US008383599B2

(12) United States Patent
Hannon et al.

(10) Patent No.: US 8,383,599 B2
(45) Date of Patent: *Feb. 26, 2013

(54) METHODS AND COMPOSITIONS FOR RNA INTERFERENCE

(75) Inventors: Gregory J. Hannon, Huntington, NY (US); Patrick J. Paddison, Seattle, WA (US); Emily Bernstein, New York, NY (US); Amy Caudy, Toronto (CA); Douglas S. Conklin, Niskayuna, NY (US); Scott Hammond, Harbor Pittsboro, NC (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 84 days.

This patent is subject to a terminal disclaimer.

(21) Appl. No.: 12/152,837

(22) Filed: May 16, 2008

(65) Prior Publication Data
US 2009/0193531 A1 Jul. 30, 2009

Related U.S. Application Data

(63) Continuation of application No. 10/055,797, filed on Jan. 22, 2002, now abandoned.

(51) Int. Cl.
*A61K 48/00* (2006.01)
(52) U.S. Cl. ...... 514/44; 536/24.5; 536/24.31; 536/24.1
(58) Field of Classification Search .................. None
See application file for complete search history.

(56) References Cited

U.S. PATENT DOCUMENTS

| | | | |
|---|---|---|---|
| 5,246,921 | A | 9/1993 | Reddy et al. |
| 5,624,803 | A | 4/1997 | Noonberg et al. |
| 5,814,500 | A | 9/1998 | Dietz |
| 5,998,148 | A | 12/1999 | Bennett et al. |
| 6,107,027 | A | 8/2000 | Kay et al. |
| 6,130,092 | A | 10/2000 | Lieber et al. |
| 6,326,193 | B1 | 12/2001 | Liu et al. |
| 6,506,559 | B1 | 1/2003 | Fire et al. |
| 6,541,248 | B1 | 4/2003 | Kingsman et al. |
| 6,573,099 | B2 | 6/2003 | Graham et al. |
| 6,605,429 | B1 | 8/2003 | Barber et al. |
| 7,691,995 | B2 | 4/2010 | Zamore et al. |
| 2002/0086356 | A1 | 7/2002 | Tuschl et al. |
| 2002/0114784 | A1 | 8/2002 | Li et al. |
| 2002/0160393 | A1 | 10/2002 | Symonds et al. |
| 2003/0051263 | A1 | 3/2003 | Fire et al. |
| 2003/0055020 | A1 | 3/2003 | Fire et al. |
| 2003/0056235 | A1 | 3/2003 | Fire et al. |
| 2003/0084471 | A1 | 5/2003 | Beach et al. |
| 2004/0001811 | A1 | 1/2004 | Kreutzer et al. |
| 2004/0018999 | A1 | 1/2004 | Beach et al. |
| 2004/0086884 | A1 | 5/2004 | Beach et al. |
| 2004/0102408 | A1 | 5/2004 | Kreutzer et al. |
| 2004/0229266 | A1 | 11/2004 | Tuschl et al. |
| 2005/0164210 | A1 | 7/2005 | Mittal et al. |
| 2005/0197315 | A1 | 9/2005 | Taira et al. |

FOREIGN PATENT DOCUMENTS

| | | |
|---|---|---|
| CA | 2470903 | 7/2003 |
| EP | 1462525 | 9/2004 |
| WO | WO-94/01550 | 1/1994 |
| WO | 99/32619 | 7/1999 |
| WO | WO-99/32619 | 7/1999 |
| WO | WO-99/49029 | 9/1999 |
| WO | WO-00/01846 | 1/2000 |
| WO | WO-00/44895 | 8/2000 |
| WO | WO-00/44914 | 8/2000 |
| WO | WO-00/63364 | 10/2000 |
| WO | WO-01/29058 | 4/2001 |
| WO | WO-01/36646 | 5/2001 |
| WO | WO-01/48183 | 7/2001 |
| WO | WO-01/49844 | 7/2001 |
| WO | 01/68836 | 9/2001 |
| WO | WO-01/75164 | 10/2001 |
| WO | WO-02/44321 | 6/2002 |
| WO | WO-02/059300 | 8/2002 |
| WO | WO-02/068635 | 9/2002 |
| WO | WO-03/010180 | 2/2003 |
| WO | WO-03/020931 | 3/2003 |
| WO | WO-2004/029219 | 4/2004 |

OTHER PUBLICATIONS

Miller et al. Improved retroviral vectors for gene transfer and expression. Biotechniques 1989, 7(9): 980-990.*
Brummelkamp et al. Science 2002: 550-553.*
Brummelkamp et al. Cancer Cell 2002, vol. 2: 243-247.*
Sorenson et al. J. Molecular Biology Apr. 2003, 761-766.*
McManus et al. RNA 2002, vol. 8, 842-850.*
Silva et al. (Nature Genetics, 2005: vol. 37: 1281-1288).*
Brummelkamp et al., "A system for stable expression of short interfering RNA's in mammalian cells," Science, vol. 296, pp. 550-553 (Apr. 2002).
European Search Result mailed on Sep. 22, 2009 for European Application No. EP 03732052 filed Jan. 22, 2003.
European Search Result mailed on Feb. 17, 2010, for European Application No. EP 03732052 filed Jan. 22, 2003.
Elbashir et al., "Duplexes of 21-nucleotide RNAs mediate RNA Interference in cultured mammalian cells," Nature vol. 411, pp. 494-498 (May 2001).
European Search Report for European Patent Application No. 05857008.6, mailed May 8, 2008.
Paddison et al., "Short hairpin activated gene silencing in mammalian cells," Methods in molecular biology, Humana Press Inc., Cifton , NJ, US, vol. 265, pp. 85-100 (Apr. 2004).
Silva Jose et al., "Second-generation shRNA libraries covering the mouse and human genomes," Nature genetics, vol. 37, No. 11, pp. 1281-1288 (Nov. 2005).
Siolas Despina et al., :Synthesis shRNAs as potent RNAi triggers, Nature Biotechnology, vol. 23, No. 2, pp. 227-231 (Feb. 2005).

(Continued)

*Primary Examiner* — Kimberly Chong
(74) *Attorney, Agent, or Firm* — Wilmer Cutler Pickering Hale and Dorr LLP

(57) ABSTRACT

The present invention provides methods for attenuating gene expression in a cell using gene-targeted double stranded RNA (dsRNA). The dsRNA contains a nucleotide sequence that hybridizes under physiologic conditions of the cell to the nucleotide sequence of at least a portion of the gene to be inhibited (the "target" gene).

20 Claims, 49 Drawing Sheets

OTHER PUBLICATIONS

Bosher et al., "RNA interference can target pre-mRNA: consequences for gene expression in a *Caenorhabditis elegans* operon," Genetics, vol. 153, No. 3, p. 1245-1256 (Nov. 1999).
European Search report for European Patent application No. 03732052.0, mailed May 23, 2008.
Hasuwa et al., "Small interfering RNA and gene silencing in transgenic mice and rats," FEBS Letters, Elsevier, Amsterdam, NL, vol. 532, pp. 227-230 (Dec. 2002).
Manche et al., "Interactions between double-stranded RNA regulators and the proteinkinase Dai," Molecular and cellular Biology, Amercian Society for Microbiology, Washington, US, vol. 12, pp. 5238-5248 (Nov. 1992).
Silva et al., Second-generation shRNA libraries to the mouse and human genomes, unpublished manuscript.
Marked-up U.S. Appl. No. 09/866,557, filed May 24, 2001.
Marked-up U.S. Appl. No. 60/243,097, filed Oct. 24, 2000.
Declaration of Dr. Vladimir Drozdoff (executed Aug. 5, 2008).
Declaration of Mr. John Maroney (executed Aug. 5, 2008).
Declaration of Professor Gregory Hannon (executed Aug. 5, 2008).
Letter of Apr. 22, 2008 from Douglass N. Ellis, Jr. of Ropes & Gray LLP to John Maroney, Esq. of Cold Spring Harbor Laboratory.
Letter of Apr. 28, 2008 from John Maroney of Cold Spring Harbor Laboratory to Douglass N. Ellis, Jr. of Robes & Gray LLP.
Letter of Apr. 29, 2008 from Douglass N. Ellis, Jr. from Robes & Gray LLP to John Maroney, Esq. of Cold Spring Harbor Laboratory.
Letter of May 9, 2008 to Eric R. Hubbard, Esq. of Robes & Gray LLP from John Maroney, Esq. of Cold Spring Harbor Laboratory.
Letter of Jun. 4, 2008 from Eric R. Hubbard of Robes & Gray LLP to John Maroney, Esq. of Cold Spring Harbor Laboratory.
Letter of Jun. 13, 2008 from John Maroney, Esq. of Cold Spring Harbor Laboratory to James Haley, Esq. of Robes & Gray LLP.
Non final office action mailed on Feb. 9, 2005 for U.S. Appl. No. 10/055,797, filed Jan. 22, 2002.
Non final office action mailed on Nov. 8, 2005 for U.S. Appl. No. 10/055,797, filed Jan. 22, 2002.
Final office action mailed on Apr. 17, 2007, for U.S. Appl. No. 10/055,797, filed Jan. 22, 2002.
Non final office action mailed on Jul. 26, 2006, for U.S. Appl. No. 10/055,797, filed Jan. 22, 2002.
Non final office action mailed on Aug. 30, 2010, for U.S. Appl. No. 11/894,676, filed Aug. 20, 2007.
Final office action mailed on Jan. 27, 2010, for U.S. Appl. No. 11/894,676, filed Aug. 20, 2007.
Non final office action mailed on May 4, 2009, for U.S. Appl. No. 11/894,676, filed Aug. 20, 2007.
Final Office Action mailed on May 12, 2009, for U.S. Appl. No. 10/997,086, filed Nov. 23, 2004.
Final Office Action mailed on Jul. 2, 2010, for U.S. Appl. No. 10/997,086, filed Nov. 23, 2004.
Non Final Office Action mailed on Aug. 26, 2009, for U.S. Appl. No. 10/997,086, filed Nov. 23, 2004.
Non Final Office Action mailed on Feb. 12, 2007, for U.S. Appl. No. 10/997,086, filed Nov. 23, 2004.
U.S. Appl. No. 60/305,185, filed Jul. 12, 2001.
U.S. Appl. No. 60/307,411, filed Jul. 23, 2001, 32 pages.
Agrawal, S. et al., "Antisense Therapeutics: Is It As Simple as Complementary Base Recognition?," Molecular Medicine Today, 61:72-81 (2000).
Ambros V, Dicing Up RNAs, Science 293:811-813 (2001).
Bass, B.L., Double-Stranded RNA as a Template for Gene Silencing, Cell 101, 235-238 (2000).
Baulcombe, D.C., Gene Silencing: RNA Makes RNA Makes No Protein, Curr. Biol. 9, R599-R601 (1999).
Baulcombe, D.C., RNA as a Target and an Initiator of Post-Transcriptional Gene Silencing in Transgenic Plants, Plant Mol. Biol. 32, 79-88 (1996).
Bernstein E. et al., Dicer is Essential for Mouse Development, Nat. Genet. 35(3):215-7 (2003); Epub Oct. 5, 2003.
Bernstein E. et al., Role for a Bidentate Ribonuclease in the Initiation Step of RNA Interference, Nature 409(6818):363-6 (2001).
Bernstein E. et al., The Rest is Silence, RNA 7(11):1509-21 (2001).
Bohmert, K. et al., AGO1 Defines a Novel Locus of Arabidopsis Controlling Leaf Development, EMBO J. 17, 170-180 (1998).

Bosher, J.M. & Labouesse, M., RNA Interference: Genetic Wand and Genetic Watchdog, Nat. Cell Biol. 2, E31-36 (2000).
Bosher, J.M. et al., RNA Interference Can Target Pre-mRNA: Consequences for Gene Expression in a *Caenorhabditis elegans* Operon, Genetics 153, 1245-1256 (Nov. 1999).
Buchholz et al., "Enzymatically prepared RNAi libraries," Nature Mathods, vol. 3, No. 9, pp. 696-700 (Sep. 2006).
Caplen et al., "Rescue of polyglutamine-mediated cytotoxicity by double-stranded RNA-mediated RNA interference," Human Molecular Genetics, vol. 11, pp. 175-184 (2002).
Caplen et al., "Specific inhibition of gene expression by small double-stranded RNAs in invertebrate and vertebrate systems," PNAS vol. 98, pp. 9742-9747 (Aug. 2001).
Caplen et al., dsRNA-Mediated Gene Silencing in Cultured Drosophila Cells: A Tissue Culture Model for the Analysis of RNA Interference, Gene (2000) 252:95-105, Elsevier.
Caplen et al.,"Specific inhibition of gene expression by small double-stranded RNA's in invertebrate and vertebrate systems," PNAS, vol. 98, pp. 9742-9747 (Aug. 2001).
Caplen, NJ, RNAi as a Gene Therapy Approach, Expert Opinion Biol. Thera. (2003), vol. 3(4):575-586, Ashley Publications Ltd.
Carmell MA et al., Germline Transmission of RNAi in Mice, Nat Struct Biol. 10(2):91-2 (2003).
Carmell MA et al., RNase III Enzymes and the Initiation of Gene Silencing, Nat Struct Mol Biol. 11(3):214-8 (2004).
Carmell MA et al., The Argonaute Family: Tentacles That Reach Into RNAi, Developmental Control, Stem Cell Maintenance, and Tumorigenesis, Genes Dev. 16(21):2733-42 (2002).
Catalanotto, C. et al., Gene Silencing in Worms and Fungi, Nature 404, 245 (2000).
Caudy AA et al., A Micrococcal Nuclease Homologue in RNAi Effector Complexes, Nature 425(6956):411-4 (2003).
Caudy AA et al., Fragile X-Related Protein and VIG Associate With the RNA Interference Machinery, Genes Dev. 16(19):2491-6 (2002).
Caudy AA et al., Induction and Biochemical Purification of RNA-Induced Silencing Complex From Drosophila S2 Cells, Methods Mol Biol. 265:59-72 (2004.
Chang et al., "Lessons from Nature:microRNA-based ShRNA libraries," Nature Methods, vol. 3, No. 9, pp. 707-714 (Sep. 2006).
Check, E., "RNA to the Rescue? Disease Therapies Based on a Technique for Gene Silencing Called RNA Interference Are Racing Towards the Clinic, Erika Check Investigates Molecular Medicine's Next Big Thing," Nature, 425:10-12 (2003).
Cleary MA et al., Production of complex Nucleic Acid Libraries Using Highly Parallel in Situ Oligonucleotide Synthesis, Nat Methods, 1(3):241-8 (2004); Epub Nov. 18, 2004.
Cogoni et al., "Post-transcriptional gene silencing across kingdoms," Current opinion in Genetics and Development, vol. 10, pp. 638-643 (2000).
Cogoni, C. & Macino, G., Gene Silencing in Neurospora Crassa Requires a Protein Homologous to RNA-Dependent RNA Polymerase, Nature 399, 166-169 (1999).
Cogoni, C. & Macino, G., Posttranscriptional Gene Silencing in Neurospora by a RecQ DNA Helicase, Science 286, 2342-2344 (1999).
Connelly, J.C. & Leach, D.R., the sbcC and sbcD genes of *Escherichia coli* Encode a Nuclease Involved in Palindrome inviability and Genetic Recombination, Genes Cell 1, 285-291 (1996).
Crooke, ST, Basic Principles of Antisense Therapeutics, Antisense Research and Application (1998), Chapter 1, Springer-Verlag, New York.
Cullen, "Enhancing and confirming the specificity of RNAi experiments," Nature Methods, vol. 3, pp. 677-681 (Sep. 2006).
Dalmay, T., et al., An RNA-Dependent RNA Polymerase Gene in Arabidopsis is Required for Posttranscriptional Gene Silencing Mediated by a Transgene But Not by a Virus, Cell 101, 543-553 (2000).
Denli AM et al., RNAi: An Ever-Growing Puzzle, Trends Biochem Sci. 28(4):196-201 (2003).
Denli et al., "Processing of primary microRNAs by the Microprocessor complex," Nature, vol. 432(7014), pp. 231-235 (2004); Epub Nov. 7, 2004.

Di Nocera, P.P. & Dawid, I.B., Transient Expression of Genes Introduced Into Cultured Cells of Drosophila, PNAS 80, 7095-7098 (1983).

Elbashir et al., "Functional anatomy of siRNAs for mediating efficient RNAi in Drosophila melanogaster embryo lysate," The EMBO Journal, vol. 20(23): pp. 6877-688 (2001).

Elbashir et al., "Duplexes of 21-nucleotide RNA's mediate RNa interferencein cultured mammalian cells," Nature, vol. 411, pp. 494-498 (May 2001).

Elbashir et al., "RNA interference is medited by 21- and 22-nucleotida RNA,s," Gene and Development, vol. 15, pp. 188-200 (2001).

Elk et al, "Gene based therapy," Goodman & Gilman's, the Pharmacological Basis of Therapeutics, 9th Edition,; 5: 77-101 (1996).

Fagard, M., et al., AG01, QDE-2, and RDE-1 Are Related Proteins Required for Posttranscriptional Gene Silencing in Plants, Quelling in Fungi, and RNA Interference in Animals, PNAS 97, 11650-11654 (Oct. 10, 2000).

Fire, A., et al., Potent and Specific Genetic Interference by Double-Stranded RNA in *Caenorhabditis elegans*, Nature 391, 806-811 (1998).

Fire, A., RNA-Triggered Gene Silencing, Trends Genet. 15, 358-363 (1999).

Fortier, E. & Belote, J.M., Temperature-Dependent Gene Silencing by an Expressed Inverted Repeat in Drosophila, Genesis 26, 240-244 (2000).

Fraser A., "Human Genes hit the big screen," Nature 428:375-378 (2004).

Gil et al., "Induction of apoptosis by the DsRNA-dependent protein Kinase (PKR): mechanism of Action," Apopsosis, vol. 5, pp. 107-114 (2000).

Gillespie, D.E. & Berg, C.A., Homeless is Required for RNA Localization in Drosophila Oogenesis and Encodes a New Member of the DE-H Family of RNA-Dependent ATPases, Genes Dev. 9, 2495-2508 (1995).

Good et al., "Expression of small, therapeutic RNA's in human cell nuclei," Gene Therapy, vol. 4, pp. 45-54, Stockton Press (1997).

Grosshans et al., "Micro-RNAs: small is plentiful," The Journal of Cell Biology, vol. 156, pp. 17-21 (2002).

Guo, S. & Kemphues, K.J., Par-1, A Gene Required for Establishing Polarity in *C. elegans* Embryos, Encodes a Putative Ser/Thr Kinase That is Asymmetrically Distributed, Cell 81, 611-620 (1995).

Gupta et al., Inducible, reversible, and stable RNA interference in mammalian cells, Proc. Natl Acd. Sci. USA 101(7): 1927-32 (2004); Epub Feb. 4, 2004.

Hamilton, J.A. & Baulcombe, D.C., A Species of Small Antisense RNA in Posttranscriptional Gene Silencing in Plants, Science 286, 950-952 (1999).

Hammond et al., "Post-Transcriptional Gene Silencing by Double-Stranded RNA", Nature Rev. Genetics 2(2):10 (2001.

Hammond, S. et al., "Argonaute2, A Link Between Genetic and Biochemical Analyses RNAi," Science, 293:5532, 1146-1150 (2001).

Hammond, S.M. et al., An RNA-Directed Nuclease Mediates Post-Transcriptional Gene Silencing in Drosophila Cells, Nature 404, 293-296 (2000).

Hannon et al., "RNA interference by short Hairpin RNAs expreseed in vertebrate cells," Methods Mol Biol 257:255-66 (2004).

Hannon G et al., "Unlocking the potential of the human genome with RNA interference," Nature, 431(7006):371-8 (2004).

Hannon GJ, "RNA Interference," Nature 418(6894): 244-51 (2002).

He et al., "A microRNA polycitron as a potential human oncogene," Nature 435(7043):828-33 (2005).

He et al., MicroRNAs: small RNAs with a big role in gene regulation, Nat Rev. Genet. 5(7):522-31 (2004).

Hemann et al., "An epi-allelic seried of p53 hypomorphs created by stable RNAi produces distinct tumor phenotypes in vivo," Nat Genet. 33(3):396-400 (2003); Epub Feb. 3, 2003.

Hunter, C., Genetics: A Touch of Elegance with RNAi, Curr. Biol. 9, R440-R442 (1999).

Hutvagner et al., A Cellular Function for the RNA-Interference Enzyme Dicer i the maturation of the let-7 Small Temporal RNA, Science, vol. 293, pp. 834-838 (Aug. 2001).

Jackson et al., "Expression profiling reveals off-target gene regulation by RNAi," Nature Biotechnology 21(6), 635-638 (Jun. 2003).

Jacobsen, S.E. et al., Disruption of an RNA helicase/RNAse III Gene in Arabidopsis Causes Unregulated Cell Division in Floral Meristems, Development 126, 5231-5243 (1999).

Jen, K.Y. et al., "Suppression of Gene Expression by Targeted Disruption of Messenger RNA: Available Options and Current Strategies," Stem Cells, 18:307-319 (2000).

Jones, A.L. et al., De Novo Methylation and Co-Suppression Induced by a Cytoplamically Replicating Plant RNA Virus, EMBO J. 17, 6385-6393 (1998).

Jones, L., et al., RNA-DNA Interactions and DNA Methylation in Post-Transcriptional Gene Silencing, Plant Cell 11, 2291-2301 (Dec. 1999).

Jorgensen et al., "An RNA-based information Superhighway in Plants," Science 279, pp. 1486-1487 (1998).

Kalejta, R.F. et al., An Integral Membrane Green Fluorescent Protein Marker, Us9-GFP, Is Quantitatively Retained in Cells During Propidium Iodide-Based Cell Cycle Analysis by Flow Cytometry, Exp. Cell. Res. 248, 322-328 (1999).

Kennerdell, J.R. & Carthew, R.W., Heritable Gene Silencing in Drosophila Using Double-Stranded RNA, Nat. Biotechnol. 17, 896-898 (2000).

Kennerdell, J.R. & Carthew, R.W., Use of dsRNA-Mediated Genetic Interference to Demonstrate That Frizzled 2 Act in the Wingless Pathway, Cell 95, 1017-1026 (1998).

Ketting et al, "Dicer functions in RNA interference and in synthesis of small RNA involved in developmental timing in *C. elegans*," Genes Dev 15, 2654-2659 (Oct. 15, 2001).

Ketting, R.F. et al., mut-7 of *C. elegans*, Required for Transposon Silencing and RNA Interference, Is a Homolog of Werner Syndrome Helicase and RNaseD, Cell 99, 133-141 (1999).

Kramer, E.R. et al., Activation of the Human Anaphase-Promoting complex by Proteins of the CDC20/Fizzy Family, Curr. Biol. 8, 1207-1210 (1998).

Lam, G. & Thummel, C.S., Inducible Expression of Double-Stranded RNA Directs Specific Genetic Interference in Drosophila, Curr. Biol. 10, 957-963 (2000).

Lee et al., Distinct Roles for Drosophila Dicer-1 and Dicer-2 in the SiRNA/miRNA silencing Pathways, Cell 117, 69-81 (Apr. 2, 2004).

Lipardi et al, "RNAi as randon Degradative PCR: SiRNA Primers Convert mRNA into dsRNAs that are degrated to generate new siRNAs," Cell, vol. 107, pp. 297-307 (2001).

Liu et al., "MicroRNA-dependent localization of targeted mRNAs to mammalian P-bodies," Nat cell Biol. 7(7): 719-23 (2005): Epub Jun. 5, 2005.

Liu et al., "Argonaute 2 is the catalytic engine of mammalian RNAI," Science 305(5689):1437-41 (2004); Epub Jul. 29, 2004.

Lohmann, J.U. et al., Silencing of Developmental Genes in Hydra, Dev. Biol. 214, 211-214 (1999).

Lund et al., "Nuclear Export of MicroRNA Precursors," Science 303, 95-98 (Jan. 2, 2004).

Matsuda, S. et al., Molecular Cloning and Characterization of a Novel Human Gene (HERNA) Which Encodes a Putative RNA-Helicase, Biochim. Biophys. Acta 1490, 163-169 (2000).

MCCaffrey et al, "RNA inference in adult mice," Nature 418(6893):38-9 (2002).

Mcmanus et al., "Gene Silencing in mammals by small interfering RNA's," Nature Reviews, vol. 3, pp. 737-747 (Oct. 2002).

Mette et al., "Transcriptional silencing and promoter methylation triggered by double stranded RNA," The EMBO Journal vol. 19(19): pp. 5194-5201 (2000).

Misquitta, L. & Paterson, B.M., Targeted Disruption of Gene Function in drosophila by RNA Interference (RNA-i): a Role for Nautilus in Embryonic Somatic muscle Formation, PNAS 96, 1451-1456 (Feb. 1999).

Montgomery, M.K. & Fire, A Double-Stranded RNA as a Mediator in Sequence-Specific Genetic Silencing and Co-Suppression, Trends Genet. 14, 255-258 (1998).

Montgomery, M.K. et al., RNA as a Target of Double-Stranded RNA-Mediated Genetic Interference in *Caenorhabditis elegans*, PNAS 95, 15502-15507 (Dec. 1998).

Moss, Eric G., "RNA Interference: It's a Small RNA World," Current Biology, 11(19), R772-R775 (2001).
Mourrain, P. et al., Arabidopsis SGS2 and SGS3 Genes Are Required for Posttranscriptional Gene Silencing and Natural Virus Resistance, Cell 101, 533-542 (2000).
Murchison et al., "miRNAs on the move; miRNA biogenesis and the RNAi machinery," Curr opinion Cell Biol. 16(3):223-9 (2004).
Ngo, H. et al., Double-Stranded RNA Induces mRNA Degradation in Trypanosoma Brucei, PNAS 95, 14687-14692 (Dec. 1998).
Novina et al., The RNAI Revolution, Nature (2004), vol. 430:161-164, Nature Publishing Group.
Opalinska et al., "Nucleic acid therapeutics: basic principals and recent applications," Nature reviews: Drug Discovery, vol. 1, pp. 503-514 (2002).
Paddison et al., "A resource for large-scale RNA-interference-based screens in mammals," Nature 428(6981):427-31 (2004).
Paddison et al., "RNA interference: the new somatic cell genetics?," Cancer cell. 2(1): 17-23 (2002).
Paddison et al., "Short hairpin activated gene silencing in mammalian cells," Methods Mol Biol. 265: 85-100 (2004).
Paddison et al., "Short hairpin RNAs (shRNAs) induce sequence-specific silencing in mammalian cells," Genes & Development 16:948-958 (2002).
Paddison et al., "Stable suppression of gene expression by RNAI in mammalian cells," 99(3) 1443-1448 (2002).
Paddison et al.m, "SiRNAs and ShRNAs: skeleton keys to the human genome," Curr Opinion Mil Ther. 5(3):217-24 (2003).
Paroo et al., Challenges for RNAi in Vivo, Trends in Biotechnology (2004), vol. 22(8), 390-394, Elsevier.
Pei et al., "On the art of identifying effective and specific siRNAs," Nature Methods, vol. 3, No. 9, pp. 670-676 (Sep. 2006).
Pham et al., "A Dicer-2-Dependent 80S complex cleaves targeted mRNAs during RNAI in Drosophilia," Cell 117, 83-94 (Apr. 2, 2004).
Piccin et al., "Efficient and Heritable Functional Knock-Out of an Adult Phenotype in Drosophila Using a GAL4-Driven Hairpin RNA Incorporating a Heterologous Spacer", Nuc. Acid Res., 29(12):E55 (2001).
Qi et al., Biochemical Specialization within Arabidopsis RNA Silencing Pathways, Mol Cell. 19(3): 421-8 (2005).
Ratcliff, F. et al., A Similarity Between Viral Defense and Gene Silencing in Plants, Science 276, 1558-1560 (1997).
Rivas et al., Purified Argonaute and an sIRNA form recombinant human RISC, Nat Struct Mol Biol, 12(4):340-9 (2005); Epub Mar. 30, 2005.
Sanchez Alvarado, A. & Newmark, P.A., Double-Stranded RNA Specifically Disrupts Gene Expression During Planarian Regeneration, PNAS 96, 5049-5054 (Apr. 1999).
Schneider, I., Cell Lines Derived from Late Embryonic Stages of Drosophila Melanogaster, J. Embryol. Exp. Morpho. 27, 353-365 (1972).
Schramke et al., "RNA-interference-directed chromatin modification coupled to RNA polymerase II transcription," Nature 435(7046:1275-9 (2005); Epub Jun. 19, 2005.
Sen et al., "A brief history of RNAi: the silence of the genes," FASEB J., vol. 20, pp. 1293-1299 (2006).
Sharp, P.A., RNAi and Double-Strand RNA, Genes Dev. 13, 139-141 (1999).
Shi, H. et al., Genetic Interference in Typanosoma Brucei by Heritable and Inducible Double-Stranded RNA, RNA 6, 1069-1076 (2000).
Shuttleworth, J. & Colman, A. Antisense Oligonucleotide-Directed Cleavage of mRNA in Xenopus Oocytes and Eggs, EMBO J. 7, 427-434 (1988).
Sijen, T. & Kooter, J.M., Post-Transcriptional Gene-Silencing: RNAs on the Attack or on the Defense? Bioessays 22, 520-531 (2000).
Silva et al., Free energy lights the path toward more effective RNAI, Nat Genet. 35: 303-5 (2003).
Silva et al., "RNA interference micro arrays: high-throughtput loss-of function genetics in mammalian cells," Proc. NAtl Acad. Sci USA, 101(17):6548-52 (2004); Epub Apr. 14, 2004.
Silva et al., "RNA interference: a promising appraoch to antiviral therapy?," Trends Mol Med. 8(11): 505-8 (2002).

Silva et al., "RNA-interfrence-based functional genomics in mammalian cells: reverse genetics coming of age," Oncogene 23(51):8401-9 (2004).
Silva et al., Second-generation shRNA libraries to the mouse and human genomes, unpublished manuscript, Nature Genetics 2005, vol. 25:1281-1288.
Singh et al., "Inverted-Repeat DNA: A New Gene-Silencing Tool for Seed Lipid Modification", Biochem Soc. Trans. 28(6):925 (2000).
Siolas et al., "Synthetic shRNAs as potent RNAi triggers," Nat Biotechnol. 23(2):227-31 (2005); Epub Dec. 26, 2004.
Smardon, A. et al., EGO-1 is Related to RNA-Directed RNA Polymerase and Functions in Germ-Line Development and RNA Interference in C. elegans, Curr. Biol. 10, 169-178 (2000).
Smith, N.A. et al., Total Silencing by Intron-Spliced Hairpin RNAs, Nature 407, 319-320 (2000).
Snove Jr et al., "Expressing short Hairpin RNAs in vivo," Nature Methods, vol. 3 No. 9, pp. 689-695 (Sep. 2006).
Song et al., "Crystal structure of Argonaute and its applications for RISC slicer activity," Science 305(5689):1434-7 (2004) Epub Jul. 29, 2004.
Song et al., "The Crystal structure of the Argonaute 2PAZ domai reveals a RNA binding motif in RNAi effector complexes," Nat Struct Biol. 10(12): 1026-32 (2003); Epub Nov. 16, 2003.
Svoboda et al., "RNAI in mouse Oocytes and Preimplantation Embryos: effectiveness of Hairpin dsRNA," Biochem. Biophys. Res. Commum. vol. 287, pp. 1099-1104 (2001).
Svoboda et al., "RNAi expression of retrotransposons MuERV-L and IAP in preimplantation mouse embryos," Dev biol 269(1):276-85 (2004).
Tabara et al., "The DsRNA binding Protein RDE-4 interacts with RDE-1, DCR-1, and a DExH-Box Helicase to direct RNAi in C. elegans," Cell 109, 861-871 (Jun. 28, 2002).
Tabara, H. et al., RNAi in C. elegans: Soaking in the Genome Sequence, Science 282, 430-432 (1998).
Tabara, H. et al., The rde-1 Gene, RNA Interference, and Transposon Silencing in C. elegans, Cell 99, 123-132 (1999).
Tavernarakis, N. et al., Heritable and Inducible Genetic Interference by Double-Stranded RNA Encoded by Transgenes, Nat. Genet. 24, 180-183 (2000).
Timmons, L. & Fire, A., Specific Interference by Ingested dsRNA, Nature 395, 854 (1998).
Tomari et al., "RISC Assembly Defects in the Drosophila RNAi Mutant armitage," Cell 116, 831-841 (Mar. 19, 2004).
Tuschl, T. et al., Targeted mRNA Degradation by Double-Stranded RNA in Vitro, Genes & Development, 13(24):3191-3197 (1999).
Tuschl, T. et al., Targeted mRNA Degradation by Double-Stranded RNA in Vitro, Genes Dev. 13, 3191-3197 (1999).
Ui-Tei et al., Sensitive Assay of RNA Interference in Drosphilia and Chinese Hamster Cultured Cells Using Firefly Luciferase Gene as Target, FEBS Letters (2000), 479:79-82, Elsevier.
Vaucheret, H. et al., Transgene-Induced Gene Silencing in Plants, Plant J. 16, 651-659 (1998).
Vermeulen et al., "The contributions of DsRNA structure to Dicer specificity and efficiency," RNA, vol. 11, pp. 674-682 (2005).
Wadhwa, R. et al., "Know-How of RNA Interference and Its Applications in Research and Therapy," Mutation Research, 567:71-84 (2004).
Wassenegger, M. & Pelissier, T., A Model for RNA-Mediated Gene Silencing in Higher Plants, Plant Mol. Biol., 37, 349-362 (1998).
Waterhouse, P.M. et al., Virus Resistance and Gene Silencing in Plants Can Be Induced by Simultaneous Expression of Sense and Antisense RNA, PNAS 95, 13959-13964 (Nov. 1998).
Wianny, F. & Zernicka-Goetz, M., Specific Interference With Gene Function by Double-Stranded RNA in Early Mouse Development, Nature Cell Biol. 2, 70-75 (2000).
Wolf, D.A. & Jackson, P.K., Cell Cycle: Oiling the Gears of Anaphase, Curr. Biol. 8, R636-R639 (1998).
Zamore, P.D. et al., RNAi: Double-Stranded RNA Directs the ATP-Dependent Cleavage of mRNA at 21 to 23 Nucleotide Intervals, Cell 101, 25-33 (2000).
Zhang et al., "Human Dicer preferentially cleaves dsRNAs at their termini withour a requirment for ATP," The EMBO Journal 21:5875-5885 (Nov. 1, 2002).

Zhang et al., "Single Processing Center Models for Human Dicer and Bacterial RNase III," Cell Vo. 118:57-68 (2004).

Zhang et al., "Targeted gene silencing by smakk interfering RNA-based knock-down technology," Curr Pharma Biotech, vol. 5, pp. 1-7 (2004).

Lingel et al., "Nucleic acid 3'-end recognition by the Argonaute2 PAZ domain," Nat. Struct & Mol. Biol, vol. 11(6):576-577 (2004).

Marshall E, "Gene Therapy's growing pains," Science 269, 1050-1055 (1995).

Paddison et al., "Cloning of short hairpin RNAs for gene knockdown in mammalian cells," Nature Meth., vol. 1(2): 163-167 (2004).

* cited by examiner

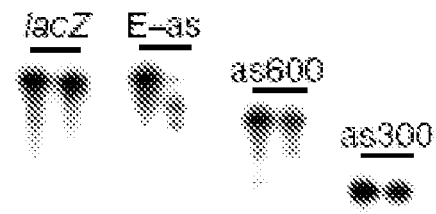
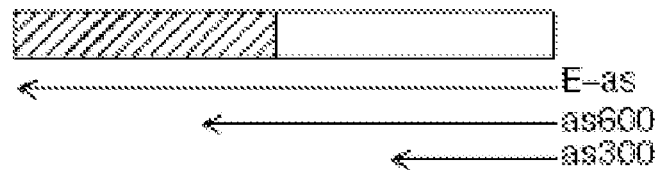
Fig. 2C

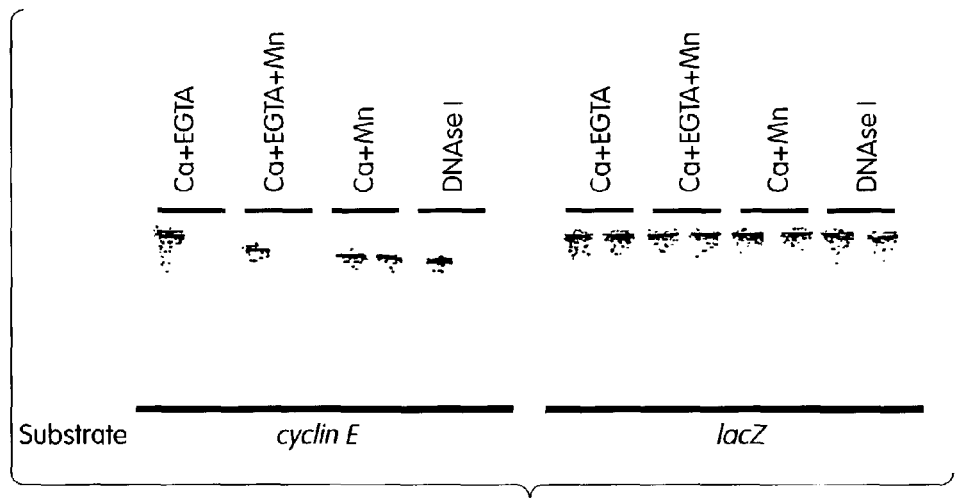
Fig. 3
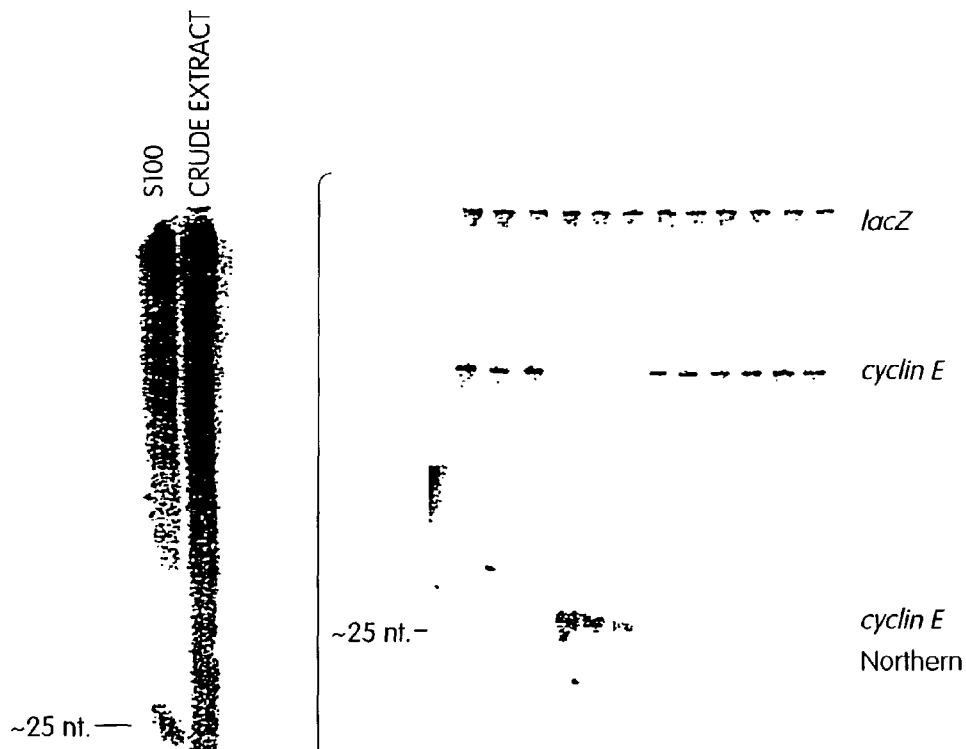
Fig. 4A
Fig. 4B

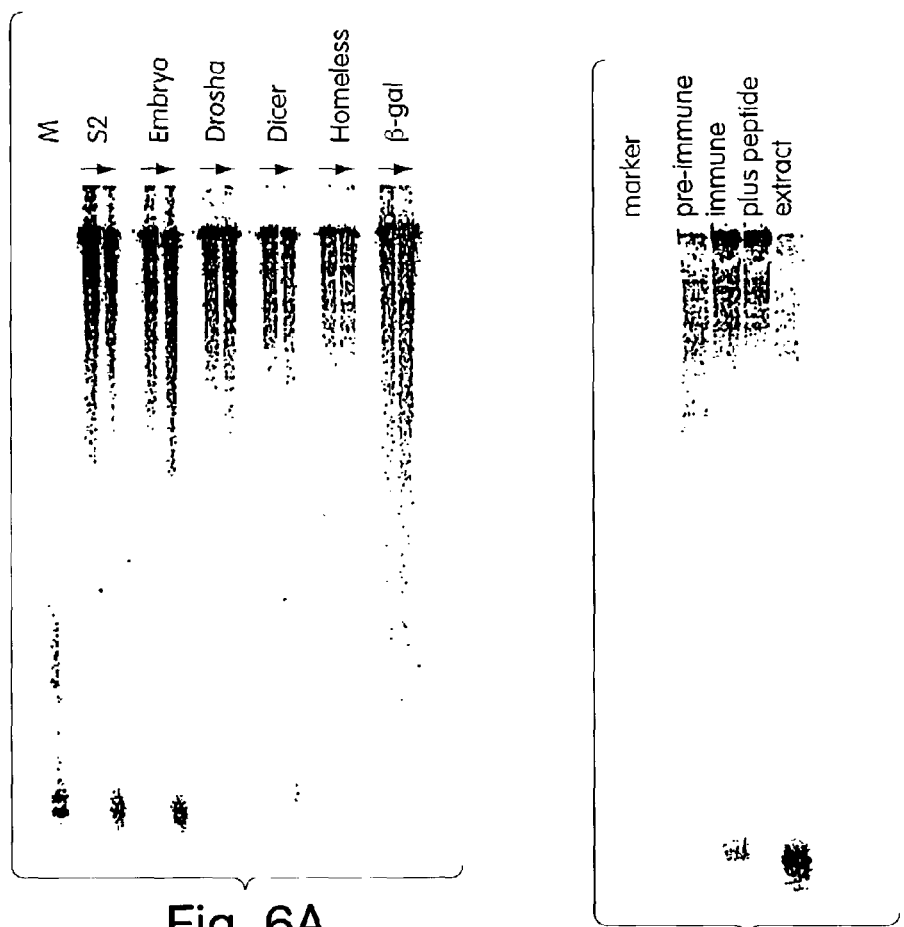
Fig. 6A
Fig. 6C
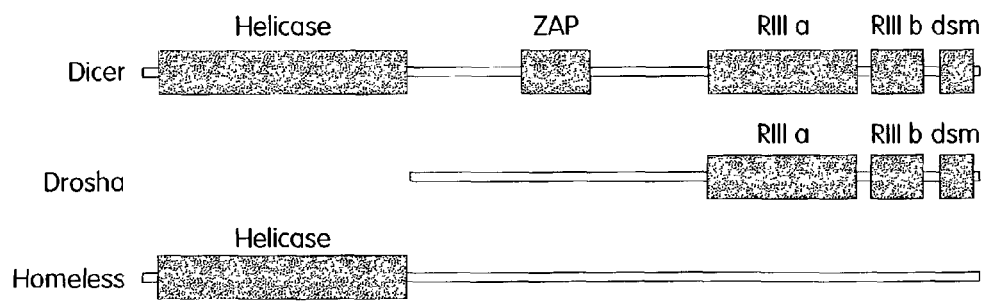
Fig. 6B

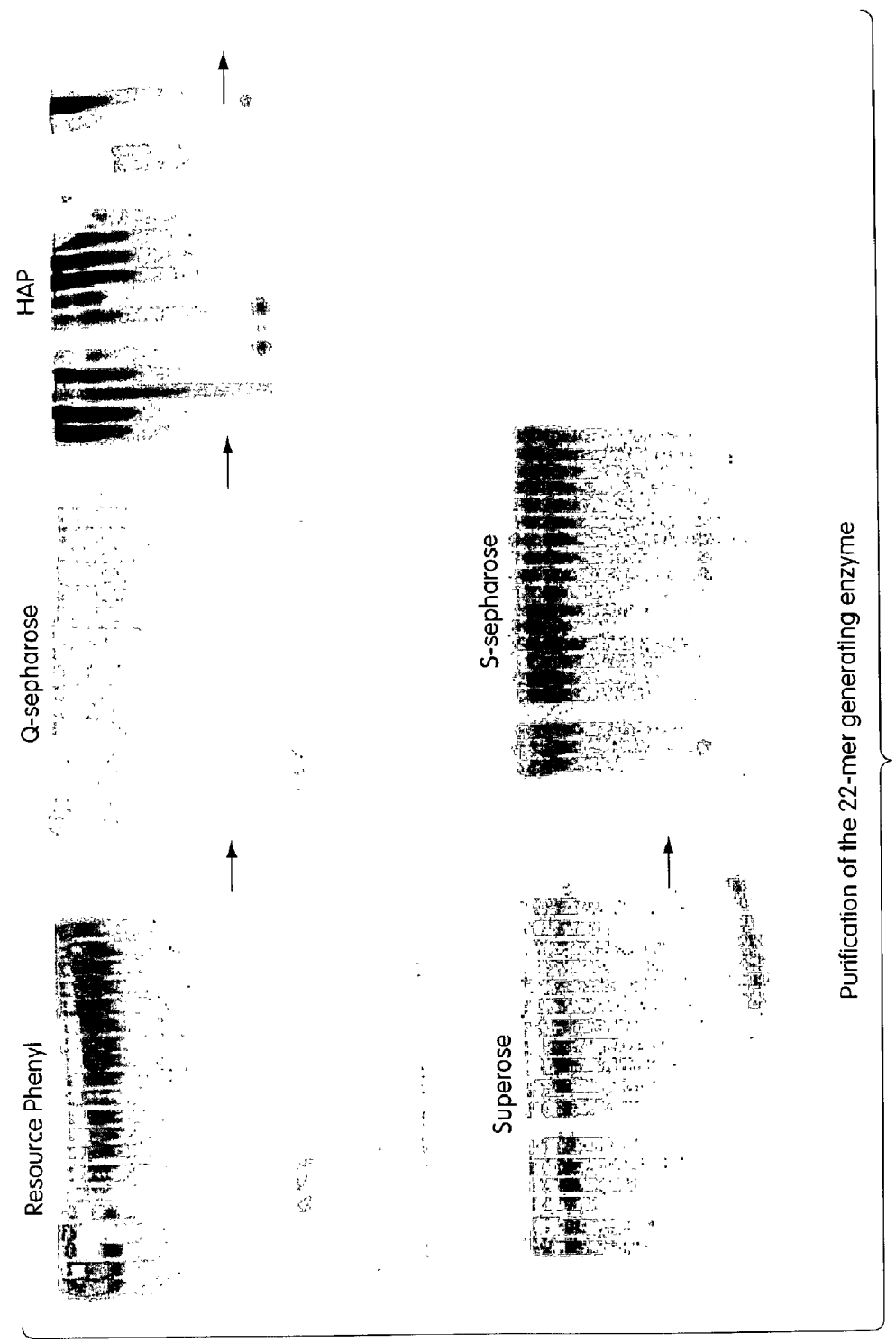

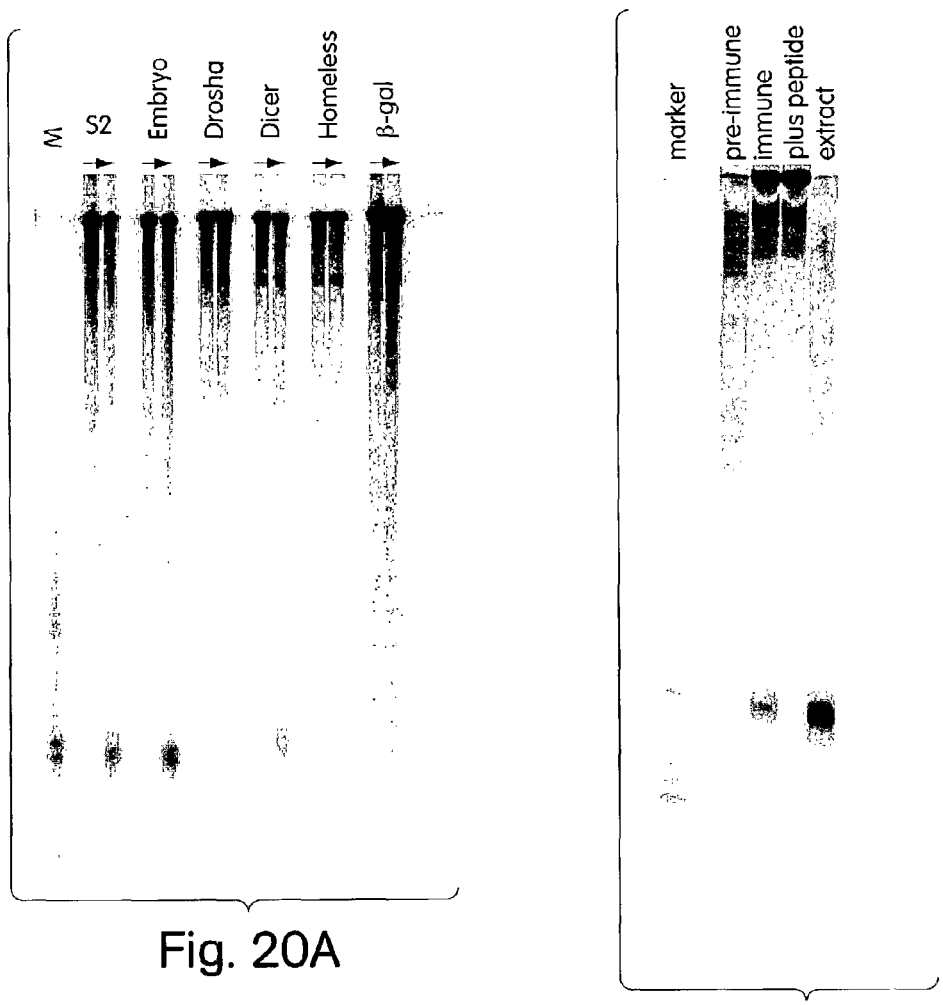
Fig. 20A
Fig. 20C
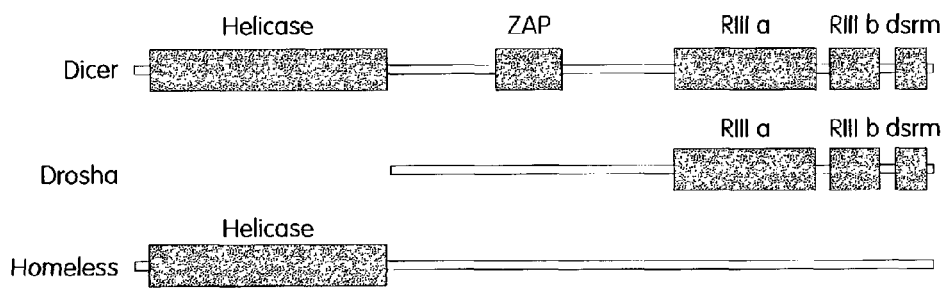
Fig. 20B

MGKKDKNKKGGQDSAAAPQPQQQQKQQQQRQQQPQQLQQPQQLQQPQQLQQPQQQQQ
QPHQQQQQSSRQQPSTSSGGSRASGFQQGGQQQKSQDAEGWTAQKKQGKQQVQGWTKQ
GQQGHQQGRQGQDGGYQQRPPGQQQGGHQQGRQGQEGGYQQRPPGQQQGGHQQGRQG
QEGGYQQRPSGQQQGGHQQGRQGQEGGYQQRPPGQQQGGHQQGRQGQEGGYQQRPSGQ
QQGHQQGRQGQEGGYQQRPSGQQQGGHQQGRQGQEGGYQQRPSGQQQGGHQQGRQGQ
EGGYQQRPPGQQPNQTQSQGQYQSRGPPQQQQAAPLPLPPQPAGSIKRGTIGKPGQVG
INYLDLDLSKMPSVAYHYDVKIMPERPKKFYRQAFEQFRVDQLGGAVLAYDGKASCYS
VDKLPLNSQNPEVTVTDRNGRTLRYTIEIKETGDSTIDLKSLTTYMNDRIFDKPMRAM
QCVEVVLASPCHNKAIRVGRSFFKMSDPNNRHELDDGYEALVGLYQAFMLGDRPFLNV
DISHKSFPISMPMIEYLERFSLKAKINNTTNLDYSRRFLEPFLRGINVVYTPPQSFQS
APRVYRVNGLSRAPASSETFEHDGKKVTIASYFHSRNYPLKFPQLHCLNVGSSIKSIL
LPIELCSIEEGQALNRKDGATQVANMIKYAATSTNVRKRKIMNLLQYFQHNLDPTISR
FGIRIANDFIVVSTRVLSPPQVEYHSKRFTMVKNGSWRMDGMKFLEPKPKAHKCAVLY
CDPRSGRKMNYTQLNDFGNLIISQGKAVNISLDSDVTYRPFTDDERSLDTIFADLKRS
QHDLAIVIIPQFRISYDTIKQKAELQHGILTQCIKQFTVERKCNNQTIGNILLKINSK
LNGINHKIKDDPRLPMMKNTMYIGADVTHPSPDQREIPSVVGVAASHDPYGASYNMQY
RLQRGALEEIEDMFSITLEHLRVYKEYRNAYPDHIIYYRDGVSDGQFPKIKNEELRCI
KQACDKVGCKPKICCVIVVKRHHTRFFPSGDVTTSNKFNNVDPGTVVDRTIVHPNEMQ
FFMVSHQAIQGTAKPTRYNVIENTGNLDIDLLQQLTYNLCHMFPRCNRSVSYPAPAYL
AHLVAARGRVYLTGTNRFLDLKKEYAKRTIVPEFMKKNPMYFV

Fig. 24

Strategy for stable expression of dsRNA in cultured mammalian cells

Production of dsRNA homologous to target mRNA

Figure 28
Stable suppression of transgene expression in ammalian cells
wt P19
Putative P19 clones stably ex-pressing 500mer GFP hairpin
*Co-transfection with pRFP and pGFP, 42 hrs post-transfection*

RNAi in ES cells

RNAi in mouse embyronic cells (P19)

RNAi is post-transcriptional

Silencing is specific and requires dsRNA

Figure 37

Luciferase siRNA

```
UCGAAGUACUAGGUAGUGA
UAAAGCUUCAUGAGUCGCAUUC
```

Luciferase Let-7 like

```
                                    U  \
                               GGGGC   C
                               UCCCG   U
                                    G /
CAUCGACUGAAAUCCCUU        UAGGGUAUCG
GUAGCUGAUUUAGGGACUAUUAGGUAAA
```

Luciferase simple hairpin

```
                            U
CAUCGACUGAAAUCCCUGGUAAAUCCGUUG  U  A
GUAGCUGACUUUAGGGACCAUUAGGCAAC   A  A
```

Short Hairpin RNAs in Drosophila S2 cells

Simultaneous introduction of multiple hairpins does not produce synergy

Encoded short hairpins function *in vivo*

Stable Suppression by short dsRNAs – stable expression strategies

Stable Suppression by short dsRNAs – cloning strategy

MaRX-R

Stable suppression by expressed RNAi

Early Passage PKR -/- MEFs: dual luciferase assay with long dsRNA (~500nt)

Mouse Tyrosinase Promoter

METHODS AND COMPOSITIONS FOR RNA INTERFERENCE

RELATED APPLICATIONS

This application is a continuation of U.S. Ser. No. 10/055,797, filed on Jan. 22, 2002, the specification of which is incorporated by reference herein.

GOVERNMENT SUPPORT

This invention was made with government support under Grant No. R01-GM62534 awarded by the National Institutes of Health (NIH). The U.S. government has certain rights in the invention.

BACKGROUND OF THE INVENTION

"RNA interference", "post-transcriptional gene silencing", "quelling"—these different names describe similar effects that result from the overexpression or misexpression of transgenes, or from the deliberate introduction of double-stranded RNA into cells (reviewed in Fire A (1999) Trends Genet. 15: 358-363; Sharp P A (1999) Genes Dev 13: 139-141; Hunter C (1999) Curr Biol 9: R440-R442; Baulcombe, D C (1999) Curr Biol 9: R599-R601; Vaucheret et al. (1998) Plant J 16: 651-659). The injection of double-stranded RNA into the nematode *Caenorhabditis elegans*, for example, acts systemically to cause the post-transcriptional depletion of the homologous endogenous RNA (Fire et al. (1998) Nature 391: 806-811; and Montgomery et al. (1998) PNAS 95: 15502-15507). RNA interference, commonly referred to as RNAi, offers a way of specifically and potently inactivating a cloned gene, and is proving a powerful tool for investigating gene function. Although the phenomenon is interesting in its own right; the mechanism has been rather mysterious, but recent research—for example that recently reported by Smardon et al. (2000) Curr Biol 10: 169-178—is beginning to shed light on the nature and evolution of the biological processes that underlie RNAi.

RNAi was discovered when researchers attempting to use the antisense RNA approach to inactivate a *C. elegans* gene found that injection of sense-strand RNA was actually as effective as the antisense RNA at inhibiting gene function (Guo et al. (1995) Cell 81: 611-620). Further investigation revealed that the active agent was modest amounts of double-stranded RNA that contaminate in vitro RNA preparations. Researchers quickly determined the 'rules' and effects of RNAi which have become the paradigm for thinking about the mechanism which mediates this affect. Exon sequences are required, whereas introns and promoter sequences, while ineffective, do not appear to compromise RNAi (though there may be gene-specific exceptions to this rule). RNAi acts systemically—injection into one tissue inhibits gene function in cells throughout the animal. The results of a variety of experiments, in *C. elegans* and other organisms, indicate that RNAi acts to destabilize cellular RNA after RNA processing.

The potency of RNAi inspired Timmons and Fire (1998 Nature 395: 854) to do a simple experiment that produced an astonishing result. They fed to nematodes bacteria that had been engineered to express double-stranded RNA corresponding to the *C. elegans* unc-22 gene. Amazingly, these nematodes developed a phenotype similar to that of unc-22 mutants that was dependent on their food source. The ability to conditionally expose large numbers of nematodes to gene-specific double-stranded RNA formed the basis for a very powerful screen to select for RNAi-defective *C. elegans* mutants and then to identify the corresponding genes.

Double-stranded RNAs (dsRNAs) can provoke gene silencing in numerous in vivo contexts including *Drosophila*, *Caenorhabditis elegans*, planaria, hydra, trypanosomes, fungi and plants. However, the ability to recapitulate this phenomenon in higher eukaryotes, particularly mammalian cells, has not been accomplished in the art. Nor has the prior art demonstrated that this phenomena can be observed in cultured eukaryotic cells. Additionally, the 'rules' established by the prior art have taught that RNAi requires exon sequences, and thus constructs consisting of intronic or promoter sequences were not believed to be effective reagents in mediating RNAi. The present invention aims to address each of these deficiencies in the prior art and provides evidence both that RNAi can be observed in cultured eukaryotic cells and that RNAi constructs consisting of non-exon sequences can effectively repress gene expression.

SUMMARY OF THE INVENTION

One aspect of the present invention provides a method for attenuating expression of a target gene in cultured cells, comprising introducing double stranded RNA (dsRNA) into the cells in an amount sufficient to attenuate expression of the target gene, wherein the dsRNA comprises a nucleotide sequence that hybridizes under stringent conditions to a nucleotide sequence of the target gene.

Another aspect of the present invention provides a method for attenuating expression of a target gene in a mammalian cell, comprising
  (i) activating one or both of a Dicer activity or an Argonaut activity in the cell, and
  (ii) introducing into the cell a double stranded RNA (dsRNA) in an amount sufficient to attenuate expression of the target gene, wherein the dsRNA comprises a nucleotide sequence that hybridizes under stringent conditions to a nucleotide sequence of the target gene.

In certain embodiments, the cell is suspended in culture; while in other embodiments the cell is in a whole animal, such as a non-human mammal.

In certain preferred embodiments, the cell is engineered with (i) a recombinant gene encoding a Dicer activity, (ii) a recombinant gene encoding an Argonaut activity, or (iii) both. For instance, the recombinant gene may encode, for a example, a protein which includes an amino acid sequence at least 50 percent identical to SEQ ID No. 2 or 4; or be defined by a coding sequence which hybridizes under wash conditions of 2×SSC at 22° C. to SEQ ID No. 1 or 3. In certain embodiments, the recombinant gene may encode, for a example, a protein which includes an amino acid sequence at least 50 percent identical to the Argonaut sequence shown in FIG. 24. In certain embodiments, the recombinant gene may encode a protein which includes an amino acid sequence at least 60 percent, 70 percent, 80 percent, 85 percent, 90 percent, or 95 percent identical to SEQ ID No. 2 or 4. In certain embodiments, the recombinant gene may be defined by a coding sequence which hybridizes under stringent conditions, including a wash step selected from 0.2×-2.0×SSC at from 50° C.-65° C., to SEQ ID No. 1 or 3.

In certain embodiments, rather than use a heterologous expression construct(s), an endogenous Dicer gene or Argonaut gene can be activated, e.g, by gene activation technology, expression of activated transcription factors or other signal transduction protein(s), which induces expression of the gene, or by treatment with an endogenous factor which upregulates the level of expression of the protein or inhibits the degradation of the protein.

In certain preferred embodiments, the target gene is an endogenous gene of the cell. In other embodiments, the target gene is a heterologous gene relative to the genome of the cell, such as a pathogen gene, e.g., a viral gene.

In certain embodiments, the cell is treated with an agent that inhibits protein kinase RNA-activated (PKR) apoptosis, such as by treatment with agents which inhibit expression of PKR, cause its destruction, and/or inhibit the kinase activity of PKR.

In certain preferred embodiments, the cell is a primate cell, such as a human cell.

In certain preferred embodiments, the length of the dsRNA is at least 20, 21 or 22 nucleotides in length, e.g., corresponding in size to RNA products produced by Dicer-dependent cleavage. In certain embodiments, the dsRNA construct is at least 25, 50, 100, 200, 300 or 400 bases. In certain embodiments, the dsRNA construct is 400-800 bases in length.

In certain preferred embodiments, expression of the target gene is attenuated by at least 5 fold, and more preferably at least 10, 20 or even 50 fold, e.g., relative to the untreated cell or a cell treated with a dsRNA construct which does not correspond to the target gene.

Yet another aspect of the present invention provides a method for attenuating expression of a target gene in cultured cells, comprising introducing an expression vector having a "coding sequence" which, when transcribed, produces double stranded RNA (dsRNA) in the cell in an amount sufficient to attenuate expression of the target gene, wherein the dsRNA comprises a nucleotide sequence that hybridizes under stringent conditions to a nucleotide sequence of the target gene. In certain embodiments, the vector includes a single coding sequence for the dsRNA which is operably linked to (two) transcriptional regulatory sequences which cause transcription in both directions to form complementary transcripts of the coding sequence. In other embodiments, the vector includes two coding sequences which, respectively, give rise to the two complementary sequences which form the dsRNA when annealed. In still other embodiments, the vector includes a coding sequence which forms a hairpin. In certain embodiments, the vectors are episomal, e.g., and transfection is transient. In other embodiments, the vectors are chromosomally integrated, e.g., to produce a stably transfected cell line. Preferred vectors for forming such stable cell lines are described in U.S. Pat. No. 6,025,192 and PCT publication WO/9812339, which are incorporated by reference herein.

Another aspect of the present invention provides a method for attenuating expression of a target gene in cultured cells, comprising introducing an expression vector having a "non-coding sequence" which, when transcribed, produces double stranded RNA (dsRNA) in the cell in an amount sufficient to attenuate expression of the target gene. The non-coding sequence may include intronic or promoter sequence of the target gene of interest, and the dsRNA comprises a nucleotide sequence that hybridizes under stringent conditions to a nucleotide sequence of the promoter or intron of the target gene. In certain embodiments, the vector includes a single sequence for the dsRNA which is operably linked to (two) transcriptional regulatory sequences which cause transcription in both directions to form complementary transcripts of the sequence. In other embodiments, the vector includes two sequences which, respectively, give rise to the two complementary sequences which form the dsRNA when annealed. In still other embodiments, the vector includes a coding sequence which forms a hairpin. In certain embodiments, the vectors are episomal, e.g., and transfection is transient. In other embodiments, the vectors are chromosomally integrated, e.g., to produce a stably transfected cell line. Preferred vectors for forming such stable cell lines are described in U.S. Pat. No. 6,025,192 and PCT publication WO/9812339, which are incorporated by reference herein.

Another aspect the present invention provides a double stranded (ds) RNA for inhibiting expression of a mammalian gene. The dsRNA comprises a first nucleotide sequence that hybridizes under stringent conditions, including a wash step of 0.2×SSC at 65° C., to a nucleotide sequence of at least one mammalian gene and a second nucleotide sequence which is complementary to the first nucleotide sequence.

In one embodiment, the first nucleotide sequence of said double-stranded RNA is at least 20, 21, 22, 25, 50, 100, 200, 300, 400, 500, 800 nucleotides in length.

In another embodiment, the first nucleotide sequence of said double-stranded RNA is identical to at least one mammalian gene. In another embodiment, the first nucleotide sequence of said double-stranded RNA is identical to one mammalian gene. In yet another embodiment, the first nucleotide sequence of said double-stranded RNA hybridizes under stringent conditions to at least one human gene. In still another embodiment, the first nucleotide sequence of said double-stranded RNA is identical to at least one human gene. In still another embodiment, the first nucleotide sequence of said double-stranded RNA is identical to one human gene.

The double-stranded RNA may be an siRNA or a hairpin, and may be expressed transiently or stably. In one embodiment, the double-stranded RNA is a hairpin comprising a first nucleotide sequence that hybridizes under stringent conditions to a nucleotide sequence of at least one mammalian gene, and a second nucleotide sequence which is a complementary inverted repeat of said first nucleotide sequence and hybridizes to said first nucleotide sequence to form a hairpin structure.

The first nucleotide sequence of said double-stranded RNA can hybridize to either coding or non-coding sequence of at least one mammalian gene. In one embodiment, the first nucleotide sequence of said double-stranded RNA hybridizes to a coding sequence of at least one mammalian gene. In another embodiment, the first nucleotide sequence of said double-stranded RNA hybridizes to a coding sequence of at least one human gene. In another embodiment, the first nucleotide sequence of said double-stranded RNA is identical to a coding sequence of at least one mammalian gene. In still another embodiment, the first nucleotide sequence of said double-stranded RNA is identical to a coding sequence of at least one human gene.

In another embodiment, the first nucleotide sequence of said double-stranded RNA hybridizes to a non-coding sequence of at least one mammalian gene. In another embodiment, the first nucleotide sequence of said double-stranded RNA hybridizes to a non-coding sequence of at least one human gene. In another embodiment, the first nucleotide sequence of said double-stranded RNA is identical to a non-coding sequence of at least one mammalian gene. In still another embodiment, the first nucleotide sequence of said double-stranded RNA is identical to a non-coding sequence of at least one human gene. In any of the foregoing embodiments, the non-coding sequence may be a non-transcribed sequence.

Still another aspect of the present invention provides an assay for identifying nucleic acid sequences, either coding or non-coding sequences, responsible for conferring a particular phenotype in a cell, comprising (i) constructing a variegated library of nucleic acid sequences from a cell in an orientation relative to a promoter to produce double stranded DNA;
(ii) introducing the variegated dsRNA library into a culture of target cells;
(iii) identifying members of the library which confer a particular phenotype on the cell, and identifying the sequence from a cell which correspond, such as being identical or homologous, to the library member.

Yet another aspect of the present invention provides a method of conducting a drug discovery business comprising:
(i) identifying, by the subject assay, a target gene which provides a phenotypically desirable response when inhibited by RNAi;
(ii) identifying agents by their ability to inhibit expression of the target gene or the activity of an expression product of the target gene;
(iii) conducting therapeutic profiling of agents identified in step (b), or further analogs thereof, for efficacy and toxicity in animals; and
(iv) formulating a pharmaceutical preparation including one or more agents identified in step (iii) as having an acceptable therapeutic profile.

The method may include an additional step of establishing a distribution system for distributing the pharmaceutical preparation for sale, and may optionally include establishing a sales group for marketing the pharmaceutical preparation.

Another aspect of the present invention provides a method of conducting a target discovery business comprising:
(i) identifying, by the subject assay, a target gene which provides a phenotypically desirable response when inhibited by RNAi;
(ii) (optionally) conducting therapeutic profiling of the target gene for efficacy and toxicity in animals; and
(iii). licensing, to a third party, the rights for further drug development of inhibitors of the target gene.

Another aspect of the invention provides a method for inhibiting RNAi by inhibiting the expression or activity of an RNAi enzyme. Thus, the subject method may include inhibiting the activity of Dicer and/or the 22-mer RNA.

Still another aspect relates to a method for altering the specificity of an RNAi by modifying the sequence of the RNA component of the RNAi enzyme.

In another aspect, gene expression in an undifferentiated stem cell, or the differentiated progeny thereof, is altered by introducing dsRNA of the present invention. In one embodiment, the stem cells are embryonic stem cells. Preferably, the embryonic stem cells are derived from mammals, more preferably from non-human primates, and most preferably from humans.

The embryonic stem cells may be isolated by methods known to one of skill in the art from the inner cell mass (ICM) of blastocyst stage embryos. In one embodiment the embryonic stem cells are obtained from previously established cell lines. In a second embodiment, the embryonic stem cells are derived de novo by standard methods.

In another aspect, the embryonic stem cells are the result of nuclear transfer. The donor nuclei are obtained from any adult, fetal, or embryonic tissue by methods well known in the art. In one embodiment, the donor nuclei is transferred to a recipient oocyte which had previously been modified. In one embodiment, the oocyte is modified using one or more dsRNAs. Exemplary modifications of the recipient oocyte include any changes in gene or protein expression that prevent an embryo derived from said modified oocyte from successfully implanting in the uterine wall. Since implantation in the uterine wall is essential for fertilized mammalian embryos to progress from beyond the blastocyst stage, embryos made from such modified oocytes could not give rise to viable organisms. Non-limiting examples of such modifications include those that decrease or eliminate expression of cell surface receptors (i.e., integrins) required for the recognition between the blastocyst and the uterine wall, modifications that decrease or eliminate expression of proteases (i.e., collagenase, stromelysin, and plasminogen activator) required to digest matrix in the uterine lining and thus allow proper implantation, and modifications that decrease or eliminate expression of proteases (i.e., strypsin) necessary for the blastocyst to hatch from the zona pellucida. Such hatching is required for implantation.

In another embodiment, embryonic stem cells, embryonic stem cells obtained from fertilization of modified oocytes, or the differentiated progeny thereof, can be modified or further modified with one or more dsRNAs. In a preferred embodiment, the modification decreases or eliminates MHC expression. Cells modified in this way will be tolerated by the recipient, thus avoiding complications arising from graft rejection. Such modified cells are suitable for transplantation into a related or unrelated patient to treat a condition characterized by cell damage or cell loss.

In another aspect of the invention, the undifferentiated stem cell is an adult stem cell. Exemplary adult stem cells include, but are not limited to, hematopoietic stem cells, mesenchymal stem cells, cardiac stem cells, pancreatic stem cells, and neural stem cells. Exemplary adult stem cells include any stem cell capable of forming differentiated ectodermal, mesodermal, or endodermal derivatives. Non-limiting examples of differentiated cell types which arise from adult stem cells include: blood, skeletal muscle, myocardium, endocardium, pericardium, bone, cartilage, tendon, ligament, connective tissue, adipose tissue, liver, pancreas, skin, neural tissue, lung, small intestine, large intestine, gall bladder, rectum, anus, bladder, female or male reproductive tract, genitals, and the linings of the body cavity.

In one embodiment, an undifferentiated adult stem cell, or the differentiated progeny thereof, is altered with one or more dsRNAs to decrease or eliminate MHC expression. Cells modified in this way will be tolerated by the recipient, thus avoiding complications arising from graft rejection. Such modified cells are suitable for transplantation into a related or unrelated patient to treat a condition characterized by cell damage or cell loss.

In another aspect of the invention, an embryonic stem cell, an undifferentiated adult stem cell, or the differentiated progeny of either an embryonic or adult stem cell is altered with one or more dsRNA to decrease or eliminate expression of genes required for HIV infection. In a preferred embodiment, the stem cell is one capable of giving rise to hematopoietic cells. Modified cells with hematopoietic potential can be transplanted into a patient as a preventative therapy or treatment for HIV or AIDS.

Another aspect of the invention relates to purified or semi-purified preparations of the RNAi enzyme or components thereof. In certain embodiments, the preparations are used for identifying compounds, especially small organic molecules, which inhibit or potentiate the RNAi activity. Small molecule inhibitors, for example, can be used to inhibit dsRNA responses in cells which are purposefully being transfected with a virus which produces double stranded RNA.

The dsRNA construct may comprise one or more strands of polymerized ribonucleotide. It may include modifications to either the phosphate-sugar backbone or the nucleoside. The double-stranded structure may be formed by a single self-complementary RNA strand or two complementary RNA strands. RNA duplex formation may be initiated either inside or outside the cell. The dsRNA construct may be introduced in an amount which allows delivery of at least one copy per cell. Higher doses of double-stranded material may yield more effective inhibition. Inhibition is sequence-specific in that nucleotide sequences corresponding to the duplex region of the RNA are targeted for genetic inhibition. In certain embodiments, dsRNA constructs containing a nucleotide sequences identical to a portion of the target gene are preferred for inhibition. RNA sequences with insertions, deletions, and single point mutations relative to the target sequence (i.e., RNA sequences similar to the target sequence) have also been found to be effective for inhibition. Thus, sequence identity may be optimized by alignment algorithms known in the art and calculating the percent difference between the nucleotide sequences. Alternatively, the duplex region of the RNA may be defined functionally as a nucleotide sequence that is capable of hybridizing with a portion of the target gene transcript. In another embodiment, dsRNA constructs containing nucleotide sequences identical to a non-coding portion of the target gene are preferred for inhibition. Exemplary non-coding regions include introns and the promoter region. Sequences with insertions, deletions, and single point mutations relative to the target non-coding sequence may also be used.

Yet another aspect of the invention pertains to transgenic non-human mammals which include a transgene encoding a dsRNA construct, wherein the dsRNA is identical or similar to either the coding or non-coding sequence of the target gene, preferably which is stably integrated into the genome of cells in which it occurs. The animals can be derived by oocyte microinjection, for example, in which case all of the nucleated cells of the animal will include the transgene, or can be derived using embryonic stem (ES) cells which have been transfected with the transgene, in which case the animal is a chimera and only a portion of its nucleated cells will include the transgene. In certain instances, the sequence-independent dsRNA response, e.g., the PKR response, is also inhibited in those cells including the transgene.

In still other embodiments, dsRNA itself can be introduced into an ES cell in order to effect gene silencing, and that phenotype will be carried for at least several rounds of division, e.g., into the progeny of that cell.

BRIEF DESCRIPTION OF THE DRAWINGS

FIG. 3: Substrate requirements of the RISC. Extracts were prepared from cells transfected with cyclin E dsRNA. Aliquots were incubated for 30 min at 30° C. before the addition of either the cyclin E (E600) or lacZ (Z800) substrate. Individual 20 µl aliquots, as indicated, were pre-incubated with 1 mM $CaCl_2$ and 5 mM EGTA, 1 mM $CaCl_2$, 5 mM EGTA and 60 U of micrococcal nuclease, 1 mM $CaCl_2$ and 60 U of micrococcal nuclease or 10 U of DNase I (Promega) and 5 mM EGTA. After the 30 min pre-incubation, EGTA was added to those samples that lacked it. Yeast tRNA (1 µg) was added to all samples. Time points were at 0 and 30 min.

FIG. 4: The RISC contains a potential guide RNA. (a) Northern blots of RNA from either a crude lysate or the S100 fraction (containing the soluble nuclease activity, see Methods) were hybridized to a riboprobe derived from the sense strand of the cyclin E mRNA. (b) Soluble cyclin-E-specific nuclease activity was fractionated as described in Methods. Fractions from the anion-exchange resin were incubated with the lacZ, control substrate (upper panel) or the cyclin E substrate (centre panel). Lower panel, RNA from each fraction was analysed by northern blotting with a uniformly labelled transcript derived from sense strand of the cyclin E cDNA. DNA oligonucleotides were used as size markers.

FIG. 19: Dicer was fractionated over several columns.

FIG. 20: Identification of dicer as enzyme which can process dsRNA into 22mers. Various RNaseIII family members were expressed with n terminal tags, immunoprecipitated, and assayed for 22mer generating activity (left panel). In right panel, antibodies to dicer could also precipitate 22mer generating activity.

FIG. 24: Sequence of *Drosophila* argonaute 2 (SEQ ID NO: 5). Peptides identified by microsequencing are shown in underline.

FIG. 28: The panels at the right show expression of either RFP or GFP following transient transfection into wild type P19 cells. The panels at the left demonstrate the specific suppression of GFP expression in P19 clones which stably express a 500 nt double stranded GFP hairpin. P19 clones which stably express the double stranded GFP hairpin were transiently transfected with RFP or GFP, and expression of RFP or GFP was assessed by visual inspection.

FIG. 37: Depicts three types of short RNAs corresponding to the coding region of firefly luciferase. The three types of RNAs are siRNAs (SEQ ID NOs: 6 and 7), let-7 like hairpins (SEQ ID NO: 8), and simple hairpins (SEQ ID NO: 9).

DETAILED DESCRIPTION OF CERTAIN PREFERRED EMBODIMENTS

I. Overview

Figure 1A:
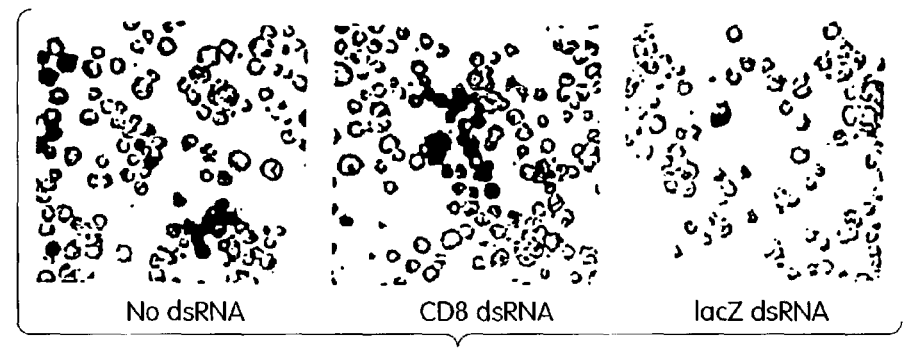
FIG. 1: RNAi in S2 cells. (a) *Drosophila* S2 cells were transfected with a plasmid that directs lacZ expression from the copia promoter in combination with dsRNAs corresponding to either human CD8 or lacZ, or with no dsRNA, as indicated. (b) S2 cells were co-transfected with a plasmid that directs expression of a GFP-US9 fusion protein and dsRNAs of either lacZ or cyclin E, as indicated. Upper panels show FACS profiles of the bulk population. Lower panels show FACS profiles from GFP-positive cells. (c) Total RNA was extracted from cells transfected with lacZ, cyclin E, fizzy or cyclin A dsRNAs, as indicated. Northern blots were hybridized with sequences not present in the transfected dsRNAs.

The present invention provides methods for attenuating gene expression in a cell using gene-targeted double stranded RNA (dsRNA). The dsRNA contains a nucleotide sequence that hybridizes under physiologic conditions of the cell to the nucleotide sequence of at least a portion of the gene to be inhibited (the "target" gene). The nucleotide sequence can hybridize to either coding or non-coding sequence of the target gene.

A significant aspect to certain embodiments of the present invention relates to the demonstration in the present application that RNAi can in fact be accomplished both in cultured mammalian cells and in whole organisms. This had not been previously described in the art.

Another salient feature of the present invention concerns the ability to carry out RNAi in higher eukaryotes, particularly in non-oocytic cells of mammals, e.g., cells from adult mammals as an example.

Furthermore, in contrast to the teachings of the prior art, we demonstrate that RNAi in mammalian systems can be mediated with dsRNA identical or similar to non-coding sequence of a target gene. It was previously believed that although dsRNA identical or similar to non-coding sequences (i.e., promoter, enhancer, or intronic sequences) did not inhibit RNAi, such dsRNAs were not thought to mediate RNAi.

As described in further detail below, the present invention(s) are based on the discovery that the RNAi phenomenum is mediated by a set of enzyme activities, including an essential RNA component, that are evolutionarily conserved in eukaryotes ranging from plants to mammals.

One enzyme contains an essential RNA component. After partial purification, a multi-component nuclease (herein "RISC nuclease") co-fractionates with a discrete, 22-nucleotide RNA species which may confer specificity to the nuclease through homology to the substrate mRNAs. The short RNA molecules are generated by a processing reaction from the longer input dsRNA. Without wishing to be bound by any particular theory, these 22mer guide RNAs may serve as guide sequences that instruct the RISC nuclease to destroy specific mRNAs corresponding to the dsRNA sequences.

As illustrated, double stranded forms of the 22-mer guide RNA can be sufficient in length to induce sequence-dependent dsRNA inhibition of gene expression. In the illustrated example, dsRNA constructs are administered to cells having a recombinant luciferase reporter gene. In the control cell, e.g., no exogenously added RNA, the level of expression of the luciferase reporter is normalized to be the value of "1". As illustrated, both long (500-mer) and short (22-mer) dsRNA constructs complementary to the luciferase gene could inhibit expression of that gene product relative to the control cell. On the other hand, similarly sized dsRNA complementary to the coding sequence for another protein, green fluorescence protein (GFP), did not significantly effect the expression of luciferase—indicating that the inhibitory phenomena was in each case sequence-dependent. Likewise, single stranded 22-mers of luciferase did not inhibit expression of that gene—indicating that the inhibitory phenomena is double stranded-dependent.

The appended examples also identify an enzyme, Dicer, that can produce the putative guide RNAs. Dicer is a member of the RNAse III family of nucleases that specifically cleave dsRNA and is evolutionarily conserved in worms, flies, plants, fungi and, as described herein, mammals. The enzyme has a distinctive structure which includes a helicase domain and dual RNAse III motifs. Dicer also contains a region of homology to the RDE1/QDE2/ARGONAUTE family, which have been genetically linked to RNAi in lower eukaryotes. Indeed, activation of, or overexpression of Dicer may be sufficient in many cases to permit RNA interference in otherwise non-receptive cells, such as cultured eukaryotic cells, or mammalian (non-oocytic) cells in culture or in whole organisms.

In certain embodiments, the cells can be treated with an agent(s) that inhibits the general double-stranded RNA response(s) by the host cells, such as may give rise to sequence-independent apoptosis. For instance, the cells can be treated with agents that inhibit the dsRNA-dependent protein kinase known as PKR (protein kinase RNA-activated). Double stranded RNAs in mammalian cells typically activate protein kinase PKR and lead to apoptosis. The mechanism of action of PKR includes phosphorylation and inactivation of eIF2α (Fire (1999) Trends Genet. 15: 358). It has also been reported that induction of NF-κB by PKR is involved in apoptosis commitment and this process is mediated through activation of the IKK complex. This sequence-independent response may reflect a form of primitive immune response, since the presence of dsRNA is a common feature of many viral lifecycles.

As described herein, Applicants have demonstrated that the PKR response can be overcome in favor of the sequence-specific RNAi response. However, in certain instances, it may be desirable to treat the cells with agents which inhibit expression of PKR, cause its destruction, and/or inhibit the kinase activity of PKR, and such methods are specifically contemplated for use in the present invention. Likewise, overexpression of agents which ectopically activate eIF2α can be used. Other agents which can be used to suppress the PKR response include inhibitors of IKK phosphorylation of IκB, inhibitors of IκB ubiquitination, inhibitors of IκB degradation, inhibitors of NF-κB nuclear translocation, and inhibitors of NF-κB interaction with κB response elements.

Other inhibitors of sequence-independent dsRNA response in cells include the gene product of the vaccinia virus E3L. The E3L gene product contains two distinct domains. A conserved carboxy-terminal domain has been shown to bind double-stranded RNA (dsRNA) and inhibit the antiviral dsRNA response by cells. Expression of at least that portion of the E3L gene in the host cell, or the use of polypeptide or peptidomimetics thereof, can be used to suppress the general dsRNA response. Caspase inhibitors sensitize cells to killing by double-stranded RNA. Accordingly, ectopic expression or activation of caspases in the host cell can be used to suppress the general dsRNA response.

In other embodiments, the subject method is carried out in cells which have little or no general response to double stranded RNA, e.g., have no PKR-dependent dsRNA response, at least under the culture conditions. As illustrated in FIGS. 28-32, CHO and P19 cells can be used without having to inhibit PKR or other general dsRNA responses.

Thus, the present invention provides a process and compositions for inhibiting expression of a target gene in a cell, especially a mammalian cell. In certain embodiments, the process comprises introduction of RNA (the "dsRNA construct") with partial or fully double-stranded character into the cell or into the extracellular environment. Inhibition is specific in that a nucleotide sequence from a portion of the target gene is chosen to produce the dsRNA construct. The dsRNA may be identical or similar to coding or non-coding sequence of the target gene. In preferred embodiments, the method utilizes a cell in which Dicer and/or Argonaute activities are recombinantly expressed or otherwise ectopically activated. This process can be (1) effective in attenuating gene expression, (2) specific to the targeted gene, and (3) general in allowing inhibition of many different types of target gene.

II. Definitions

For convenience, certain terms employed in the specification, examples, and appended claims are collected here.

As used herein, the term "vector" refers to a nucleic acid molecule capable of transporting another nucleic acid to which it has been linked. One type of vector is a genomic integrated vector, or "integrated vector", which can become integrated into the chromosomal DNA of the host cell. Another type of vector is an episomal vector, i.e., a nucleic acid capable of extra-chromosomal replication. Vectors capable of directing the expression of genes to which they are operatively linked are referred to herein as "expression vectors". In the present specification, "plasmid" and "vector" are used interchangeably unless otherwise clear from the context.

As used herein, the term "nucleic acid" refers to polynucleotides such as deoxyribonucleic acid (DNA), and, where appropriate, ribonucleic acid (RNA). The term should also be understood to include, as applicable to the embodiment being described, single-stranded (such as sense or antisense) and double-stranded polynucleotides.

As used herein, the term "gene" or "recombinant gene" refers to a nucleic acid comprising an open reading frame encoding a polypeptide of the present invention, including both exon and (optionally) intron sequences. The nucleic acid may also optionally include non-coding sequences such as promoter or enhancer sequences. A "recombinant gene" refers to nucleic acid encoding such regulatory polypeptides, that may optionally include intron sequences that are derived from chromosomal DNA. The term "intron" refers to a DNA sequence present in a given gene that is not translated into protein and is generally found between exons.

A "protein coding sequence" or a sequence that "encodes" a particular polypeptide or peptide, is a nucleic acid sequence that is transcribed (in the case of DNA) and is translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from procaryotic or eukaryotic mRNA, genomic DNA sequences from procaryotic or eukaryotic DNA, and even synthetic DNA sequences. A transcription termination sequence will usually be located 3' to the coding sequence.

Likewise, "encodes", unless evident from its context, will be meant to include DNA sequences that encode a polypeptide, as the term is typically used, as well as DNA sequences that are transcribed into inhibitory antisense molecules.

The term "loss-of-function", as it refers to genes inhibited by the subject RNAi method, refers to a diminishment in the level of expression of a gene(s) in the presence of one or more dsRNA construct(s) when compared to the level in the absense of such dsRNA construct(s).

The term "expression" with respect to a gene sequence refers to transcription of the gene and, as appropriate, translation of the resulting mRNA transcript to a protein. Thus, as will be clear from the context, expression of a protein coding sequence results from transcription and translation of the coding sequence.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "cultured cells" refers to cells suspended in culture, e.g., dispersed in culture or in the form tissue. It does not, however, include oocytes or whole embryos (including blastocysts and the like) which may be provided in culture. In certain embodiments, the cultured cells are adults cells, e.g., non-embryonic.

By "recombinant virus" is meant a virus that has been genetically altered, e.g., by the addition or insertion of a heterologous nucleic acid construct into the particle.

As used herein, the terms "transduction" and "transfection" are art recognized and mean the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a dsRNA construct.

"Transient transfection" refers to cases where exogenous DNA does not integrate into the genome of a transfected cell, e.g., where episomal DNA is transcribed into mRNA and translated into protein.

A cell has been "stably transfected" with a nucleic acid construct when the nucleic acid construct is capable of being inherited by daughter cells.

As used herein, a "reporter gene construct" is a nucleic acid that includes a "reporter gene" operatively linked to at least one transcriptional regulatory sequence. Transcription of the reporter gene is controlled by these sequences to which they are linked. The activity of at least one or more of these control sequences can be directly or indirectly regulated by the target receptor protein. Exemplary transcriptional control sequences are promoter sequences. A reporter gene is meant to include a promoter-reporter gene construct that is heterologously expressed in a cell.

As used herein, "transformed cells" refers to cells that have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control. For purposes of this invention, the terms "transformed phenotype of malignant mammalian cells" and "transformed phenotype" are intended to encompass, but not be limited to, any of the following phenotypic traits associated with cellular transformation of mammalian cells: immortalization, morphological or growth transformation, and tumorigenicity, as detected by prolonged growth in cell culture, growth in semi-solid media, or tumorigenic growth in immuno-incompetent or syngeneic animals.

As used herein, "proliferating" and "proliferation" refer to cells undergoing mitosis.

As used herein, "immortalized cells" refers to cells that have been altered via chemical, genetic, and/or recombinant means such that the cells have the ability to grow through an indefinite number of divisions in culture.

The "growth state" of a cell refers to the rate of proliferation of the cell and the state of differentiation of the cell.

III. Exemplary Embodiments of Isolation Method

One aspect of the invention provides a method for potentiating RNAi by induction or ectopic activation of an RNAi enzyme in a cell (in vivo or in vitro) or cell-free mixtures. In preferred embodiments, the RNAi activity is activated or added to a mammalian cell, e.g., a human cell, which cell may be provided in vitro or as part of a whole organism. In other embodiments, the subject method is carried out using eukaryotic cells generally (except for oocytes) in culture. For instance, the Dicer enzyme may be activated by virtue of being recombinantly expressed or it may be activated by use of an agent which (i) induces expression of the endogenous gene, (ii) stabilizes the protein from degradation, and/or (iii) allosterically modifies the enzyme to increase its activity (by altering its Kcat, Km or both).

A. Dicer and Argonaut Activities

In certain embodiments, at least one of the activated RNAi enzymes is Dicer, or a homolog thereof. In certain preferred embodiments, the present method provides for ectopic activation of Dicer. As used herein, the term "Dicer" refers to a protein which (a) mediates an RNAi response and (b) has an amino acid sequence at least 50 percent identical, and more preferably at least 75, 85, 90 or 95 percent identical to SEQ ID No. 2 or 4, and/or which can be encoded by a nucleic acid which hybridizes under wash conditions of 2×SSC at 22° C., and more preferably 0.2×SSC at 65° C., to a nucleotide represented by SEQ ID No. 1 or 3. Accordingly, the method may comprise introducing a dsRNA construct into a cell in which Dicer has been recombinantly expressed or otherwise ectopically activated.

In certain embodiment, at least one of the activated RNAi enzymes is Argonaut, or a homolog thereof. In certain preferred embodiments, the present method provides for ectopic activation of Argonaut. As used herein, the term "Argonaut" refers to a protein which (a) mediates an RNAi response and (b) has an amino acid sequence at least 50 percent identical, and more preferably at least 75, 85, 90 or 95 percent identical to the amino acid sequence shown in FIG. 24. Accordingly, the method may comprise introducing a dsRNA construct into a cell in which Argonaut has been recombinantly expressed or otherwise ectopically activated.

This invention also provides expression vectors containing a nucleic acid encoding a Dicer or Argonaut polypeptide, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of the subject Dicer or Argonaut proteins. Accordingly, the term transcriptional regulatory sequence includes promoters, enhancers and other expression control elements. Such regulatory sequences are described in Goeddel; Gene Expression Technology: Methods in Enzymology 185, Academic Press, San Diego, Calif. (1990). For instance, any of a wide variety of expression control sequences, sequences that control the expression of a DNA sequence when operatively linked to it, may be used in these vectors to express DNA sequences encoding Dicer or Argonaut polypeptides of this invention. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage λ, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed.

Moreover, the vector's copy number, the ability to control that copy number and the expression of any other proteins encoded by the vector, such as antibiotic markers, should also be considered.

The recombinant Dicer or Argonaut genes can be produced by ligating a nucleic acid encoding a Dicer or Argonaut polypeptide into a vector suitable for expression in either prokaryotic cells, eukaryotic cells, or both. Expression vectors for production of recombinant forms of the subject Dicer or Argonaut polypeptides include plasmids and other vectors. For instance, suitable vectors for the expression of a Dicer or Argonaut polypeptide include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in Experimental Manipulation of Gene Expression, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used. In an illustrative embodiment, a Dicer or Argonaut polypeptide is produced recombinantly utilizing an expression vector generated by sub-cloning the coding sequence of a Dicer or Argonaut gene.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

In yet another embodiment, the subject invention provides a "gene activation" construct which, by homologous recombination with a genomic DNA, alters the transcriptional regulatory sequences of an endogenous Dicer or Argonaut gene. For instance, the gene activation construct can replace the endogenous promoter of a Dicer or Argonaut gene with a heterologous promoter, e.g., one which causes constitutive expression of the Dicer or Argonaut gene or which causes inducible expression of the gene under conditions different from the normal expression pattern of Dicer or Argonaut. A variety of different formats for the gene activation constructs are available. See, for example, the Transkaryotic Therapies, Inc PCT publications WO93/09222, WO95/31560, WO96/29411, WO95/31560 and WO94/12650.

In preferred embodiments, the nucleotide sequence used as the gene activation construct can be comprised of (1) DNA from some portion of the endogenous Dicer or Argonaut gene (exon sequence, intron sequence, promoter sequences, etc.) which direct recombination and (2) heterologous transcriptional regulatory sequence(s) which is to be operably linked to the coding sequence for the genomic Dicer or Argonaut gene upon recombination of the gene activation construct. For use in generating cultures of Dicer or Argonaut producing cells, the construct may further include a reporter gene to detect the presence of the knockout construct in the cell.

The gene activation construct is inserted into a cell, and integrates with the genomic DNA of the cell in such a position so as to provide the heterologous regulatory sequences in operative association with the native Dicer or Argonaut gene. Such insertion occurs by homologous recombination, i.e., recombination regions of the activation construct that are homologous to the endogenous Dicer or Argonaut gene sequence hybridize to the genomic DNA and recombine with the genomic sequences so that the construct is incorporated into the corresponding position of the genomic DNA.

The terms "recombination region" or "targeting sequence" refer to a segment (i.e., a portion) of a gene activation construct having a sequence that is substantially identical to or substantially complementary to a genomic gene sequence, e.g., including 5' flanking sequences of the genomic gene, and can facilitate homologous recombination between the genomic sequence and the targeting transgene construct.

As used herein, the term "replacement region" refers to a portion of a activation construct which becomes integrated into an endogenous chromosomal location following homologous recombination between a recombination region and a genomic sequence.

The heterologous regulatory sequences, e.g., which are provided in the replacement region, can include one or more of a variety of elements, including: promoters (such as constitutive or inducible promoters), enhancers, negative regulatory elements, locus control regions, transcription factor binding sites, or combinations thereof.

Promoters/enhancers which may be used to control the expression of the targeted gene in vivo include, but are not limited to, the cytomegalovirus (CMV) promoter/enhancer (Karasuyama et al. (1989) J. Exp. Med. 169: 13), the human β-actin promoter (Gunning et al. (1987) PNAS 84: 4831-4835), the glucocorticoid-inducible promoter present in the mouse mammary tumor virus long terminal repeat (MMTV LTR) (Klessig et al. (1984) Mol. Cell. Biol. 4: 1354-1362), the long terminal repeat sequences of Moloney murine leukemia virus (MuLV LTR) (Weiss et al. (1985) RNA Tumor Viruses, Cold Spring Harbor Laboratory, Cold Spring Harbor, N.Y.), the SV40 early or late region promoter (Bemoist et al. (1981) Nature 290: 304-310; Templeton et al. (1984) Mol. Cell. Biol. 4: 817; and Sprague et al. (1983) J. Virol. 45: 773), the promoter contained in the 3' long terminal repeat of Rous sarcoma virus (RSV) (Yamamoto et al. (1980) Cell 22: 787-797), the herpes simplex virus (HSV) thymidine kinase promoter/enhancer (Wagner et al. (1981) PNAS 82: 3567-71), and the herpes simplex virus LAT promoter (Wolfe et al. (1992) Nature Genetics 1: 379-384).

In still other embodiments, the replacement region merely deletes a negative transcriptional control element of the native gene, e.g., to activate expression, or ablates a positive control element, e.g., to inhibit expression of the targeted gene.

B. Cell/Organism

The cell with the target gene may be derived from or contained in any organism (e.g., plant, animal, protozoan, virus, bacterium, or fungus). The dsRNA construct may be synthesized either in vivo or in vitro. Endogenous RNA polymerase of the cell may mediate transcription in vivo, or cloned RNA polymerase can be used for transcription in vivo or in vitro. For generating double stranded transcripts from a transgene in vivo, a regulatory region may be used to transcribe the RNA strand (or strands). Furthermore, dsRNA can be generated by transcribing an RNA strand which forms a hairpin, thus producing a dsRNA.

Genetic manipulation becomes possible in organisms that are not classical genetic models. Breeding and screening programs may be accelerated by the ability to rapidly assay the consequences of a specific, targeted gene disruption. Gene disruptions may be used to discover the function of the target gene, to produce disease models in which the target gene are involved in causing or preventing a pathological condition, and to produce organisms with improved economic properties.

The cell with the target gene may be derived from or contained in any organism. The organism may be a plant, animal, protozoan, bacterium, virus, or fungus. The plant may be a monocot, dicot or gymnosperm; the animal may be a vertebrate or invertebrate. Preferred microbes are those used in agriculture or by industry, and those that are pathogenic for plants or animals. Fungi include organisms in both the mold and yeast morphologies.

Plants include *arabidopsis*; field crops (e.g., alfalfa, barley, bean, corn, cotton, flax, pea, rape, rice, rye, safflower, sorghum, soybean, sunflower, tobacco, and wheat); vegetable crops (e.g., asparagus, beet, broccoli, cabbage, carrot, cauliflower, celery, cucumber, eggplant, lettuce, onion, pepper, potato, pumpkin, radish, spinach, squash, taro, tomato, and zucchini); fruit and nut crops (e.g., almond, apple, apricot, banana, blackberry, blueberry, cacao, cherry, coconut, cranberry, date, faJoa, filbert, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut, and watermelon); and ornamentals (e.g., alder, ash, aspen, azalea, birch, boxwood, camellia, carnation, chrysanthemum, elm, fir, ivy, jasmine, juniper, oak, palm, poplar, pine, redwood, rhododendron, rose, and rubber).

Examples of vertebrate animals include fish, mammal, cattle, goat, pig, sheep, rodent, hamster, mouse, rat, primate, and human.

Invertebrate animals include nematodes, other worms, *drosophila*, and other insects. Representative generae of nematodes include those that infect animals (e.g., *Ancylostoma, Ascaridia, Ascaris, Bunostomum, Caenorhabditis, Capillaria, Chabertia, Cooperia, Dictyocaulus, Haernonchus, Heterakis, Nematodirus, Oesophagostomum, Ostertagia, Oxyuris, Parascaris, Strongylus, Toxascaris, Trichuris, Trichostrongylus, Tflichonema, Toxocara, Uncinaria*) and those that infect plants (e.g., *Bursaphalenchus, Criconerriella, Diiylenchus, Ditylenchus, Globodera, Helicotylenchus, Heterodera, Longidorus, Melodoigyne, Nacobbus, Paratylenchus, Pratylenchus, Radopholus, Rotelynchus, Tylenchus,* and *Xiphinema*). Representative orders of insects include Coleoptera, Diptera, Lepidoptera, and Homoptera.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

C. Targeted Genes

The target gene may be a gene derived from the cell, an endogenous gene, a transgene, or a gene of a pathogen which is present in the cell after infection thereof. Depending on the particular target gene and the dose of double stranded RNA material delivered, the procedure may provide partial or complete loss of function for the target gene. Lower doses of injected material and longer times after administration of dsRNA may result in inhibition in a smaller fraction of cells. Quantitation of gene expression in a cell may show similar amounts of inhibition at the level of accumulation of target mRNA or translation of target protein.

"Inhibition of gene expression" refers to the absence (or observable decrease) in the level of protein and/or mRNA product from a target gene. "Specificity" refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin.

Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of dsRNA may result in inhibition in a smaller fraction of cells (e.g., at least 10%, 20%, 50%, 75%, 90%, or 95% of targeted cells). Quantitation of gene expression in a cell may show similar amounts of inhibition at the level of accumulation of target mRNA or translation of target protein. As an example, the efficiency of inhibition may be determined by assessing the amount of gene product in the cell: mRNA may be detected with a hybridization probe having a nucleotide sequence outside the region used for the inhibitory double-stranded RNA, or translated polypeptide may be detected with an antibody raised against the polypeptide sequence of that region.

As disclosed herein, the present invention is not limited to any type of target gene or nucleotide sequence. But the following classes of possible target genes are listed for illustrative purposes: developmental genes (e.g., adhesion molecules, cyclin kinase inhibitors, Writ family members, Pax family members, Winged helix family members, Hox family members, cytokines/lymphokines and their receptors, growth/differentiation factors and their receptors, neurotransmitters and their receptors); oncogenes (e.g., ABLI, BCLI, BCL2, BCL6, CBFA2, CBL, CSFIR, ERBA, ERBB, EBRB2, ETSI, ETS1, ETV6, FGR, FOS, FYN, HCR, HRAS, JUN, KRAS, LCK, LYN, MDM2, MLL, MYB, MYC, MYCLI, MYCN, NRAS, PIM 1, PML, RET, SRC, TALI, TCL3, and YES); tumor suppressor genes (e.g., APC, BRCA 1, BRCA2, MADH4, MCC, NF 1, NF2, RB 1, TP53, and WTI); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases).

D. dsRNA Constructs

The dsRNA construct may comprise one or more strands of polymerized ribonucleotide. It may include modifications to either the phosphate-sugar backbone or the nucleoside. For example, the phosphodiester linkages of natural RNA may be modified to include at least one of a nitrogen or sulfur heteroatom. Modifications in RNA structure may be tailored to allow specific genetic inhibition while avoiding a general panic response in some organisms which is generated by dsRNA. Likewise, bases may be modified to block the activity of adenosine deaminase. The dsRNA construct may be produced enzymatically or by partial/total organic synthesis, any modified ribonucleotide can be introduced by in vitro enzymatic or organic synthesis.

The dsRNA construct may be directly introduced into the cell (i.e., intracellularly); or introduced extracellularly into a cavity, interstitial space, into the circulation of an organism, introduced orally, or may be introduced by bathing an organism in a solution containing RNA. Methods for oral introduction include direct mixing of RNA with food of the organism, as well as engineered approaches in which a species that is used as food is engineered to express an RNA, then fed to the organism to be affected. Physical methods of introducing nucleic acids include injection of an RNA solution directly into the cell or extracellular injection into the organism.

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition; lower doses may also be useful for specific applications. Inhibition is sequence-specific in that nucleotide sequences corresponding to the duplex region of the RNA are targeted for genetic inhibition.

dsRNA constructs containing a nucleotide sequences identical to a portion, of either coding or non-coding sequence, of the target gene are preferred for inhibition. RNA sequences with insertions, deletions, and single point mutations relative to the target sequence (ds RNA similar to the target gene) have also been found to be effective for inhibition. Thus, sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing). In certain preferred embodiments, the length of the dsRNA is at least 20, 21 or 22 nucleotides in length, e.g., corresponding in size to RNA products produced by Dicer-dependent cleavage. In certain embodiments, the dsRNA construct is at least 25, 50, 100, 200, 300 or 400 bases. In certain embodiments, the dsRNA construct is 400-800 bases in length.

100% sequence identity between the RNA and the target gene is not required to practice the present invention. Thus the invention has the advantage of being able to tolerate sequence variations that might be expected due to genetic mutation, strain polymorphism, or evolutionary divergence.

The dsRNA construct may be synthesized either in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the dsRNA strand (or strands). Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus. The dsRNA construct may be chemically or enzymatically synthesized by manual or automated reactions. The dsRNA construct may be synthesized by a cellular RNA polymerase or a bacteriophage RNA polymerase (e.g., T3, T7, SP6). The use and production of an expression construct are known in the art (see also WO 97/32016; U.S. Pat. Nos. 5,593,874, 5,698,425, 5,712,135, 5,789,214, and 5,804,693; and the references cited therein). If synthesized chemically or by in vitro enzymatic synthesis, the RNA may be purified prior to introduction into the cell. For example, RNA can be purified from a mixture by extraction with a solvent or resin, precipitation, electrophoresis, chromatography or a combination thereof. Alternatively, the dsRNA construct may be used with no or a minimum of purification to avoid losses due to sample processing. The dsRNA construct may be dried for storage or dissolved in an aqueous solution. The solution may contain buffers or salts to promote annealing, and/or stabilization of the duplex strands.

Physical methods of introducing nucleic acids include injection of a solution containing the dsRNA construct, bombardment by particles covered by the dsRNA construct, soaking the cell or organism in a solution of the RNA, or electroporation of cell membranes in the presence of the dsRNA construct. A viral construct packaged into a viral particle would accomplish both efficient introduction of an expression construct into the cell and transcription of dsRNA construct encoded by the expression construct. Other methods known in the art for introducing nucleic acids to cells may be used, such as lipid-mediated carrier transport, chemical mediated transport, such as calcium phosphate, and the like. Thus the dsRNA construct may be introduced along with components that perform one or more of the following activities: enhance RNA uptake by the cell, promote annealing of the duplex strands, stabilize the annealed strands, or other-wise increase inhibition of the target gene.

E. Illustrative Uses

One utility of the present invention is as a method of identifying gene function in an organism, especially higher eukaryotes, comprising the use of double-stranded RNA to inhibit the activity of a target gene of previously unknown function. Instead of the time consuming and laborious isolation of mutants by traditional genetic screening, functional genomics would envision determining the function of uncharacterized genes by employing the invention to reduce the amount and/or alter the timing of target gene activity. The invention could be used in determining potential targets for pharmaceuticals, understanding normal and pathological events associated with development, determining signaling pathways responsible for postnatal development/aging, and the like. The increasing speed of acquiring nucleotide sequence information from genomic and expressed gene sources, including total sequences for mammalian genomes, can be coupled with the invention to determine gene function in a cell or in a whole organism. The preference of different organisms to use particular codons, searching sequence databases for related gene products, correlating the linkage map of genetic traits with the physical map from which the nucleotide sequences are derived, and artificial intelligence methods may be used to define putative open reading frames from the nucleotide sequences acquired in such sequencing projects.

A simple assay would be to inhibit gene expression according to the partial sequence available from an expressed sequence tag (EST). Functional alterations in growth, development, metabolism, disease resistance, or other biological processes would be indicative of the normal role of the EST's gene product.

The ease with which the dsRNA construct can be introduced into an intact cell/organism containing the target gene allows the present invention to be used in high throughput screening (HTS). For example, duplex RNA can be produced by an amplification reaction using primers flanking the inserts of any gene library derived from the target cell or organism. Inserts may be derived from genomic DNA or mRNA (e.g., cDNA and cRNA). Individual clones from the library can be replicated and then isolated in separate reactions, but preferably the library is maintained in individual reaction vessels (e.g., a 96 well microtiter plate) to minimize the number of steps required to practice the invention and to allow automation of the process.

In an exemplary embodiment, the subject invention provides an arrayed library of RNAi constructs. The array may be in the form of solutions, such as multi-well plates, or may be "printed" on solid substrates upon which cells can be grown. To illustrate, solutions containing duplex RNAs that are capable of inhibiting the different expressed genes can be placed into individual wells positioned on a microtiter plate as an ordered array, and intact cells/organisms in each well can be assayed for any changes or modifications in behavior or development due to inhibition of target gene activity.

In one embodiment, the subject method uses an arrayed library of RNAi constructs to screen for combinations of RNAi that are lethal to host cells. Synthetic lethality is a bedrock principle of experimental genetics. A synthetic lethality describes the properties of two mutations which, individually, are tolerated by the organism but which, in combination, are lethal. The subject arrays can be used to identify loss-of-function mutations that are lethal in combination with alterations in other genes, such as activated oncogenes or loss-of-function mutations to tumor suppressors. To achieve this, one can create "phenotype arrays" using cultured cells. Expression of each of a set of genes, such as the host cell's genome, can be individually systematically disrupted using RNA interference. Combination with alterations in oncogene and tumor suppressor pathways can be used to identify synthetic lethal interactions that may identify novel therapeutic targets.

In certain embodiments, the RNAi constructs can be fed directly to, or injected into, the cell/organism containing the target gene. Alternatively, the duplex RNA can be produced by in vivo or in vitro transcription from an expression construct used to produce the library. The construct can be replicated as individual clones of the library and transcribed to produce the RNA; each clone can then be fed to, injected into, or delivered by another method known in the art to, the cell/organism containing the target gene. The function of the target gene can be assayed from the effects it has on the cell/organism when gene activity is inhibited. This screening could be amenable to small subjects that can be processed in large number, for example, tissue culture cells derived from mammals, especially primates, and most preferably humans.

If a characteristic of an organism is determined to be genetically linked to a polymorphism through RFLP or QTL analysis, the present invention can be used to gain insight regarding whether that genetic polymorphism might be directly responsible for the characteristic. For example, a fragment defining the genetic polymorphism or sequences in the vicinity of such a genetic polymorphism can be amplified to produce an RNA, the duplex RNA can be introduced to the organism or cell, and whether an alteration in the characteristic is correlated with inhibition can be determined. Of course, there may be trivial explanations for negative results with this type of assay, for example: inhibition of the target gene causes lethality, inhibition of the target gene may not result in any observable alteration, the fragment contains nucleotide sequences that are not capable of inhibiting the target gene, or the target gene's activity is redundant.

The present invention may be useful in allowing the inhibition of essential genes. Such genes may be required for cell or organism viability at only particular stages of development or only in specific cellular compartments or tissues. The functional equivalent of conditional mutations may be produced by inhibiting activity of the target gene when or where it is not required for viability. The invention allows addition of RNA at specific times of development and locations in the organism without introducing permanent mutations into the target genome.

The present invention may be useful in allowing the inhibition of genes that have been difficult to inhibit using other methods due to gene redundancy. Since the present methods may be used to deliver more than one dsRNA to a cell or organism, dsRNA identical or similar to more than one gene, wherein the genes have a redundant function during normal development, may be delivered.

If alternative splicing produced a family of transcripts that were distinguished by usage of characteristic exons, the present invention can target inhibition through the appropriate exons to specifically inhibit or to distinguish among the functions of family members. For example, a protein factor that contained an alternatively spliced transmembrane domain may be expressed in both membrane bound and secreted forms. Instead of isolating a nonsense mutation that terminates translation before the transmembrane domain, the functional consequences of having only secreted hormone can be determined according to the invention by targeting the exon containing the transmembrane domain and thereby inhibiting expression of membrane-bound hormone. That is, the subject method can be used for selected ablation of splicing variants.

The present invention may be used alone or as a component of a kit having at least one of the reagents necessary to carry out the in vitro or in vivo introduction of RNA to test samples or subjects. Preferred components are the dsRNA and a vehicle that promotes introduction of the dsRNA. Such a kit may also include instructions to allow a user of the kit to practice the invention.

Alternatively, an organism may be engineered to produce dsRNA which produces commercially or medically beneficial results, for example, resistance to a pathogen or its pathogenic effects, improved growth, or novel developmental patterns.

IV. Exemplification

The invention, now being generally described, will be more readily understood by reference to the following examples, which are included merely for purposes of illustration of certain aspects and embodiments of the present invention and are not intended to limit the invention.

Example 1

An RNA-Directed Nuclease Mediates RNAi Gene Silencing

In a diverse group of organisms that includes *Caenorhabditis elegans, Drosophila*, planaria, hydra, trypanosomes, fungi and plants, the introduction of double-stranded RNAs inhibits gene expression in a sequence-specific manner (Sharp (1999) Genes and Development 13: 139-141; Sanchez-Alvarado and Newmark (1999) PNAS 96: 5049-5054; Lohman et al. (1999) Developmental Biology 214: 211-214; Cogoni and Macino (1999) Nature 399: 166-169; Waterhouse et al. (1998) PNAS 95: 13959-13964; Montgomery and Fire (1998) Trends Genet. 14: 225-228; Ngo et al. (1998) PNAS 95: 14687-14692). These responses, called RNA interference or post-transcriptional gene silencing, may provide anti-viral defence, modulate transposition or regulate gene expression (Sharp (1999) Genes and Development 13: 139-141; Montgomery and Fire (1998) Trends Genet. 14: 225-228; Tabara et al. (1999) Cell 99: 123-132; Ketting et al. (1999) Cell 99: 133-141; Ratcliff et al. (1997) Science 276: 1558-1560). We have taken a biochemical approach towards elucidating the mechanisms underlying this genetic phenomenon. Here we show that 'loss-of-function' phenotypes can be created in cultured *Drosophila* cells by transfection with specific double-stranded RNAs. This coincides with a marked reduction in the level of cognate cellular messenger RNAs. Extracts of transfected cells contain a nuclease activity that specifically degrades exogenous transcripts homologous to transfected double-stranded RNA. This enzyme contains an essential RNA component. After partial purification, the sequence-specific nuclease co-fractionates with a discrete, ~25-nucleotide RNA species which may confer specificity to the enzyme through homology to the substrate mRNAs.

Although double-stranded RNAs (dsRNAs) can provoke gene silencing in numerous biological contexts including *Drosophila* (Kennerdell et al. (1998) Cell 95: 1017-1026; Misquitta and Paterson (1999) PNAS 96: 1451-1456), the mechanisms underlying this phenomenon have remained mostly unknown. We therefore wanted to establish a biochemically tractable model in which such mechanisms could be investigated.

Transient transfection of cultured, *Drosophila* S2 cells with a lacZ expression vector resulted in β-galactosidase activity that was easily detectable by an in situ assay (FIG. 1a). This activity was greatly reduced by co-transfection with a dsRNA corresponding to the first 300 nucleotides of the lacZ sequence, whereas co-transfection with a control dsRNA (CD8) (FIG. 1a) or with single-stranded RNAs of either sense or antisense orientation (data not shown) had little or no effect. This indicated that dsRNAs could interfere, in a sequence-specific fashion, with gene expression in cultured cells.

Figure 1B:
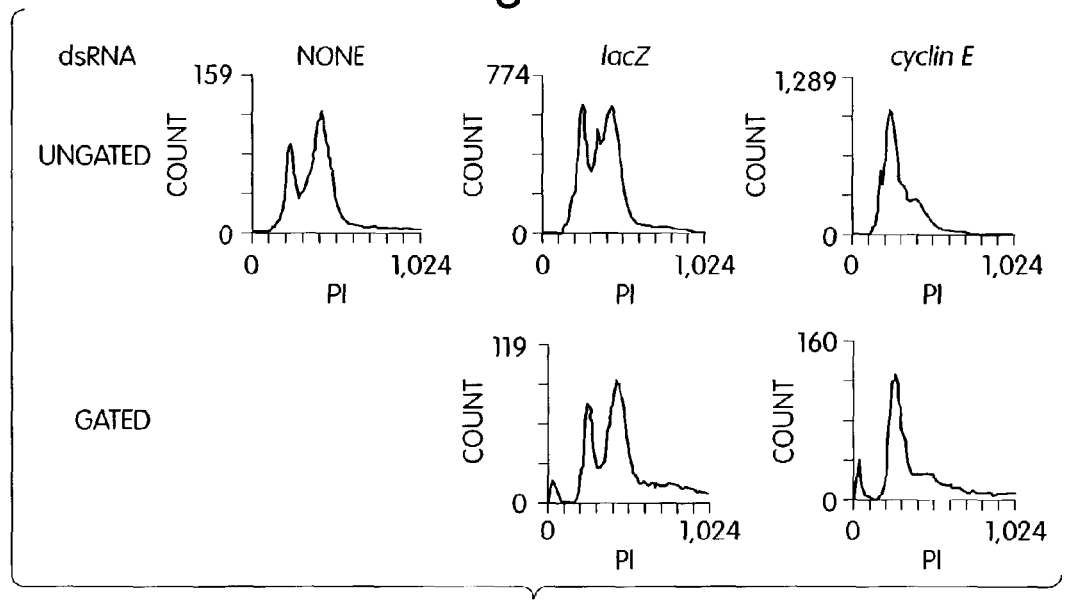

To determine whether RNA interference (RNAi) could be used to target endogenous genes, we transfected S2 cells with a dsRNA corresponding to the first 540 nucleotides of *Drosophila* cyclin E, a gene that is essential for progression into S phase of the cell cycle. During log-phase growth, untreated S2 cells reside primarily in G2/M (FIG. 1b). Transfection with lacZ dsRNA had no effect on cell-cycle distribution, but transfection with the cyclin E dsRNA caused a G1-phase cell-cycle arrest (FIG. 1b). The ability of cyclin E dsRNA to provoke this response was length-dependent. Double-stranded RNAs of 540 and 400 nucleotides were quite effective, whereas dsRNAs of 200 and 300 nucleotides were less potent. Double-stranded cyclin E RNAs of 50 or 100 nucleotides were inert in our assay, and transfection with a single-stranded, antisense cyclin E RNA had virtually no effect.

Figure 1C:
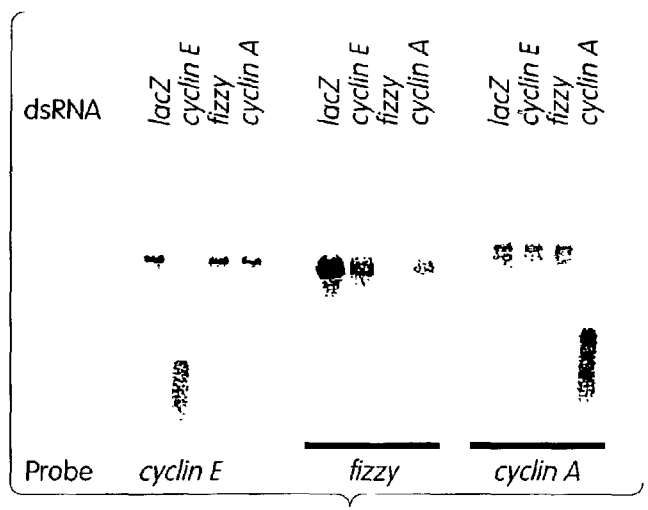

One hallmark of RNAi is a reduction in the level of mRNAs that are homologous to the dsRNA. Cells transfected with the cyclin E dsRNA (bulk population) showed diminished endogenous cyclin E mRNA as compared with control cells (FIG. 1c). Similarly, transfection of cells with dsRNAs homologous to fizzy, a component of the anaphase-promoting complex (APC) or cyclin A, a cyclin that acts in S, G2 and M, also caused reduction of their cognate mRNAs (FIG. 1c). The modest reduction in fizzy mRNA levels in cells transfected with cyclin A dsRNA probably resulted from arrest at a point in the division cycle at which fizzy transcription is low (Wolf and Jackson (1998) Current Biology 8: R637-R639; Kramer et al. (1998) Current Biology 8: 1207-1210). These results indicate that RNAi may be a generally applicable method for probing gene function in cultured *Drosophila* cells.

The decrease in mRNA levels observed upon transfection of specific dsRNAs into *Drosophila* cells could be explained by effects at transcriptional or post-transcriptional levels. Data from other systems have indicated that some elements of the dsRNA response may affect mRNA directly (reviewed in Sharp (1999) Genes and Development 13: 139-141; Montgomery and Fire (1998) Trends Genet. 14: 225-228). We therefore sought to develop a cell-free assay that reflected, at least in part, RNAi.

Figure 2A:
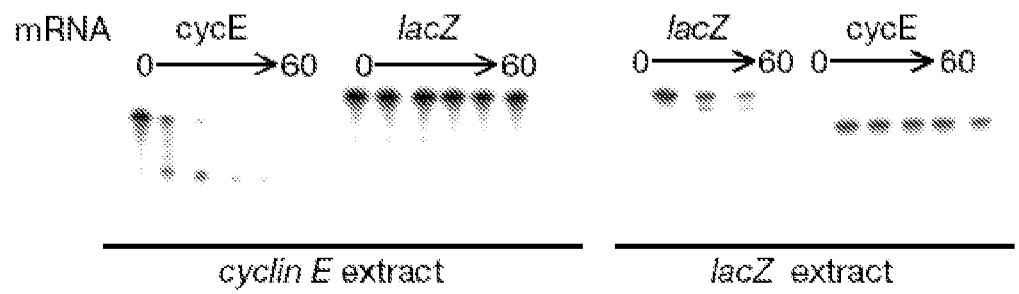
FIG. 2: RNAi in vitro. (a) Transcripts corresponding to either the first 600 nucleotides of *Drosophila* cyclin E (E600) or the first 800 nucleotides of lacZ (Z800) were incubated in lysates derived from cells that had been transfected with either lacZ or cyclin E (cycE) dsRNAs, as indicated. Time points were 0, 10, 20, 30, 40 and 60 min for cyclin E and 0, 10, 20, 30 and 60 min for lacZ. (b) Transcripts were incubated in an extract of S2 cells that had been transfected with cyclin E dsRNA (cross-hatched box, below). Transcripts corresponded to the first 800 nucleotides of lacZ or the first 600, 300, 220 or 100 nucleotides of cyclin E, as indicated. Eout is a transcript derived from the portion of the cyclin E cDNA not contained within the transfected dsRNA. E-ds is identical to the dsRNA that had been transfected into S2 cells. Time points were 0 and 30 min. (c) Synthetic transcripts complementary to the complete cyclin E cDNA (Eas) or the final 600 nucleotides (Eas600) or 300 nucleotides (Eas300) were incubated in extract for 0 or 30 min.

S2 cells were transfected with dsRNAs corresponding to either cyclin E or lacZ. Cellular extracts were incubated with synthetic mRNAs of lacZ or cyclin E. Extracts prepared from cells transfected with the 540-nucleotide cyclin E dsRNA efficiently degraded the cyclin E transcript; however, the lacZ transcript was stable in these lysates (FIG. 2a). Conversely, lysates from cells transfected with the lacZ dsRNA degraded the lacZ transcript but left the cyclin E mRNA intact. These results indicate that RNAi ablates target mRNAs through the generation of a sequence-specific nuclease activity. We have termed this enzyme RISC(RNA-induced silencing complex). Although we occasionally observed possible intermediates in the degradation process (see FIG. 2), the absence of stable cleavage end-products indicates an exonuclease (perhaps coupled to an endonuclease). However, it is possible that the RNAi nuclease makes an initial endonucleolytic cut and that non-specific exonucleases in the extract complete the degradation process (Shuttleworth and Colman (1988) EMBO J. 7: 427-434). In addition, our ability to create an extract that targets lacZ in vitro indicates that the presence of an endogenous gene is not required for the RNAi response.

Figure 2B:
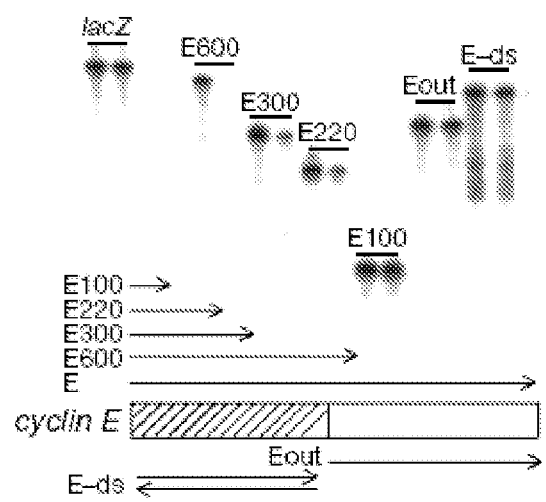

To examine the substrate requirements for the dsRNA-induced, sequence-specific nuclease activity, we incubated a variety of cyclin-E-derived transcripts with an extract derived from cells that had been transfected with the 540-nucleotide cyclin E dsRNA (FIGS. 2b, c). Just as a length requirement was observed for the transfected dsRNA, the RNAi nuclease activity showed a dependence on the size of the RNA substrate. Both a 600-nucleotide transcript that extends slightly beyond the targeted region (FIG. 2b) and an ~1-kilobase (kb) transcript that contains the entire coding sequence (data not shown) were completely destroyed by the extract. Surprisingly, shorter substrates were not degraded as efficiently. Reduced activity was observed against either a 300- or a 220-nucleotide transcript, and a 100-nucleotide transcript was resistant to nuclease in our assay. This was not due solely to position effects because ~100-nucleotide transcripts derived from other portions of the transfected dsRNA behaved similarly (data not shown). As expected, the nuclease activity (or activities) present in the extract could also recognize the antisense strand of the cyclin E mRNA. Again, substrates that contained a substantial portion of the targeted region were degraded efficiently whereas those that contained a shorter stretch of homologous sequence (~130 nucleotides) were recognized inefficiently (FIG. 2c, as600). For both the sense and antisense strands, transcripts that had no homology with the transfected dsRNA (FIG. 2b, Eout; FIG. 2c, as300) were not degraded. Although we cannot exclude the possibility that nuclease specificity could have migrated beyond the targeted region, the resistance of transcripts that do not contain homology to the dsRNA is consistent with data from *C. elegans*. Double-stranded RNAs homologous to an upstream cistron have little or no effect on a linked downstream cistron, despite the fact that unprocessed, polycistronic mRNAs can be readily detected (Tabara et al. (1998) Science 282: 430-432; Bosher et al. (1999) Genetics 153: 1245-1256). Furthermore, the nuclease was inactive against a dsRNA identical to that used to provoke the RNAi response in vivo (FIG. 2b). In the in vitro system, neither a 5' cap nor a poly(A) tail was required, as such transcripts were degraded as efficiently as uncapped and non-polyadenylated RNAs.

Gene silencing provoked by dsRNA is sequence specific. A plausible mechanism for determining specificity would be incorporation of nucleic-acid guide sequences into the complexes that accomplish silencing (Hamilton and Baulcombe (1999) Science 286: 950-952). In accord with this idea, pretreatment of extracts with a $Ca^{2+}$-dependent nuclease (micrococcal nuclease) abolished the ability of these extracts to degrade cognate mRNAs (FIG. 3). Activity could not be rescued by addition of non-specific RNAs such as yeast transfer RNA. Although micrococcal nuclease can degrade both DNA and RNA, treatment of the extract with DNAse I had no effect (FIG. 3). Sequence-specific nuclease activity, however, did require protein (data not shown). Together, our results support the possibility that the RNAi nuclease is a ribonucleoprotein, requiring both RNA and protein components. Biochemical fractionation (see below) is consistent with these components being associated in extract rather than being assembled on the target mRNA after its addition.

Figure 2D:
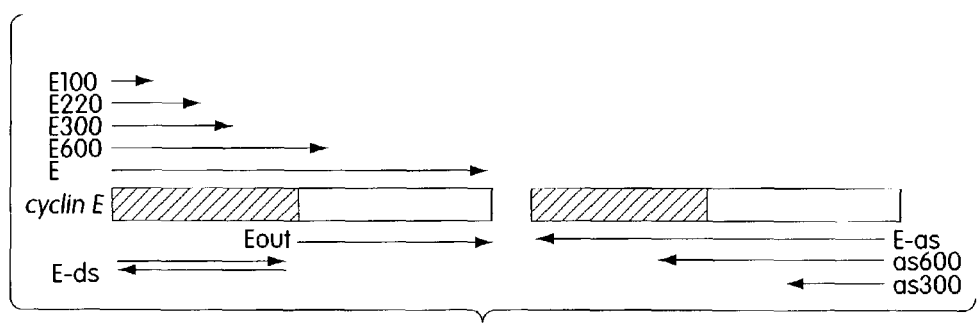

In plants, the phenomenon of co-suppression has been associated with the existence of small (~25-nucleotide) RNAs that correspond to the gene that is being silenced (Hamilton and Baulcombe (1999) Science 286: 950-952). To address the possibility that a similar RNA might exist in *Drosophila* and guide the sequence-specific nuclease in the choice of substrate, we partially purified our activity through several fractionation steps. Crude extracts contained both sequence-specific nuclease activity and abundant, heterogeneous RNAs homologous to the transfected dsRNA (FIGS. 2 and 4a). The RNAi nuclease fractionated with ribosomes in a high-speed centrifugation step. Activity could be extracted by treatment with high salt, and ribosomes could be removed by an additional centrifugation step. Chromatography of soluble nuclease over an anion-exchange column resulted in a discrete peak of activity (FIG. 4b, cyclin E). This retained specificity as it was inactive against a heterologous mRNA (FIG. 4b, lacZ). Active fractions also contained an RNA species of 25 nucleotides that is homologous to the cyclin E target (FIG. 4b, northern). The band observed on northern blots may represent a family of discrete RNAs because it could be detected with probes specific for both the sense and antisense cyclin E sequences and with probes derived from distinct segments of the dsRNA (data not shown). At present, we cannot determine whether the 25-nucleotide RNA is present in the nuclease complex in a double-stranded or single-stranded form.

RNA interference allows an adaptive defence against both exogenous and endogenous dsRNAs, providing something akin to a dsRNA immune response. Our data, and that of others (Hamilton and Baulcombe (1999) Science 286: 950-952), is consistent with a model in which dsRNAs present in a cell are converted, either through processing or replication, into small specificity determinants of discrete size in a manner analogous to antigen processing. Our results suggest that the post-transcriptional component of dsRNA-dependent gene silencing is accomplished by a sequence-specific nuclease that incorporates these small RNAs as guides that target specific messages based upon sequence recognition. The identical size of putative specificity determinants in plants (Hamilton and Baulcombe (1999) Science 286: 950-952) and animals predicts a conservation of both the mechanisms and the components of dsRNA-induced, post-transcriptional gene silencing in diverse organisms. In plants, dsRNAs provoke not only post-transcriptional gene silencing but also chromatin remodelling and transcriptional repression (Jones et al. (1998) EMBO J. 17: 6385-6393; Jones et al. (1999) Plant Cell 11: 2291-2301). It is now critical to determine whether conservation of gene-silencing mechanisms also exists at the transcriptional level and whether chromatin remodelling can be directed in a sequence-specific fashion by these same dsRNA-derived guide sequences.

Methods

Cell culture and RNA methods S2 cells (Schneider (1972) J. Embryol Exp Morpho 27: 353-365) were cultured at 27° C. in 90% Schneider's insect media (Sigma), 10% heat inactivated fetal bovine serum (FBS). Cells were transfected with dsRNA and plasmid DNA by calcium phosphate co-precipitation (DiNocera and Dawid (1983) PNAS 80: 7095-7098). Identical results were observed when cells were transfected using lipid reagents (for example, Superfect, Qiagen). For FACS analysis, cells were additionally transfected with a vector that directs expression of a green fluorescent protein (GFP)—US9 fusion protein (Kalejta et al. (1999) Exp Cell Res. 248: 322-328). These cells were fixed in 90% ice-cold ethanol and stained with propidium iodide at 25 μg/ml. FACS was performed on an Elite flow cytometer (Coulter). For northern blotting, equal loading was ensured by over-probing blots with a control complementary DNA (RP49). For the production of dsRNA, transcription templates were generated by polymerase chain reaction such that they contained T7 promoter sequences on each end of the template. RNA was prepared using the RiboMax kit (Promega). Confirmation that RNAs were double stranded came from their complete sensitivity to RNAse III (a gift from A. Nicholson). Target mRNA transcripts were synthesized using the Riboprobe kit (Promega) and were gel purified before use.

Extract preparation Log-phase S2 cells were plated on 15-cm tissue culture dishes and transfected with 30 μg dsRNA and 30 μg carrier plasmid DNA. Seventy-two hours after transfection, cells were harvested in PBS containing 5 mM EGTA, washed twice in PBS and once in hypotonic buffer (10 mM HEPES pH 7.3, 6 mM β-mercaptoethanol). Cells were suspended in 0.7 packed-cell volumes of hypotonic buffer containing Complete protease inhibitors (Boehringer) and 0.5 units/ml of RNasin (Promega). Cells were disrupted in a dounce homogenizer with a type B pestle, and lysates were centrifuged at 30,000 g for 20 min. Supernatants were used in an in vitro assay containing 20 mM HEPES pH 7.3, 110 mM KOAc, 1 mM $Mg(OAc)_2$, 3 mM EGTA, 2 mM CaCl$_2$, 1 mM DTT. Typically, 5 µl extract was used in a 10 µl assay that contained also 10,000 c.p.m. synthetic mRNA substrate.

Extract fractionation Extracts were centrifuged at 200,000 g for 3 h and the resulting pellet (containing ribosomes) was extracted in hypotonic buffer containing also 1 mM MgCl$_2$ and 300 mM KOAc. The extracted material was spun at 100,000 g for 1 h and the resulting supernatant was fractionated on Source 15Q column (Pharmacia) using a KCl gradient in buffer A (20 mM HEPES pH 7.0, 1 mM dithiothreitol, 1 mM MgCl$_2$). Fractions were assayed for nuclease activity as described above. For northern blotting, fractions were proteinase K/SDS treated, phenol extracted, and resolved on 15% acrylamide 8M urea gels. RNA was electroblotted onto Hybond N+ and probed with strand-specific riboprobes derived from cyclin E mRNA. Hybridization was carried out in 500 mM NaPO$_4$ pH 7.0, 15% formamide, 7% SDS, 1% BSA. Blots were washed in 1×SSC at 37-45° C.

Example 2

Role for a Bidentate Ribonuclease in the Initiation Step of RNA Interference

Figure 5B:
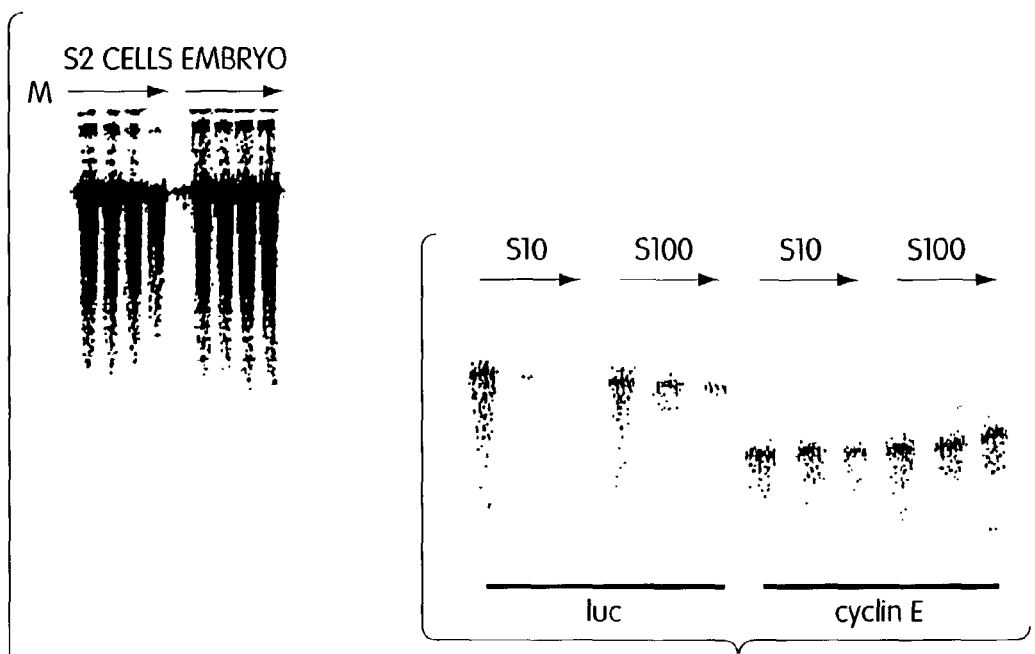
FIG. 5: Generation of 22mers and degradation of mRNA are carried out by distinct enzymatic complexes. (a) Extracts prepared either from 0-12 hour *Drosophila* embryos or *Drosophila* S2 cells (see Methods) were incubated for 0, 15, 30, or 60 minutes (left to right) with a uniformly-labeled double-stranded RNA corresponding to the first 500 nucleotides of the *Drosophila* cyclin E coding region. M indicates a marker prepared by in vitro transcription of a synthetic template. The template was designed to yield a 22 nucleotide transcript. The doublet most probably results from improper initiation at the +1 position. (b) Whole-cell extracts were prepared from S2 cells that had been transfected with a dsRNA corresponding to the first 500 nt. of the luciferase coding region. S10 extracts were spun at 30,000×g for 20 minutes which represents our standard RISC extract. S100 extracts were prepared by further centrifugation of S10 extracts for 60 minutes at 100,000×g. Assays for mRNA degradation were carried out as described previously for 0, 30 or 60 minutes (left to right in each set) with either a single-stranded luciferase mRNA or a single-stranded cyclin E mRNA, as indicated. (c) S10 or S100 extracts were incubated with cyclin E dsRNAs for 0, 60 or 120 minutes (L to R).
Figure 5A:
Figure 5C:
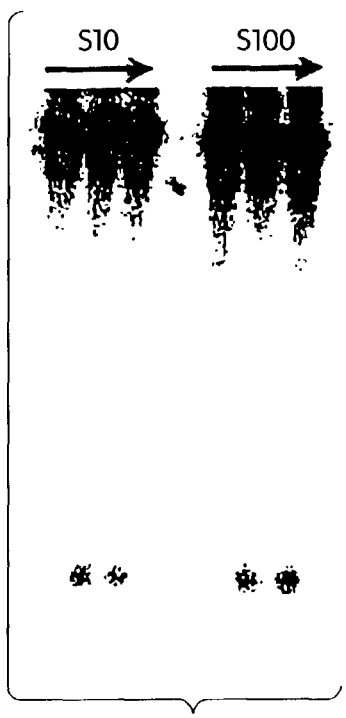

Genetic approaches in worms, fungi and plants have identified a group of proteins that are essential for double-stranded RNA-induced gene silencing. Among these are ARGONAUTE family members (e.g. RDE1, QDE2) (Tabara et al. (1999) Cell 99: 123-132; Catalanotto et al. (2000) Nature 404: 245; Fagard et al. (2000) PNAS 97: 11650-11654), recQ-family helicases (MUT-7, QDE3) (Ketting et al. (1999) Cell 99: 133-141; Cogoni and Macino. (1999) Science 286: 2342-2344), and RNA-dependent RNA polymerases (e.g. EGO-1, QDE1, SGS2/SDE1) (Cogoni and Macino (1999) Nature 399: 166-169; Smardon et al. (2000) Current Biology 10: 169-178; Mourrain et al. (2000) Cell 101: 533-542; Dalmay et al. (2000) Cell 101: 543-553). While potential roles have been proposed, none of these genes has been assigned a definitive function in the silencing process. Biochemical studies have suggested that PTGS is accomplished by a multicomponent nuclease that targets mRNAs for degradation (Hammond et al. (2000) Nature 404: 293-296; Zamore et al. (2000) Cell 101 25-33; Tuschl et al. (1999) Genes and Development 13: 3191-3197). We have shown that the specificity of this complex may derive from the incorporation of a small guide sequence that is homologous to the mRNA substrate (Hammond et al. (2000) Nature 404: 293-296). Originally identified in plants that were actively silencing transgenes (Hamilton and Baulcombe (1999) Science 286: 950-952), these ~22 nt. RNAs have been produced during RNAi in vitro using an extract prepared from *Drosophila* embryos (Zamore et al. (2000) Cell 101 25-33). Putative guide RNAs can also be produced in extracts from *Drosophila* S2 cells (FIG. 5a). With the goal of understanding the mechanism of post-transcriptional gene silencing, we have undertaken both biochemical fractionation and candidate gene approaches to identify the enzymes that execute each step of RNAi.

Our previous studies resulted in the partial purification of a nuclease, RISC, that is an effector of RNA interference. See Example 1. This enzyme was isolated from *Drosophila* S2 cells in which RNAi had been initiated in vivo by transfection with dsRNA. We first sought to determine whether the RISC enzyme and the enzyme that initiates RNAi via processing of dsRNA into 22mers are distinct activities. RISC activity could be largely cleared from extracts by high-speed centrifugation (100,000×g for 60 min.) while the activity that produces 22mers remained in the supernatant (FIGS. 5b,c). This simple fractionation indicated that RISC and the 22mer-generating activity are separable and thus distinct enzymes. However, it seems likely that they might interact at some point during the silencing process.

RNAse III family members are among the few nucleases that show specificity for double-stranded RNA (Nicholson (1999) FEMS Microbiol Rev 23: 371-390). Analysis of the *Drosophila* and *C. elegans* genomes reveals several types of RNAse III enzymes. First is the canonical RNAse III which contains a single RNAse III signature motif and a double-stranded RNA binding domain (dsRBD; e.g. RNC_CAEEL). Second is a class represented by Drosha (Filippov et al. (2000) Gene 245: 213-221), a *Drosophila* enzyme that contains two RNAse III motifs and a dsRBD (CeDrosha in *C. elegans*). A third class contains two RNAse III signatures and an amino terminal helicase domain (e.g. *Drosophila* CG4792, CG6493, *C. elegans* K12H4.8), and these had previously been proposed by Bass as candidate RNAi nucleases (Bass (2000) Cell 101: 235-238). Representatives of all three classes were tested for the ability to produce discrete, ~22 nt. RNAs from dsRNA substrates.

Partial digestion of a 500 nt. cyclin E dsRNA with purified, bacterial RNAse III produced a smear of products while nearly complete digestion produced a heterogeneous group of ~11-17 nucleotide RNAs (not shown). In order to test the dual-RNAse III enzymes, we prepared T7 epitope-tagged versions of Drosha and CG4792. These were expressed in transfected S2 cells and isolated by immunoprecipitation using antibody-agarose conjugates. Treatment of the dsRNA with the CG4792 immunoprecipitate yielded ~22 nt. fragments similar to those produced in either S2 or embryo extracts (FIG. 6a). Neither activity in extract nor activity in immunoprecipitates depended on the sequence of the RNA substrate since dsRNAs derived from several genes were processed equivalently (see Supplement 1). Negative results were obtained with Drosha and with immunoprecipitates of a DExH box helicase (Homeless (Gillespie et al. (1995) Genes and Development 9: 2495-2508); see FIGS. 6a,b). Western blotting confirmed that each of the tagged proteins was expressed and immunoprecipitated similarly (see Supplement 2). Thus, we conclude that CG4792 may carry out the initiation step of RNA interference by producing ~22 nt. guide sequences from dsRNAs. Because of its ability to digest dsRNA into uniformly sized, small RNAs, we have named this enzyme Dicer (Dcr). Dicer mRNA is expressed in embryos, in S2 cells, and in adult flies, consistent with the presence of functional RNAi machinery in all of these contexts (see Supplement 3).

Figure 6D:
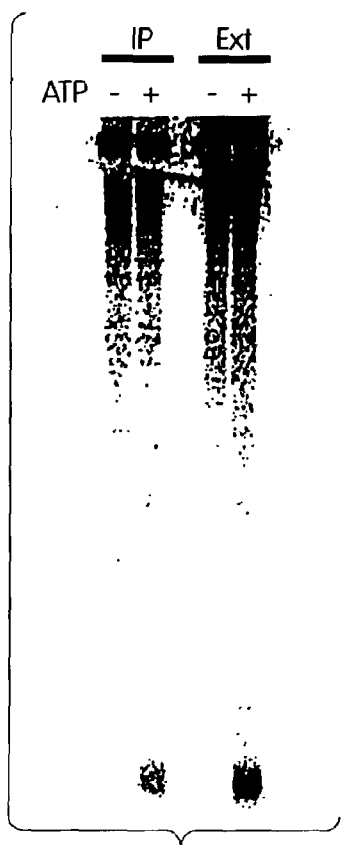
FIG. 6: Production of 22mers by recombinant CG4792/ Dicer. (a) *Drosophila* S2 cells were transfected with plasmids that direct the expression of T7-epitope tagged versions of Drosha, CG4792/Dicer-1 and Homeless. Tagged proteins were purified from cell lysates by immunoprecipitation and were incubated with cyclin E dsRNA. For comparison, reactions were also performed in *Drosophila* embryo and S2 cell extracts. As a negative control, immunoprecipitates were prepared from cells transfected with a β-galactosidase expression vector. Pairs of lanes show reactions performed for 0 or 60 minutes. The synthetic marker (M) is as described in the legend to FIG. 1. (b) Diagrammatic representations of the domain structures of CG4792/Dicer-1, Drosha and Homeless are shown. (c) Immunoprecipitates were prepared from detergent lysates of S2 cells using an antiserum raised against the C-terminal 8 amino acids of *Drosophila* Dicer-1 (CG4792). As controls, similar preparations were made with a pre-immune serum and with an immune serum that had been pre-incubated with an excess of antigenic peptide. Cleavage reactions in which each of these precipitates was incubated with an ~500 nt. fragment of *Drosophila* cyclin E are shown. For comparison, an incubation of the substrate in *Drosophila* embryo extract was electrophoresed in parallel. (d) Dicer immunoprecipitates were incubated with dsRNA substrates in the presence or absence of ATP. For comparison, the same substrate was incubated with S2 extracts that either contained added ATP or that were depleted of ATP using glucose and hexokinase (see methods). (e) *Drosophila* S2 cells were transfected with uniformly, $^{32}$P-labelled dsRNA corresponding to the first 500 nt. of GFP. RISC complex was affinity purified using a histidine-tagged version of *Drosophila* Ago-2, a recently identified component of the RISC complex (Hammond et al., in prep). RISC was isolated either under conditions in which it remains ribosome associated (ls, low salt) or under conditions that extract it from the ribosome in a soluble form (hs, high salt). For comparison, the spectrum of labelled RNAs in the total lysate is shown. (f) Guide RNAs produced by incubation of dsRNA with a Dicer immunoprecipitate are compared to guide RNAs present in an affinity-purified RISC complex. These precisely comigrate on a gel that has single-nucleotide resolution. The lane labelled control is an affinity selection for RISC from a cell that had been transfected with labeled dsRNA but not with the epitope-tagged *Drosophila* Ago-2.
Figure 6E:
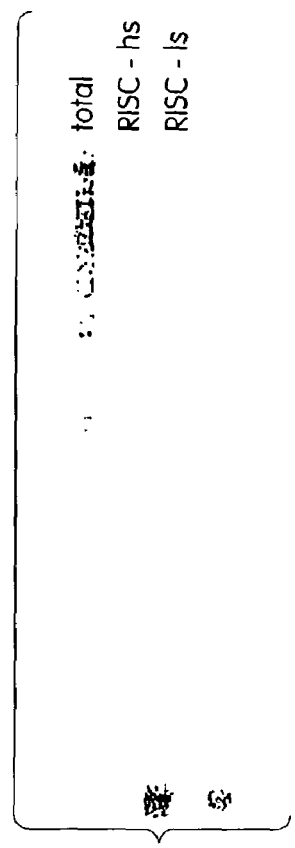
Figure 6F:
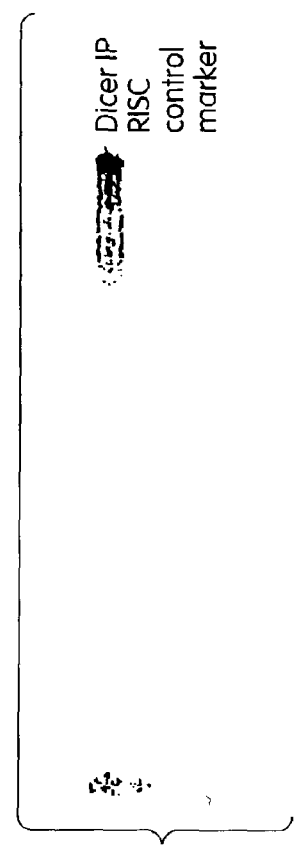

The possibility that Dicer might be the nuclease responsible for the production of guide RNAs from dsRNAs prompted us to raise an antiserum directed against the carboxy-terminus of the Dicer protein (Dicer-1, CG4792). This antiserum could immunoprecipitate a nuclease activity from either *Drosophila* embryo extracts or from S2 cell lysates that produced ~22 nt. RNAs from dsRNA substrates (FIG. 6C). The putative guide RNAs that are produced by the Dicer-1 enzyme precisely comigrate with 22mers that are produced in extract and with 22mers that are associated with the RISC enzyme (FIGS. 6 D,F). It had previously been shown that the enzyme that produced guide RNAs in *Drosophila* embryo extracts was ATP-dependent (Zamore et al. (2000) Cell 101 25-33). Depletion of this cofactor resulted in an ~6-fold lower rate of dsRNA cleavage and in the production of RNAs with a slightly lower mobility. Of interest was the fact that both Dicer-1 immunoprecipitates and extracts from S2 cells require ATP for the production of ~22mers (FIG. 6D). We do not observe the accumulation of lower mobility products in these cases, although we do routinely observe these in ATP-depleted embryo extracts. The requirement of this nuclease for ATP is a quite unusual property. We hypothesize that this requirement could indicate that the enzyme may act processively on the dsRNA, with the helicase domain harnessing the energy of ATP hydrolysis both for unwinding guide RNAs and for translocation along the substrate.

Efficient induction of RNA interference in *C. elegans* and in *Drosophila* has several requirements. For example, the initiating RNA must be double-stranded, and it must be several hundred nucleotides in length. To determine whether these requirements are dictated by Dicer, we characterized the ability of extracts and of immunoprecipitated enzyme to digest various RNA substrates. Dicer was inactive against single stranded RNAs regardless of length (see Supplement 4). The enzyme could digest both 200 and 500 nucleotide dsRNAs but was significantly less active with shorter substrates (see Supplement 4). Double-stranded RNAs as short as 35 nucleotides could be cut by the enzyme, albeit very inefficiently (data not shown). In contrast, *E. coli* RNAse III could digest to completion dsRNAs of 35 or 22 nucleotides (not shown). This suggests that the substrate preferences of the Dicer enzyme may contribute to but not wholly determine the size dependence of RNAi.

Figures 7A, 7B:
FIG. 7: Dicer participates in RNAi. (a) *Drosophila* S2 cells were transfected with dsRNAs corresponding to the two *Drosophila* Dicers (CG4792 and CG6493) or with a control dsRNA corresponding to murine caspase 9. Cytoplasmic extracts of these cells were tested for Dicer activity. Transfection with Dicer dsRNA reduced activity in lysates by 7.4-fold. (b) The Dicer-1 antiserum (CG4792) was used to prepare immunoprecipitates from S2 cells that had been treated as described above. Dicer dsRNA reduced the activity of Dicer-1 in this assay by 6.2-fold. (c) Cells that had been transfected two days previously with either mouse caspase 9 dsRNA or with Dicer dsRNA were cotransfected with a GFP expression plasmid and either control, luciferase dsRNA or GFP dsRNA. Three independent experiments were quantified by FACS. A comparison of the relative percentage of GFP-positive cells is shown for control (GFP plasmid plus luciferase dsRNA) or silenced (GFP plasmid plus GFP dsRNA) populations in cells that had previously been transfected with either control (caspase 9) or Dicer dsRNAs.
Figure 7C:
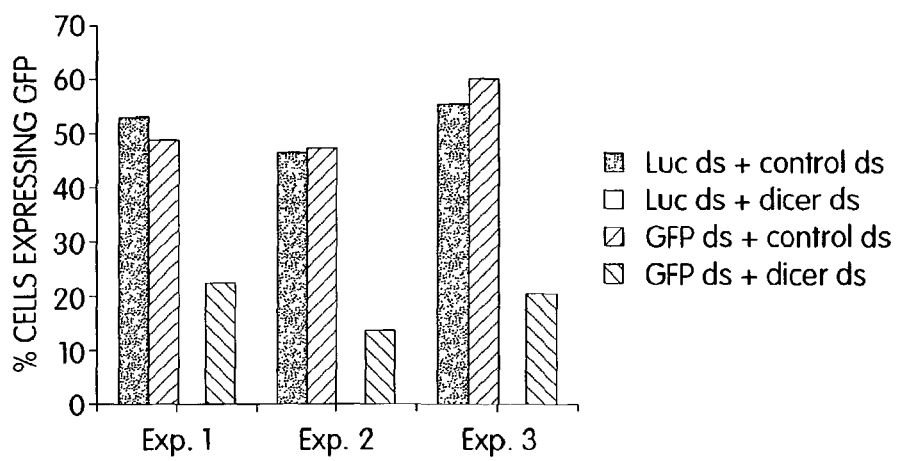

To determine whether the Dicer enzyme indeed played a role in RNAi in vivo, we sought to deplete Dicer activity from S2 cells and test the effect on dsRNA-induced gene silencing. Transfection of S2 cells with a mixture of dsRNAs homologous to the two *Drosophila* Dicer genes (CG4792 and CG6493) resulted in an ~6-7 fold reduction of Dicer activity either in whole cell lysates or in Dicer-1 immunoprecipitates (FIGS. 7A,B). Transfection with a control dsRNA (murine caspase 9) had no effect. Qualitatively similar results were seen if Dicer was examined by Northern blotting (not shown). Depletion of Dicer in this manner substantially compromised the ability of cells to silence subsequently an exogenous, GFP transgene by RNAi (FIG. 7C). These results indicate that Dicer is involved in RNAi in vivo. The lack of complete inhibition of silencing could result from an incomplete suppression of Dicer (which is itself required for RNAi) or could indicate that in vivo, guide RNAs can be produced by more than one mechanism (e.g. through the action of RNA-dependent RNA polymerases).

Our results indicate that the process of RNA interference can be divided into at least two distinct steps. According to this model, initiation of PTGS would occur upon processing of a double-stranded RNA by Dicer into ~22 nucleotide guide sequences, although we cannot formally exclude the possibility that another, Dicer-associated nuclease may participate in this process. These guide RNAs would be incorporated into a distinct nuclease complex (RISC) that targets single-stranded mRNAs for degradation. An implication of this model is that guide sequences are themselves derived directly from the dsRNA that triggers the response. In accord with this model, we have demonstrated that $^{32}$P-labeled, exogenous dsRNAs that have been introduced into S2 cells by transfection are incorporated into the RISC enzyme as 22 mers (FIG. 7E). However, we cannot exclude the possibility that RNA-dependent RNA polymerases might amplify 22mers once they have been generated or provide an alternative method for producing guide RNAs.

Figure 8A:
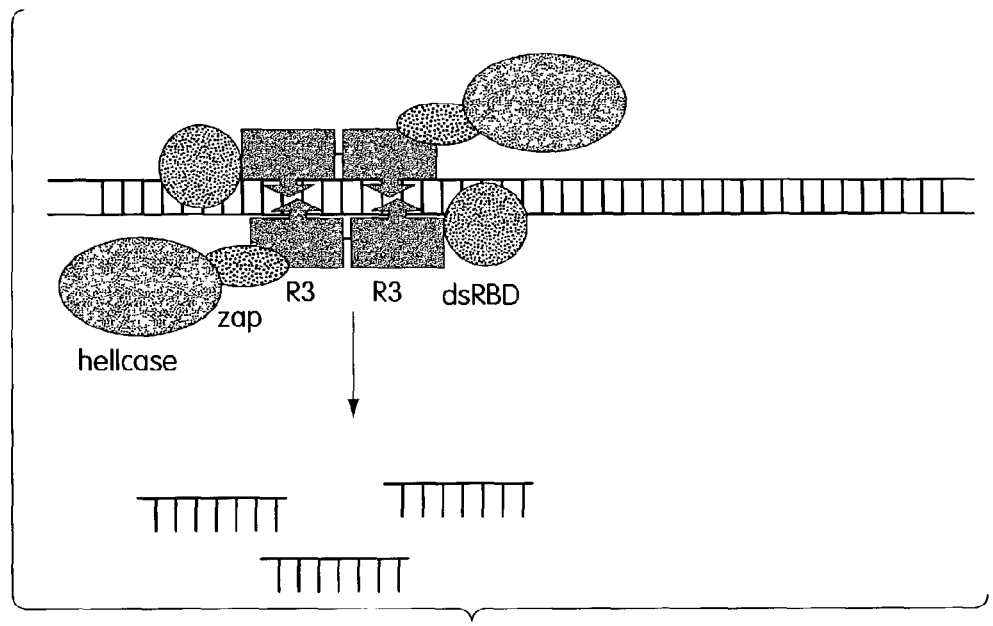
FIG. 8: Dicer is an evolutionarily conserved ribonuclease. (a) A model for production of 22mers by Dicer. Based upon the proposed mechanism of action of Ribonuclease III, we propose that Dicer acts on its substrate as a dimer. The positioning of the two ribonuclease domains (RIIIa and RIIIb) within the enzyme would thus determine the size of the cleavage product. An equally plausible alternative model could be derived in which the RIIIa and RIIIb domains of each Dicer enzyme would cleave in concert at a single position. In this model, the size of the cleavage product would be determined by interaction between two neighboring Dicer enzymes. (b) Comparison of the domain structures of potential Dicer homologs in various organisms (*Drosophila*—CG4792, CG6493, *C. elegans*-K12H4.8, *Arabidopsis*—CARPEL FACTORY, T25K16.4, AC012328_1, human Helicase-MOI and *S. pombe*—YC9A_SCHPO). The ZAP domains were identified both by analysis of individual sequences with Pfam and by Psi-blast searches. The ZAP domain in the putative *S. pombe* Dicer is not detected by PFAM but is identified by Psi-Blast and is thus shown in a different color. For comparison, a domain structure of the RDE1/QDE2/ARGONAUTE family is shown. It should be noted that the ZAP domains are more similar within each of the Dicer and ARGONAUTE families than they are between the two groups. (c) An alignment of the ZAP domains in selected Dicer and Argonaute family members is shown. The alignment was produced using ClustalW.

The structure of the Dicer enzyme provokes speculation on the mechanism by which the enzyme might produce discretely sized fragments irrespective of the sequence of the dsRNA (see Supplement 1, FIG. 8a). It has been established that bacterial RNAse III acts on its substrate as a dimer (Nicholson (1999) FEMS Microbiol Rev 23: 371-390; Robertson et al. (1968) J Biol Chem 243: 82-91; Dunn (1976) J Biol Chem 251: 3807-3814). Similarly, a dimer of Dicer enzymes may be required for cleavage of dsRNAs into ~22 nt. pieces. According to one model, the cleavage interval would be determined by the physical arrangement of the two RNAse III domains within Dicer enzyme (FIG. 8a). A plausible alternative model would dictate that cleavage was directed at a single position by the two RIII domains in a single Dicer protein. The 22 nucleotide interval could be dictated by interaction of neighboring Dicer enzymes or by translocation along the mRNA substrate. The presence of an integral helicase domain suggests that the products of Dicer cleavage might be single-stranded 22 mers that are incorporated into the RISC enzyme as such.

Figure 8B:
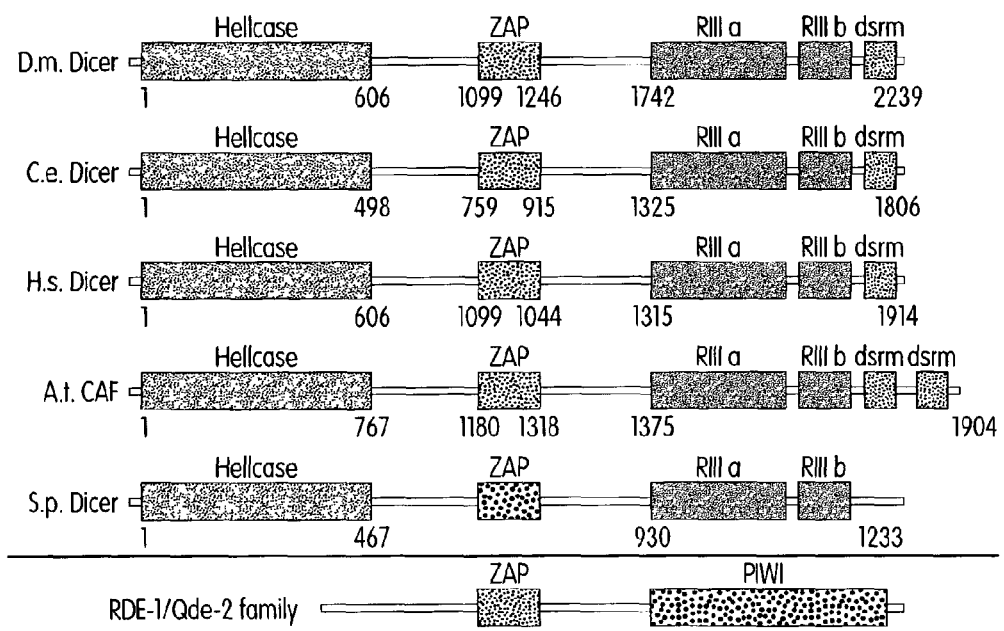
Figure 9:
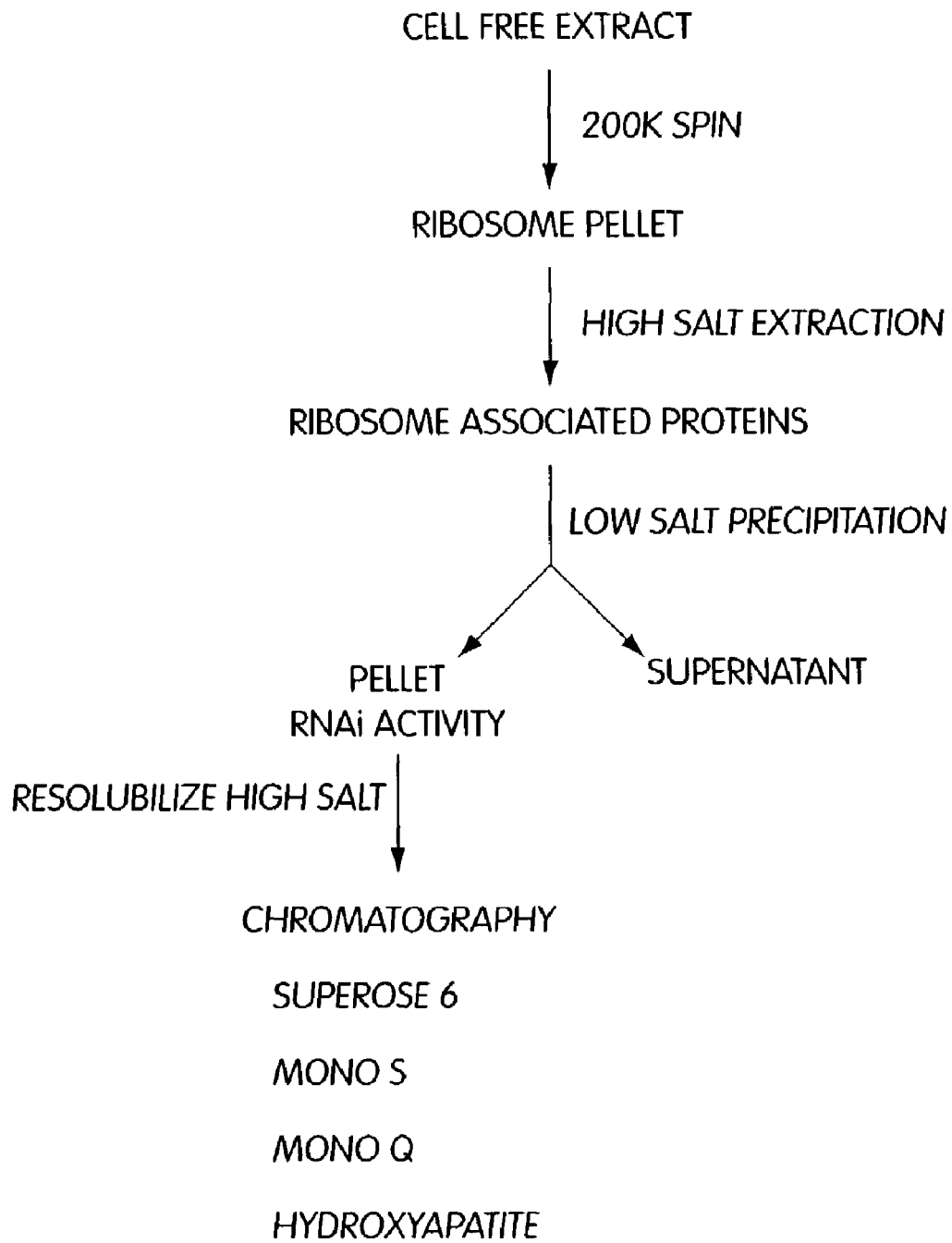
FIG. 9: Purification strategy for RISC. (second step in RNAi model).
Figure 10:
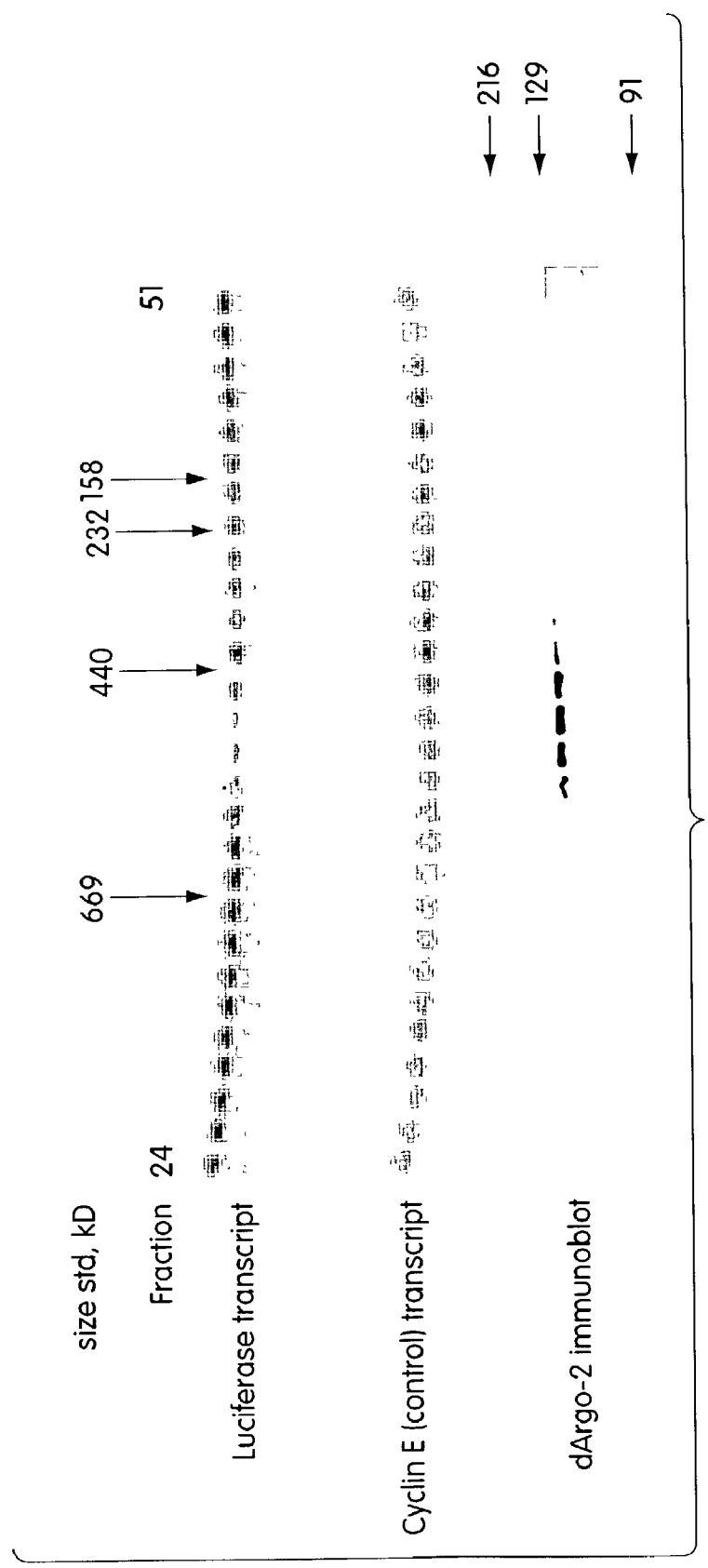
FIG. 10: Fractionation of RISC activity over sizing column. Activity fractionates as 500 KDa complex. Also, antibody to *Drosophila* argonaute 2 cofractionates with activity.
Figure 11:
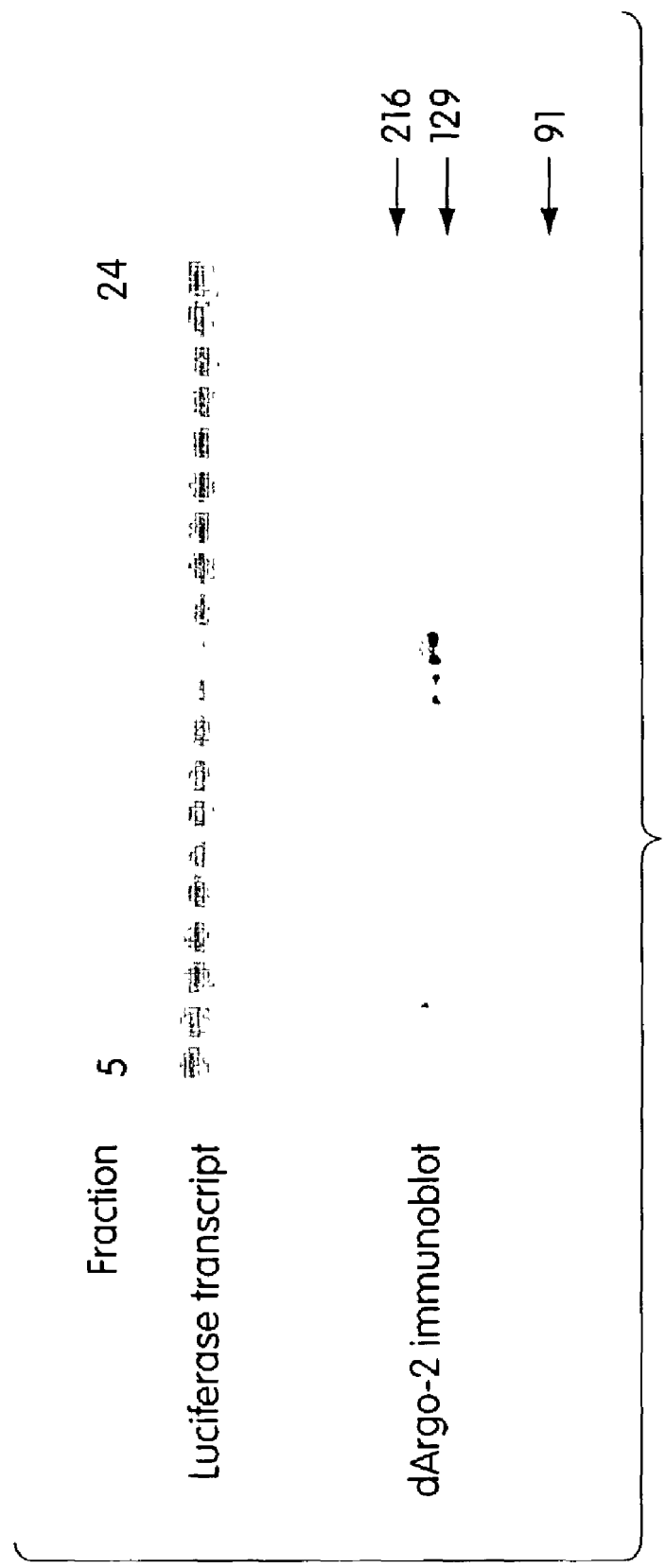
FIG. 11-13: Fractionation of RISC over monoS, monoQ, Hydroxyapatite columns. *Drosophila* argonaute 2 protein also cofractionates.
Figure 12:
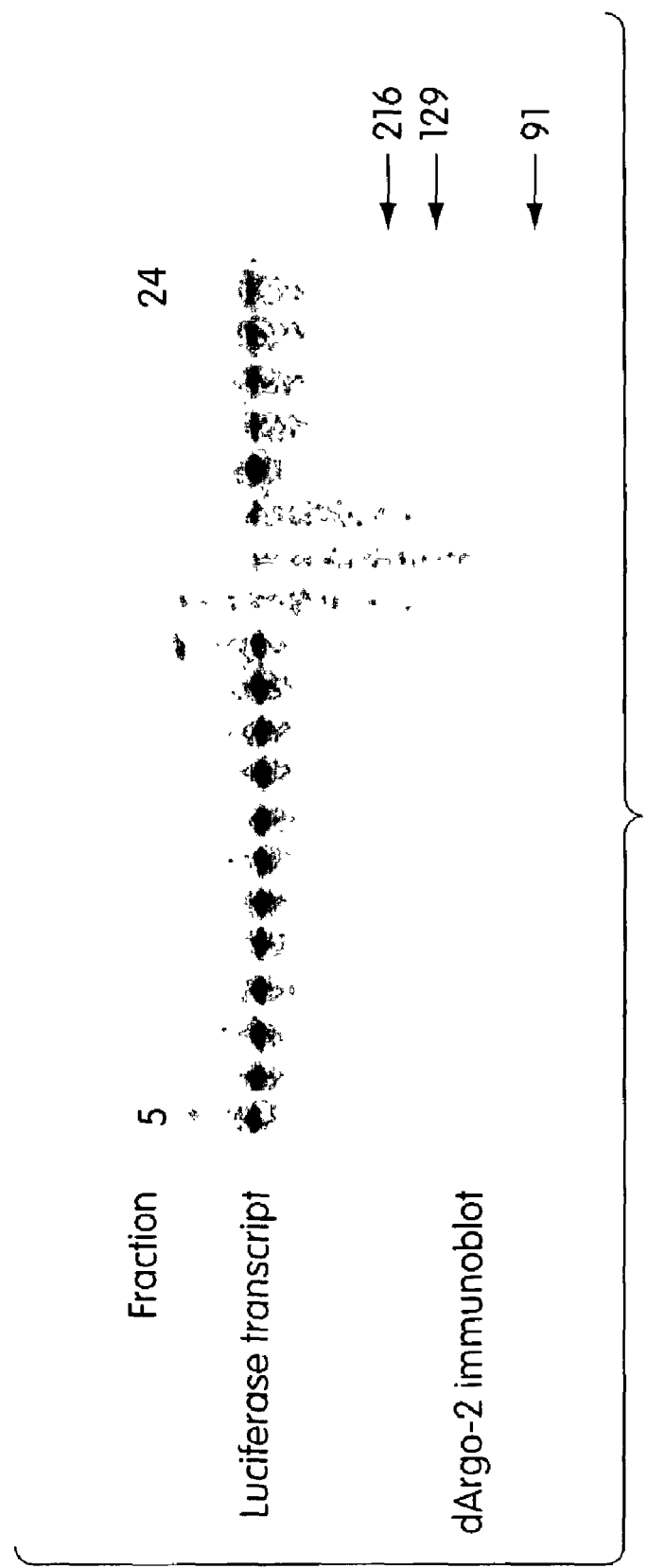
Figure 13:
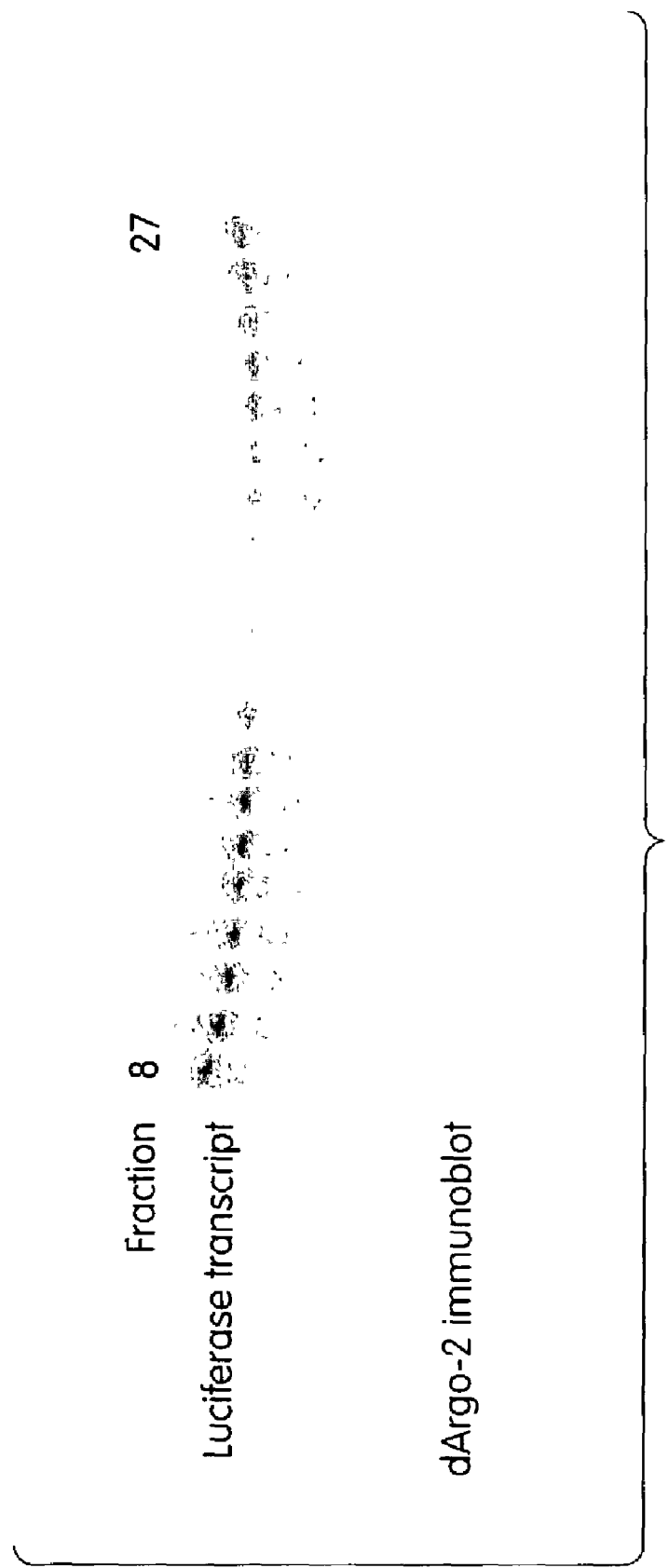
Figure 14:
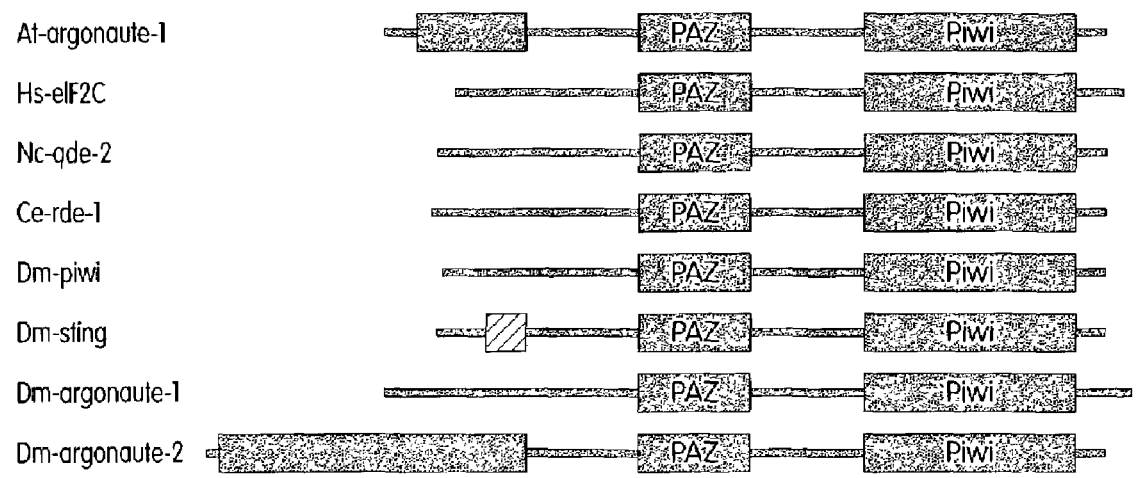
FIG. 14: Alignment of *Drosophila* argonaute 2 with other family members.
Figure 15:
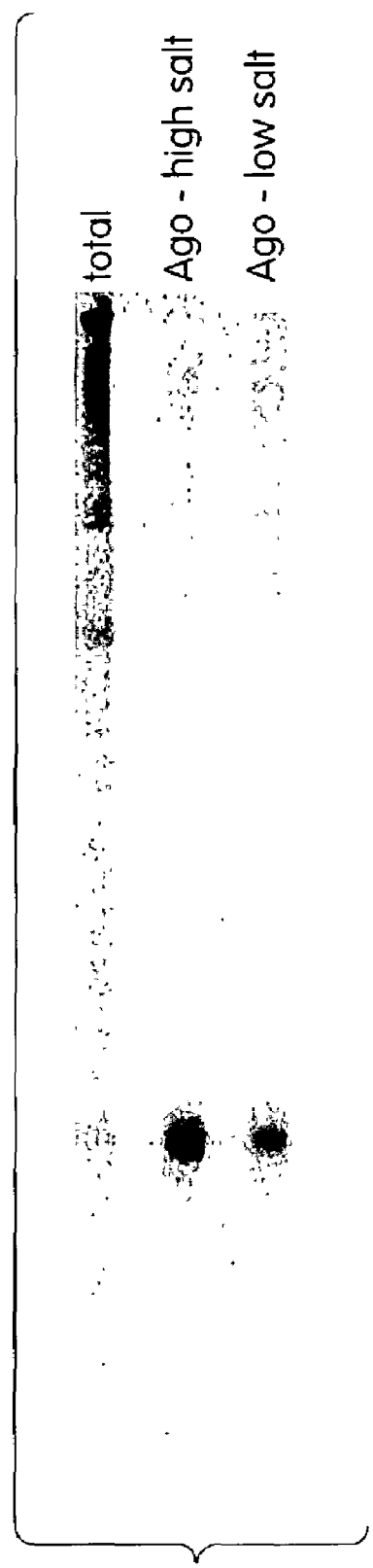
FIG. 15: Confirmation of *Drosophila* argonaute 2. S2 cells were transfected with labeled dsRNA and His tagged argonaute. Argonaute was isolated on nickel agarose and RNA component was identified on 15% acrylamide gel.
Figure 16:
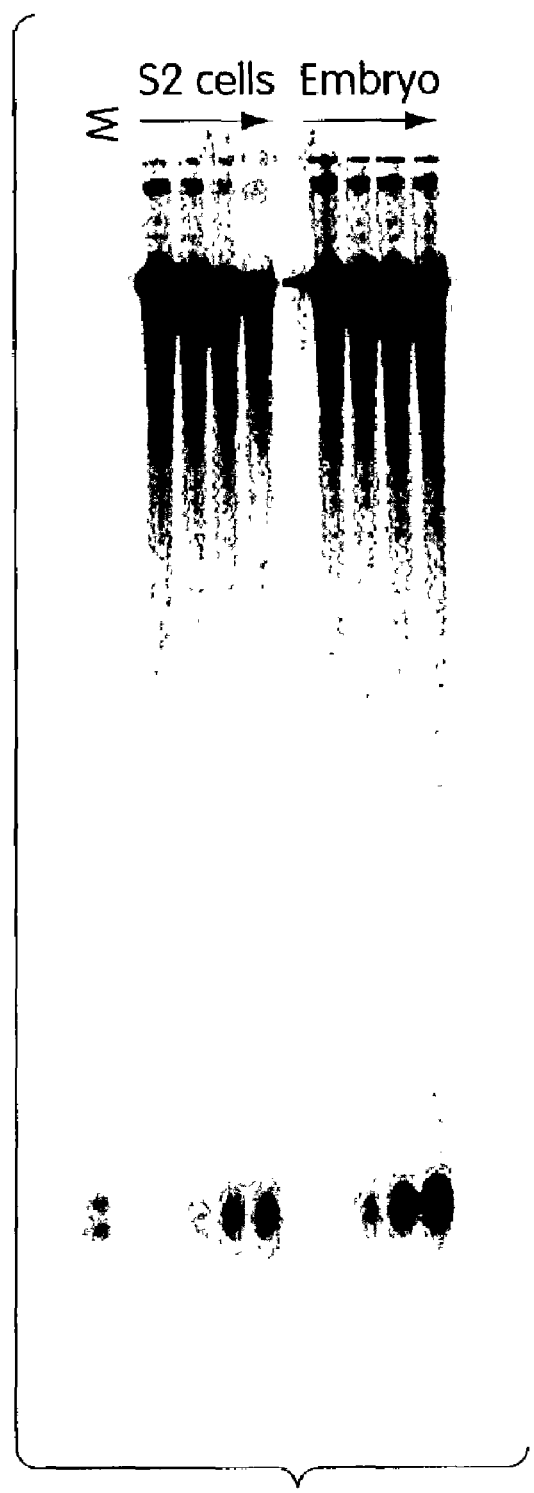
FIG. 16: S2 cell and embryo extracts were assayed for 22mer generating activity.
Figure 17:
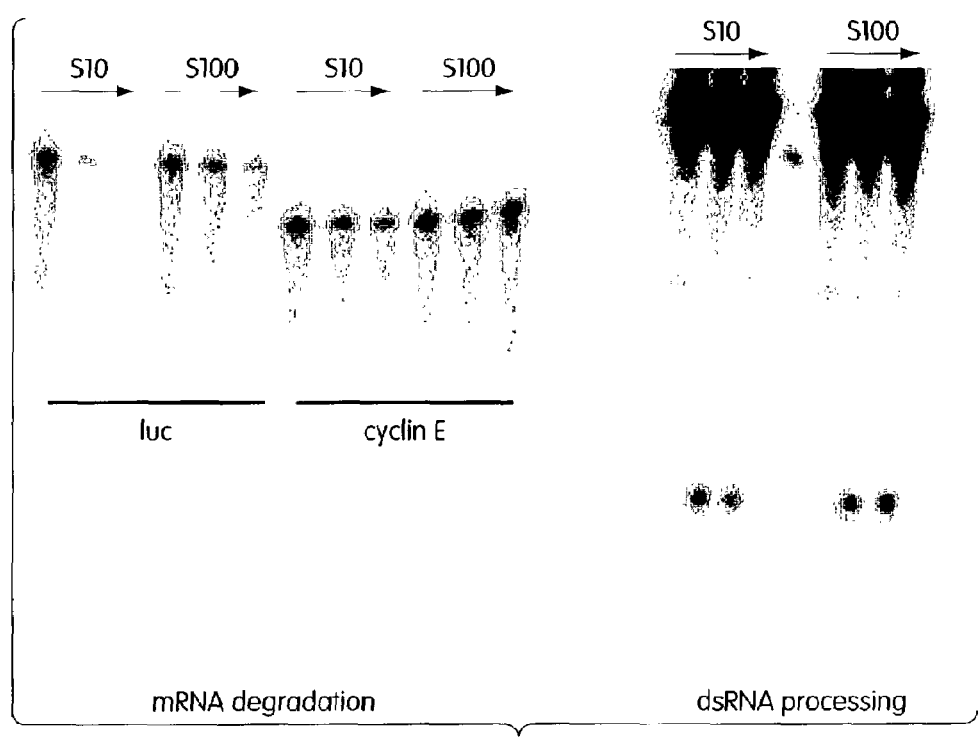
FIG. 17: RISC can be separated from 22mer generating activity (dicer). Spinning extracts (S100) can clear RISC activity from supernatant (left panel) however, S100 spins still contain dicer activity (right panel).
Figure 18:
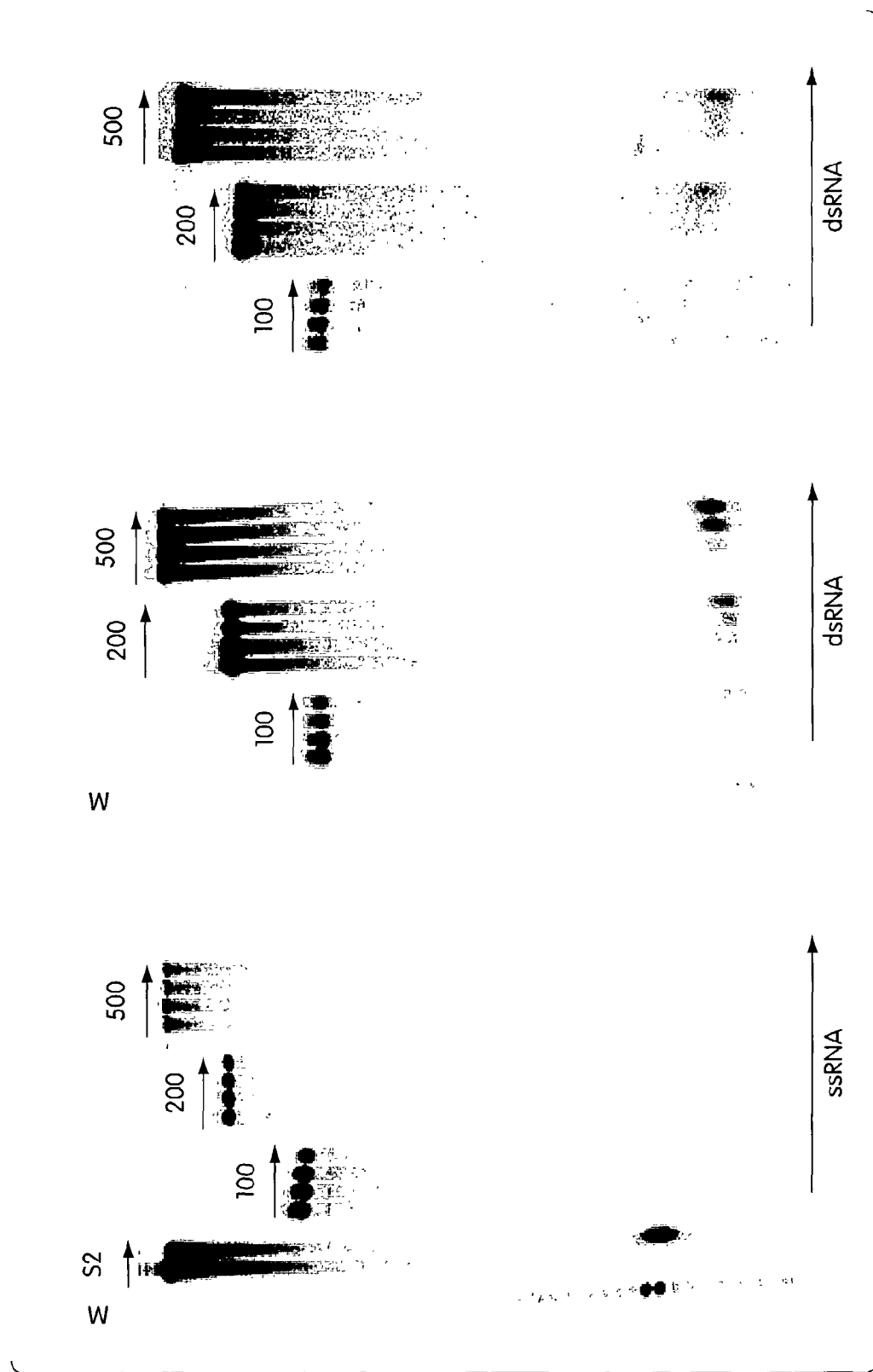
FIG. 18: Dicer is specific for dsRNA and prefers longer substrates.
Figure 21:
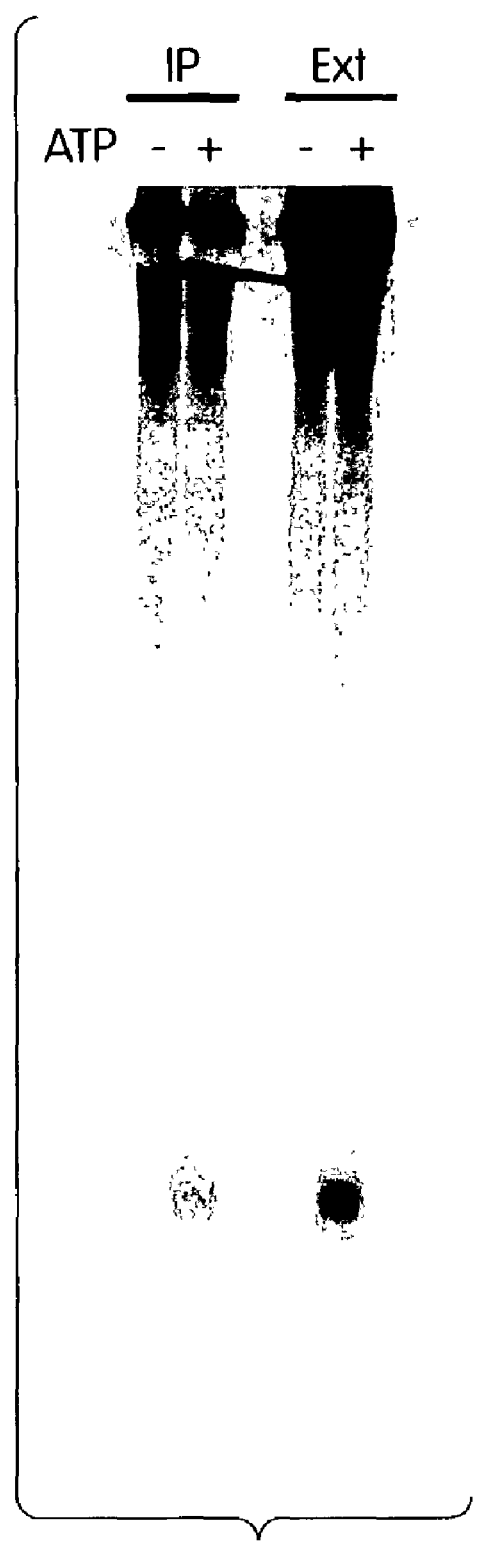
FIG. 21: Dicer requires ATP.
Figures 22A, 22B:
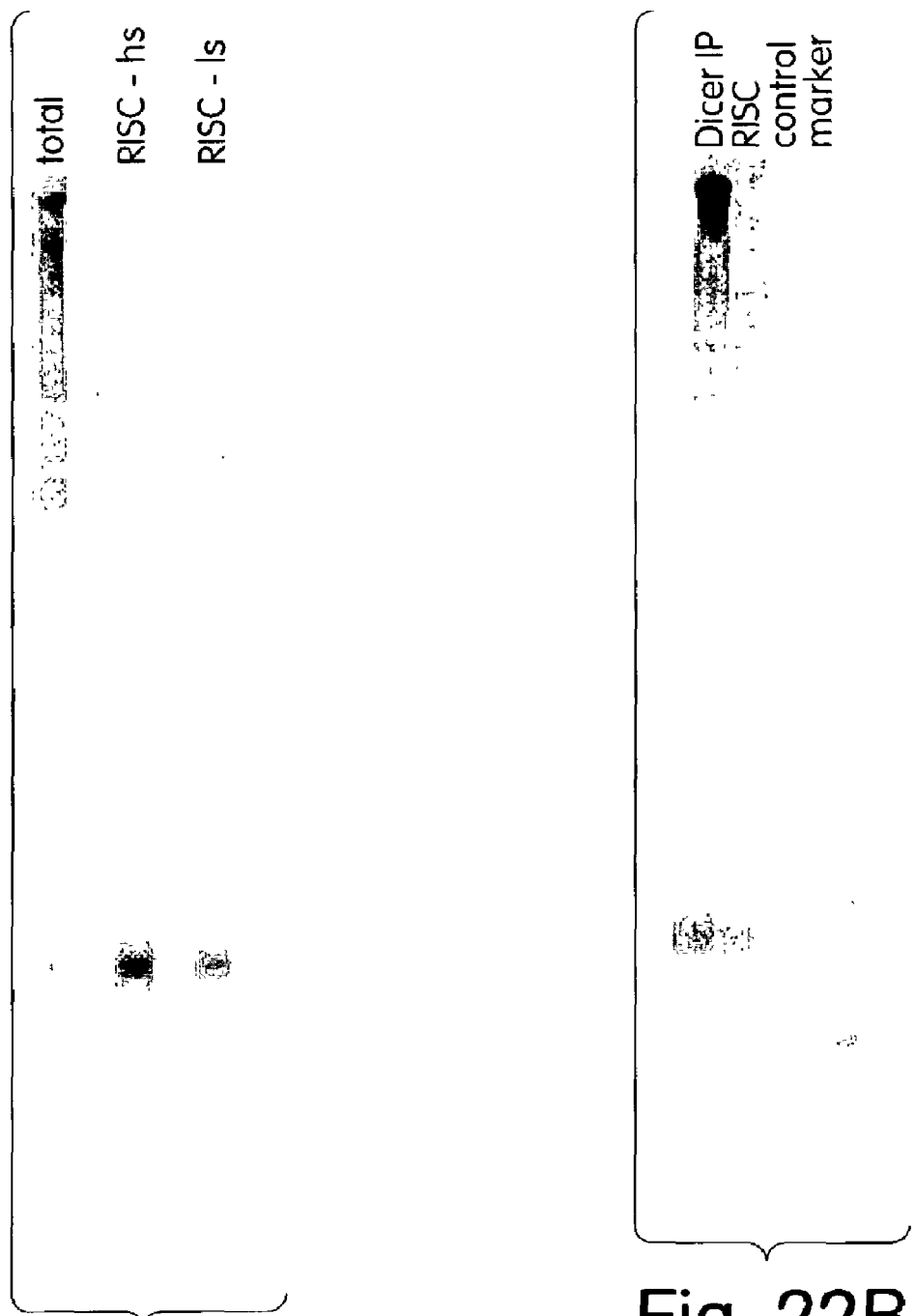
FIG. 22: Dicer produces RNAs that are the same size as RNAs present in RISC.
Figure 23:
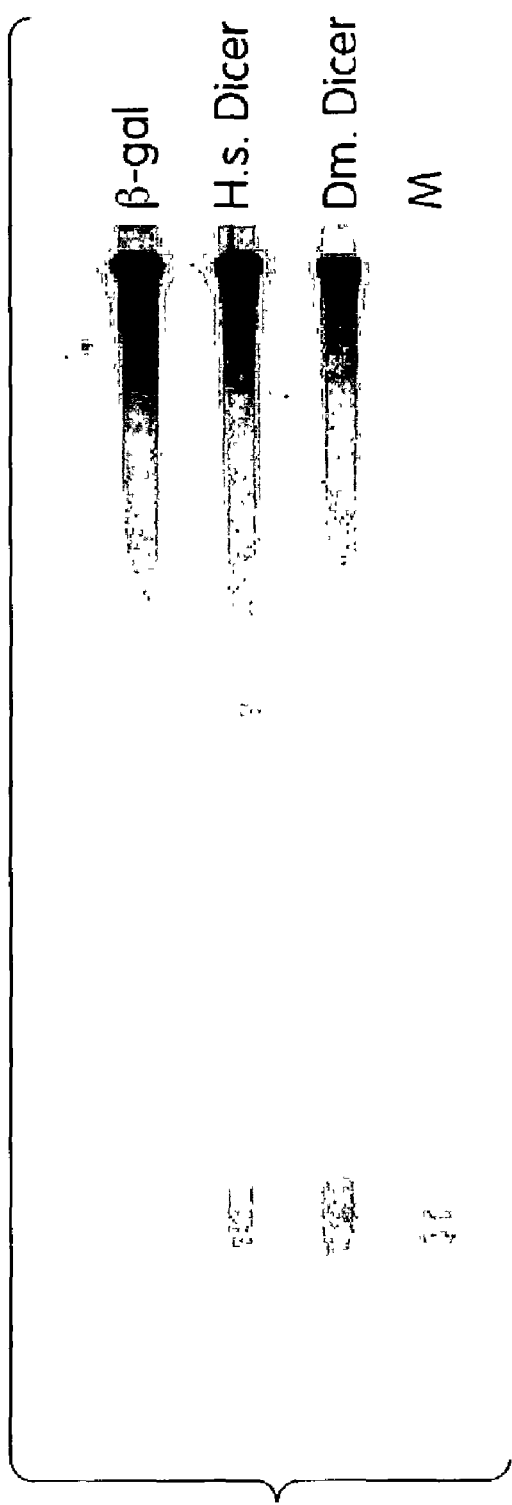
FIG. 23: Human dicer homolog when expressed and immunoprecipitated has 22mer generating activity.
Figure 25:
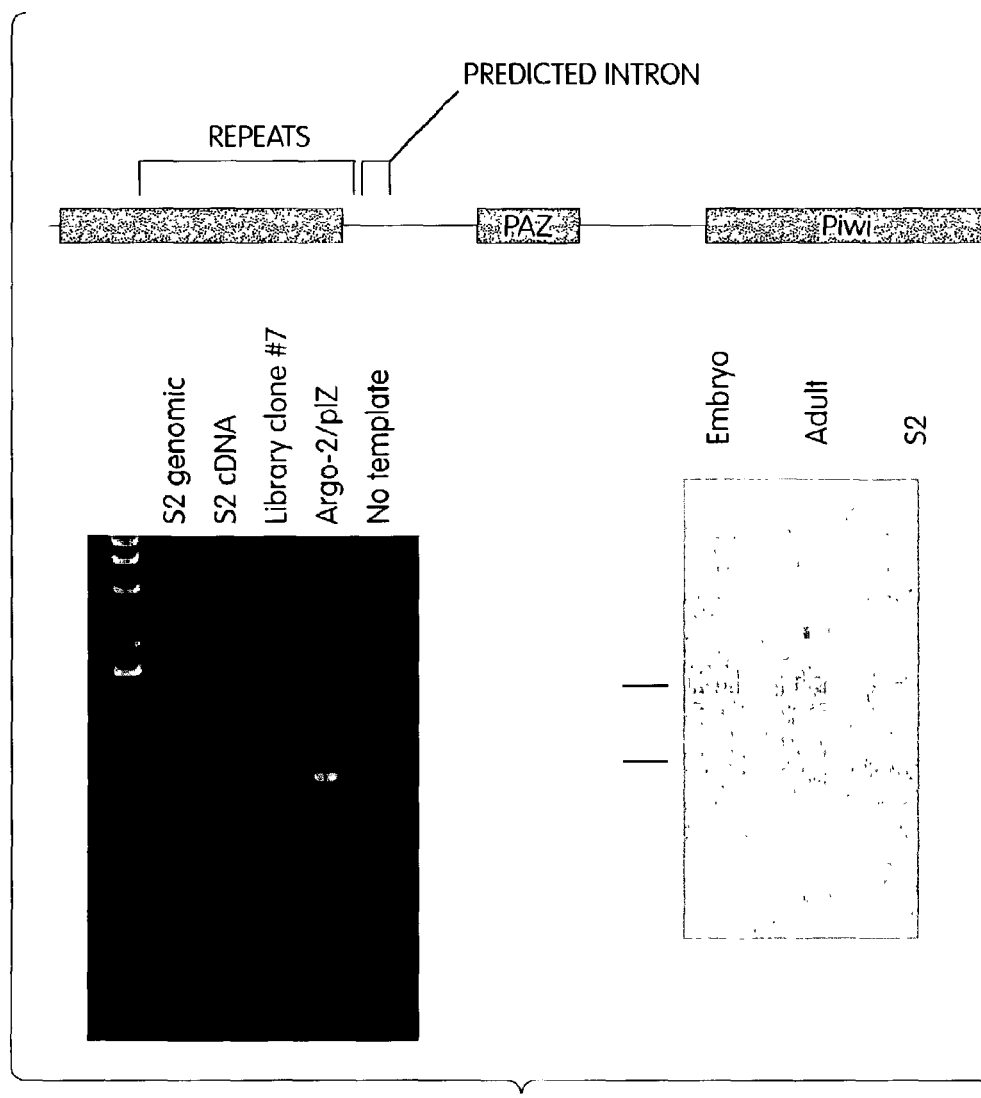
FIG. 25: Molecular characterization of *Drosophila* argonaute 2. The presence of an intron in coding sequence was determined by northern blotting using intron probe. This results in a different 5' reading frame then the published genome sequence. Number of polyglutamine repeats was determined by genomic PCR.
Figure 26:
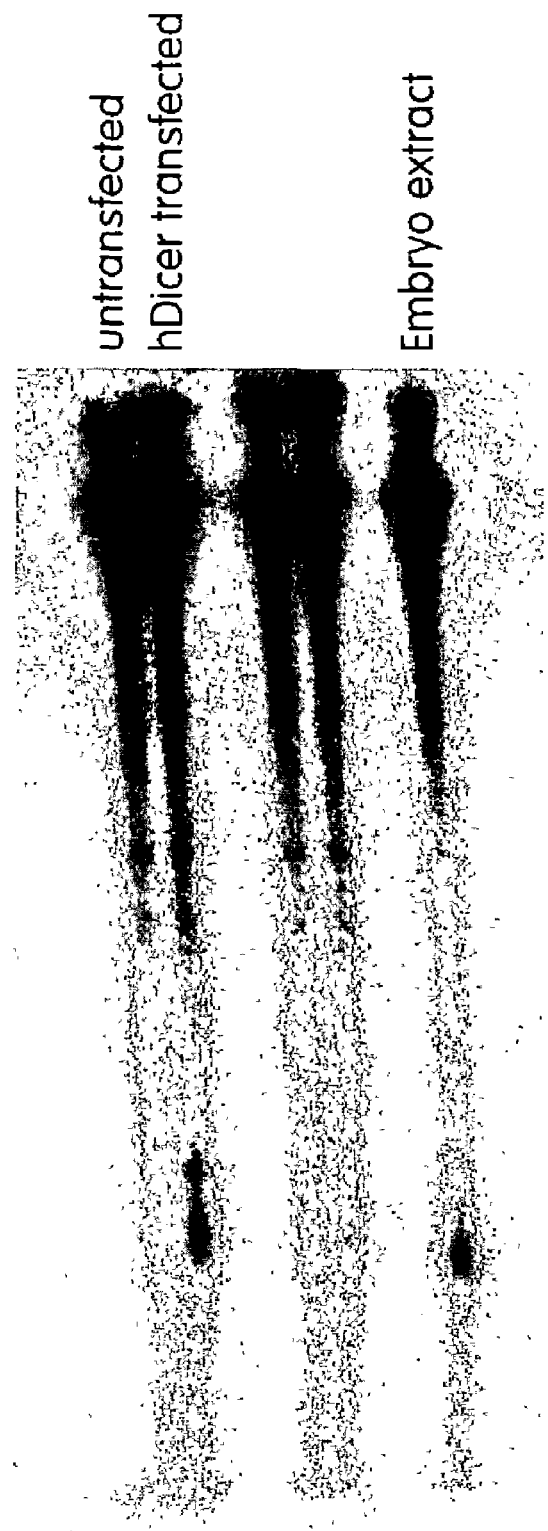
FIG. 26: Dicer activity can be created in human cells by expression of human dicer gene. Host cell was 293. Crude extracts had dicer activity, while activity was absent from untransfected cells. Activity is not dissimilar to that seen in *drosophila* embryo extracts.

A notable feature of the Dicer family is its evolutionary conservation. Homologs are found in *C. elegans* (K12H4.8), *Arabidopsis* (e.g., CARPEL FACTORY (Jacobson et al. (1999) Development 126: 5231-5243), T25K16.4, AC012328_1), mammals (Helicase-MOI (Matsuda et al. (2000) Biochim Biophys Acta 1490: 163-169) and *S. pombe* (YC9A_SCHPO) (FIG. 8b, see Supplements 6,7 for sequence comparisons). In fact, the human Dicer family member is capable of generating ~22 nt. RNAs from dsRNA substrates (Supplement 5) suggesting that these structurally similar proteins may all share similar biochemical functions. It has been demonstrated that exogenous dsRNAs can affect gene function in early mouse embryos (Wianny et al. (2000) Nature Cell Biology 2: 70-75), and our results suggest that this regulation may be accomplished by an evolutionarily conserved RNAi machinery.

In addition to RNAseIII and helicase motifs, searches of the PFAM database indicate that each Dicer family member also contains a ZAP domain (FIG. 8c) (Sonnhammer et al. (1997) Proteins 28: 405-420). This sequence was defined based solely upon its conservation in the Zwille/ARGONAUTE/Piwi family that has been implicated in RNAi by mutations in *C. elegans* (Rde-1) and *Neurospora* (Qde-2) (Tabara et al. (1999) Cell 99: 123-132; Catalanotto et al (2000) Nature 404: 245). Although the function of this domain is unknown, it is intriguing that this region of homology is restricted to two gene families that participate in dsRNA-dependent silencing. Both the ARGONAUTE and Dicer families have also been implicated in common biological processes, namely the determination of stem-cell fates. A hypomorphic allele of carpel factory, a member of the Dicer family in *Arabidopsis*, is characterized by increased proliferation in floral meristems (Jacobsen et al. (1999) Development 126 5231-5243). This phenotype and a number of other characteristic features are also shared by *Arabidopsis* ARGONAUTE (ago1-1) mutants (Bohmert et al. (1998) EMBO J. 17: 170-180; C. Kidner and R. Martiennsen, pers. comm.). These genetic analyses begin to provide evidence that RNAi may be more than a defensive response to unusual RNAs but may also play important roles in the regulation of endogenous genes.

With the identification of Dicer as a catalyst of the initiation step of RNAi, we have begun to unravel the biochemical basis of this unusual mechanism of gene regulation. It will be of critical importance to determine whether the conserved family members from other organisms, particularly mammals, also play a role in dsRNA-mediated gene regulation.

Methods

Plasmid constructs. A full-length cDNA encoding Drosha was obtained by PCR from an EST sequenced by the Berkeley *Drosophila* genome project. The Homeless clone was a gift from Gillespie and Berg (Univ. Washington). The T7 epitope-tag was added to the amino terminus of each by PCR, and the tagged cDNAs were cloned into pRIP, a retroviral vector designed specifically for expression in insect cells (E. Bernstein, unpublished). In this vector, expression is driven by the *Orgyia pseudotsugata* IE2 promoter (Invitrogen). Since no cDNA was available for CG4792/Dicer, a genomic clone was amplified from a bacmid (BACR23F10; obtained from the BACPAC Resource Center in the Dept. of Human Genetics at the Roswell Park Cancer Institute). Again, during amplification, a T7 epitope tag was added at the amino terminus of the coding sequence. The human Dicer gene was isolated from a cDNA library prepared from HaCaT cells (GJH, unpublished). A T7-tagged version of the complete coding sequence was cloned into pcDNA3 (Invitrogen) for expression in human cells (LinX-A).

Cell culture and extract preparation. S2 and embryo culture. S2 cells were cultured at 27° C. in 5% $CO_2$ in Schneider's insect media supplemented with 10% heat inactivated fetal bovine serum (Gemini) and 1% antibiotic-antimycotic solution (Gibco BRL). Cells were harvested for extract preparation at $10 \times 10^6$ cells/ml. The cells were washed 1× in PBS and were resuspended in a hypotonic buffer (10 mM Hepes pH 7.0, 2 mM $MgCl_2$, 6 mM βME) and dounced. Cell lysates were spun 20,000×g for 20 minutes. Extracts were stored at −80° C. *Drosophila* embryos were reared in fly cages by standard methodologies and were collected every 12 hours. The embryos were dechorionated in 50% chlorox bleach and washed thoroughly with distilled water. Lysis buffer (10 mM Hepes, 10 mM KCl, 1.5 mM $MgCl_2$, 0.5 mM EGTA, 10 mM β-glycerophosphate, 1 mM DTT, 0.2 mM PMSF) was added to the embryos, and extracts were prepared by homogenization in a tissue grinder. Lysates were spun for two hours at 200,000×g and were frozen at −80° C. LinX-A cells, a highly-transfectable derivative of human 293 cells, (Lin Xie and GJH, unpublished) were maintained in DMEM/ 10% FCS.

Transfections and immunoprecipitations. S2 cells were transfected using a calcium phosphate procedure essentially as previously described (Hammond et al. (2000) Nature 404: 293-296). Transfection rates were ~90% as monitored in controls using an in situ β-galactosidase assay. LinX-A cells were also transfected by calcium phosphate co-precipitation. For immunoprecipitations, cells (~$5 \times 10^6$ per IP) were transfected with various clones and lysed three days later in IP buffer (125 mM KOAc, 1 mM MgOAc, 1 mM $CaCl_2$, 5 mM EGTA, 20 mM Hepes pH 7.0, 1 mM DTT, 1% NP-40 plus Complete protease inhibitors (Roche)). Lysates were spun for 10 minutes at 14,000×g and supernatants were added to T7 antibody-agarose beads (Novagen). Antibody binding proceeded for 4 hours at 4° C. Beads were centrifuged and washed in lysis buffer three times, and once in reaction buffer. The Dicer antiserum was raised in rabbits using a KLH-conjugated peptide corresponding to the C-terminal 8 amino acids of *Drosophila* Dicer-1 (CG4792).

Cleavage reactions. RNA preparation. Templates to be transcribed into dsRNA were generated by PCR with forward and reverse primers, each containing a T7 promoter sequence. RNAs were produced using Riboprobe (Promega) kits and were uniformly labeling during the transcription reaction with $^{32}$P-UTP. Single-stranded RNAs were purified from 1% agarose gels. dsRNA cleavage. Five microliters of embryo or S2 extracts were incubated for one hour at 30° C. with dsRNA in a reaction containing 20 mM Hepes pH 7.0, 2 mM MgOAc, 2 mM DTT, 1 mM ATP and 5% Superasin (Ambion). Immunoprecipitates were treated similarly except that a minimal volume of reaction buffer (including ATP and Superasin) and dsRNA were added to beads that had been washed in reaction buffer (see above). For ATP depletion, *Drosophila* embryo extracts were incubated for 20 minutes at 30° C. with 2 mM glucose and 0.375 U of hexokinase (Roche) prior to the addition of dsRNA.

Northern and Western analysis. Total RNA was prepared from *Drosophila* embryos (0-12 hour), from adult flies, and from S2 cells using Trizol (Lifetech). Messenger RNA was isolated by affinity selection using magnetic oligo-dT beads (Dynal). RNAs were electrophoresed on denaturing formaldehyde/agarose gels, blotted and probed with randomly primed DNAs corresponding to Dicer. For Western analysis, T7-tagged proteins were immunoprecipitated from whole cell lysates in IP buffer using anti-T7-antibody-agarose conjugates. Proteins were released from the beads by boiling in Laemmli buffer and were separated by electrophoresis on 8% SDS PAGE. Following transfer to nitrocellulose, proteins were visualized using an HRP-conjugated anti-T7 antibody (Novagen) and chemiluminescent detection (Supersignal, Pierce).

RNAi of Dicer. *Drosophila* S2 cells were transfected either with a dsRNA corresponding to mouse caspase 9 or with a mixture of two dsRNAs corresponding to *Drosophila* Dicer-1 and Dicer-2 (CG4792 and CG6493). Two days after the initial transfection, cells were again transfected with a mixture containing a GFP expression plasmid and either luciferase dsRNA or GFP dsRNA as previously described (Hammond et al. (2000) Nature 404: 293-296). Cells were assayed for Dicer activity or fluorescence three days after the second transfection. Quantification of fluorescent cells was done on a Coulter EPICS cell sorter after fixation. Control transfections indicated that Dicer activity was not affected by the introduction of caspase 9 dsRNA.

Example 3

A Simplified Method for the Creation of Hairpin Constructs for RNA Interference

In numerous model organisms, double stranded RNAs have been shown to cause effective and specific suppression of gene function (Bosher and Labouesse (2000) Nature Cell Biology 2: E31-E36). This response, termed RNA interference or post-transcriptional gene silencing, has evolved into a highly effective reverse genetic tool in *C. elegans*, *Drosophila*, plants and numerous other systems. In these cases, double-stranded RNAs can be introduced by injection, transfection or feeding; however, in all cases, the response is both transient and systemic. Recently, stable interference with gene expression has been achieved by expression of RNAs that form snap-back or hairpin structures (Fortier and Belote (2000) Genesis 26: 240-244; Kennerdell and Carthew (2000) Nature Biotechnology 18: 896-898; Lam and Thummel (2000) Current Biology 10: 957-963; Shi et al. (2000) RNA 6: 1069-1076; Smith et al. (2000) Nature 407: 319-320; Tavemarakis et al. (2000) Nature Genetics 24: 180-183). This has the potential not only to allow stable silencing of gene expression but also inducible silencing as has been observed in trypanosomes and adult *Drosophila* (Fortier and Belote (2000) Genesis 26: 240-244; Lam and Thummel (2000) Current Biology 10: 957-963; Shi et al. (2000) RNA 6: 1069-1076). The utility of this approach is somewhat hampered by the difficulties that arise in the construction of bacterial plasmids containing the long inverted repeats that are necessary to provoke silencing. In a recent report, it was stated that more than 1,000 putative clones were screened to identify the desired construct (Tavemarakis et al. (2000) Nature Genetics 24: 180-183).

Figure 27:
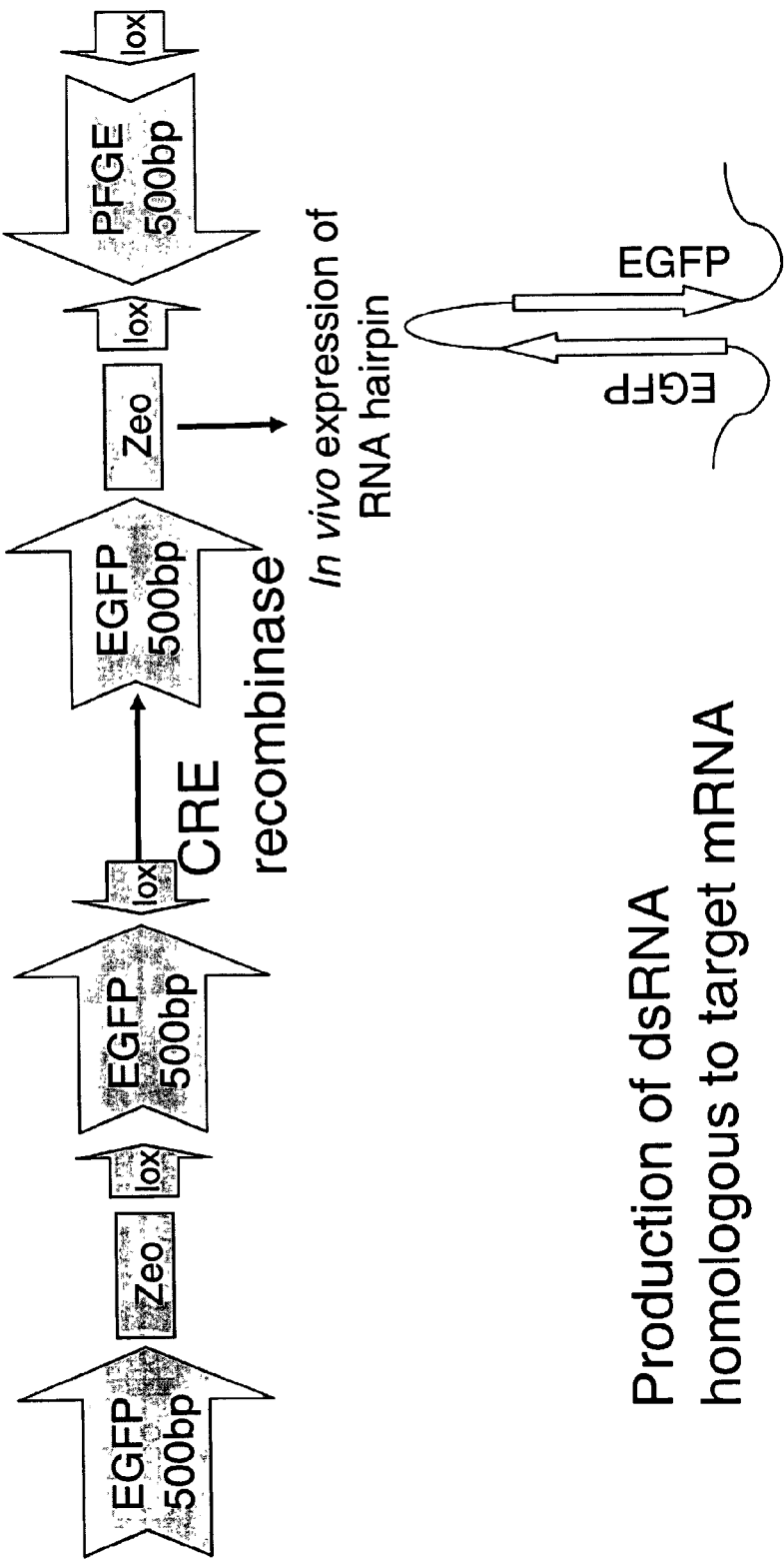
FIG. 27: A ~500 nt. fragment of the gene that is to be silenced (X) is inserted into the modified vector as a stable direct repeat using standard cloning procedures. Treatment with commercially available cre recombinase reverses sequences within the loxP sites (L) to create an inverted repeat. This can be stably maintained and amplified in an sbc mutant bacterial strain (DL759). Transcription in vivo from the promoter of choice (P) yields a hairpin RNA that causes silencing. A zeocin resistance marker is included to insure maintenance of the direct and inverted repeat structures; however this is non-essential in vivo and could be removed by pre-mRNA splicing if desired. (Smith et al. (2000) Nature 407: 319-20).

The presence of hairpin structures often induces plasmid rearrangement, in part due to the *E. coli* sbc proteins that recognize and cleave cruciform DNA structures (Connelly et al. (1996) Genes Cell 1: 285-291). We have developed a method for the construction of hairpins that does not require cloning of inverted repeats, per se. Instead, the fragment of the gene that is to be silenced is cloned as a direct repeat, and the inversion is accomplished by treatment with a site-specific recombinase, either in vitro (or potentially in vivo) (see FIG. 27). Following recombination, the inverted repeat structure is stable in a bacterial strain that lacks an intact SBC system (DL759). We have successfully used this strategy to construct numerous hairpin expression constructs that have been successfully used to provoke gene silencing in *Drosophila* cells.

In the following examples, we use this method to express long dsRNAs in a variety of mammalian cell types. We show that such long dsRNAs mediate RNAi in a variety of cell types. Additionally, since the vector described in FIG. 27 contains a selectable marker, dsRNAs produced in this manner can be stably expressed in cells. Accordingly, this method allows not only the examination of transient effects of RNA suppression in a cell, but also the effects of stable and prolonged RNA suppression.

Methods:

Plasmids expressing hairpin RNAs were constructed by cloning the first 500 basepairs of the GFP coding region into the FLIP cassette of pRIP-FLIP as a direct repeat. The FLIP cassette contains two directional cloning sites, the second of which is flanked by LoxP sites. The Zeocin gene, present between the cloning sites, maintains selection and stability. To create an inverted repeat for hairpin production, the direct repeat clones were exposed to Cre recombinase (Stratagene) in vitro and, afterwards, transformed into DL759 *E. Coli*. These bacteria permit the replication of DNA containing cruciform structures, which tend to form inverted repeats.

Example 4

Long dsRNAs Suppress Gene Expression in Mammalian Cells

Previous experiments have demonstrated that dsRNA, produced using a variety of methods including via the construction of hairpins, can suppress gene expression in *Drosophila* cells. We now demonstrate that dsRNA can also suppress gene expression in mammalian cells in culture. Additionally, we demonstrate that RNA suppression can be mediated by stably expressing a long hairpin in a mammalian cell line. The ability to engineer stable silencing of gene expression in cultured mammalian cells, in addition to the ability to transiently silence gene expression, has many important applications.

A. FIG. 28 shows wildtype P19 cells which have been co-transfected with either RFP or GFP (FIG. 28, right panel). Note the robust expression of RFP or GFR respectively approximately 42 hours post-transfection. We isolated P19 clones which stably express a 500 nt. GFP hairpin. Such clones were then transfected with either RFP or GFP, and expression of RFP or GFP was assessed by visual inspection of the cells. The left panel of FIG. 28 demonstrates that a 500 nt GFP hairpin specifically suppresses expression of GFP in P19 cells.

Figure 29:
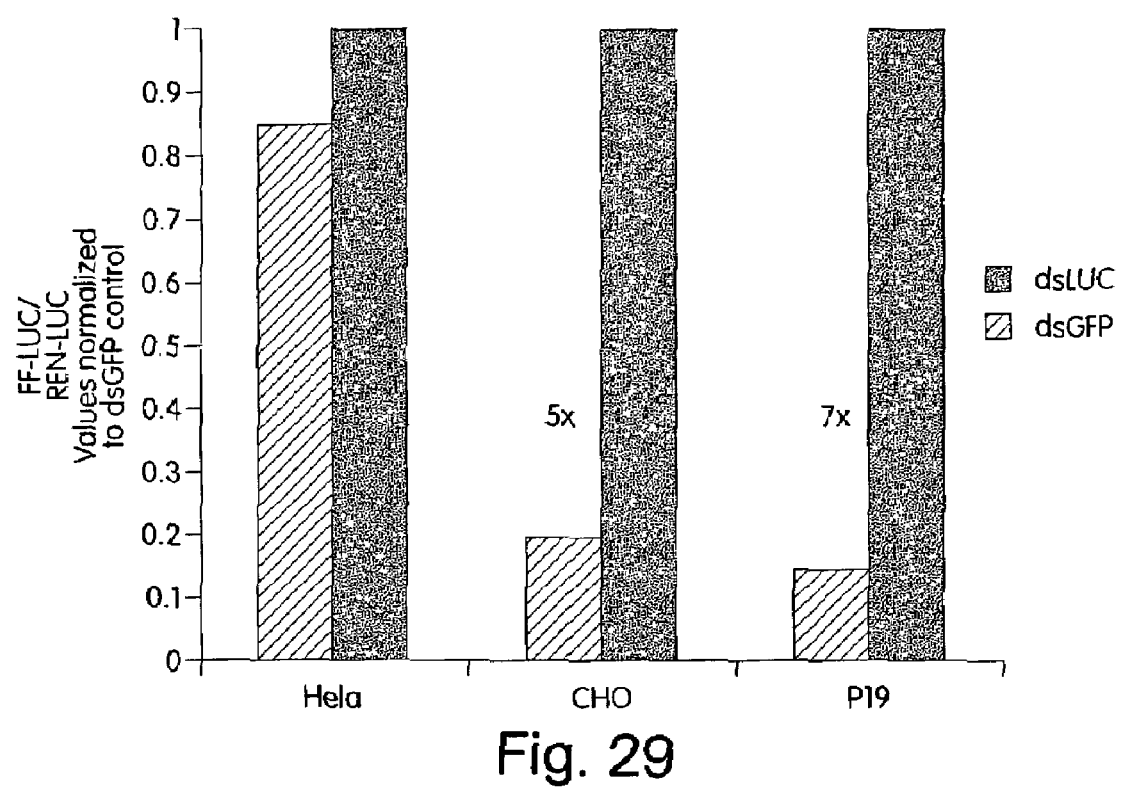
FIG. 29: Hela, Chinese hamster ovary, and P19 (pluripotent, mouse embryonic carcinoma) cell lines transfected with plasmids expressing *Photinus pyralis* (firefly) and *Renilla reniformis* (sea pansy) luciferases and with dsRNA 500mers (400 ng), homologous to either firefly luciferase mRNA (dsLUC) or non-homologous (dsGFP). Dual luciferase assays were carried out using an Analytical Scientific Instruments model 3010 Luminometer. In this assay *Renilla* luciferase serves as an internal control for dsRNA-specific suppression of firefly luciferase activity. These data demonstrate that 500mer dsRNA can specifically suppress cognate gene expression in vivo.

B. Similar experiments were performed using several cell lines in order to demonstrate that dsRNA can suppress gene expression generally in mammalian cells. FIG. 29 shows the results of a transient co-transfection assay performed in Hela cells, CHO cells and P19 cells. The cell lines were each transfected with plasmids expressing *Photinus pyralis* (firefly) and *Renila reniformis* (sea pansy) luciferases. The cells lines were additionally transfected with 400 ng of 500 nt dsRNAs corresponding to either firefly luciferase (dsLUC) or dsGFP. Dual luciferase assays were carried out using an Analytical Scientific Instruments model 3010 Luminometer. *Renilla* luciferase serves as an internal control for dsRNA specific suppression of firefly luciferase activity. All values are normalized to dsGFP control.

Figure 30:
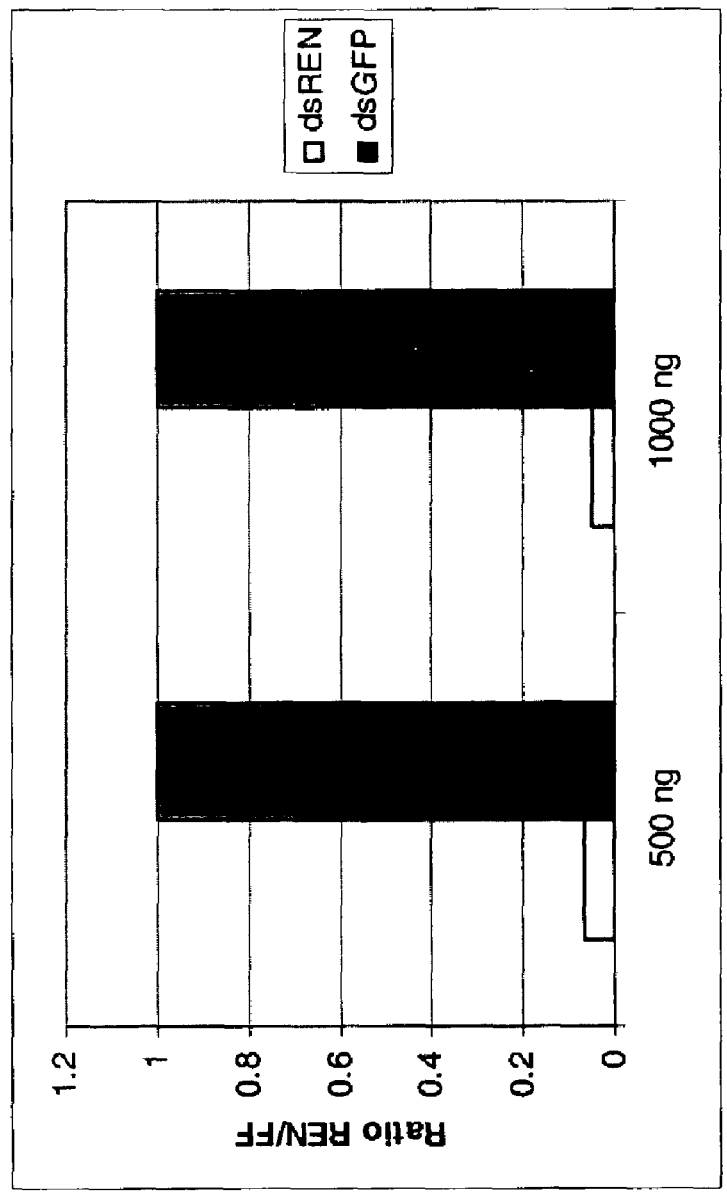
FIG. 30: Mouse embryonic stem cells (ES cells) were transfected with plasmids expressing *Photinus pyralis* (firefly) and *Renilla reniformis* (sea pansy) luciferases and with dsRNA 500mers (400 ng), homologous to either firefly luciferase mRNA (dsLUC) or non-homologous (dsGFP). Dual luciferase assays were carried out using an Analytical Scientific Instruments model 3010 Luminometer. In this assay firefly luciferase serves as an internal control for dsRNA-specific suppression of *Renilla* luciferase activity. These data demonstrate that 500mer dsRNA can specifically suppress cognate gene expression in vivo.

The results summarized in FIG. 29 demonstrate that dsRNA can specifically mediate suppression in a multiple mammalian cells types in culture. Additionally, such experiments were successfully carried out in mouse ES cells (FIG. 30). Our ability to successfully manipulate ES cell via RNAi allows the use of RNAi in the generation of transgenic and knock-out mice.

Figure 31:
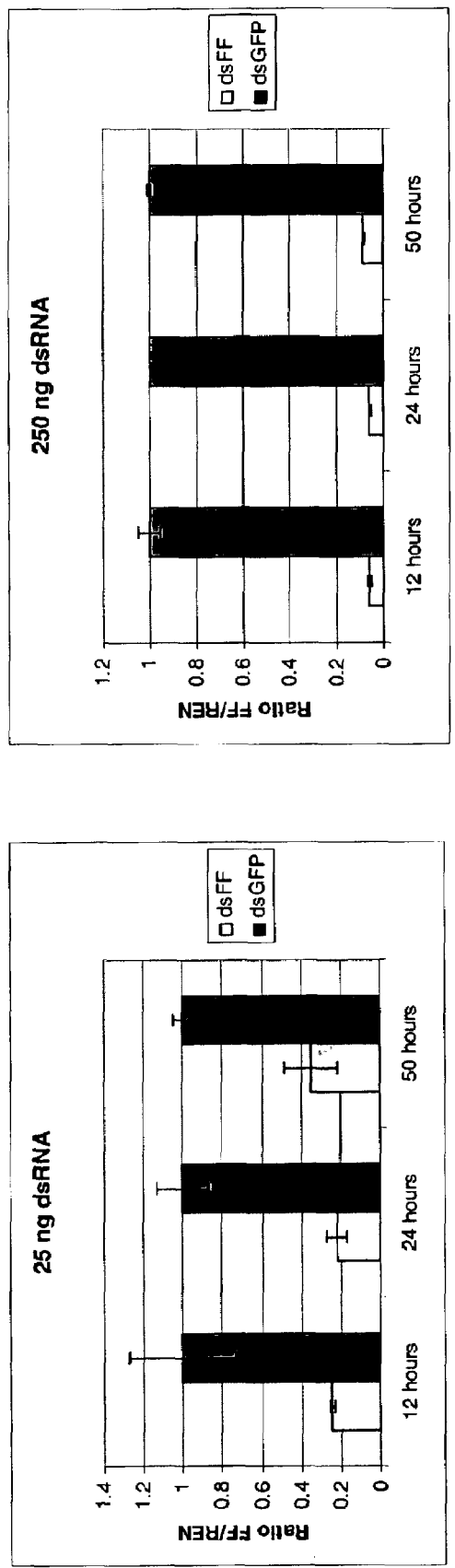
FIG. 31: P19 (a pluripontent, mouse embryonic cell line) cells transfected with plasmids expressing *Photinus pyralis* (firefly) and *Renilla reniformis* (sea pansy) luciferases and with dsRNA 500mers (500 ng), homologous to either firefly luciferase mRNA (dsLUC) or non-homologous (dsGFP). Dual luciferase assays were carried out using an Analytical Scientific Instruments model 3010 Luminometer. In this assay *Renilla* luciferase serves as an internal control for dsRNA-specific suppression of firefly luciferase activity. These data further demonstrate that 500mer dsRNA can specifically suppress cognate gene expression in vivo and that the effect is stable over time.

C. FIG. 31 demonstrates that dsRNA can mediate suppression of gene expression in mammalian cells, and that this suppression is stable over time. Experiments were carried out largely as described in part B. Briefly, P19 cells were transfected with plasmids expressing *Photinus pyralis* (firefly) and *Renila reniformis* (sea pansy) luciferases, and 500 nt dsRNA corresponding to either firefly luciferase or to GFP. Dual luciferase assays were carried out using an Analytical Scientific Instruments model 3010 Luminometer.

The results summarized in FIG. 31 demonstrate that dsRNA can mediate suppression in mammalian cells in culture, and that this suppression is stable over time. A comparable level of suppression of firefly gene expression was observed at 12 hours, 24 hours, and 50 hours post-transfection.

D. Although the above experiments demonstrate the ability to suppress gene expression in mammalian cells using dsRNA, such experiments do not address the mechanisms by which such suppression occurs. To begin to address whether dsRNA mediated suppression of gene expression in mammalian cells is mechanistically similar to dsRNA suppression in invertebrates, we examined the ability of the 500 nt dsRNA constructs described above to suppress gene expression in vitro in extracts from P19 cells.

S10 fractions from P19 cell lysates were used for in vitro translation of mRNA encoding *Photinus pyralis* (firefly) and *Renila reniformis* (sea pansy) luciferases. dsRNA corresponding to firefly luciferase or to GFP was added to the reactions. Following reactions performed at 30° C. for 1 hour, dual luciferase assays were performed using an Analytical Scientific Instruments model 3010 Luminometer.

Figure 32:
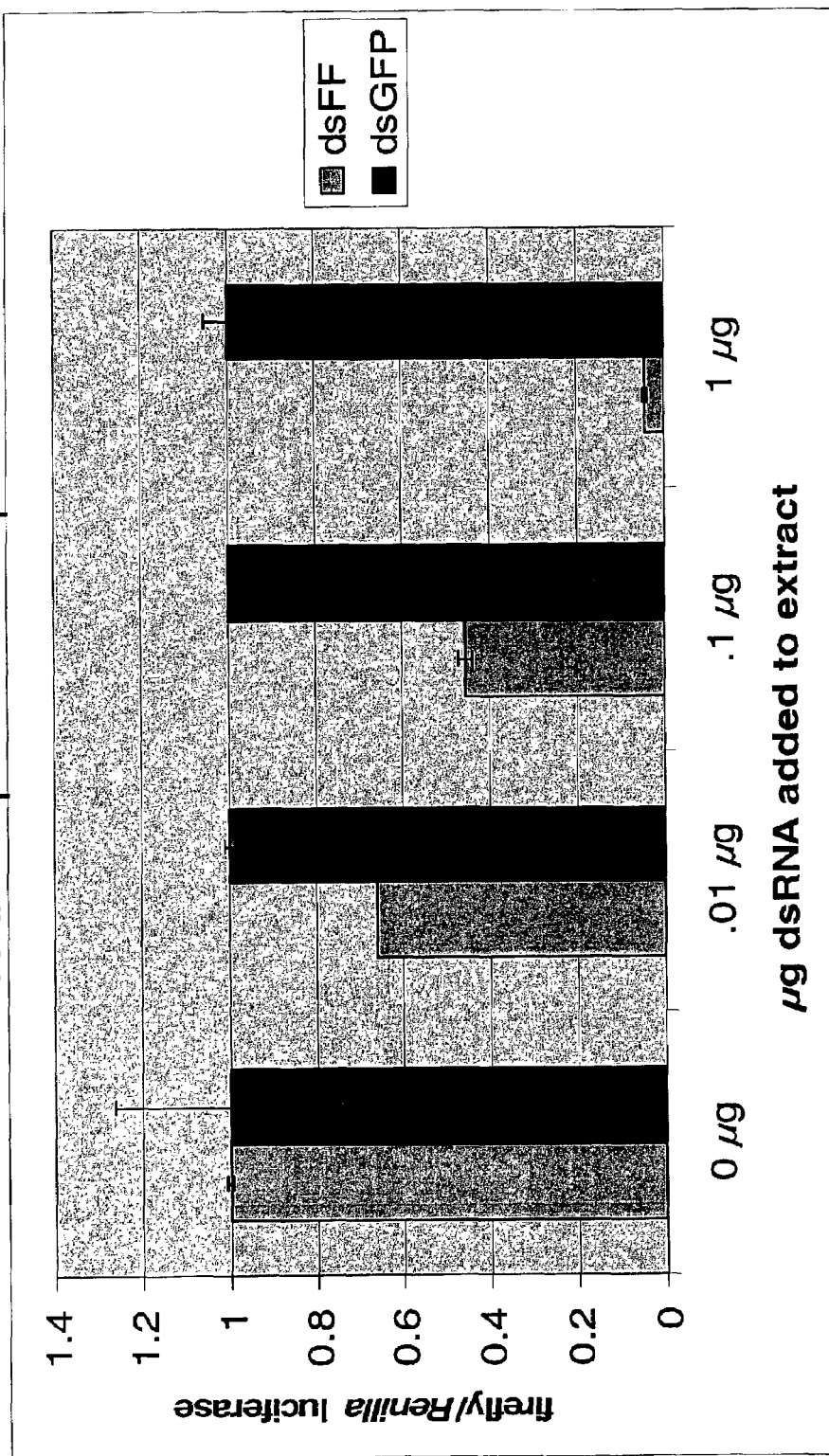
FIG. 32: S10 fractions from P19 cell lysates were used for in vitro translations of mRNA coding for *Photinus pyralis* (firefly) and *Renilla reniformis* (sea pansy) luciferases. Translation reactions were programmed with various amounts of dsRNA 500mers, either homologous to firefly luciferase mRNA (dsLUC) or non-homologous (dsGFP). Reactions were carried out at 30° C. for 1 hour, after which dual luciferase assays were carried out using an Analytical Scientific Instruments model 3010 Luminometer. In this assay *Renilla* luciferase serves as an internal control for dsRNA-specific suppression of firefly luciferase activity. These data demonstrate that 500mer dsRNA can specifically suppress cognate gene expression in vitro in a manner consistent with post-transcriptional gene silencing. Anti-sense firefly RNA did not differ significantly from dsGFP control (approximately 10%) (data not shown).

FIG. 32 summarizes the results of these experiments which demonstrate that dsRNA can specifically suppress gene expression in an in vitro mammalian cell system in a manner which is consistent with post-transcriptional gene silencing.

E. To further confirm that the dsRNA mediated suppression observed was consistent with post-transcriptional gene silencing, we examined RNA suppression in the absence of Dicer expression. As detailed herein, Dicer has been identified as an important factor in post-transcriptional gene silencing. Accordingly, if the effects described here are consistent with our understanding of post-transcriptional gene silencing, then you would not expect robust and specific suppression to occur in the absence of Dicer expression.

Figure 33:
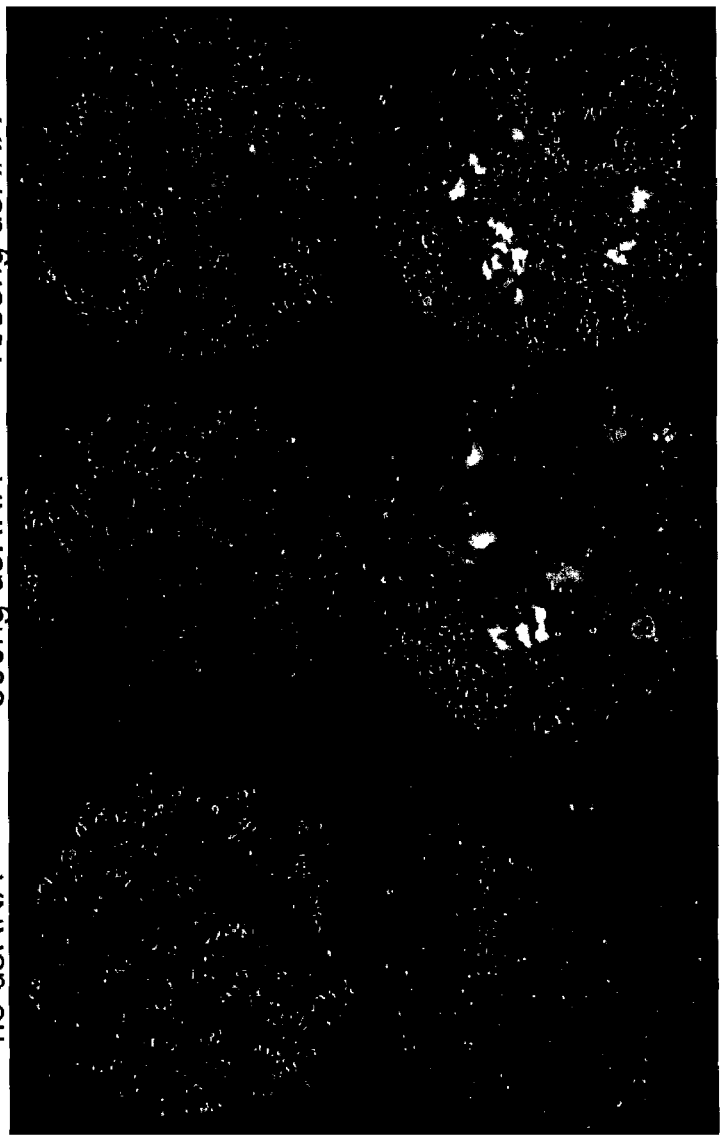
FIG. 33: Provides additional evidence that stable dsRNA suppresses gene expression in vivo in a manner consistant with post-transcriptional gene silencing. P19 cells were stably transfected with a construct expressing a long dsRNA specific for GFP. Cells were then transiently transfected with a plasmid expressing GFP or with both a plasmid expressing GFP and a plasmid expressing dsRNA specific for Dicer.

FIG. 33 summarizes these results. Briefly, P19 cells stably expressing the long dsRNA for GFP were transfected with either GFP or with GFP plus dsDicer RNA. The top panels demonstrate that stably expressed long dsRNA to GFP specifically suppresses GFP expression in P19 cells (as detailed in previous examples). However, in the presence of dsDicer RNA, GFP expression is observed in these cells.

This experiment provides further evidence indicating that the RNA mediated suppression observed upon stable expression of long dsRNAs functions by a mechanism consistent with post-transcriptional gene silencing.

F. Although the results summarized in FIGS. 32-33 appear to demonstrate that dsRNA can specifically suppress gene expression in a manner consistent with post-transcriptional silencing, we wanted to verify that the suppressive effects observed in the in vitro system were specific to double stranded RNA.

Briefly, experiments were performed in accordance with the methods outlined above. Either dsRNA (ds), single-stranded RNA (ss), or antisense-RNA (as) corresponding to firefly (FF) or *Renilla* (Ren) luciferase was added to the translation reaction. Following reactions performed at 30° C. for 1 hour, dual luciferase assays were performed using an Analytical Scientific Instruments model 3010 Luminometer.

Figure 34:
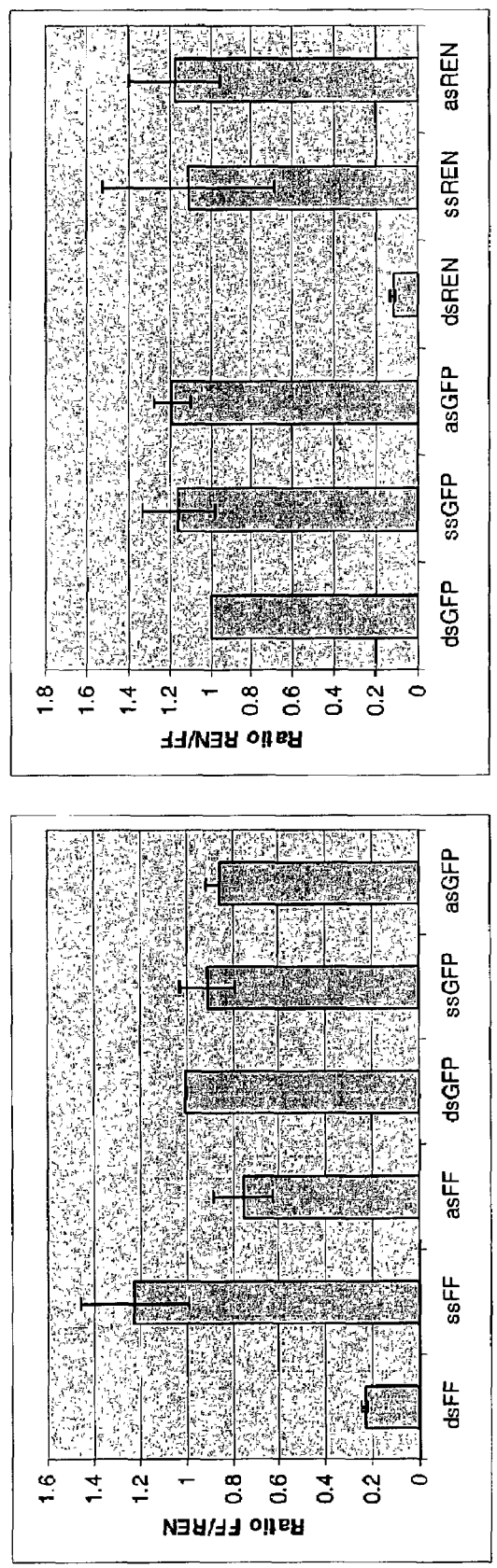
FIG. 34: S10 fractions from P19 cell lysates were used for in vitro translations of mRNA coding for *Photinus pyralis* (firefly) and *Renilla reniformis* (sea pansy) luciferases. Translation reactions were programmed with dsRNA, ssRNA, or asRNA 500mers, either complementary to firefly luciferase mRNA (dsFF, ssFF, or asFF), complementary to *Renilla* luciferase (dsREN, ssREN, or asREN) or non-complementary (dsGFP). Reactions were carried out at 30° C. for 1 hour, after a 30 min preincubation with dsRNA, ssRNA, or asRNA. Dual luciferase assays were carried out using an Analytical Scientific Instruments model 3010 Luminometer. On the left, *Renilla* luciferase serves as an internal control for dsRNA-specific suppression of firefly luciferase activity. On the right, firefly luciferase serves as an internal control for dsRNA-specific suppression of *Renilla* luciferase activity. These data demonstrate that 500mer double-stranded RNA (dsRNA) but not single-stranded (ssRNA) or anti-sense RNA (asRNA) suppresses cognate gene expression in vitro in a manner consistent with post-transcriptional gene silencing.

FIG. 34 summarizes the results of these experiments which demonstrate that the suppression of gene expression observed in this in vitro assay is specific for dsRNA. These results further support the conclusion that dsRNA suppresses gene expression in this mammalian in vitro system in a manner consistent with post-transcriptional silencing.

G. Studies of post-transcriptional silencing in invertebrates have demonstrated that transfection or injection of the dsRNA is not necessary to achieve the suppressive affects. For example, dsRNA suppression in *C. elegans* can be observed by either soaking the worms in dsRNA, or by feeding the worms bacteria expressing the dsRNA of interest. We addressed whether dsRNA suppression in mammalian cells could be observed without transfection of the dsRNA. Such a result would present additional potential for easily using dsRNA suppression in mammalian cells, and would also allow the use of dsRNA to suppress gene expression in cell types which have been difficult to transfect (i.e., cell types with a low transfection efficiency, or cell types which have proven difficult to transfect at all).

P19 cells were grown in 6-well tissue culture plates to approximately 60% confluency in growth media (αMEM/10% FBS). Varying concentrations of firefly dsRNA were added to the cultures, and cells were cultured for 12 hours in growth media+dsRNA. Cells were then transfected with plasmids expressing firefly or sea pansy luciferase, as described in detail above. Dual luciferase assays were carried out 12 hours post-transfection using an Analytical Scientific Instruments model 3010 Luminometer.

Figure 35:
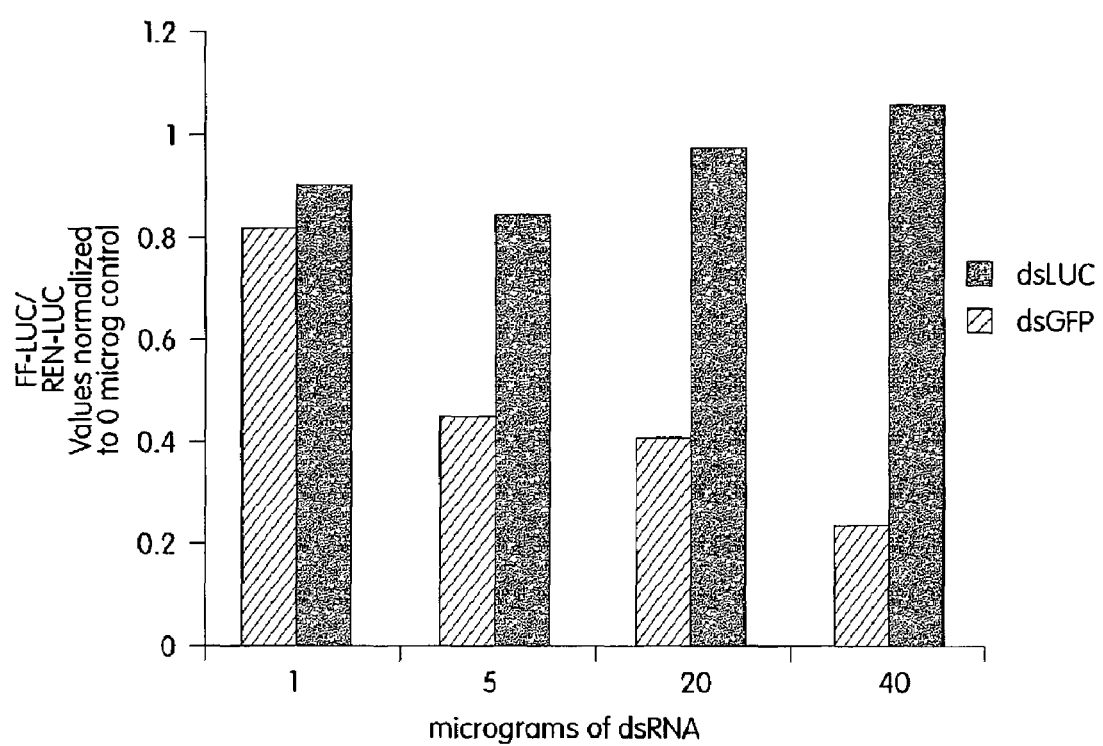
FIG. 35: P19 cells were grown in 6-well tissue culture plates to approximately 60% confluence. Various amounts of dsRNA, either homologous to firefly luciferase mRNA (dsLUC) or non-homologous (dsGFP), were added to each well and incubated for 12 hrs under normal tissue culture conditions. Cells were then transfected with plasmids expressing *Photinus pyralis* (firefly) and *Renilla reniformis* (sea pansy) luciferases and with dsRNA 500mers (500 ng). Dual luciferase assays were carried out 12 hrs post-transfection using an Analytical Scientific Instruments model 3010 Luminometer. In this assay *Renilla* luciferase serves as an internal control for dsRNA-specific suppression of firefly luciferase activity. These data show that 500mer dsRNA can specifically suppress cognate gene expression in vivo without transfection under normal tissue culture conditions.

FIG. 35 summarizes these results which demonstrate that dsRNA can suppress gene expression in mammalian cells without transfection. Culturing cells in the presence of dsRNA resulted in a dose dependent suppression of firefly luciferase gene expression.

Example 5

Compositions and Methods for Synthesizing siRNAs

Previous results have indicated that short synthetic RNAs (siRNAs) can efficiently induce RNA suppression. Since short RNAs do not activate the non-specific PKR response, they offer a means for efficiently silencing gene expression in a range of cell types. However, the current state of the art with respect to siRNAs has several limitations. Firstly, siRNAs are currently chemically synthesized at great cost (approx. $400/siRNA). Such high costs make siRNAs impractical for either small laboratories or for use in large scale screening efforts. Accordingly, there is a need in the art for methods for generating siRNAs at reduced cost.

We provide compositions and methods for synthesizing siRNAs by T7 polymerase. This approach allows for the efficient synthesis of siRNAs at a cost consistent with standard RNA transcription reactions (approx. $16/siRNA). This greatly reduced cost makes the use of siRNA a reasonable approach for small laboratories, and also will facilitate their use in large-scale screening projects.

Figure 36:
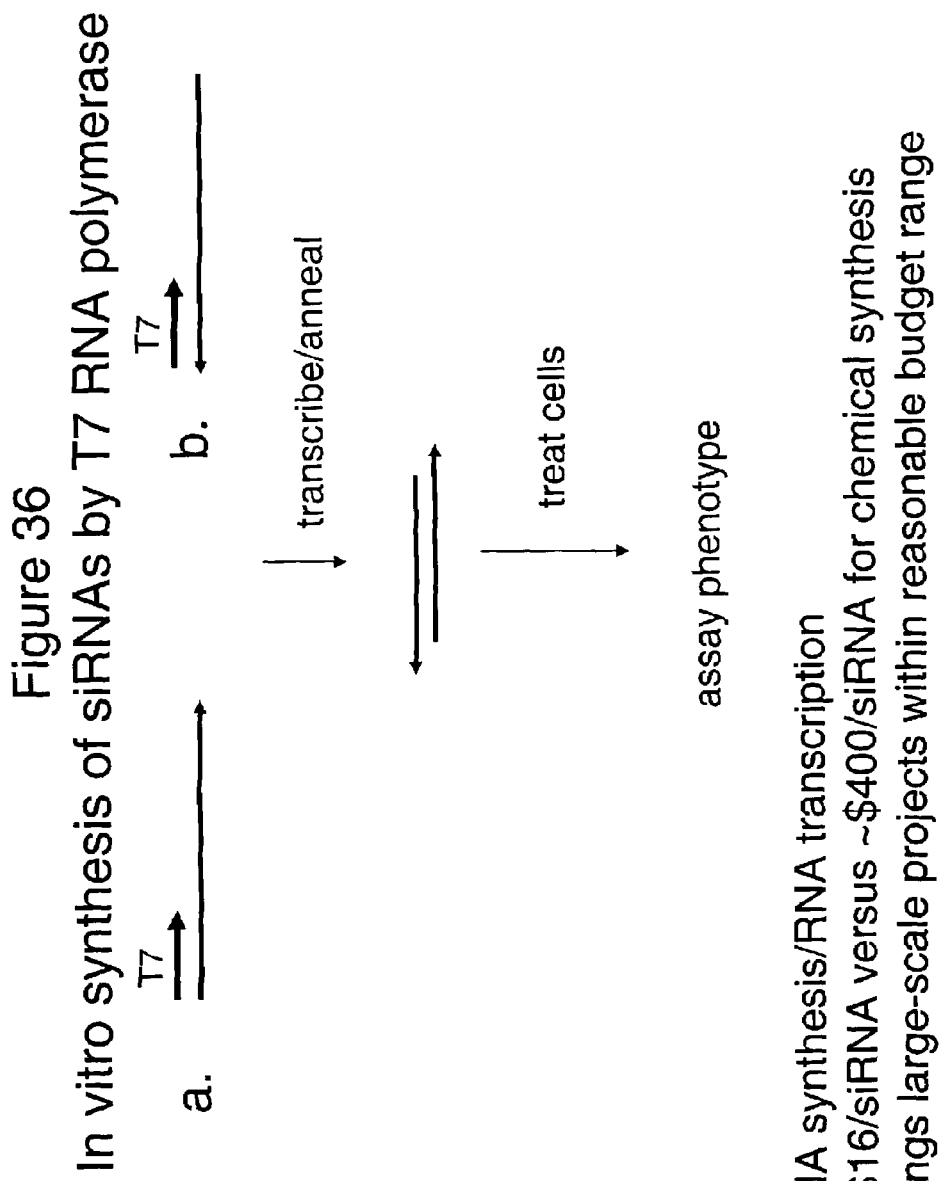
FIG. 36: Previous methods for generating siRNAs required costly chemical synthesis. The invention provides an in vitro method for synthesizing siRNAs using standard RNA transcription reactions.

FIG. 36 shows the method for producing siRNAs using T7 polymerase. Briefly, T7 polymerase is used to transcribe both a sense and antisense transcript. The transcripts are then annealed to provide an siRNA. One of skill in the art will recognize that any one of the available RNA polymerases can be readily substituted for T7 to practice the invention (i.e., T3, Sp6, etc.).

This approach is amenable to the generation of a single siRNA species, as well as to the generation of a library of siRNAs. Such a library of siRNAs can be used in any number of high-throughput screens including cell based phenotypic screens and gene array based screens.

Example 6

Generation of Short Hairpin dsRNA and Suppression of Gene Expression Using Such Short Hairpins We have generated several types of short dsRNAs corresponding to the coding region of firefly or *Renilla* luciferase (as outlined in detail above for long dsRNAs). Accordingly, the specificity of short dsRNAs in suppressing gene expression can be evaluated in much the same way the specificity of long dsRNAs was evaluated. FIG. 37 details the structure of three types of short dsRNAs tested for their efficacy in specifically suppressing gene expression in cell culture. The three basic types of short RNAs are siRNAs, let-7 like hairpin RNAs, and simple hairpins.

Figure 38:
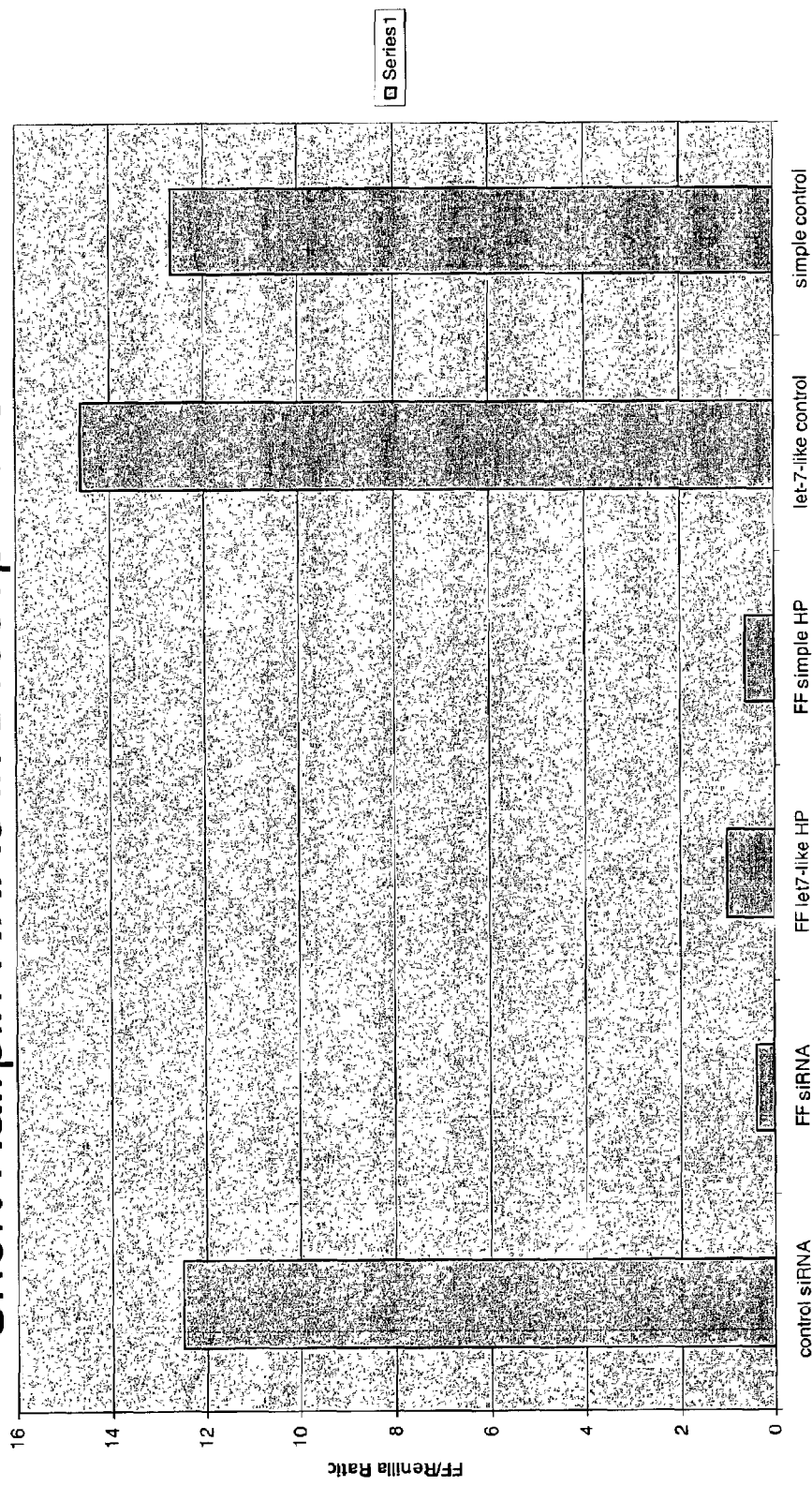
FIG. 38: The three types of short RNAs depicted in FIG. 37 were analyzed in *Drosophila* S2 cells for their ability to specifically suppress firefly luciferase gene expression. All three short RNAs (siRNA, let-7 like hairpin, and simple hairpin) specifically suppress firefly luciferase gene expression.

A. The ability of short dsRNAs to specifically suppress gene expression was analyzed in *Drosophila* S2 cells. FIG. 38 summarizes experiments which demonstrate that short hairpins corresponding to firefly luciferase specifically suppress firefly luciferase gene expression. All three types of short dsRNAs (siRNA, let-7 like hairpins, and simple hairpins) dramatically and specifically suppress gene expression in comparison to *Renilla* luciferase control RNAs. Note that the siRNA and the simple hairpin appear to suppress gene expression a little more effectively than the let-7 like hairpin.

Figure 39:
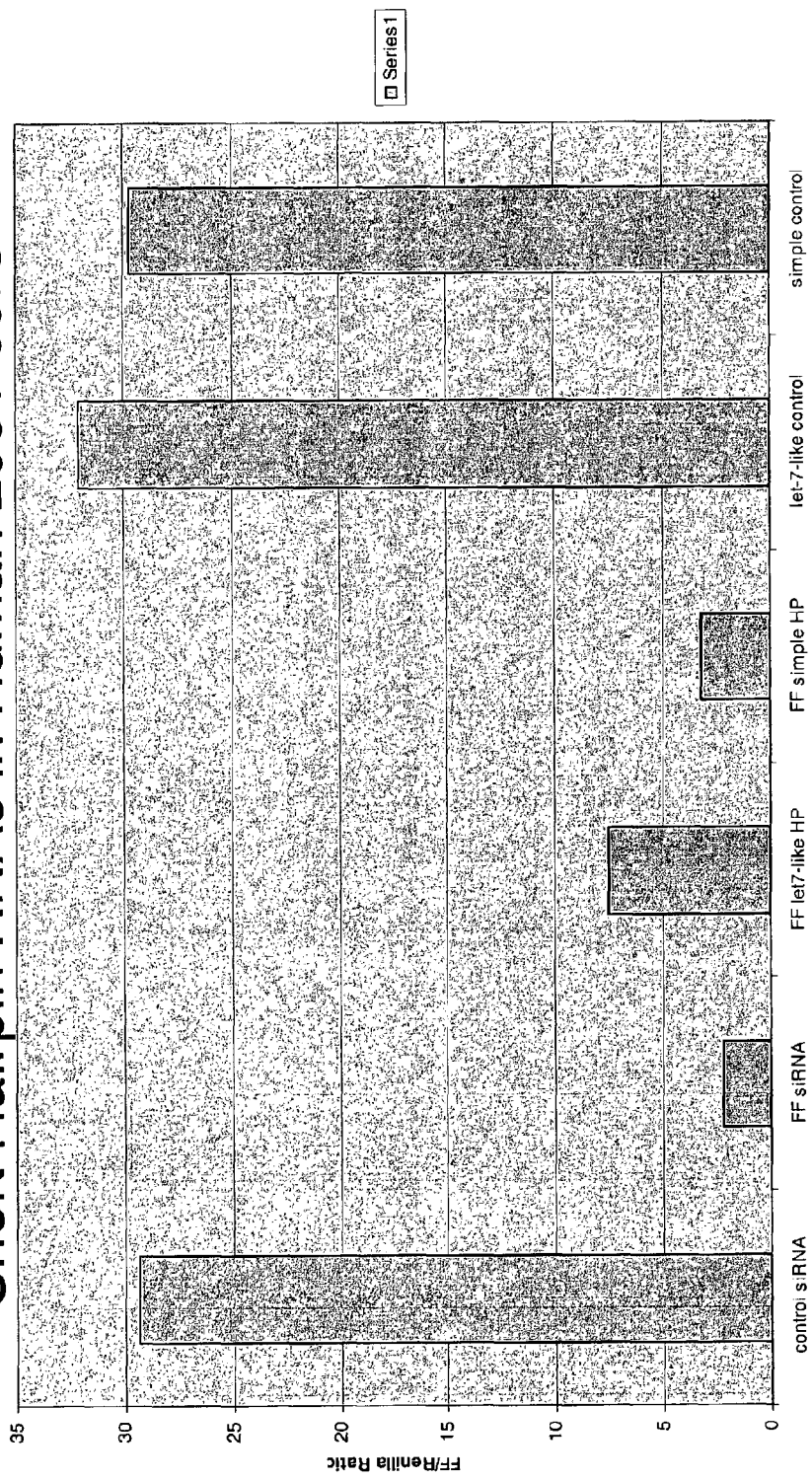
FIG. 39: The three types of short RNAs depicted in FIG. 37 were analyzed in human 293T cells for their ability to specifically suppress firefly luciferase gene expression. All three short RNAs (siRNA, let-7 like hairpin, and simple hairpin) specifically suppress firefly luciferase gene expression.

B. FIG. 39 summarizes experiments which demonstrate that short dsRNAs corresponding to firefly luciferase specifically suppress gene expression in human 293T cells. All three types of short dsRNAs (siRNA, let-7 like hairpins, and simple hairpind) dramatically and specifically suppress gene expression in comparison to *Renilla* luciferase control RNAs. Note however, consistent with the results observed in *Drosophila* S2 cells, the siRNA and the simple hairpin appear to suppress gene expression a more effectively than the let-7 like hairpin.

Figure 40:
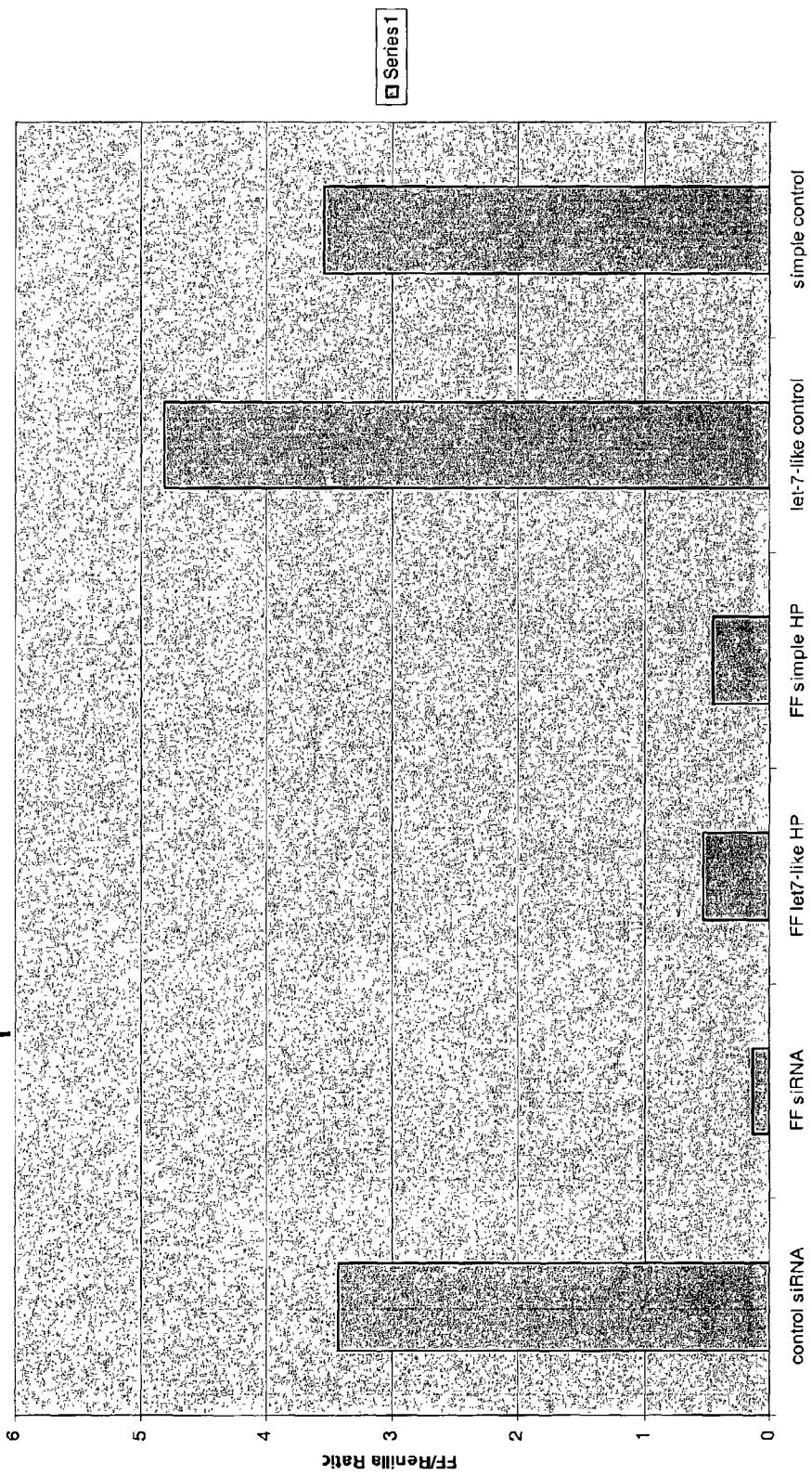
FIG. 40: The three types of short RNAs depicted in FIG. 37 were analyzed in human HeLa cells for their ability to specifically suppress firefly luciferase gene expression. All three short RNAs (siRNA, let-7 like hairpin, and simple hairpin) specifically suppress firefly luciferase gene expression.

C. FIG. 39 demonstrates that several types of short dsRNAs can specifically suppress gene expression in mammalian cells. We wanted to confirm that short dsRNAs can suppress gene expression in other mammalian cells. Additionally, we wanted to demonstrate that unlike long dsRNAs, short dsRNAs do not provoke a non-specific PKR or PKR-like response. FIG. 40 summarizes experiments performed in HeLa cells which demonstrate that short dsRNAs specifically suppress gene expression in HeLa cells. The specific suppression observed in HeLa cells in the presence of short dsRNAs is contrary to the non-specific effects observed when HeLa cells were treated with long dsRNAs, and demonstrate that short dsRNAs do not provoke a non-specific PKR or PKR-like response.

Figure 41:
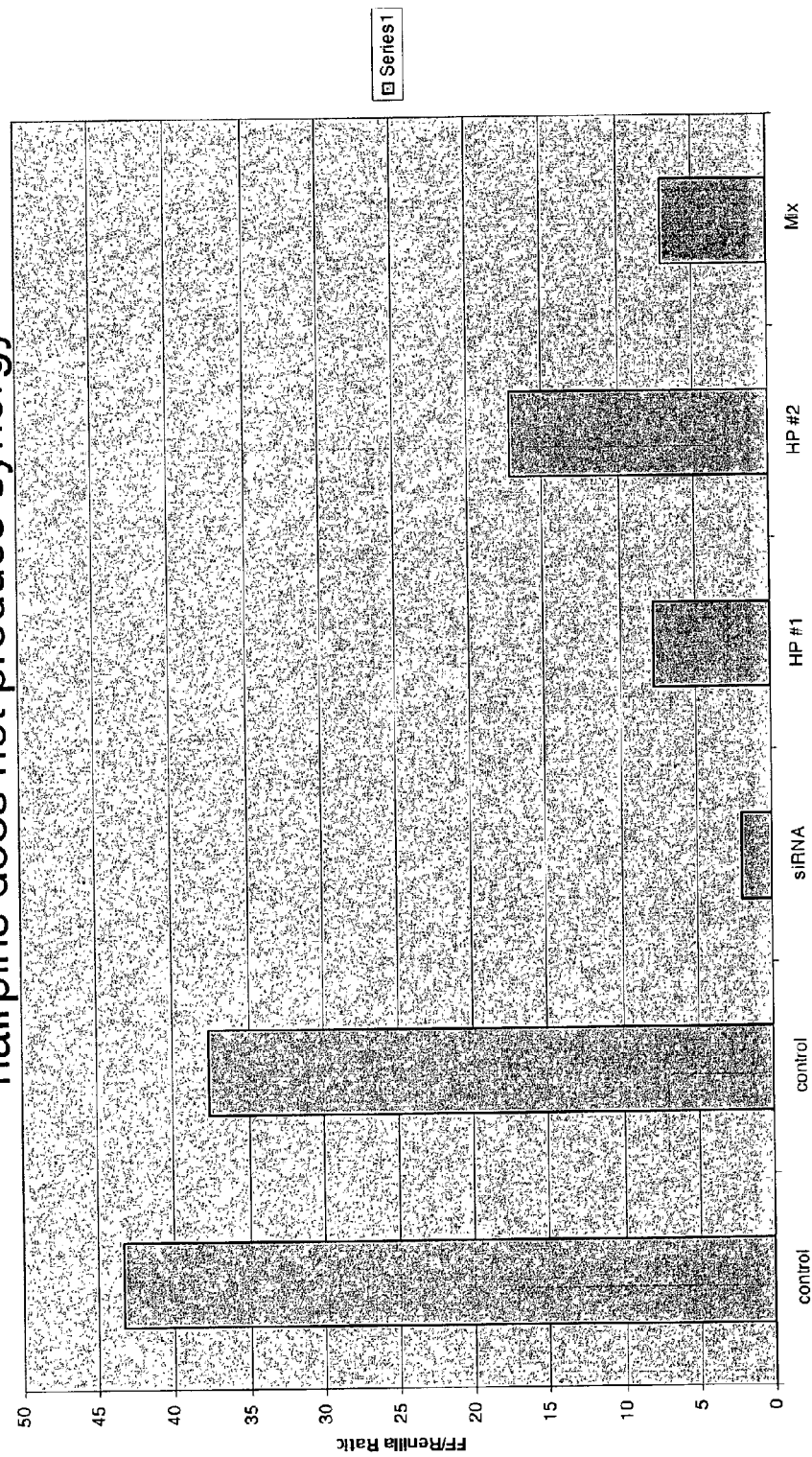
FIG. 41: A mixture of two short hairpins, both corresponding to firefly luciferase, does not result in a synergistic suppression of gene expression. Suppression of firefly luciferase gene expression resulting from transfection of a mixture of two different short hairpins (HP #1 and HP #2) was examined. The mixture of HP #1 and HP #2 did not have a more robust effect on the suppression of firefly luciferase gene expression than expression of HP #1 alone.

D. In an attempt to further understand the mechanisms by which short hairpins suppress gene expression, we examined the effects of transfecting cells with a mixture of two different short hairpins corresponding to firefly luciferase. FIG. 41 summarizes the results of experiments which suggest that there is no synergistic affects on suppression of firefly luciferase gene expression obtained when cells are exposed to a mixture of such short hairpins.

Example 7

Encoded Short Hairpins Function In Vivo

An object of the present invention is to improve methods for generating siRNAs and short hairpins for use in specifically suppressing gene expression. Example 6 demonstrates that siRNAs and short hairpins are highly effective in specifically suppressing gene expression. Accordingly, it would be advantageous to combine the efficient suppression of gene expression attainable using short hairpins and siRNAs with a method to encode such RNA on a plasmid and express it either transiently or stably.

Figure 42:
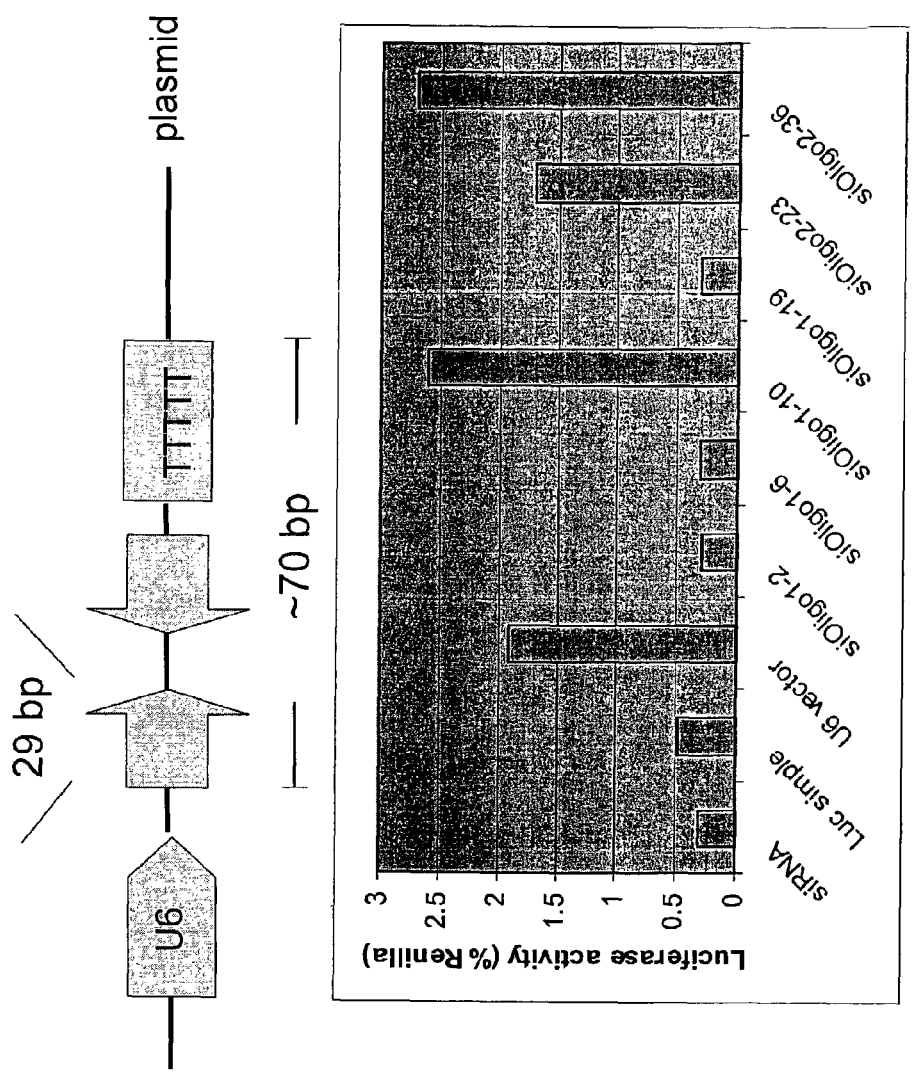
FIG. 42: Encoded short hairpins specifically suppress gene expression in vivo. DNA oligonucleotides encoding 29 nucleotide hairpins corresponding to firefly luciferase were inserted into a vector containing the U6 promoter. Three independent constructs were examined for their ability to specifically suppress firefly luciferase gene expression in 293T cells. SiOligo1-2, SiOligo1-6, and SiOligo1-19 (construct in the correct orientation) each suppressed gene expression as effectively as siRNA. In contrast, SiOligo1-10 (construct in the incorrect orientation) did not suppress gene expression. An independent construct targeted to a different is portion of the firefly luciferase gene did not effectively suppress gene expression in either orientation (SiOligo2-23, SiOligo2-36).

FIG. 42 demonstrates that short hairpins encoded on a plasmid are effective in suppressing gene expression. DNA oligonucleotides encoding 29 nucleotide hairpins corresponding to firefly luciferase were inserted into a vector containing the U6 promoter. Three independent constructs were examined for their ability to specifically suppress firefly luciferase gene expression in 293T cells. SiOligo1-2, SiOligo1-6, and SiOligo1-19 (construct in the correct orientation) each suppressed gene expression as effectively as siRNA. In contrast, SiOligo1-10 (construct in the incorrect orientation) did not suppress gene expression. Additionally, an independent construct targeted to a different portion of the firefly luciferase gene did not effectively suppress gene expression in either orientation (SiOligo2-23, SiOligo2-36).

Figure 43:
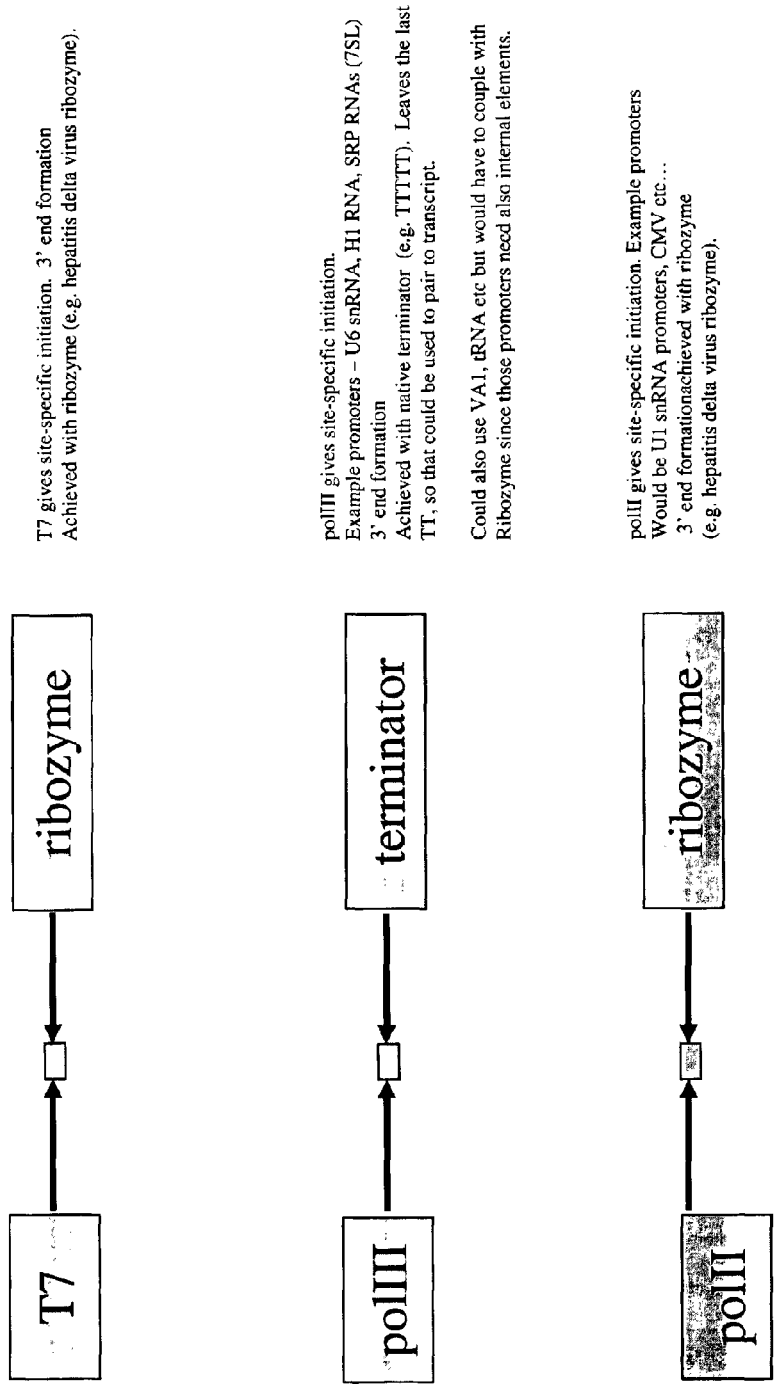
FIGS. 43-45: Strategies for stable expression of short dsRNAs.
Figure 44:
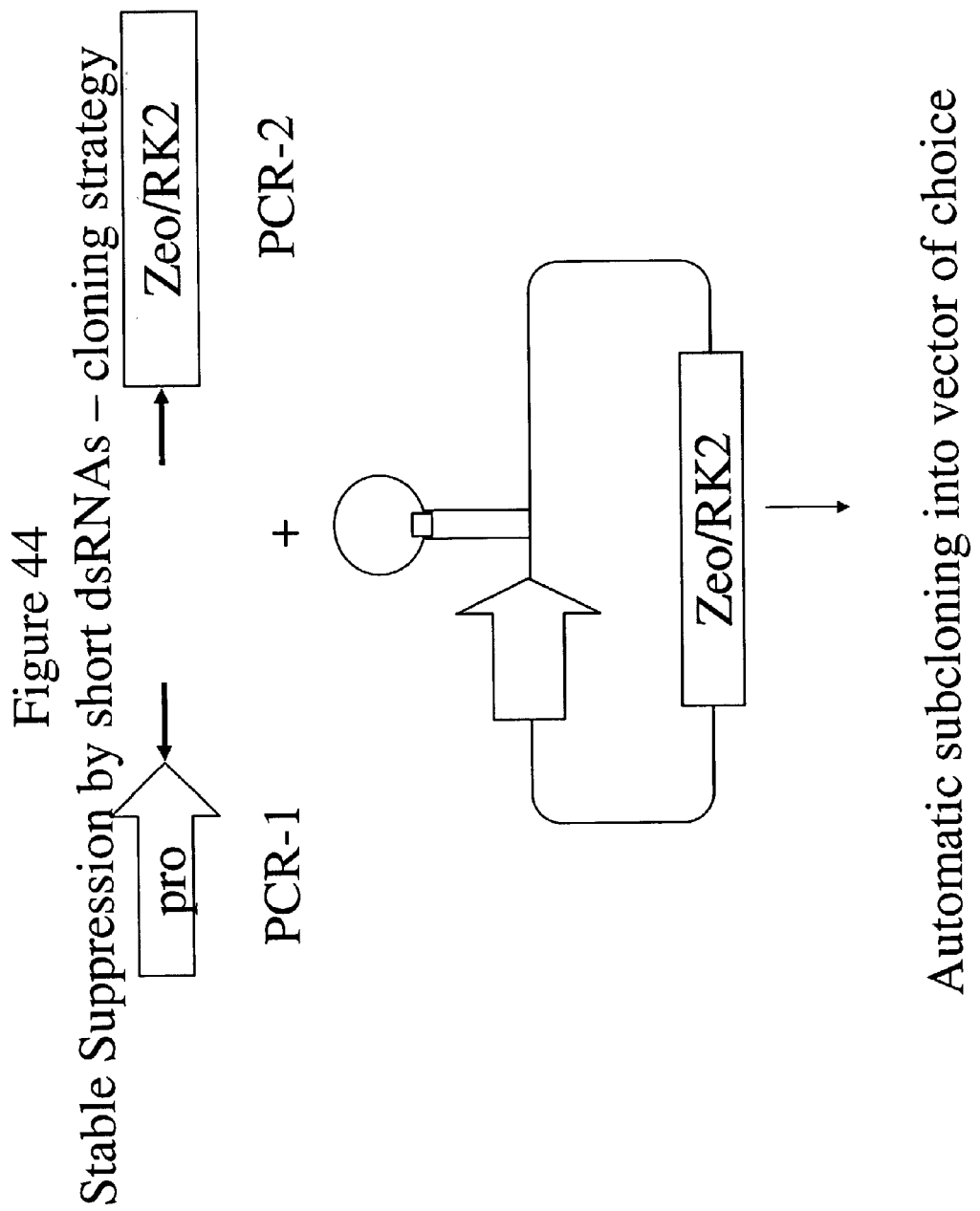
Figure 45:
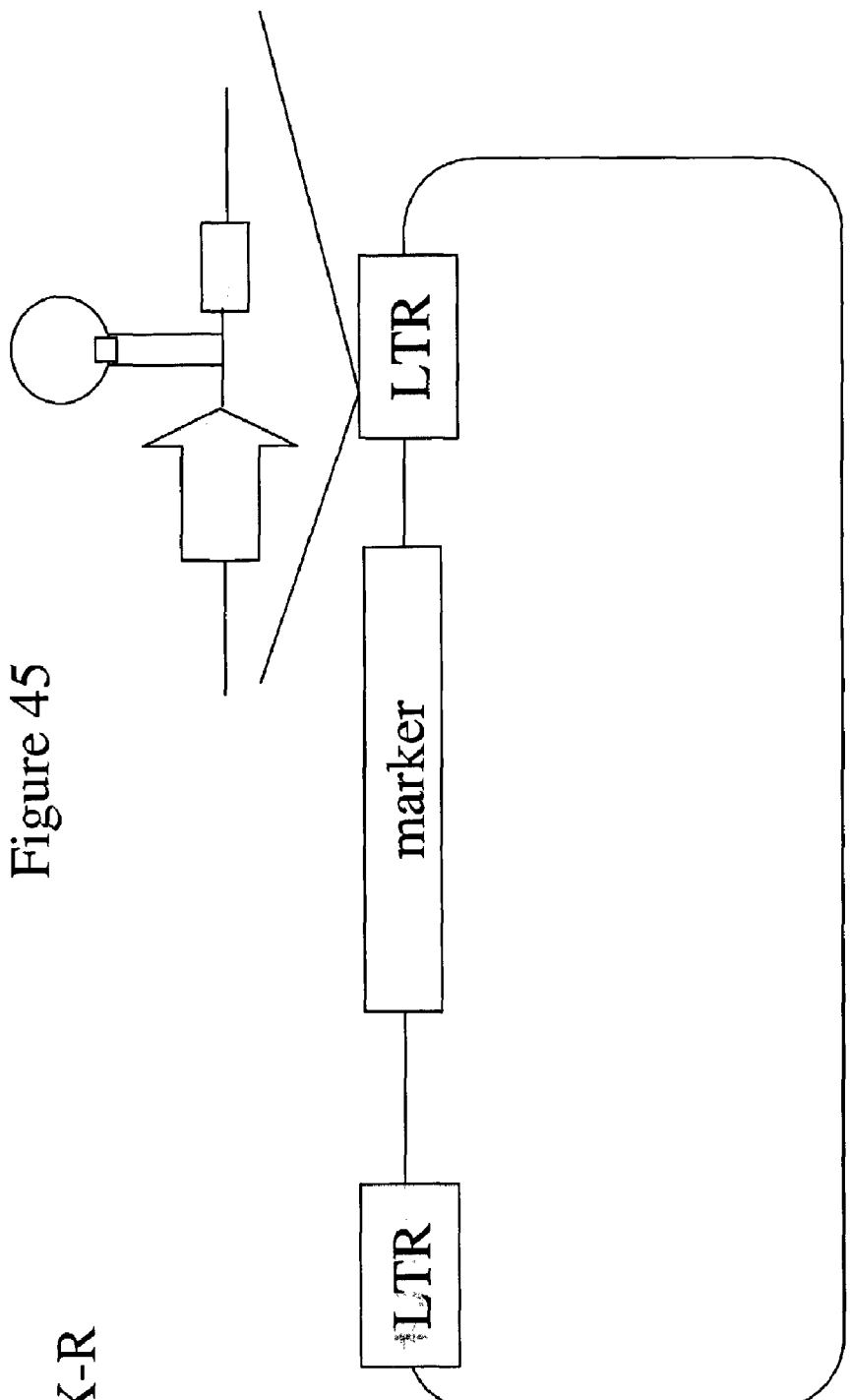

The results summarized in FIG. 42 demonstrate that transient expression of siRNAs and short hairpins encoded on a plasmid can efficiently suppress gene expression. One of skill can choose from amongst a range of vectors to either transiently or stably express an siRNA or short hairpin. Non-limiting examples of vectors and strategies to stably express short dsRNAs are presented in FIGS. 43-45.

Example 8 dsRNA Suppression in the Absence of a PKR Response

One potential impediment to the use of RNAi to suppress gene expression in some cell types, is the non-specific PKR response that can be triggered by long dsRNAs. Numerous mammalian viruses have evolved the ability to block PKR in order to aid in the infection of potential host cells. For example, adenoviruses express RNAs which mimic dsRNA but do not activate the PKR response. Vaccinia virus uses two strategies to evade PKR: the expression of E3L which binds and masks dsRNA; the expression of K3L to mimic the natural PKR substrate eIF2α.

Our understanding of the mechanisms by which viruses avoid the PKR response allows us to design approaches to circumvent the PKR response in cell types in which in might be advantageous to suppression gene expression with long dsRNAs. Possible approaches include treating cells with an agent that inhibits protein kinase RNA-activated (PKR) apoptosis, such as by treatment with agents which inhibit expression of PKR, cause its destruction, and/or inhibit the kinase activity of PKR. Accordingly, RNAi suppression of gene expression in such cell types could involve first inhibiting the PKR response, and then delivering a dsRNA identical or similar to a target gene.

A. In a murine myoblast cell line, C2C12, we noted that the cells responded to long dsRNAs with a mixture of specific and non-specific (presumably PKR) responses. In order to attenuate the non-specific PKR response while maintaining the robust and specific suppression due to the long dsRNA, C2C12 cells were transfected with a vector that directs K3L expression. This additional step successfully attenuated the PKR response, however expression of K3L protein had no effect on the magnitude of specific inhibition.

Figure 46:
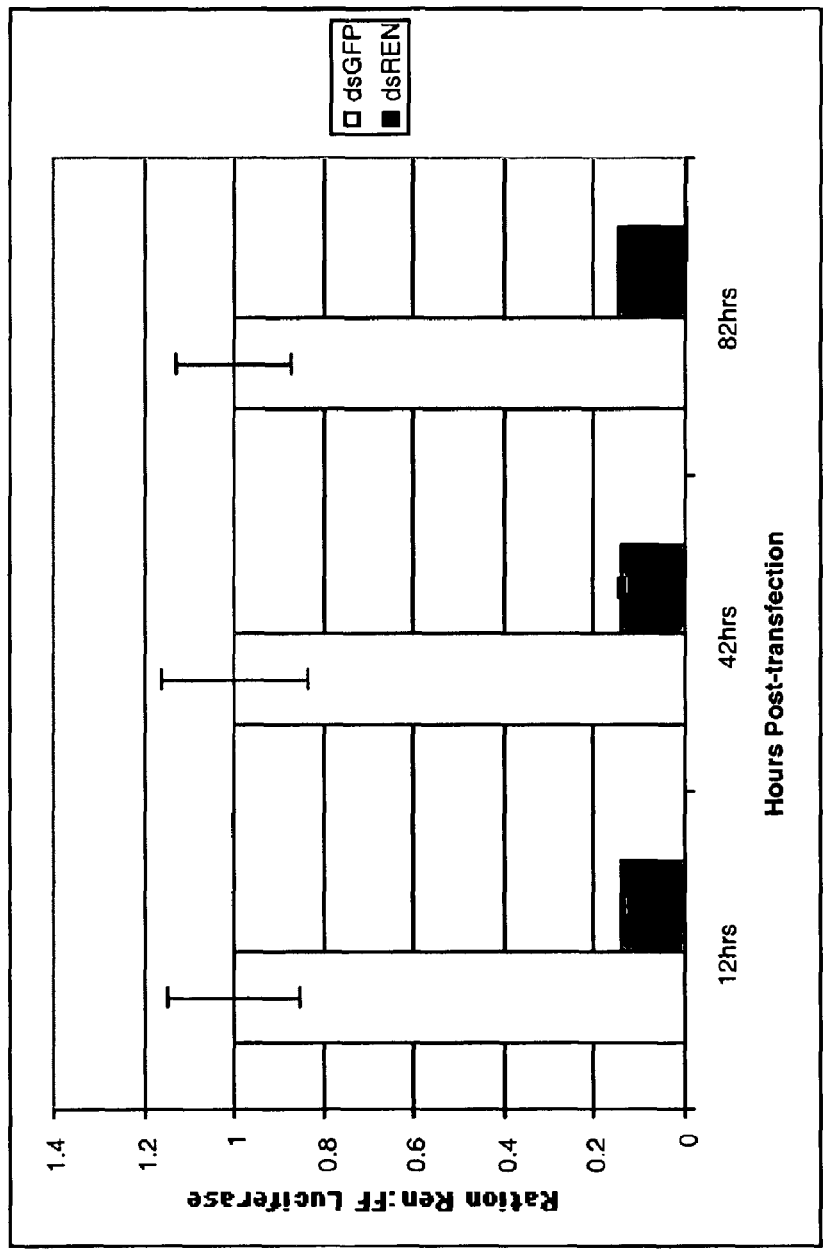
FIG. 46: Dual luciferase assays were performed as described in detail in FIGS. 28-35, however the cells used in these experiments were PKR−/− murine embryonic fibroblasts (MEFs). Briefly, RNAi using long dsRNAs typically envokes a non-specific response in MEFs (due to PKR activity). To evaluate the effect of long dsRNA constructs to specifically inhibit gene expression in MEFs, RNAi was examined in PKR −/− MEFs. Such cells do not respond to dsRNA with a non-specific response. The data summarized in this figure demonstrates that in the absence of the non-specific PKR response, long dsRNA constructs specifically suppress gene expression in MEFs.

B. However, since the efficacy of such a two step approach had not been previously demonstrated, it was formerly possible that dsRNA suppression would not be possible in cells with a PKR response. FIG. 46 summarizes results which demonstrate that such a two step approach is possible, and that robust and specific dsRNA mediated suppression is possible in cells which had formerly possessed a robust PKR response.

Briefly, dual luciferase assay were carried out as described in detail above. The experiments were carried out using PKR −/− MEFs harvested from E13.5 PKR−/− mouse embryos. MEFs typically have a robust PKR response, and thus treatment with long dsRNAs typically results in non-specific suppression of gene expression and apoptosis. However, in PKR −/− cells examined 12, 42, and 82 hours after transfection, expression of ds *Renilla* luciferase RNA specifically suppresses expression *Renilla reniformis* (sea pansy) luciferase. This suppression is stable over time.

These results demonstrate that the non-specific PKR response can be blocked without affecting specific suppression of gene expression mediated by dsRNA. This allows the use of long dsRNAs to suppress gene expression in a diverse range of cell types, including those that would be previously intractable due to the confounding influences of the non-specific PKR response to long dsRNA.

Example 9

Suppression of Gene Expression using dsRNA which Corresponds to Non-Coding Sequence Current models for the mechanisms which drive RNAi have suggested that the dsRNA construct must contain coding sequence corresponding to the gene of interest. Although evidence has demonstrated that such coding sequence need not be a perfect match to the endogenous coding sequence (i.e., it may be similar), it has been widely held that the dsRNA construct must correspond to coding sequence. We present evidence that contradicts the teachings of the prior art, and demonstrate that dsRNA corresponding to non-coding regions of a gene can suppress gene function in vivo. These results are significant not only because they demonstrate that dsRNA identical or similar to non-coding sequences (i.e., promoter sequences, enhancer sequences, or intronic sequences) can mediate suppression, but also because we demonstrate the in vivo suppression of gene expression using dsRNA technology in a mouse model.

Figure 47:
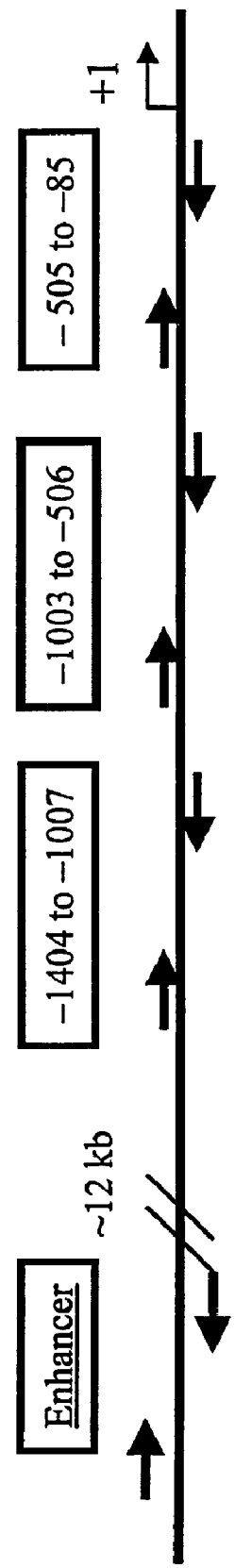
FIG. 47: Is a schematic representation of the mouse tyrosinase promoter. Primers were used to amplify three separate regions in the proximal promoter, or to amplify sequence corresponding to an enhancer located approximately 12 kb upstream.

We generated doubled stranded RNA corresponding to four segments of the mouse tyrosinase gene promoter. Three of these segments correspond to the proximal promoter and one corresponds to an enhancer (FIG. 47). The tyrosinase gene encodes the rate limiting enzyme involved in the melanin biosynthetic pathway (Bilodeau et al. (2001) Pigment Cell Research 14: 328-336). Accordingly, suppression of the tyrosinase gene is expected to inhibit pigmentation.

Double stranded RNA corresponding to each of the above promoter segments was injected into the pronuclei of fertilized eggs. Pups were born after 19 days. In total 42/136 (31%) of the embryos were carried to term. This number is within the expected range for transgenesis (30-40%). Two pups out of 42 (5%) appear totally unpigmented at birth, consistent with suppression of tyrosinase function.

Methods:

dsRNA from non-coding promoter region of tyrosinase gene. Four segments of the mouse tyrosinase gene promoter were amplified by PCR using primers which incorporated T7 RNA polymerase promoters into the PCR products (shown in bold—FIG. 47). Sequences of the mouse tyrosinase gene 5' flanking regions were obtained from GenBank (accession number D00439 and X51743). The sequence of the tyrosinase enhancer, located approximately 12 kb upstream of the transcriptional start site, was also obtained from GenBank (accession number X76647).

The sequences of the primers used were as follows: note the sequence of the T7 RNA polymerase promoter is shown in bold

```
Tyrosinase enhancer (~12 kb upstream)
5' TAATACGACTCACTATAGGGCAAGGTCATAGTTCCTGCCAGCTG 3'

5' TAATACGACTCACTATAGGGCAGATATTTTCTTACCACCCACCC 3'

-1404 to -1007
5' TAATACGACTCACTATAGGGTTAAGTTTAACAGGAGAAGCTGGA 3'

5' TAATACGACTCACTATAGGGAAATCATTGCTTTCCTGATAATGC 3'

-1003 to -506
5' TAATACGACTCACTATAGGGTAGATTTCCGCAGCCCCAGTGTTC 3'

5' TAATACGACTCACTATAGGGGTTGCCTCTCATTTTTCCTTGATT 3'

-505 to -85
5' TAATACGACTCACTATAGGGTATTTTAGACTGATTACTTTTATAA 3'

5' TAATACGACTCACTATAGGGTCACATGTTTTGGCTAAGACCTAT 3'
```

PCR products were gel purified from 1% TAE agarose gels using QiaExII Gel Extraction Kit (Qiagen). Double stranded RNA was produced from these templates using T7-Megashortscript Kit (Ambion). Enzymes and unincorporated nucleotides were removed using Qiaquick MinElute PCR Purification Kit. RNA was phenol/chloroform extracted twice, and ethanol precipitated. Pellets were resuspended in injection buffer ((10 mM Tris (pH 7.5), 0.15 nM EDTA (pH 8.0)) at a concentration of 20 ng/ul and run on a 1% TAE agarose gel to confirm integrity.

Generation of mice: An equal mixture of double stranded RNA from each of the above primer sets was injected into the pronuclei of fertilized eggs from C57BL6J mice. A total of 136 injections was performed, and 34 embryos were implanted into each of 4 pseudopregnant CD-1 females. Pups were born after 19 days. In total, 42/136 (31%) of the embryos were carried to term. 2/42 pups (5%) appear totally unpigmented at birth.

It is not clear whether the RNAi mediated by dsRNA identical or similar to non-coding sequence works via the same mechanism as PTGS observed in the presence of dsRNA identical or similar to coding sequence. However, whether these results ultimately reveal similar or differing mechanisms does not diminish the tremendous utility of the compositions and methods of the present invention to suppress expression of one or more genes in vitro or in vivo.

The present invention demonstrates that dsRNA ranging in length from 20-500 nt can readily suppress expression of target genes both in vitro and in vivo. Furthermore, the present invention demonstrates that the dsRNAs can be generated using a variety of methods including the formation of hairpins, and that these dsRNAs can be expressed either stably or transiently. Finally, the present invention demonstrates that dsRNA identical or similar to non-coding sequences can suppress target gene expression.

V. Equivalents

Those skilled in the art will recognize, or be able to ascertain using no more than routine experimentation, many equivalents to the specific embodiments of the invention described herein. Such equivalents are intended to be encompassed by the following claims.

All of the above-cited references and publications are hereby incorporated by reference.

We claim:

1. A population of mammalian cells stably transfected or stably transduced with a library of expression constructs, wherein each expression construct encodes a short hairpin RNA, each expression construct comprising:
   (i) an RNA polymerase promoter, and
   (ii) a sequence encoding a short hairpin RNA molecule comprising a double-stranded region wherein the double-stranded region consists of at least 20 nucleotides but not more than 29 nucleotides,
   wherein the short hairpin RNA molecule is a substrate for Dicer-dependent cleavage and does not trigger a protein kinase RNA-activated (PKR) response in the mammalian cells,
   wherein the double-stranded region of the short hairpin RNA molecule comprises a sequence that is complementary to a portion of a target gene in the mammalian cells, wherein the target gene is an endogenous gene of the mammalian cells, and
   wherein said population of mammalian cells comprises cells in which the short hairpin RNA molecule is stably expressed in an amount sufficient to attenuate expression of the target gene in a sequence specific manner without use of a PKR inhibitor.

2. The population of mammalian cells of claim 1, wherein the expression construct further comprises LTR sequences located 5' and 3' of the sequence encoding the short hairpin RNA molecule.

3. The population of mammalian cells of claim 1, wherein the short hairpin RNA molecule comprises a double-stranded region consisting of at least 21 nucleotides.

4. The population of mammalian cells of claim 1, wherein the short hairpin RNA molecule comprises a double-stranded region consisting of at least 22 nucleotides.

5. The population of mammalian cells of claim 1, wherein the short hairpin RNA molecule comprises a double-stranded region consisting of at least 25 nucleotides.

6. The population of mammalian cells of claim 1, wherein the short hairpin RNA molecule comprises a double-stranded region consisting of 29 nucleotides.

7. The population of mammalian cells of claim 1, wherein the short hairpin RNA molecule has a total length of 70 nucleotides.

8. The population of mammalian cells of claim 1, wherein the RNA polymerase promoter comprises a pol II promoter or a pol III promoter.

9. The population of mammalian cells of claim 8, wherein the pol III promoter comprises a U6, an HI, or an SRP promoter.

10. The population of mammalian cells of claim 8, wherein the pol II promoter comprises a U1 or a CMV promoter.

11. A mammalian cell stably transfected or stably transduced with an expression construct encoding a short hairpin RNA molecule, the expression construct comprising:
- (i) an RNA polymerase promoter, and
- (ii) a sequence encoding a short hairpin RNA molecule comprising a double-stranded region wherein the double-stranded region consists of at least 20 nucleotides but not more than 29 nucleotides, wherein the short hairpin RNA molecule is a substrate for Dicer-dependent cleavage and does not trigger a protein kinase RNA-activated (PKR) response in the mammalian cell, wherein the double-stranded region of the short hairpin RNA molecule comprises a sequence that is complementary to a portion of a target gene in the mammalian cell, wherein the target gene is an endogenous gene of the mammalian cell, and wherein the short hairpin RNA is stably expressed in an amount sufficient to attenuate expression of the target gene in a sequence specific manner without use of a PKR inhibitor.

12. The mammalian cell of claim 11, wherein the expression construct further comprises LTR sequences located 5' and 3' of the sequence encoding the short hairpin RNA molecule.

13. The mammalian cell of claim 11, wherein the short hairpin RNA molecule comprises a double-stranded region consisting of at least 21 nucleotides.

14. The mammalian cell of claim 11, wherein the short hairpin RNA molecule comprises a double-stranded region consisting of at least 22 nucleotides.

15. The mammalian cell of claim 11, wherein the short hairpin RNA molecule comprises a double-stranded region consisting of at least 25 nucleotides.

16. The mammalian cell of claim 11, wherein the short hairpin RNA molecule comprises a double-stranded region consisting of 29 nucleotides.

17. The mammalian cell of claim 11, wherein the short hairpin RNA molecule has a total length of 70 nucleotides.

18. The mammalian cell of claim 11, wherein the RNA polymerase promoter comprises a pol II promoter or a pol III promoter.

19. The mammalian cell of claim 18, wherein the pol III promoter comprises a U6, an HI, or an SRP promoter.

20. The mammalian cell of claim 18, wherein the pol II promoter comprises a U1 or a CMV promoter.

\* \* \* \* \*

SEQUENCE LISTING

```
<160> NUMBER OF SEQ ID NOS: 17

<210> SEQ ID NO 1
<211> LENGTH: 5775
<212> TYPE: DNA
<213> ORGANISM: Homo sapiens
<220> FEATURE:
<221> NAME/KEY: CDS
<222> LOCATION: (1)..(5772)

<400> SEQUENCE: 1 atg aaa agc cct gct ttg caa ccc ctc agc atg gca ggc ctg cag ctc    48
Met Lys Ser Pro Ala Leu Gln Pro Leu Ser Met Ala Gly Leu Gln Leu
1               5                   10                  15 atg acc cct gct tcc tca cca atg ggt cct ttc ttt gga ctg cca tgg    96
Met Thr Pro Ala Ser Ser Pro Met Gly Pro Phe Phe Gly Leu Pro Trp
            20                  25                  30 caa caa gaa gca att cat gat aac att tat acg cca aga aaa tat cag   144
```

|  |  |  |  |  |  |  |  |  |  |  |  |  |  |  |  |
|---|---|---|---|---|---|---|---|---|---|---|---|---|---|---|---|
| Gln | Gln | Glu | Ala | Ile | His | Asp | Asn | Ile | Tyr | Thr | Pro | Arg | Lys | Tyr | Gln |
|  |  | 35 |  |  |  | 40 |  |  |  | 45 |  |  |  |  |  |

```
gtt gaa ctg ctt gaa gca gct ctg gat cat aat acc atc gtc tgt tta      192
Val Glu Leu Leu Glu Ala Ala Leu Asp His Asn Thr Ile Val Cys Leu
    50              55                  60 aac act ggc tca ggg aag aca ttt att gct agt act act cta cta aag      240
Asn Thr Gly Ser Gly Lys Thr Phe Ile Ala Ser Thr Thr Leu Leu Lys
65              70                  75                  80 agc tgt ctc tat cta gat cta ggg gag act tca gct aga aat gga aaa      288
Ser Cys Leu Tyr Leu Asp Leu Gly Glu Thr Ser Ala Arg Asn Gly Lys
                85                  90                  95 agg acg gtg ttc ttg gtc aac tct gca aac cag gtt gct caa caa gtg      336
Arg Thr Val Phe Leu Val Asn Ser Ala Asn Gln Val Ala Gln Gln Val
            100                 105                 110 tca gct gtc aga act cat tca gat ctc aag gtt ggg gaa tac tca aac      384
Ser Ala Val Arg Thr His Ser Asp Leu Lys Val Gly Glu Tyr Ser Asn
        115                 120                 125 cta gaa gta aat gca tct tgg aca aaa gag aga tgg aac caa gag ttt      432
Leu Glu Val Asn Ala Ser Trp Thr Lys Glu Arg Trp Asn Gln Glu Phe
130                 135                 140 act aag cac cag gtt ctc att atg act tgc tat gtc gcc ttg aat gtt      480
Thr Lys His Gln Val Leu Ile Met Thr Cys Tyr Val Ala Leu Asn Val
145                 150                 155                 160 ttg aaa aat ggt tac tta tca ctg tca gac att aac ctt ttg gtg ttt      528
Leu Lys Asn Gly Tyr Leu Ser Leu Ser Asp Ile Asn Leu Leu Val Phe
                165                 170                 175 gat gag tgt cat ctt gca atc cta gac cac ccc tat cga gaa ttt atg      576
Asp Glu Cys His Leu Ala Ile Leu Asp His Pro Tyr Arg Glu Phe Met
            180                 185                 190 aag ctc tgt gaa att tgt cca tca tgt cct cgc att ttg gga cta act      624
Lys Leu Cys Glu Ile Cys Pro Ser Cys Pro Arg Ile Leu Gly Leu Thr
        195                 200                 205 gct tcc att tta aat ggg aaa tgg gat cca gag gat ttg gaa gaa aag      672
Ala Ser Ile Leu Asn Gly Lys Trp Asp Pro Glu Asp Leu Glu Glu Lys
210                 215                 220 ttt cag aaa cta gag aaa att ctt aag agt aat gct gaa act gca act      720
Phe Gln Lys Leu Glu Lys Ile Leu Lys Ser Asn Ala Glu Thr Ala Thr
225                 230                 235                 240 gac ctg gtg gtc tta gac agg tat act tct cag cca tgt gag att gtg      768
Asp Leu Val Val Leu Asp Arg Tyr Thr Ser Gln Pro Cys Glu Ile Val
                245                 250                 255 gtg gat tgt gga cca ttt act gac aga agt ggg ctt tat gaa aga ctg      816
Val Asp Cys Gly Pro Phe Thr Asp Arg Ser Gly Leu Tyr Glu Arg Leu
            260                 265                 270 ctg atg gaa tta gaa gaa gca ctt aat ttt atc aat gat tgt aat ata      864
Leu Met Glu Leu Glu Glu Ala Leu Asn Phe Ile Asn Asp Cys Asn Ile
        275                 280                 285 tct gta cat tca aaa gaa aga gat tct act tta att tcg aaa cag ata      912
Ser Val His Ser Lys Glu Arg Asp Ser Thr Leu Ile Ser Lys Gln Ile
290                 295                 300 cta tca gac tgt cgt gcc gta ttg gta gtt ctg gga ccc tgg tgt gca      960
Leu Ser Asp Cys Arg Ala Val Leu Val Val Leu Gly Pro Trp Cys Ala
305                 310                 315                 320 gat aaa gta gct gga atg atg gta aga gaa cta cag aaa tac atc aaa     1008
Asp Lys Val Ala Gly Met Met Val Arg Glu Leu Gln Lys Tyr Ile Lys
                325                 330                 335 cat gag caa gag gag ctg cac agg aaa ttt tta ttg ttt aca gac act     1056
His Glu Gln Glu Glu Leu His Arg Lys Phe Leu Leu Phe Thr Asp Thr
            340                 345                 350 ttc cta agg aaa ata cat gca cta tgt gaa gag cac ttc tca cct gcc     1104
```

```
                    -continued

Phe Leu Arg Lys Ile His Ala Leu Cys Glu Glu His Phe Ser Pro Ala
            355                 360                 365 tca ctt gac ctg aaa ttt gta act cct aaa gta atc aaa ctg ctc gaa      1152
Ser Leu Asp Leu Lys Phe Val Thr Pro Lys Val Ile Lys Leu Leu Glu
    370                 375                 380 atc tta cgc aaa tat aaa cca tat gag cga cac agt ttt gaa agc gtt      1200
Ile Leu Arg Lys Tyr Lys Pro Tyr Glu Arg His Ser Phe Glu Ser Val
385                 390                 395                 400 gag tgg tat aat aat aga aat cag gat aat tat gtg tca tgg agt gat      1248
Glu Trp Tyr Asn Asn Arg Asn Gln Asp Asn Tyr Val Ser Trp Ser Asp
                405                 410                 415 tct gag gat gat gat gag gat gaa gaa att gaa gaa aaa gag aag cca      1296
Ser Glu Asp Asp Asp Glu Asp Glu Glu Ile Glu Glu Lys Glu Lys Pro
            420                 425                 430 gag aca aat ttt cct tct cct ttt acc aac att ttg tgc gga att att      1344
Glu Thr Asn Phe Pro Ser Pro Phe Thr Asn Ile Leu Cys Gly Ile Ile
        435                 440                 445 ttt gtg gaa aga aga tac aca gca gtt gtc tta aac aga ttg ata aag      1392
Phe Val Glu Arg Arg Tyr Thr Ala Val Val Leu Asn Arg Leu Ile Lys
    450                 455                 460 gaa gct ggc aaa caa gat cca gag ctg gct tat atc agt agc aat ttc      1440
Glu Ala Gly Lys Gln Asp Pro Glu Leu Ala Tyr Ile Ser Ser Asn Phe
465                 470                 475                 480 ata act gga cat ggc att ggg aag aat cag cct cgc aac aac acg atg      1488
Ile Thr Gly His Gly Ile Gly Lys Asn Gln Pro Arg Asn Asn Thr Met
                485                 490                 495 gaa gca gaa ttc aga aaa cag gaa gag gta ctt agg aaa ttt cga gca      1536
Glu Ala Glu Phe Arg Lys Gln Glu Glu Val Leu Arg Lys Phe Arg Ala
            500                 505                 510 cat gag acc aac ctg ctt att gca aca agt att gta gaa gag ggt gtt      1584
His Glu Thr Asn Leu Leu Ile Ala Thr Ser Ile Val Glu Glu Gly Val
        515                 520                 525 gat ata cca aaa tgc aac ttg gtg gtt cgt ttt gat ttg ccc aca gaa      1632
Asp Ile Pro Lys Cys Asn Leu Val Val Arg Phe Asp Leu Pro Thr Glu
    530                 535                 540 tat cga tcc tat gtt caa tct aaa gga aga gca agg gca ccc atc tct      1680
Tyr Arg Ser Tyr Val Gln Ser Lys Gly Arg Ala Arg Ala Pro Ile Ser
545                 550                 555                 560 aat tat ata atg tta gcg gat aca gac aaa ata aaa agt ttt gaa gaa      1728
Asn Tyr Ile Met Leu Ala Asp Thr Asp Lys Ile Lys Ser Phe Glu Glu
                565                 570                 575 gac ctt aaa acc tac aaa gct att gaa aag atc ttg aga aac aag tgt      1776
Asp Leu Lys Thr Tyr Lys Ala Ile Glu Lys Ile Leu Arg Asn Lys Cys
            580                 585                 590 tcc aag tcg gtt gat act ggt gag act gac att gat cct gtc atg gat      1824
Ser Lys Ser Val Asp Thr Gly Glu Thr Asp Ile Asp Pro Val Met Asp
        595                 600                 605 gat gat cac gtt ttc cca cca tat gtg ttg agg cct gac gat ggt ggt      1872
Asp Asp His Val Phe Pro Pro Tyr Val Leu Arg Pro Asp Asp Gly Gly
    610                 615                 620 cca cga gtc aca atc aac acg gcc att gga cac atc aat aga tac tgt      1920
Pro Arg Val Thr Ile Asn Thr Ala Ile Gly His Ile Asn Arg Tyr Cys
625                 630                 635                 640 gct aga tta cca agt gat ccg ttt act cat cta gct cct aaa tgc aga      1968
Ala Arg Leu Pro Ser Asp Pro Phe Thr His Leu Ala Pro Lys Cys Arg
                645                 650                 655 acc cga gag ttg cct gat ggt aca ttt tat tca act ctt tat ctg cca      2016
Thr Arg Glu Leu Pro Asp Gly Thr Phe Tyr Ser Thr Leu Tyr Leu Pro
            660                 665                 670 att aac tca cct ctt cga gcc tcc att gtt ggt cca cca atg agc tgt      2064
```

```
Ile Asn Ser Pro Leu Arg Ala Ser Ile Val Gly Pro Pro Met Ser Cys
        675                 680                 685 gta cga ttg gct gaa aga gtt gtc gct ctc att tgc tgt gag aaa ctg      2112
Val Arg Leu Ala Glu Arg Val Val Ala Leu Ile Cys Cys Glu Lys Leu
        690                 695                 700 cac aaa att ggc gaa ctg gat gac cat ttg atg cca gtt ggg aaa gag      2160
His Lys Ile Gly Glu Leu Asp Asp His Leu Met Pro Val Gly Lys Glu
705                 710                 715                 720 act gtt aaa tat gaa gag gag ctt gat ttg cat gat gaa gaa gag acc      2208
Thr Val Lys Tyr Glu Glu Glu Leu Asp Leu His Asp Glu Glu Glu Thr
                725                 730                 735 agt gtt cca gga aga cca ggt tcc acg aaa cga agg cag tgc tac cca      2256
Ser Val Pro Gly Arg Pro Gly Ser Thr Lys Arg Arg Gln Cys Tyr Pro
        740                 745                 750 aaa gca att cca gag tgt ttg agg gat agt tat ccc aga cct gat cag      2304
Lys Ala Ile Pro Glu Cys Leu Arg Asp Ser Tyr Pro Arg Pro Asp Gln
        755                 760                 765 ccc tgt tac ctg tat gtg ata gga atg gtt tta act aca cct tta cct      2352
Pro Cys Tyr Leu Tyr Val Ile Gly Met Val Leu Thr Thr Pro Leu Pro
770                 775                 780 gat gaa ctc aac ttt aga agg cgg aag ctc tat cct cct gaa gat acc      2400
Asp Glu Leu Asn Phe Arg Arg Arg Lys Leu Tyr Pro Pro Glu Asp Thr
785                 790                 795                 800 aca aga tgc ttt gga ata ctg acg gcc aaa ccc ata cct cag att cca      2448
Thr Arg Cys Phe Gly Ile Leu Thr Ala Lys Pro Ile Pro Gln Ile Pro
                805                 810                 815 cac ttt cct gtg tac aca cgc tct gga gag gtt acc ata tcc att gag      2496
His Phe Pro Val Tyr Thr Arg Ser Gly Glu Val Thr Ile Ser Ile Glu
        820                 825                 830 ttg aag aag tct ggt ttc atg ttg tct cta caa atg ctt gag ttg att      2544
Leu Lys Lys Ser Gly Phe Met Leu Ser Leu Gln Met Leu Glu Leu Ile
        835                 840                 845 aca aga ctt cac cag tat ata ttc tca cat att ctt cgg ctt gaa aaa      2592
Thr Arg Leu His Gln Tyr Ile Phe Ser His Ile Leu Arg Leu Glu Lys
850                 855                 860 cct gca cta gaa ttt aaa cct aca gac gct gat tca gca tac tgt gtt      2640
Pro Ala Leu Glu Phe Lys Pro Thr Asp Ala Asp Ser Ala Tyr Cys Val
865                 870                 875                 880 cta cct ctt aat gtt gtt aat gac tcc agc act ttg gat att gac ttt      2688
Leu Pro Leu Asn Val Val Asn Asp Ser Ser Thr Leu Asp Ile Asp Phe
                885                 890                 895 aaa ttc atg gaa gat att gag aag tct gaa gct cgc ata ggc att ccc      2736
Lys Phe Met Glu Asp Ile Glu Lys Ser Glu Ala Arg Ile Gly Ile Pro
        900                 905                 910 agt aca aag tat aca aaa gaa aca ccc ttt gtt ttt aaa tta gaa gat      2784
Ser Thr Lys Tyr Thr Lys Glu Thr Pro Phe Val Phe Lys Leu Glu Asp
        915                 920                 925 tac caa gat gcc gtt atc att cca aga tat cgc aat ttt gat cag cct      2832
Tyr Gln Asp Ala Val Ile Ile Pro Arg Tyr Arg Asn Phe Asp Gln Pro
930                 935                 940 cat cga ttt tat gta gct gat gtg tac act gat ctt acc cca ctc agt      2880
His Arg Phe Tyr Val Ala Asp Val Tyr Thr Asp Leu Thr Pro Leu Ser
945                 950                 955                 960 aaa ttt cct tcc cct gag tat gaa act ttt gca gaa tat tat aaa aca      2928
Lys Phe Pro Ser Pro Glu Tyr Glu Thr Phe Ala Glu Tyr Tyr Lys Thr
                965                 970                 975 aag tac aac ctt gac cta acc aat ctc aac cag cca ctg ctg gat gtg      2976
Lys Tyr Asn Leu Asp Leu Thr Asn Leu Asn Gln Pro Leu Leu Asp Val
        980                 985                 990 gac cac aca tct tca aga ctt aat  ctt ttg aca cct cga  cat ttg aat    3024
```

```
            Asp His Thr Ser Ser Arg Leu Asn  Leu Leu Thr Pro Arg  His Leu Asn
                995                 1000                    1005 cag aag  ggg aaa gcg ctt cct  tta agc agt gct gag  aag agg aaa         3069
Gln Lys  Gly Lys Ala Leu Pro  Leu Ser Ser Ala Glu  Lys Arg Lys
    1010             1015                    1020 gcc aaa  tgg gaa agt ctg cag  aat aaa cag ata ctg  gtt cca gaa         3114
Ala Lys  Trp Glu Ser Leu Gln  Asn Lys Gln Ile Leu  Val Pro Glu
    1025             1030                    1035 ctc tgt  gct ata cat cca att  cca gca tca ctg tgg  aga aaa gct         3159
Leu Cys  Ala Ile His Pro Ile  Pro Ala Ser Leu Trp  Arg Lys Ala
    1040             1045                    1050 gtt tgt  ctc ccc agc ata ctt  tat cgc ctt cac tgc  ctt ttg act         3204
Val Cys  Leu Pro Ser Ile Leu  Tyr Arg Leu His Cys  Leu Leu Thr
    1055             1060                    1065 gca gag  gag cta aga gcc cag  act gcc agc gat gct  ggc gtg gga         3249
Ala Glu  Glu Leu Arg Ala Gln  Thr Ala Ser Asp Ala  Gly Val Gly
    1070             1075                    1080 gtc aga  tca ctt cct gcg gat  ttt aga tac cct aac  tta gac ttc         3294
Val Arg  Ser Leu Pro Ala Asp  Phe Arg Tyr Pro Asn  Leu Asp Phe
    1085             1090                    1095 ggg tgg  aaa aaa tct att gac  agc aaa tct ttc atc  tca att tct         3339
Gly Trp  Lys Lys Ser Ile Asp  Ser Lys Ser Phe Ile  Ser Ile Ser
    1100             1105                    1110 aac tcc  tct tca gct gaa aat  gat aat tac tgt aag  cac agc aca         3384
Asn Ser  Ser Ser Ala Glu Asn  Asp Asn Tyr Cys Lys  His Ser Thr
    1115             1120                    1125 att gtc  cct gaa aat gct gca  cat caa ggt gct aat  aga acc tcc         3429
Ile Val  Pro Glu Asn Ala Ala  His Gln Gly Ala Asn  Arg Thr Ser
    1130             1135                    1140 tct cta  gaa aat cat gac caa  atg tct gtg aac tgc  aga acg ttg         3474
Ser Leu  Glu Asn His Asp Gln  Met Ser Val Asn Cys  Arg Thr Leu
    1145             1150                    1155 ctc agc  gag tcc cct ggt aag  ctc cac gtt gaa gtt  tca gca gat         3519
Leu Ser  Glu Ser Pro Gly Lys  Leu His Val Glu Val  Ser Ala Asp
    1160             1165                    1170 ctt aca  gca att aat ggt ctt  tct tac aat caa aat  ctc gcc aat         3564
Leu Thr  Ala Ile Asn Gly Leu  Ser Tyr Asn Gln Asn  Leu Ala Asn
    1175             1180                    1185 ggc agt  tat gat tta gct aac  aga gac ttt tgc caa  gga aat cag         3609
Gly Ser  Tyr Asp Leu Ala Asn  Arg Asp Phe Cys Gln  Gly Asn Gln
    1190             1195                    1200 cta aat  tac tac aag cag gaa  ata ccc gtg caa cca  act acc tca         3654
Leu Asn  Tyr Tyr Lys Gln Glu  Ile Pro Val Gln Pro  Thr Thr Ser
    1205             1210                    1215 tat tcc  att cag aat tta tac  agt tac gag aac cag  ccc cag ccc         3699
Tyr Ser  Ile Gln Asn Leu Tyr  Ser Tyr Glu Asn Gln  Pro Gln Pro
    1220             1225                    1230 agc gat  gaa tgt act ctc ctg  agt aat aaa tac ctt  gat gga aat         3744
Ser Asp  Glu Cys Thr Leu Leu  Ser Asn Lys Tyr Leu  Asp Gly Asn
    1235             1240                    1245 gct aac  aaa tct acc tca gat  gga agt cct gtg atg  gcc gta atg         3789
Ala Asn  Lys Ser Thr Ser Asp  Gly Ser Pro Val Met  Ala Val Met
    1250             1255                    1260 cct ggt  acg aca gac act att  caa gtg ctc aag ggc  agg atg gat         3834
Pro Gly  Thr Thr Asp Thr Ile  Gln Val Leu Lys Gly  Arg Met Asp
    1265             1270                    1275 tct gag  cag agc cct tct att  ggg tac tcc tca agg  act ctt ggc         3879
Ser Glu  Gln Ser Pro Ser Ile  Gly Tyr Ser Ser Arg  Thr Leu Gly
    1280             1285                    1290 ccc aat  cct gga ctt att ctt  cag gct ttg act ctg  tca aac gct         3924
```

```
                                              -continued
Pro Asn Pro Gly Leu Ile Leu Gln Ala Leu Thr Leu Ser Asn Ala
    1295            1300                1305 agt gat gga ttt aac ctg gag cgg ctt gaa atg ctt ggc gac tcc    3969
Ser Asp Gly Phe Asn Leu Glu Arg Leu Glu Met Leu Gly Asp Ser
1310            1315                1320 ttt tta aag cat gcc atc acc aca tat cta ttt tgc act tac cct    4014
Phe Leu Lys His Ala Ile Thr Thr Tyr Leu Phe Cys Thr Tyr Pro
1325            1330                1335 gat gcg cat gag ggc cgc ctt tca tat atg aga agc aaa aag gtc    4059
Asp Ala His Glu Gly Arg Leu Ser Tyr Met Arg Ser Lys Lys Val
1340            1345                1350 agc aac tgt aat ctg tat cgc ctt gga aaa aag aag gga cta ccc    4104
Ser Asn Cys Asn Leu Tyr Arg Leu Gly Lys Lys Lys Gly Leu Pro
1355            1360                1365 agc cgc atg gtg gtg tca ata ttt gat ccc cct gtg aat tgg ctt    4149
Ser Arg Met Val Val Ser Ile Phe Asp Pro Pro Val Asn Trp Leu
1370            1375                1380 cct cct ggt tat gta gta aat caa gac aaa agc aac aca gat aaa    4194
Pro Pro Gly Tyr Val Val Asn Gln Asp Lys Ser Asn Thr Asp Lys
1385            1390                1395 tgg gaa aaa gat gaa atg aca aaa gac tgc atg ctg gcg aat ggc    4239
Trp Glu Lys Asp Glu Met Thr Lys Asp Cys Met Leu Ala Asn Gly
1400            1405                1410 aaa ctg gat gag gat tac gag gag gag gat gag gag gag gag agc    4284
Lys Leu Asp Glu Asp Tyr Glu Glu Glu Asp Glu Glu Glu Glu Ser
1415            1420                1425 ctg atg tgg agg gct ccg aag gaa gag gct gac tat gaa gat gat    4329
Leu Met Trp Arg Ala Pro Lys Glu Glu Ala Asp Tyr Glu Asp Asp
1430            1435                1440 ttc ctg gag tat gat cag gaa cat atc aga ttt ata gat aat atg    4374
Phe Leu Glu Tyr Asp Gln Glu His Ile Arg Phe Ile Asp Asn Met
1445            1450                1455 tta atg ggg tca gga gct ttt gta aag aaa atc tct ctt tct cct    4419
Leu Met Gly Ser Gly Ala Phe Val Lys Lys Ile Ser Leu Ser Pro
1460            1465                1470 ttt tca acc act gat tct gca tat gaa tgg aaa atg ccc aaa aaa    4464
Phe Ser Thr Thr Asp Ser Ala Tyr Glu Trp Lys Met Pro Lys Lys
1475            1480                1485 tcc tcc tta ggt agt atg cca ttt tca tca gat ttt gag gat ttt    4509
Ser Ser Leu Gly Ser Met Pro Phe Ser Ser Asp Phe Glu Asp Phe
1490            1495                1500 gac tac agc tct tgg gat gca atg tgc tat ctg gat cct agc aaa    4554
Asp Tyr Ser Ser Trp Asp Ala Met Cys Tyr Leu Asp Pro Ser Lys
1505            1510                1515 gct gtt gaa gaa gat gac ttt gtg gtg ggg ttc tgg aat cca tca    4599
Ala Val Glu Glu Asp Asp Phe Val Val Gly Phe Trp Asn Pro Ser
1520            1525                1530 gaa gaa aac tgt ggt gtt gac acg gga aag cag tcc att tct tac    4644
Glu Glu Asn Cys Gly Val Asp Thr Gly Lys Gln Ser Ile Ser Tyr
1535            1540                1545 gac ttg cac act gag cag tgt att gct gac aaa agc ata gcg gac    4689
Asp Leu His Thr Glu Gln Cys Ile Ala Asp Lys Ser Ile Ala Asp
1550            1555                1560 tgt gtg gaa gcc ctg ctg ggc tgc tat tta acc agc tgt ggg gag    4734
Cys Val Glu Ala Leu Leu Gly Cys Tyr Leu Thr Ser Cys Gly Glu
1565            1570                1575 agg gct gct cag ctt ttc ctc tgt tca ctg ggg ctg aag gtg ctc    4779
Arg Ala Ala Gln Leu Phe Leu Cys Ser Leu Gly Leu Lys Val Leu
1580            1585                1590 ccg gta att aaa agg act gat cgg gaa aag gcc ctg tgc cct act    4824
```

-continued

| | | | | | | | | | | | | |
|---|---|---|---|---|---|---|---|---|---|---|---|---|
| Pro | Val | Ile | Lys | Arg | Thr | Asp | Arg | Glu | Lys | Ala | Leu | Cys | Pro | Thr |
| | 1595 | | | | 1600 | | | | | 1605 | | | | |

| cgg | gag | aat | ttc | aac | agc | caa | caa | aag | aac | ctt | tca | gtg | agc | tgt | 4869 |
|---|---|---|---|---|---|---|---|---|---|---|---|---|---|---|---|
| Arg | Glu | Asn | Phe | Asn | Ser | Gln | Gln | Lys | Asn | Leu | Ser | Val | Ser | Cys | |
| 1610 | | | | | 1615 | | | | | 1620 | | | | | |

| gct | gct | gct | tct | gtg | gcc | agt | tca | cgc | tct | tct | gta | ttg | aaa | gac | 4914 |
|---|---|---|---|---|---|---|---|---|---|---|---|---|---|---|---|
| Ala | Ala | Ala | Ser | Val | Ala | Ser | Ser | Arg | Ser | Ser | Val | Leu | Lys | Asp | |
| 1625 | | | | | 1630 | | | | | 1635 | | | | | |

| tcg | gaa | tat | ggt | tgt | ttg | aag | att | cca | cca | aga | tgt | atg | ttt | gat | 4959 |
|---|---|---|---|---|---|---|---|---|---|---|---|---|---|---|---|
| Ser | Glu | Tyr | Gly | Cys | Leu | Lys | Ile | Pro | Pro | Arg | Cys | Met | Phe | Asp | |
| 1640 | | | | | 1645 | | | | | 1650 | | | | | |

| cat | cca | gat | gca | gat | aaa | aca | ctg | aat | cac | ctt | ata | tcg | ggg | ttt | 5004 |
|---|---|---|---|---|---|---|---|---|---|---|---|---|---|---|---|
| His | Pro | Asp | Ala | Asp | Lys | Thr | Leu | Asn | His | Leu | Ile | Ser | Gly | Phe | |
| 1655 | | | | | 1660 | | | | | 1665 | | | | | |

| gaa | aat | ttt | gaa | aag | aaa | atc | aac | tac | aga | ttc | aag | aat | aag | gct | 5049 |
|---|---|---|---|---|---|---|---|---|---|---|---|---|---|---|---|
| Glu | Asn | Phe | Glu | Lys | Lys | Ile | Asn | Tyr | Arg | Phe | Lys | Asn | Lys | Ala | |
| 1670 | | | | | 1675 | | | | | 1680 | | | | | |

| tac | ctc | ctc | cag | gct | ttt | aca | cat | gcc | tcc | tac | cac | tac | aat | act | 5094 |
|---|---|---|---|---|---|---|---|---|---|---|---|---|---|---|---|
| Tyr | Leu | Leu | Gln | Ala | Phe | Thr | His | Ala | Ser | Tyr | His | Tyr | Asn | Thr | |
| 1685 | | | | | 1690 | | | | | 1695 | | | | | |

| atc | act | gat | tgt | tac | cag | cgc | tta | gaa | ttc | ctg | gga | gat | gcg | att | 5139 |
|---|---|---|---|---|---|---|---|---|---|---|---|---|---|---|---|
| Ile | Thr | Asp | Cys | Tyr | Gln | Arg | Leu | Glu | Phe | Leu | Gly | Asp | Ala | Ile | |
| 1700 | | | | | 1705 | | | | | 1710 | | | | | |

| ttg | gac | tac | ctc | ata | acc | aag | cac | ctt | tat | gaa | gac | ccg | cgg | cag | 5184 |
|---|---|---|---|---|---|---|---|---|---|---|---|---|---|---|---|
| Leu | Asp | Tyr | Leu | Ile | Thr | Lys | His | Leu | Tyr | Glu | Asp | Pro | Arg | Gln | |
| 1715 | | | | | 1720 | | | | | 1725 | | | | | |

| cac | tcc | ccg | ggg | gtc | ctg | aca | gac | ctg | cgg | tct | gcc | ctg | gtc | aac | 5229 |
|---|---|---|---|---|---|---|---|---|---|---|---|---|---|---|---|
| His | Ser | Pro | Gly | Val | Leu | Thr | Asp | Leu | Arg | Ser | Ala | Leu | Val | Asn | |
| 1730 | | | | | 1735 | | | | | 1740 | | | | | |

| aac | acc | atc | ttt | gca | tcg | ctg | gct | gta | aag | tac | gac | tac | cac | aag | 5274 |
|---|---|---|---|---|---|---|---|---|---|---|---|---|---|---|---|
| Asn | Thr | Ile | Phe | Ala | Ser | Leu | Ala | Val | Lys | Tyr | Asp | Tyr | His | Lys | |
| 1745 | | | | | 1750 | | | | | 1755 | | | | | |

| tac | ttc | aaa | gct | gtc | tct | cct | gag | ctc | ttc | cat | gtc | att | gat | gac | 5319 |
|---|---|---|---|---|---|---|---|---|---|---|---|---|---|---|---|
| Tyr | Phe | Lys | Ala | Val | Ser | Pro | Glu | Leu | Phe | His | Val | Ile | Asp | Asp | |
| 1760 | | | | | 1765 | | | | | 1770 | | | | | |

| ttt | gtg | cag | ttt | cag | ctt | gag | aag | aat | gaa | atg | caa | gga | atg | gat | 5364 |
|---|---|---|---|---|---|---|---|---|---|---|---|---|---|---|---|
| Phe | Val | Gln | Phe | Gln | Leu | Glu | Lys | Asn | Glu | Met | Gln | Gly | Met | Asp | |
| 1775 | | | | | 1780 | | | | | 1785 | | | | | |

| tct | gag | ctt | agg | aga | tct | gag | gag | gat | gaa | gag | aaa | gaa | gag | gat | 5409 |
|---|---|---|---|---|---|---|---|---|---|---|---|---|---|---|---|
| Ser | Glu | Leu | Arg | Arg | Ser | Glu | Glu | Asp | Glu | Glu | Lys | Glu | Glu | Asp | |
| 1790 | | | | | 1795 | | | | | 1800 | | | | | |

| att | gaa | gtt | cca | aag | gcc | atg | ggg | gat | att | ttt | gag | tcg | ctt | gct | 5454 |
|---|---|---|---|---|---|---|---|---|---|---|---|---|---|---|---|
| Ile | Glu | Val | Pro | Lys | Ala | Met | Gly | Asp | Ile | Phe | Glu | Ser | Leu | Ala | |
| 1805 | | | | | 1810 | | | | | 1815 | | | | | |

| ggt | gcc | att | tac | atg | gat | agt | ggg | atg | tca | ctg | gag | aca | gtc | tgg | 5499 |
|---|---|---|---|---|---|---|---|---|---|---|---|---|---|---|---|
| Gly | Ala | Ile | Tyr | Met | Asp | Ser | Gly | Met | Ser | Leu | Glu | Thr | Val | Trp | |
| 1820 | | | | | 1825 | | | | | 1830 | | | | | |

| cag | gtg | tac | tat | ccc | atg | atg | cgg | cca | cta | ata | gaa | aag | ttt | tct | 5544 |
|---|---|---|---|---|---|---|---|---|---|---|---|---|---|---|---|
| Gln | Val | Tyr | Tyr | Pro | Met | Met | Arg | Pro | Leu | Ile | Glu | Lys | Phe | Ser | |
| 1835 | | | | | 1840 | | | | | 1845 | | | | | |

| gca | aat | gta | ccc | cgt | tcc | cct | gtg | cga | gaa | ttg | ctt | gaa | atg | gaa | 5589 |
|---|---|---|---|---|---|---|---|---|---|---|---|---|---|---|---|
| Ala | Asn | Val | Pro | Arg | Ser | Pro | Val | Arg | Glu | Leu | Leu | Glu | Met | Glu | |
| 1850 | | | | | 1855 | | | | | 1860 | | | | | |

| cca | gaa | act | gcc | aaa | ttt | agc | ccg | gct | gag | aga | act | tac | gac | ggg | 5634 |
|---|---|---|---|---|---|---|---|---|---|---|---|---|---|---|---|
| Pro | Glu | Thr | Ala | Lys | Phe | Ser | Pro | Ala | Glu | Arg | Thr | Tyr | Asp | Gly | |
| 1865 | | | | | 1870 | | | | | 1875 | | | | | |

| aag | gtc | aga | gtc | act | gtg | gaa | gta | gta | gga | aag | ggg | aaa | ttt | aaa | 5679 |
|---|---|---|---|---|---|---|---|---|---|---|---|---|---|---|---|
| Lys | Val | Arg | Val | Thr | Val | Glu | Val | Val | Gly | Lys | Gly | Lys | Phe | Lys | |
| 1880 | | | | | 1885 | | | | | 1890 | | | | | |

| ggt | gtt | ggt | cga | agt | tac | agg | att | gcc | aaa | tct | gca | gca | gca | aga | 5724 |
|---|---|---|---|---|---|---|---|---|---|---|---|---|---|---|---|

-continued

```
Gly Val Gly Arg Ser Tyr Arg Ile Ala Lys Ser Ala Ala Ala Arg
    1895                1900                1905 aga gcc ctc cga agc ctc aaa gct aat caa cct cag gtt ccc aat      5769
Arg Ala Leu Arg Ser Leu Lys Ala Asn Gln Pro Gln Val Pro Asn
    1910                1915                1920 agc tga                                                           5775
Ser
```

<210> SEQ ID NO 2
<211> LENGTH: 1924
<212> TYPE: PRT
<213> ORGANISM: Homo sapiens

<400> SEQUENCE: 2

```
Met Lys Ser Pro Ala Leu Gln Pro Leu Ser Met Ala Gly Leu Gln Leu
1               5                   10                  15

Met Thr Pro Ala Ser Ser Pro Met Gly Pro Phe Phe Gly Leu Pro Trp
                20                  25                  30

Gln Gln Glu Ala Ile His Asp Asn Ile Tyr Thr Pro Arg Lys Tyr Gln
            35                  40                  45

Val Glu Leu Leu Glu Ala Ala Leu Asp His Asn Thr Ile Val Cys Leu
        50                  55                  60

Asn Thr Gly Ser Gly Lys Thr Phe Ile Ala Ser Thr Thr Leu Leu Lys
65                  70                  75                  80

Ser Cys Leu Tyr Leu Asp Leu Gly Glu Thr Ser Ala Arg Asn Gly Lys
                85                  90                  95

Arg Thr Val Phe Leu Val Asn Ser Ala Asn Gln Val Ala Gln Gln Val
            100                 105                 110

Ser Ala Val Arg Thr His Ser Asp Leu Lys Val Gly Glu Tyr Ser Asn
        115                 120                 125

Leu Glu Val Asn Ala Ser Trp Thr Lys Glu Arg Trp Asn Gln Glu Phe
    130                 135                 140

Thr Lys His Gln Val Leu Ile Met Thr Cys Tyr Val Ala Leu Asn Val
145                 150                 155                 160

Leu Lys Asn Gly Tyr Leu Ser Leu Ser Asp Ile Asn Leu Leu Val Phe
                165                 170                 175

Asp Glu Cys His Leu Ala Ile Leu Asp His Pro Tyr Arg Glu Phe Met
            180                 185                 190

Lys Leu Cys Glu Ile Cys Pro Ser Cys Pro Arg Ile Leu Gly Leu Thr
        195                 200                 205

Ala Ser Ile Leu Asn Gly Lys Trp Asp Pro Glu Asp Leu Glu Glu Lys
    210                 215                 220

Phe Gln Lys Leu Glu Lys Ile Leu Lys Ser Asn Ala Glu Thr Ala Thr
225                 230                 235                 240

Asp Leu Val Val Leu Asp Arg Tyr Thr Ser Gln Pro Cys Glu Ile Val
                245                 250                 255

Val Asp Cys Gly Pro Phe Thr Asp Arg Ser Gly Leu Tyr Glu Arg Leu
            260                 265                 270

Leu Met Glu Leu Glu Glu Ala Leu Asn Phe Ile Asn Asp Cys Asn Ile
        275                 280                 285

Ser Val His Ser Lys Glu Arg Asp Ser Thr Leu Ile Ser Lys Gln Ile
    290                 295                 300

Leu Ser Asp Cys Arg Ala Val Leu Val Val Leu Gly Pro Trp Cys Ala
305                 310                 315                 320

Asp Lys Val Ala Gly Met Met Val Arg Glu Leu Gln Lys Tyr Ile Lys
                325                 330                 335
```

-continued

His Glu Gln Glu Glu Leu His Arg Lys Phe Leu Leu Phe Thr Asp Thr
                340                 345                 350

Phe Leu Arg Lys Ile His Ala Leu Cys Glu Glu His Phe Ser Pro Ala
            355                 360                 365

Ser Leu Asp Leu Lys Phe Val Thr Pro Lys Val Ile Lys Leu Leu Glu
370                 375                 380

Ile Leu Arg Lys Tyr Lys Pro Tyr Glu Arg His Ser Phe Glu Ser Val
385                 390                 395                 400

Glu Trp Tyr Asn Asn Arg Asn Gln Asp Asn Tyr Val Ser Trp Ser Asp
                405                 410                 415

Ser Glu Asp Asp Asp Glu Asp Glu Glu Ile Glu Lys Glu Lys Pro
            420                 425                 430

Glu Thr Asn Phe Pro Ser Pro Phe Thr Asn Ile Leu Cys Gly Ile Ile
                435                 440                 445

Phe Val Glu Arg Arg Tyr Thr Ala Val Val Leu Asn Arg Leu Ile Lys
450                 455                 460

Glu Ala Gly Lys Gln Asp Pro Glu Leu Ala Tyr Ile Ser Ser Asn Phe
465                 470                 475                 480

Ile Thr Gly His Gly Ile Gly Lys Asn Gln Pro Arg Asn Asn Thr Met
                485                 490                 495

Glu Ala Glu Phe Arg Lys Gln Glu Glu Val Leu Arg Lys Phe Arg Ala
            500                 505                 510

His Glu Thr Asn Leu Leu Ile Ala Thr Ser Ile Val Glu Glu Gly Val
            515                 520                 525

Asp Ile Pro Lys Cys Asn Leu Val Val Arg Phe Asp Leu Pro Thr Glu
530                 535                 540

Tyr Arg Ser Tyr Val Gln Ser Lys Gly Arg Ala Arg Ala Pro Ile Ser
545                 550                 555                 560

Asn Tyr Ile Met Leu Ala Asp Thr Asp Lys Ile Lys Ser Phe Glu Glu
                565                 570                 575

Asp Leu Lys Thr Tyr Lys Ala Ile Glu Lys Ile Leu Arg Asn Lys Cys
            580                 585                 590

Ser Lys Ser Val Asp Thr Gly Glu Thr Asp Ile Asp Pro Val Met Asp
            595                 600                 605

Asp Asp His Val Phe Pro Pro Tyr Val Leu Arg Pro Asp Asp Gly Gly
610                 615                 620

Pro Arg Val Thr Ile Asn Thr Ala Ile Gly His Ile Asn Arg Tyr Cys
625                 630                 635                 640

Ala Arg Leu Pro Ser Asp Pro Phe Thr His Leu Ala Pro Lys Cys Arg
                645                 650                 655

Thr Arg Glu Leu Pro Asp Gly Thr Phe Tyr Ser Thr Leu Tyr Leu Pro
            660                 665                 670

Ile Asn Ser Pro Leu Arg Ala Ser Ile Val Gly Pro Pro Met Ser Cys
            675                 680                 685

Val Arg Leu Ala Glu Arg Val Val Ala Leu Ile Cys Cys Glu Lys Leu
690                 695                 700

His Lys Ile Gly Glu Leu Asp Asp His Leu Met Pro Val Gly Lys Glu
705                 710                 715                 720

Thr Val Lys Tyr Glu Glu Glu Leu Asp Leu His Asp Glu Glu Thr
                725                 730                 735

Ser Val Pro Gly Arg Pro Gly Ser Thr Lys Arg Arg Gln Cys Tyr Pro
            740                 745                 750

Lys Ala Ile Pro Glu Cys Leu Arg Asp Ser Tyr Pro Arg Pro Asp Gln

-continued

```
            755                 760                765
Pro Cys Tyr Leu Tyr Val Ile Gly Met Val Leu Thr Thr Pro Leu Pro
770                     775                 780

Asp Glu Leu Asn Phe Arg Arg Arg Lys Leu Tyr Pro Pro Glu Asp Thr
785                     790             795                 800

Thr Arg Cys Phe Gly Ile Leu Thr Ala Lys Pro Ile Pro Gln Ile Pro
                    805                 810              815

His Phe Pro Val Tyr Thr Arg Ser Gly Glu Val Thr Ile Ser Ile Glu
                820                 825                 830

Leu Lys Lys Ser Gly Phe Met Leu Ser Leu Gln Met Leu Glu Leu Ile
                835                 840                 845

Thr Arg Leu His Gln Tyr Ile Phe Ser His Ile Leu Arg Leu Glu Lys
            850                 855                 860

Pro Ala Leu Glu Phe Lys Pro Thr Asp Ala Asp Ser Ala Tyr Cys Val
865                 870                 875                 880

Leu Pro Leu Asn Val Val Asn Asp Ser Ser Thr Leu Asp Ile Asp Phe
                        885                 890                 895

Lys Phe Met Glu Asp Ile Glu Lys Ser Glu Ala Arg Ile Gly Ile Pro
                900                 905                 910

Ser Thr Lys Tyr Thr Lys Glu Thr Pro Phe Val Phe Lys Leu Glu Asp
            915                 920                 925

Tyr Gln Asp Ala Val Ile Ile Pro Arg Tyr Arg Asn Phe Asp Gln Pro
                930                 935                 940

His Arg Phe Tyr Val Ala Asp Val Tyr Thr Asp Leu Thr Pro Leu Ser
945                 950                 955                 960

Lys Phe Pro Ser Pro Glu Tyr Glu Thr Phe Ala Glu Tyr Tyr Lys Thr
                    965                 970                 975

Lys Tyr Asn Leu Asp Leu Thr Asn Leu Asn Gln Pro Leu Leu Asp Val
                980                 985                 990

Asp His Thr Ser Ser Arg Leu Asn  Leu Leu Thr Pro Arg  His Leu Asn
                995                 1000                1005

Gln Lys  Gly Lys Ala Leu Pro  Leu Ser Ser Ala Glu  Lys Arg Lys
   1010                 1015                1020

Ala Lys  Trp Glu Ser Leu Gln  Asn Lys Gln Ile Leu  Val Pro Glu
1025                    1030                1035

Leu Cys  Ala Ile His Pro Ile  Pro Ala Ser Leu Trp  Arg Lys Ala
                    1040                1045                1050

Val Cys  Leu Pro Ser Ile Leu  Tyr Arg Leu His Cys  Leu Leu Thr
            1055                1060                1065

Ala Glu  Glu Leu Arg Ala Gln  Thr Ala Ser Asp Ala  Gly Val Gly
        1070                    1075                1080

Val Arg  Ser Leu Pro Ala Asp  Phe Arg Tyr Pro Asn  Leu Asp Phe
    1085                    1090                1095

Gly Trp  Lys Lys Ser Ile Asp  Ser Lys Ser Phe Ile  Ser Ile Ser
            1100                1105                1110

Asn Ser  Ser Ser Ala Glu Asn  Asp Asn Tyr Cys Lys  His Ser Thr
    1115                    1120                1125

Ile Val  Pro Glu Asn Ala Ala  His Gln Gly Ala Asn  Arg Thr Ser
    1130                    1135                1140

Ser Leu  Glu Asn His Asp Gln  Met Ser Val Asn Cys  Arg Thr Leu
    1145                    1150                1155

Leu Ser  Glu Ser Pro Gly Lys  Leu His Val Glu Val  Ser Ala Asp
    1160                    1165                1170
```

-continued

```
Leu Thr Ala Ile Asn Gly Leu Ser Tyr Asn Gln Asn Leu Ala Asn
1175                1180                1185

Gly Ser Tyr Asp Leu Ala Asn Arg Asp Phe Cys Gln Gly Asn Gln
1190                1195                1200

Leu Asn Tyr Tyr Lys Gln Glu Ile Pro Val Gln Pro Thr Thr Ser
1205                1210                1215

Tyr Ser Ile Gln Asn Leu Tyr Ser Tyr Glu Asn Gln Pro Gln Pro
1220                1225                1230

Ser Asp Glu Cys Thr Leu Leu Ser Asn Lys Tyr Leu Asp Gly Asn
1235                1240                1245

Ala Asn Lys Ser Thr Ser Asp Gly Ser Pro Val Met Ala Val Met
1250                1255                1260

Pro Gly Thr Thr Asp Thr Ile Gln Val Leu Lys Gly Arg Met Asp
1265                1270                1275

Ser Glu Gln Ser Pro Ser Ile Gly Tyr Ser Ser Arg Thr Leu Gly
1280                1285                1290

Pro Asn Pro Gly Leu Ile Leu Gln Ala Leu Thr Leu Ser Asn Ala
1295                1300                1305

Ser Asp Gly Phe Asn Leu Glu Arg Leu Glu Met Leu Gly Asp Ser
1310                1315                1320

Phe Leu Lys His Ala Ile Thr Thr Tyr Leu Phe Cys Thr Tyr Pro
1325                1330                1335

Asp Ala His Glu Gly Arg Leu Ser Tyr Met Arg Ser Lys Lys Val
1340                1345                1350

Ser Asn Cys Asn Leu Tyr Arg Leu Gly Lys Lys Lys Gly Leu Pro
1355                1360                1365

Ser Arg Met Val Val Ser Ile Phe Asp Pro Pro Val Asn Trp Leu
1370                1375                1380

Pro Pro Gly Tyr Val Val Asn Gln Asp Lys Ser Asn Thr Asp Lys
1385                1390                1395

Trp Glu Lys Asp Glu Met Thr Lys Asp Cys Met Leu Ala Asn Gly
1400                1405                1410

Lys Leu Asp Glu Asp Tyr Glu Glu Glu Asp Glu Glu Glu Glu Ser
1415                1420                1425

Leu Met Trp Arg Ala Pro Lys Glu Glu Ala Asp Tyr Glu Asp Asp
1430                1435                1440

Phe Leu Glu Tyr Asp Gln Glu His Ile Arg Phe Ile Asp Asn Met
1445                1450                1455

Leu Met Gly Ser Gly Ala Phe Val Lys Lys Ile Ser Leu Ser Pro
1460                1465                1470

Phe Ser Thr Thr Asp Ser Ala Tyr Glu Trp Lys Met Pro Lys Lys
1475                1480                1485

Ser Ser Leu Gly Ser Met Pro Phe Ser Ser Asp Phe Glu Asp Phe
1490                1495                1500

Asp Tyr Ser Ser Trp Asp Ala Met Cys Tyr Leu Asp Pro Ser Lys
1505                1510                1515

Ala Val Glu Glu Asp Asp Phe Val Val Gly Phe Trp Asn Pro Ser
1520                1525                1530

Glu Glu Asn Cys Gly Val Asp Thr Gly Lys Gln Ser Ile Ser Tyr
1535                1540                1545

Asp Leu His Thr Glu Gln Cys Ile Ala Asp Lys Ser Ile Ala Asp
1550                1555                1560

Cys Val Glu Ala Leu Leu Gly Cys Tyr Leu Thr Ser Cys Gly Glu
1565                1570                1575
```

```
Arg Ala Ala Gln Leu Phe Leu Cys Ser Leu Gly Leu Lys Val Leu
    1580                1585                1590

Pro Val Ile Lys Arg Thr Asp Arg Glu Lys Ala Leu Cys Pro Thr
    1595                1600                1605

Arg Glu Asn Phe Asn Ser Gln Gln Lys Asn Leu Ser Val Ser Cys
    1610                1615                1620

Ala Ala Ala Ser Val Ala Ser Ser Arg Ser Ser Val Leu Lys Asp
    1625                1630                1635

Ser Glu Tyr Gly Cys Leu Lys Ile Pro Pro Arg Cys Met Phe Asp
    1640                1645                1650

His Pro Asp Ala Asp Lys Thr Leu Asn His Leu Ile Ser Gly Phe
    1655                1660                1665

Glu Asn Phe Glu Lys Lys Ile Asn Tyr Arg Phe Lys Asn Lys Ala
    1670                1675                1680

Tyr Leu Leu Gln Ala Phe Thr His Ala Ser Tyr His Tyr Asn Thr
    1685                1690                1695

Ile Thr Asp Cys Tyr Gln Arg Leu Glu Phe Leu Gly Asp Ala Ile
    1700                1705                1710

Leu Asp Tyr Leu Ile Thr Lys His Leu Tyr Glu Asp Pro Arg Gln
    1715                1720                1725

His Ser Pro Gly Val Leu Thr Asp Leu Arg Ser Ala Leu Val Asn
    1730                1735                1740

Asn Thr Ile Phe Ala Ser Leu Ala Val Lys Tyr Asp Tyr His Lys
    1745                1750                1755

Tyr Phe Lys Ala Val Ser Pro Glu Leu Phe His Val Ile Asp Asp
    1760                1765                1770

Phe Val Gln Phe Gln Leu Glu Lys Asn Glu Met Gln Gly Met Asp
    1775                1780                1785

Ser Glu Leu Arg Arg Ser Glu Asp Glu Glu Lys Glu Glu Asp
    1790                1795                1800

Ile Glu Val Pro Lys Ala Met Gly Asp Ile Phe Glu Ser Leu Ala
    1805                1810                1815

Gly Ala Ile Tyr Met Asp Ser Gly Met Ser Leu Glu Thr Val Trp
    1820                1825                1830

Gln Val Tyr Tyr Pro Met Met Arg Pro Leu Ile Glu Lys Phe Ser
    1835                1840                1845

Ala Asn Val Pro Arg Ser Pro Val Arg Glu Leu Leu Glu Met Glu
    1850                1855                1860

Pro Glu Thr Ala Lys Phe Ser Pro Ala Glu Arg Thr Tyr Asp Gly
    1865                1870                1875

Lys Val Arg Val Thr Val Glu Val Val Gly Lys Gly Lys Phe Lys
    1880                1885                1890

Gly Val Gly Arg Ser Tyr Arg Ile Ala Lys Ser Ala Ala Ala Arg
    1895                1900                1905

Arg Ala Leu Arg Ser Leu Lys Ala Asn Gln Pro Gln Val Pro Asn
    1910                1915                1920

Ser

<210> SEQ ID NO 3
<211> LENGTH: 6750
<212> TYPE: DNA
<213> ORGANISM: Drosophila melanogaster
<220> FEATURE:
<221> NAME/KEY: CDS
<222> LOCATION: (1)..(6747)
```

<400> SEQUENCE: 3

```
atg gcg ttc cac tgg tgc gac aac aat ctg cac acc acc gtg ttc acg     48
Met Ala Phe His Trp Cys Asp Asn Asn Leu His Thr Thr Val Phe Thr
 1               5                  10                  15 ccg cgc gac ttt cag gtg gag cta ctg gcc acc gcc tac gag cgg aac     96
Pro Arg Asp Phe Gln Val Glu Leu Leu Ala Thr Ala Tyr Glu Arg Asn
             20                  25                  30 acg att att tgc ctg ggc cat cga agt tcc aag gag ttt ata gcc ctc    144
Thr Ile Ile Cys Leu Gly His Arg Ser Ser Lys Glu Phe Ile Ala Leu
         35                  40                  45 aag ctg ctc cag gag ctg tcg cgt cga gca cgc cga cat ggt cgt gtc    192
Lys Leu Leu Gln Glu Leu Ser Arg Arg Ala Arg Arg His Gly Arg Val
     50                  55                  60 agt gtc tat ctc agt tgc gag gtt ggc acc agc acg gaa cca tgc tcc    240
Ser Val Tyr Leu Ser Cys Glu Val Gly Thr Ser Thr Glu Pro Cys Ser
 65                  70                  75                  80 atc tac acg atg ctc acc cac ttg act gac ctg cgg gtg tgg cag gag    288
Ile Tyr Thr Met Leu Thr His Leu Thr Asp Leu Arg Val Trp Gln Glu
                 85                  90                  95 cag ccg gat atg caa att ccc ttt gat cat tgc tgg acg gac tat cac    336
Gln Pro Asp Met Gln Ile Pro Phe Asp His Cys Trp Thr Asp Tyr His
            100                 105                 110 gtt tcc atc cta cgg cca gag gga ttt ctt tat ctg ctc gaa act cgc    384
Val Ser Ile Leu Arg Pro Glu Gly Phe Leu Tyr Leu Leu Glu Thr Arg
        115                 120                 125 gag ctg ctg ctg agc agc gtc gaa ctg atc gtg ctg gaa gat tgt cat    432
Glu Leu Leu Leu Ser Ser Val Glu Leu Ile Val Leu Glu Asp Cys His
    130                 135                 140 gac agc gcc gtt tat cag agg ata agg cct ctg ttc gag aat cac att    480
Asp Ser Ala Val Tyr Gln Arg Ile Arg Pro Leu Phe Glu Asn His Ile
145                 150                 155                 160 atg cca gcg cca ccg gcg gac agg cca cgg att ctc gga ctc gct gga    528
Met Pro Ala Pro Pro Ala Asp Arg Pro Arg Ile Leu Gly Leu Ala Gly
                165                 170                 175 ccg ctg cac agc gcc gga tgt gag ctg cag caa ctg agc gcc atg ctg    576
Pro Leu His Ser Ala Gly Cys Glu Leu Gln Gln Leu Ser Ala Met Leu
            180                 185                 190 gcc acc ctg gag cag agt gtg ctt tgc cag atc gag acg gcc agt gat    624
Ala Thr Leu Glu Gln Ser Val Leu Cys Gln Ile Glu Thr Ala Ser Asp
        195                 200                 205 att gtc acc gtg ttg cgt tac tgt tcc cga ccg cac gaa tac atc gta    672
Ile Val Thr Val Leu Arg Tyr Cys Ser Arg Pro His Glu Tyr Ile Val
    210                 215                 220 cag tgc gcc ccc ttc gag atg gac gaa ctg tcc ctg gtg ctt gcc gat    720
Gln Cys Ala Pro Phe Glu Met Asp Glu Leu Ser Leu Val Leu Ala Asp
225                 230                 235                 240 gtg ctc aac aca cac aag tcc ttt tta ttg gac cac cgc tac gat ccc    768
Val Leu Asn Thr His Lys Ser Phe Leu Leu Asp His Arg Tyr Asp Pro
                245                 250                 255 tac gaa atc tac ggc aca gac cag ttt atg gac gaa ctg aaa gac ata    816
Tyr Glu Ile Tyr Gly Thr Asp Gln Phe Met Asp Glu Leu Lys Asp Ile
            260                 265                 270 ccc gat ccc aag gtg gac ccc ctg aac gtc atc aac tca cta ctg gtc    864
Pro Asp Pro Lys Val Asp Pro Leu Asn Val Ile Asn Ser Leu Leu Val
        275                 280                 285 gtg ctg cac gag atg ggt cct tgg tgc acg cag cgg gct gca cat cac    912
Val Leu His Glu Met Gly Pro Trp Cys Thr Gln Arg Ala Ala His His
    290                 295                 300 ttt tac caa tgc aat gag aag tta aag gtg aag acg ccg cac gaa cgt    960
```

```
             Phe Tyr Gln Cys Asn Glu Lys Leu Lys Val Lys Thr Pro His Glu Arg
             305                 310                 315                 320 cac tac ttg ctg tac tgc cta gtg agc acg gcc ctt atc caa ctg tac          1008
His Tyr Leu Leu Tyr Cys Leu Val Ser Thr Ala Leu Ile Gln Leu Tyr
                    325                 330                 335 tcc ctc tgc gaa cac gca ttc cat cga cat tta gga agt ggc agc gat          1056
Ser Leu Cys Glu His Ala Phe His Arg His Leu Gly Ser Gly Ser Asp
                340                 345                 350 tca cgc cag acc atc gaa cgc tat tcc agc ccc aag gtg cga cgt ctg          1104
Ser Arg Gln Thr Ile Glu Arg Tyr Ser Ser Pro Lys Val Arg Arg Leu
            355                 360                 365 ttg cag aca ctg agg tgc ttc aag ccg gaa gag gtg cac acc caa gcg          1152
Leu Gln Thr Leu Arg Cys Phe Lys Pro Glu Glu Val His Thr Gln Ala
        370                 375                 380 gac gga ctg cgc aga atg cgg cat cag gtg gat cag gcg gac ttc aat          1200
Asp Gly Leu Arg Arg Met Arg His Gln Val Asp Gln Ala Asp Phe Asn
    385                 390                 395                 400 cgg tta tct cat acg ctg gaa agc aag tgc cga atg gtg gat caa atg          1248
Arg Leu Ser His Thr Leu Glu Ser Lys Cys Arg Met Val Asp Gln Met
                    405                 410                 415 gac caa ccg ccg acg gag aca cga gcc ctg gtg gcc act ctt gag cag          1296
Asp Gln Pro Pro Thr Glu Thr Arg Ala Leu Val Ala Thr Leu Glu Gln
                420                 425                 430 att ctg cac acg aca gag gac agg cag acg aac aga agc gcc gct cgg          1344
Ile Leu His Thr Thr Glu Asp Arg Gln Thr Asn Arg Ser Ala Ala Arg
            435                 440                 445 gtg act cct act cct act ccc gct cat gcg aag ccg aaa cct agc tct          1392
Val Thr Pro Thr Pro Thr Pro Ala His Ala Lys Pro Lys Pro Ser Ser
        450                 455                 460 ggt gcc aac act gca caa cca cga act cgt aga cgt gtg tac acc agg          1440
Gly Ala Asn Thr Ala Gln Pro Arg Thr Arg Arg Val Tyr Thr Arg
    465                 470                 475                 480 cgc cac cac cgg gat cac aat gat ggc agc gac acg ctc tgc gca ctg          1488
Arg His His Arg Asp His Asn Asp Gly Ser Asp Thr Leu Cys Ala Leu
                    485                 490                 495 att tac tgc aac cag aac cac acg gct cgc gtg ctc ttt gag ctt cta          1536
Ile Tyr Cys Asn Gln Asn His Thr Ala Arg Val Leu Phe Glu Leu Leu
                500                 505                 510 gcg gag att agc aga cgt gat ccc gat ctc aag ttc cta cgc tgc cag          1584
Ala Glu Ile Ser Arg Arg Asp Pro Asp Leu Lys Phe Leu Arg Cys Gln
            515                 520                 525 tac acc acg gac cgg gtg gca gat ccc acc acg gag ccc aaa gag gct          1632
Tyr Thr Thr Asp Arg Val Ala Asp Pro Thr Thr Glu Pro Lys Glu Ala
        530                 535                 540 gag ttg gag cac cgg cgg cag gaa gag gtg cta aag cgc ttc cgc atg          1680
Glu Leu Glu His Arg Arg Gln Glu Glu Val Leu Lys Arg Phe Arg Met
545                 550                 555                 560 cat gac tgc aat gtc ctg atc ggt act tcg gtg ctg gaa gag ggc atc          1728
His Asp Cys Asn Val Leu Ile Gly Thr Ser Val Leu Glu Glu Gly Ile
                    565                 570                 575 gat gtg ccc aag tgc aat ttg gtt gtg cgc tgg gat ccg cca acc aca          1776
Asp Val Pro Lys Cys Asn Leu Val Val Arg Trp Asp Pro Pro Thr Thr
                580                 585                 590 tat cgc agt tac gtt cag tgc aaa ggt cga gcc cgt gct gct cca gcc          1824
Tyr Arg Ser Tyr Val Gln Cys Lys Gly Arg Ala Arg Ala Ala Pro Ala
            595                 600                 605 tat cat gtc att ctc gtc gct ccg agt tat aaa agc cca act gtg ggg          1872
Tyr His Val Ile Leu Val Ala Pro Ser Tyr Lys Ser Pro Thr Val Gly
        610                 615                 620 tca gtg cag ctg acc gat cgg agt cat cgg tat att tgc gcg act ggt          1920
```

```
Ser Val Gln Leu Thr Asp Arg Ser His Arg Tyr Ile Cys Ala Thr Gly
625                 630                 635                 640 gat act aca gag gcg gac agc gac tct gat gat tca gcg atg cca aac    1968
Asp Thr Thr Glu Ala Asp Ser Asp Ser Asp Asp Ser Ala Met Pro Asn
                    645                 650                 655 tcg tcc ggc tcg gat ccc tat act ttt ggc acg gca cgc gga acc gtg    2016
Ser Ser Gly Ser Asp Pro Tyr Thr Phe Gly Thr Ala Arg Gly Thr Val
660                 665                 670 aag atc ctc aac ccc gaa gtg ttc agt aaa caa cca ccg aca gcg tgc    2064
Lys Ile Leu Asn Pro Glu Val Phe Ser Lys Gln Pro Pro Thr Ala Cys
            675                 680                 685 gac att aag ctg cag gag atc cag gac gaa ttg cca gcc gca gcg cag    2112
Asp Ile Lys Leu Gln Glu Ile Gln Asp Glu Leu Pro Ala Ala Ala Gln
        690                 695                 700 ctg gat acg agc aac tcc agc gac gaa gcc gtc agc atg agt aac acg    2160
Leu Asp Thr Ser Asn Ser Ser Asp Glu Ala Val Ser Met Ser Asn Thr
705                 710                 715                 720 tct cca agc gag agc agt aca gaa caa aaa tcc aga cgc ttc cag tgc    2208
Ser Pro Ser Glu Ser Ser Thr Glu Gln Lys Ser Arg Arg Phe Gln Cys
                725                 730                 735 gag ctg agc tct tta acg gag cca gaa gac aca agt gat act aca gcc    2256
Glu Leu Ser Ser Leu Thr Glu Pro Glu Asp Thr Ser Asp Thr Thr Ala
            740                 745                 750 gaa atc gat act gct cat agt tta gcc agc acc acg aag gac ttg gtg    2304
Glu Ile Asp Thr Ala His Ser Leu Ala Ser Thr Thr Lys Asp Leu Val
        755                 760                 765 cat caa atg gca cag tat cgc gaa atc gag cag atg ctg cta tcc aag    2352
His Gln Met Ala Gln Tyr Arg Glu Ile Glu Gln Met Leu Leu Ser Lys
770                 775                 780 tgc gcc aac aca gag ccg ccg gag cag gag cag agt gag gcg gaa cgt    2400
Cys Ala Asn Thr Glu Pro Pro Glu Gln Glu Gln Ser Glu Ala Glu Arg
785                 790                 795                 800 ttt agt gcc tgc ctg gcc gca tac cga ccc aag ccg cac ctg cta aca    2448
Phe Ser Ala Cys Leu Ala Ala Tyr Arg Pro Lys Pro His Leu Leu Thr
                805                 810                 815 ggc gcc tcc gtg gat ctg ggt tct gct ata gct ttg gtc aac aag tac    2496
Gly Ala Ser Val Asp Leu Gly Ser Ala Ile Ala Leu Val Asn Lys Tyr
            820                 825                 830 tgc gcc cga ctg cca agc gac acg ttc acc aag ttg acg gcg ttg tgg    2544
Cys Ala Arg Leu Pro Ser Asp Thr Phe Thr Lys Leu Thr Ala Leu Trp
        835                 840                 845 cgc tgc acc cga aac gaa agg gct gga gtg acc ctg ttt cag tac aca    2592
Arg Cys Thr Arg Asn Glu Arg Ala Gly Val Thr Leu Phe Gln Tyr Thr
850                 855                 860 ctc cgt ctg ccc atc aac tcg cca ttg aag cat gac att gtg ggt ctt    2640
Leu Arg Leu Pro Ile Asn Ser Pro Leu Lys His Asp Ile Val Gly Leu
865                 870                 875                 880 ccg atg cca act caa aca ttg gcc cgc cga ctg gct gcc ttg cag gct    2688
Pro Met Pro Thr Gln Thr Leu Ala Arg Arg Leu Ala Ala Leu Gln Ala
                885                 890                 895 tgc gtg gaa ctg cac agg atc ggt gag tta gac gat cag ttg cag cct    2736
Cys Val Glu Leu His Arg Ile Gly Glu Leu Asp Asp Gln Leu Gln Pro
            900                 905                 910 atc ggc aag gag gga ttt cgt gcc ctg gag ccg gac tgg gag tgc ttt    2784
Ile Gly Lys Glu Gly Phe Arg Ala Leu Glu Pro Asp Trp Glu Cys Phe
        915                 920                 925 gaa ctg gag cca gag gac gaa cag att gtg cag cta agc gat gaa cca    2832
Glu Leu Glu Pro Glu Asp Glu Gln Ile Val Gln Leu Ser Asp Glu Pro
930                 935                 940 cgt ccg gga aca acg aag cgt cgt cag tac tat tac aaa cgc att gca    2880
```

-continued

| | | |
|---|---|---|
| Arg Pro Gly Thr Thr Lys Arg Arg Gln Tyr Tyr Tyr Lys Arg Ile Ala<br>945                          950                     955                     960 | |

```
tcc gaa ttt tgc gat tgc cgt ccc gtt gcc gga gcg cca tgc tat ttg     2928
Ser Glu Phe Cys Asp Cys Arg Pro Val Ala Gly Ala Pro Cys Tyr Leu
            965                 970                 975 tac ttt atc caa ctg acg ctc caa tgt ccg att ccc gaa gag caa aac     2976
Tyr Phe Ile Gln Leu Thr Leu Gln Cys Pro Ile Pro Glu Glu Gln Asn
        980                 985                 990 acg cgg gga cgc aag att tat ccg ccc gaa gat gcg cag cag gga ttc     3024
Thr Arg Gly Arg Lys Ile Tyr Pro Pro Glu Asp Ala Gln Gln Gly Phe
    995                 1000                1005 ggc att cta acc acc aaa cgg ata ccc aag ctg agt gct ttc tcg         3069
Gly Ile Leu Thr Thr Lys Arg Ile Pro Lys Leu Ser Ala Phe Ser
    1010            1015            1020 ata ttc acg cgt tcc ggt gag gtg aag gtt tcc ctg gag tta gct         3114
Ile Phe Thr Arg Ser Gly Glu Val Lys Val Ser Leu Glu Leu Ala
    1025            1030            1035 aag gaa cgc gtg att cta act agc gaa caa ata gtc tgc atc aac         3159
Lys Glu Arg Val Ile Leu Thr Ser Glu Gln Ile Val Cys Ile Asn
    1040            1045            1050 gga ttt tta aac tac acg ttc acc aat gta ctg cgt ttg caa aag         3204
Gly Phe Leu Asn Tyr Thr Phe Thr Asn Val Leu Arg Leu Gln Lys
    1055            1060            1065 ttt ctg atg ctc ttc gat ccg gac tcc acg gaa aat tgt gta ttc         3249
Phe Leu Met Leu Phe Asp Pro Asp Ser Thr Glu Asn Cys Val Phe
    1070            1075            1080 att gtg ccc acc gtg aag gca cca gct ggc ggc aag cac atc gac         3294
Ile Val Pro Thr Val Lys Ala Pro Ala Gly Gly Lys His Ile Asp
    1085            1090            1095 tgg cag ttt ctg gag ctg atc caa gcg aat gga aat aca atg cca         3339
Trp Gln Phe Leu Glu Leu Ile Gln Ala Asn Gly Asn Thr Met Pro
    1100            1105            1110 cgg gca gtg ccc gat gag gag cgc cag gcg cag ccg ttt gat ccg         3384
Arg Ala Val Pro Asp Glu Glu Arg Gln Ala Gln Pro Phe Asp Pro
    1115            1120            1125 caa cgc ttc cag gat gcc gtc gtt atg ccg tgg tat cgc aac cag         3429
Gln Arg Phe Gln Asp Ala Val Val Met Pro Trp Tyr Arg Asn Gln
    1130            1135            1140 gat caa ccg cag tat ttc tat gtg gcg gag ata tgt cca cat cta         3474
Asp Gln Pro Gln Tyr Phe Tyr Val Ala Glu Ile Cys Pro His Leu
    1145            1150            1155 tcc cca ctc agc tgc ttc cct ggt gac aac tac cgc acg ttc aag         3519
Ser Pro Leu Ser Cys Phe Pro Gly Asp Asn Tyr Arg Thr Phe Lys
    1160            1165            1170 cac tac tac ctc gtc aag tat ggt ctg acc ata cag aat acc tcg         3564
His Tyr Tyr Leu Val Lys Tyr Gly Leu Thr Ile Gln Asn Thr Ser
    1175            1180            1185 cag ccg cta ttg gac gtg gat cac acc agt gcg cgg tta aac ttc         3609
Gln Pro Leu Leu Asp Val Asp His Thr Ser Ala Arg Leu Asn Phe
    1190            1195            1200 ctc acg cca cga tac gtt aat cgc aag ggc gtt gct ctg ccc act         3654
Leu Thr Pro Arg Tyr Val Asn Arg Lys Gly Val Ala Leu Pro Thr
    1205            1210            1215 agt tcg gag gag aca aag cgg gca aag cgc gag aat ctc gaa cag         3699
Ser Ser Glu Glu Thr Lys Arg Ala Lys Arg Glu Asn Leu Glu Gln
    1220            1225            1230 aag cag atc ctt gtg cca gag ctc tgc act gtg cat cca ttc ccc         3744
Lys Gln Ile Leu Val Pro Glu Leu Cys Thr Val His Pro Phe Pro
    1235            1240            1245 gcc tcc ttg tgg cga act gcc gtg tgc ctg ccc tgc atc ctg tac         3789
```

```
Ala Ser Leu Trp Arg Thr Ala Val Cys Leu Pro Cys Ile Leu Tyr
    1250            1255            1260 cgc ata aat ggt ctt cta ttg gcc gac gat att cgg aaa cag gtt           3834
Arg Ile Asn Gly Leu Leu Leu Ala Asp Asp Ile Arg Lys Gln Val
    1265            1270            1275 tct gcg gat ctg ggg ctg gga agg caa cag atc gaa gat gag gat           3879
Ser Ala Asp Leu Gly Leu Gly Arg Gln Gln Ile Glu Asp Glu Asp
    1280            1285            1290 ttc gag tgg ccc atg ctg gac ttt ggg tgg agt cta tcg gag gtg           3924
Phe Glu Trp Pro Met Leu Asp Phe Gly Trp Ser Leu Ser Glu Val
    1295            1300            1305 ctc aag aaa tcg cgg gag tcc aaa caa aag gag tcc ctt aag gat           3969
Leu Lys Lys Ser Arg Glu Ser Lys Gln Lys Glu Ser Leu Lys Asp
    1310            1315            1320 gat act att aat ggc aaa gac tta gct gat gtt gaa aag aaa ccg           4014
Asp Thr Ile Asn Gly Lys Asp Leu Ala Asp Val Glu Lys Lys Pro
    1325            1330            1335 act agc gag gag acc caa cta gat aag gat tca aaa gac gat aag           4059
Thr Ser Glu Glu Thr Gln Leu Asp Lys Asp Ser Lys Asp Asp Lys
    1340            1345            1350 gtt gag aaa agt gct att gaa cta atc att gag gga gag gag aag           4104
Val Glu Lys Ser Ala Ile Glu Leu Ile Ile Glu Gly Glu Glu Lys
    1355            1360            1365 ctg caa gag gct gat gac ttc att gag ata ggc act tgg tca aac           4149
Leu Gln Glu Ala Asp Asp Phe Ile Glu Ile Gly Thr Trp Ser Asn
    1370            1375            1380 gat atg gcc gac gat ata gct agt ttt aac caa gaa gac gac gac           4194
Asp Met Ala Asp Asp Ile Ala Ser Phe Asn Gln Glu Asp Asp Asp
    1385            1390            1395 gag gat gac gcc ttc cat ctc cca gtt tta ccg gca aac gtt aag           4239
Glu Asp Asp Ala Phe His Leu Pro Val Leu Pro Ala Asn Val Lys
    1400            1405            1410 ttc tgt gat cag caa acg cgc tac ggt tcg ccc aca ttt tgg gat           4284
Phe Cys Asp Gln Gln Thr Arg Tyr Gly Ser Pro Thr Phe Trp Asp
    1415            1420            1425 gtg agc aat ggc gaa agc ggc ttc aag ggt cca aag agc agt cag           4329
Val Ser Asn Gly Glu Ser Gly Phe Lys Gly Pro Lys Ser Ser Gln
    1430            1435            1440 aat aag cag ggt ggc aag ggc aaa gca aag ggt ccg gca aag ccc           4374
Asn Lys Gln Gly Gly Lys Gly Lys Ala Lys Gly Pro Ala Lys Pro
    1445            1450            1455 aca ttt aac tat tat gac tcg gac aat tcg ctg ggt tcc agc tac           4419
Thr Phe Asn Tyr Tyr Asp Ser Asp Asn Ser Leu Gly Ser Ser Tyr
    1460            1465            1470 gat gac gac gat aac gca ggt ccg ctc aat tac atg cat cac aac           4464
Asp Asp Asp Asp Asn Ala Gly Pro Leu Asn Tyr Met His His Asn
    1475            1480            1485 tac agt tcg gat gac gac gat gtg gca gat gat atc gat gcg gga           4509
Tyr Ser Ser Asp Asp Asp Asp Val Ala Asp Asp Ile Asp Ala Gly
    1490            1495            1500 cgc att gcg ttc acc tcc aag aat gaa gcg gag act att gaa acc           4554
Arg Ile Ala Phe Thr Ser Lys Asn Glu Ala Glu Thr Ile Glu Thr
    1505            1510            1515 gca cag gaa gtg gaa aag cgc cag aag cag ctg tcc atc atc cag           4599
Ala Gln Glu Val Glu Lys Arg Gln Lys Gln Leu Ser Ile Ile Gln
    1520            1525            1530 gcg acc aat gct aac gag cgg cag tat cag cag aca aag aac ctg           4644
Ala Thr Asn Ala Asn Glu Arg Gln Tyr Gln Gln Thr Lys Asn Leu
    1535            1540            1545 ctc att gga ttc aat ttt aag cat gag gac cag aag gaa cct gcc           4689
```

|     |     |     |     |     |     |     |     |     |     |     |     |      |
|---|---|---|---|---|---|---|---|---|---|---|---|---|
| Leu | Ile | Gly | Phe | Asn | Phe | Lys | His | Glu | Asp | Gln | Lys | |
|     | 1550 |     |     |     | 1555 |     |     |     | 1560 |     |     | |
| Glu | Pro | Ala |     |     |     |     |     |     |     |     |     | |
| act | ata | aga | tat | gaa | gaa | tcc | ata | gct | aag | ctc | aaa | 4734 |
| Thr | Ile | Arg | Tyr | Glu | Glu | Ser | Ile | Ala | Lys | Leu | Lys | |
|     | 1565 |     |     |     | 1570 |     |     |     | 1575 |     |     | |
| acg | gaa | ata | | | | | | | | | | |
| Thr | Glu | Ile | | | | | | | | | | |
| gaa | tcc | ggc | ggc | atg | ttg | gtg | ccg | cac | gac | cag | cag | 4779 |
| Glu | Ser | Gly | Gly | Met | Leu | Val | Pro | His | Asp | Gln | Gln | |
|     | 1580 |     |     |     | 1585 |     |     |     | 1590 |     |     | |
| ttg | gtt | cta | | | | | | | | | | |
| Leu | Val | Leu | | | | | | | | | | |
| aaa | aga | agt | gat | gcc | gct | gag | gct | cag | gtt | gca | aag | 4824 |
| Lys | Arg | Ser | Asp | Ala | Ala | Glu | Ala | Gln | Val | Ala | Lys | |
|     | 1595 |     |     |     | 1600 |     |     |     | 1605 |     |     | |
| gta | tcg | atg | | | | | | | | | | |
| Val | Ser | Met | | | | | | | | | | |
| atg | gag | cta | ttg | aag | cag | ctg | ctg | ccg | tat | gta | aat | 4869 |
| Met | Glu | Leu | Leu | Lys | Gln | Leu | Leu | Pro | Tyr | Val | Asn | |
|     | 1610 |     |     |     | 1615 |     |     |     | 1620 |     |     | |
| gaa | gat | gtg | | | | | | | | | | |
| Glu | Asp | Val | | | | | | | | | | |
| ctg | gcc | aaa | aag | ctg | ggt | gat | agg | cgc | gag | ctt | ctg | 4914 |
| Leu | Ala | Lys | Lys | Leu | Gly | Asp | Arg | Arg | Glu | Leu | Leu | |
|     | 1625 |     |     |     | 1630 |     |     |     | 1635 |     |     | |
| ctg | tcg | gat | | | | | | | | | | |
| Leu | Ser | Asp | | | | | | | | | | |
| ttg | gta | gag | cta | aat | gca | gat | tgg | gta | gcg | cga | cat | 4959 |
| Leu | Val | Glu | Leu | Asn | Ala | Asp | Trp | Val | Ala | Arg | His | |
|     | 1640 |     |     |     | 1645 |     |     |     | 1650 |     |     | |
| gag | cag | gag | | | | | | | | | | |
| Glu | Gln | Glu | | | | | | | | | | |
| acc | tac | aat | gta | atg | gga | tgc | gga | gat | agt | ttt | gac | 5004 |
| Thr | Tyr | Asn | Val | Met | Gly | Cys | Gly | Asp | Ser | Phe | Asp | |
|     | 1655 |     |     |     | 1660 |     |     |     | 1665 |     |     | |
| aac | tat | aac | | | | | | | | | | |
| Asn | Tyr | Asn | | | | | | | | | | |
| gat | cat | cat | cgg | ctg | aac | ttg | gat | gaa | aag | caa | ctg | 5049 |
| Asp | His | His | Arg | Leu | Asn | Leu | Asp | Glu | Lys | Gln | Leu | |
|     | 1670 |     |     |     | 1675 |     |     |     | 1680 |     |     | |
| aaa | ctg | caa | | | | | | | | | | |
| Lys | Leu | Gln | | | | | | | | | | |
| tac | gaa | cga | att | gaa | att | gag | cca | cct | act | tcc | acg | 5094 |
| Tyr | Glu | Arg | Ile | Glu | Ile | Glu | Pro | Pro | Thr | Ser | Thr | |
|     | 1685 |     |     |     | 1690 |     |     |     | 1695 |     |     | |
| aag | gcc | ata | | | | | | | | | | |
| Lys | Ala | Ile | | | | | | | | | | |
| acc | tca | gcc | ata | tta | cca | gct | ggc | ttc | agt | ttc | gat | 5139 |
| Thr | Ser | Ala | Ile | Leu | Pro | Ala | Gly | Phe | Ser | Phe | Asp | |
|     | 1700 |     |     |     | 1705 |     |     |     | 1710 |     |     | |
| cga | caa | ccg | | | | | | | | | | |
| Arg | Gln | Pro | | | | | | | | | | |
| gat | cta | gtg | ggc | cat | cca | gga | ccc | agt | ccc | agc | atc | 5184 |
| Asp | Leu | Val | Gly | His | Pro | Gly | Pro | Ser | Pro | Ser | Ile | |
|     | 1715 |     |     |     | 1720 |     |     |     | 1725 |     |     | |
| att | ttg | caa | | | | | | | | | | |
| Ile | Leu | Gln | | | | | | | | | | |
| gcc | ctc | aca | atg | tcc | aat | gct | aac | gat | ggc | atc | aat | 5229 |
| Ala | Leu | Thr | Met | Ser | Asn | Ala | Asn | Asp | Gly | Ile | Asn | |
|     | 1730 |     |     |     | 1735 |     |     |     | 1740 |     |     | |
| ctg | gag | cga | | | | | | | | | | |
| Leu | Glu | Arg | | | | | | | | | | |
| ctg | gag | aca | att | gga | gat | tcc | ttt | cta | aag | tat | gcc | 5274 |
| Leu | Glu | Thr | Ile | Gly | Asp | Ser | Phe | Leu | Lys | Tyr | Ala | |
|     | 1745 |     |     |     | 1750 |     |     |     | 1755 |     |     | |
| att | acc | acc | | | | | | | | | | |
| Ile | Thr | Thr | | | | | | | | | | |
| tac | ttg | tac | atc | acc | tac | gag | aat | gtg | cac | gag | gga | 5319 |
| Tyr | Leu | Tyr | Ile | Thr | Tyr | Glu | Asn | Val | His | Glu | Gly | |
|     | 1760 |     |     |     | 1765 |     |     |     | 1770 |     |     | |
| aaa | cta | agt | | | | | | | | | | |
| Lys | Leu | Ser | | | | | | | | | | |
| cac | ctg | cgc | tcc | aag | cag | gtt | gcc | aat | ctc | aat | ctc | 5364 |
| His | Leu | Arg | Ser | Lys | Gln | Val | Ala | Asn | Leu | Asn | Leu | |
|     | 1775 |     |     |     | 1780 |     |     |     | 1785 |     |     | |
| tat | cgt | ctg | | | | | | | | | | |
| Tyr | Arg | Leu | | | | | | | | | | |
| ggc | aga | cgt | aag | aga | ctg | ggt | gaa | tat | atg | ata | gcc | 5409 |
| Gly | Arg | Arg | Lys | Arg | Leu | Gly | Glu | Tyr | Met | Ile | Ala | |
|     | 1790 |     |     |     | 1795 |     |     |     | 1800 |     |     | |
| act | aaa | ttc | | | | | | | | | | |
| Thr | Lys | Phe | | | | | | | | | | |
| gag | ccg | cac | gac | aat | tgg | ctg | cca | ccc | tgc | tac | tac | 5454 |
| Glu | Pro | His | Asp | Asn | Trp | Leu | Pro | Pro | Cys | Tyr | Tyr | |
|     | 1805 |     |     |     | 1810 |     |     |     | 1815 |     |     | |
| gtg | cca | aag | | | | | | | | | | |
| Val | Pro | Lys | | | | | | | | | | |
| gag | cta | gag | aag | gcg | ctc | atc | gag | gcg | aag | atc | ccc | 5499 |
| Glu | Leu | Glu | Lys | Ala | Leu | Ile | Glu | Ala | Lys | Ile | Pro | |
|     | 1820 |     |     |     | 1825 |     |     |     | 1830 |     |     | |
| act | cac | cat | | | | | | | | | | |
| Thr | His | His | | | | | | | | | | |
| tgg | aag | ctg | gcc | gat | ctg | cta | gac | att | aag | aac | cta | 5544 |
| Trp | Lys | Leu | Ala | Asp | Leu | Leu | Asp | Ile | Lys | Asn | Leu | |
|     | 1835 |     |     |     | 1840 |     |     |     | 1845 |     |     | |
| agc | agt | gtg | | | | | | | | | | |
| Ser | Ser | Val | | | | | | | | | | |
| caa | atc | tgc | gag | atg | gtt | cgc | gaa | aaa | gcc | gat | gcc | 5589 |
| Gln | Ile | Cys | Glu | Met | Val | Arg | Glu | Lys | Ala | Asp | Ala | |
| ctg | ggc | ttg | | | | | | | | | | |
| Leu | Gly | Leu | | | | | | | | | | |

```
                Gln Ile Cys Glu Met Val Arg Glu Lys Ala Asp Ala Leu Gly Leu
                    1850            1855            1860 gag cag aat ggg ggt gcc caa aat gga caa ctt gac gac tcc aat              5634
Glu Gln Asn Gly Gly Ala Gln Asn Gly Gln Leu Asp Asp Ser Asn
            1865            1870            1875 gat agc tgc aat gat ttt agc tgt ttt att ccc tac aac ctt gtt              5679
Asp Ser Cys Asn Asp Phe Ser Cys Phe Ile Pro Tyr Asn Leu Val
1880            1885            1890 tcg caa cac agc att ccg gat aag tct att gcc gat tgc gtc gaa              5724
Ser Gln His Ser Ile Pro Asp Lys Ser Ile Ala Asp Cys Val Glu
        1895            1900            1905 gcc ctc att gga gcc tat ctc att gag tgc gga ccc cga ggg gct              5769
Ala Leu Ile Gly Ala Tyr Leu Ile Glu Cys Gly Pro Arg Gly Ala
    1910            1915            1920 tta ctc ttt atg gcc tgg ctg ggc gtg aga gtg ctc cct atc aca              5814
Leu Leu Phe Met Ala Trp Leu Gly Val Arg Val Leu Pro Ile Thr
1925            1930            1935 agg cag ttg gac ggg ggt aac cag gag caa cga ata ccc ggt agc              5859
Arg Gln Leu Asp Gly Gly Asn Gln Glu Gln Arg Ile Pro Gly Ser
        1940            1945            1950 aca aaa ccg aat gcc gaa aat gtg gtc acc gtt tac ggt gca tgg              5904
Thr Lys Pro Asn Ala Glu Asn Val Val Thr Val Tyr Gly Ala Trp
    1955            1960            1965 ccc acg ccg cgt agt cca ctg ctg cac ttt gct cca aat gct acg              5949
Pro Thr Pro Arg Ser Pro Leu Leu His Phe Ala Pro Asn Ala Thr
1970            1975            1980 gag gag ctg gac cag tta cta agc ggc ttt gag gag ttt gag gag              5994
Glu Glu Leu Asp Gln Leu Leu Ser Gly Phe Glu Glu Phe Glu Glu
        1985            1990            1995 agt ttg gga tac aag ttc cgg gat cgg tcg tac ctg ttg caa gcc              6039
Ser Leu Gly Tyr Lys Phe Arg Asp Arg Ser Tyr Leu Leu Gln Ala
    2000            2005            2010 atg aca cat gcc agt tac acg ccc aat cga ttg acg gat tgc tat              6084
Met Thr His Ala Ser Tyr Thr Pro Asn Arg Leu Thr Asp Cys Tyr
2015            2020            2025 cag cgt ctg gag ttc ctg ggc gat gct gtt cta gat tac ctc att              6129
Gln Arg Leu Glu Phe Leu Gly Asp Ala Val Leu Asp Tyr Leu Ile
        2030            2035            2040 acg cgg cat tta tac gaa gat ccc cgc cag cat tct cca ggc gca              6174
Thr Arg His Leu Tyr Glu Asp Pro Arg Gln His Ser Pro Gly Ala
    2045            2050            2055 tta acg gat ttg cgg tca gca ctg gtg aat aat aca ata ttc gcc              6219
Leu Thr Asp Leu Arg Ser Ala Leu Val Asn Asn Thr Ile Phe Ala
2060            2065            2070 tcc ctg gct gtt cgc cat ggc ttc cac aag ttc ttc cgg cac ctc              6264
Ser Leu Ala Val Arg His Gly Phe His Lys Phe Phe Arg His Leu
        2075            2080            2085 tcg ccg ggc ctt aac gat gtg att gac cgt ttt gtg cgg atc cag              6309
Ser Pro Gly Leu Asn Asp Val Ile Asp Arg Phe Val Arg Ile Gln
    2090            2095            2100 cag gag aat gga cac tgc atc agt gag gag tac tac tta ttg tcc              6354
Gln Glu Asn Gly His Cys Ile Ser Glu Glu Tyr Tyr Leu Leu Ser
2105            2110            2115 gag gag gag tgc gat gac gcc gag gac gtt gag gtg ccc aag gca              6399
Glu Glu Glu Cys Asp Asp Ala Glu Asp Val Glu Val Pro Lys Ala
        2120            2125            2130 ttg ggc gac gtt ttc gag tcg atc gca ggt gcc att ttt ctc gac              6444
Leu Gly Asp Val Phe Glu Ser Ile Ala Gly Ala Ile Phe Leu Asp
    2135            2140            2145 tca aac atg tcg ctg gac gtg gtt tgg cac gta tat agc aac atg              6489
```

-continued

```
Ser Asn Met Ser Leu Asp Val Val Trp His Val Tyr Ser Asn Met
    2150                2155                2160 atg agc ccg gag atc gag cag ttc agc aac tca gtg cca aaa tcg      6534
Met Ser Pro Glu Ile Glu Gln Phe Ser Asn Ser Val Pro Lys Ser
    2165                2170                2175 ccc att cgg gag ctc ctc gag ctg gag ccg gaa acc gcc aag ttc      6579
Pro Ile Arg Glu Leu Leu Glu Leu Glu Pro Glu Thr Ala Lys Phe
    2180                2185                2190 ggc aag ccc gag aag ctg gcg gat ggg cga cgg gtg cgc gtt acc      6624
Gly Lys Pro Glu Lys Leu Ala Asp Gly Arg Arg Val Arg Val Thr
    2195                2200                2205 gtg gat gtc ttc tgc aaa gga acc ttc cgt ggc atc gga cgc aac      6669
Val Asp Val Phe Cys Lys Gly Thr Phe Arg Gly Ile Gly Arg Asn
    2210                2215                2220 tat cgc att gcc aag tgc acg gcg gcc aaa tgc gca ttg cgc caa      6714
Tyr Arg Ile Ala Lys Cys Thr Ala Ala Lys Cys Ala Leu Arg Gln
    2225                2230                2235 ctc aaa aag cag ggc ttg ata gcc aaa aaa gac taa                  6750
Leu Lys Lys Gln Gly Leu Ile Ala Lys Lys Asp
    2240                2245
```

<210> SEQ ID NO 4
<211> LENGTH: 2249
<212> TYPE: PRT
<213> ORGANISM: Drosophila melanogaster

<400> SEQUENCE: 4

```
Met Ala Phe His Trp Cys Asp Asn Asn Leu His Thr Thr Val Phe Thr
1               5                   10                  15

Pro Arg Asp Phe Gln Val Glu Leu Leu Ala Thr Ala Tyr Glu Arg Asn
                20                  25                  30

Thr Ile Ile Cys Leu Gly His Arg Ser Ser Lys Glu Phe Ile Ala Leu
            35                  40                  45

Lys Leu Leu Gln Glu Leu Ser Arg Arg Ala Arg Arg His Gly Arg Val
        50                  55                  60

Ser Val Tyr Leu Ser Cys Glu Val Gly Thr Ser Thr Glu Pro Cys Ser
65                  70                  75                  80

Ile Tyr Thr Met Leu Thr His Leu Thr Asp Leu Arg Val Trp Gln Glu
                85                  90                  95

Gln Pro Asp Met Gln Ile Pro Phe Asp His Cys Trp Thr Asp Tyr His
                100                 105                 110

Val Ser Ile Leu Arg Pro Glu Gly Phe Leu Tyr Leu Leu Glu Thr Arg
            115                 120                 125

Glu Leu Leu Leu Ser Ser Val Glu Leu Ile Val Leu Glu Asp Cys His
        130                 135                 140

Asp Ser Ala Val Tyr Gln Arg Ile Arg Pro Leu Phe Glu Asn His Ile
145                 150                 155                 160

Met Pro Ala Pro Ala Asp Arg Pro Arg Ile Leu Gly Leu Ala Gly
                165                 170                 175

Pro Leu His Ser Ala Gly Cys Glu Leu Gln Gln Leu Ser Ala Met Leu
            180                 185                 190

Ala Thr Leu Glu Gln Ser Val Leu Cys Gln Ile Glu Thr Ala Ser Asp
        195                 200                 205

Ile Val Thr Val Leu Arg Tyr Cys Ser Arg Pro His Glu Tyr Ile Val
    210                 215                 220

Gln Cys Ala Pro Phe Glu Met Asp Glu Leu Ser Leu Val Leu Ala Asp
225                 230                 235                 240
```

-continued

```
Val Leu Asn Thr His Lys Ser Phe Leu Leu Asp His Arg Tyr Asp Pro
                245                 250                 255

Tyr Glu Ile Tyr Gly Thr Asp Gln Phe Met Asp Glu Leu Lys Asp Ile
            260                 265                 270

Pro Asp Pro Lys Val Asp Pro Leu Asn Val Ile Asn Ser Leu Leu Val
        275                 280                 285

Val Leu His Glu Met Gly Pro Trp Cys Thr Gln Arg Ala Ala His His
    290                 295                 300

Phe Tyr Gln Cys Asn Glu Lys Leu Lys Val Lys Thr Pro His Glu Arg
305                 310                 315                 320

His Tyr Leu Leu Tyr Cys Leu Val Ser Thr Ala Leu Ile Gln Leu Tyr
                325                 330                 335

Ser Leu Cys Glu His Ala Phe His Arg His Leu Gly Ser Gly Ser Asp
            340                 345                 350

Ser Arg Gln Thr Ile Glu Arg Tyr Ser Ser Pro Lys Val Arg Arg Leu
        355                 360                 365

Leu Gln Thr Leu Arg Cys Phe Lys Pro Glu Glu Val His Thr Gln Ala
    370                 375                 380

Asp Gly Leu Arg Arg Met Arg His Gln Val Asp Gln Ala Asp Phe Asn
385                 390                 395                 400

Arg Leu Ser His Thr Leu Glu Ser Lys Cys Arg Met Val Asp Gln Met
                405                 410                 415

Asp Gln Pro Pro Thr Glu Thr Arg Ala Leu Val Ala Thr Leu Glu Gln
            420                 425                 430

Ile Leu His Thr Thr Glu Asp Arg Gln Thr Asn Arg Ser Ala Ala Arg
        435                 440                 445

Val Thr Pro Thr Pro Thr Pro Ala His Ala Lys Pro Lys Pro Ser Ser
    450                 455                 460

Gly Ala Asn Thr Ala Gln Pro Arg Thr Arg Arg Val Tyr Thr Arg
465                 470                 475                 480

Arg His His Arg Asp His Asn Asp Gly Ser Asp Thr Leu Cys Ala Leu
                485                 490                 495

Ile Tyr Cys Asn Gln Asn His Thr Ala Arg Val Leu Phe Glu Leu Leu
            500                 505                 510

Ala Glu Ile Ser Arg Arg Asp Pro Asp Leu Lys Phe Leu Arg Cys Gln
        515                 520                 525

Tyr Thr Thr Asp Arg Val Ala Asp Pro Thr Thr Glu Pro Lys Glu Ala
    530                 535                 540

Glu Leu Glu His Arg Arg Gln Glu Glu Val Leu Lys Arg Phe Arg Met
545                 550                 555                 560

His Asp Cys Asn Val Leu Ile Gly Thr Ser Val Leu Glu Glu Gly Ile
                565                 570                 575

Asp Val Pro Lys Cys Asn Leu Val Val Arg Trp Asp Pro Pro Thr Thr
            580                 585                 590

Tyr Arg Ser Tyr Val Gln Cys Lys Gly Arg Ala Arg Ala Ala Pro Ala
        595                 600                 605

Tyr His Val Ile Leu Val Ala Pro Ser Tyr Lys Ser Pro Thr Val Gly
    610                 615                 620

Ser Val Gln Leu Thr Asp Arg Ser His Arg Tyr Ile Cys Ala Thr Gly
625                 630                 635                 640

Asp Thr Thr Glu Ala Asp Ser Asp Ser Asp Ser Ala Met Pro Asn
                645                 650                 655

Ser Ser Gly Ser Asp Pro Tyr Thr Phe Gly Thr Ala Arg Gly Thr Val
            660                 665                 670
```

```
Lys Ile Leu Asn Pro Glu Val Phe Ser Lys Gln Pro Thr Ala Cys
        675                 680                 685

Asp Ile Lys Leu Gln Glu Ile Gln Asp Glu Leu Pro Ala Ala Ala Gln
        690                 695                 700

Leu Asp Thr Ser Asn Ser Ser Asp Glu Ala Val Ser Met Ser Asn Thr
705                 710                 715                 720

Ser Pro Ser Glu Ser Ser Thr Glu Gln Lys Ser Arg Arg Phe Gln Cys
        725                 730                 735

Glu Leu Ser Ser Leu Thr Glu Pro Glu Asp Thr Ser Asp Thr Thr Ala
        740                 745                 750

Glu Ile Asp Thr Ala His Ser Leu Ala Ser Thr Thr Lys Asp Leu Val
        755                 760                 765

His Gln Met Ala Gln Tyr Arg Glu Ile Glu Gln Met Leu Leu Ser Lys
        770                 775                 780

Cys Ala Asn Thr Glu Pro Pro Glu Gln Glu Gln Ser Glu Ala Glu Arg
785                 790                 795                 800

Phe Ser Ala Cys Leu Ala Ala Tyr Arg Pro Lys Pro His Leu Leu Thr
        805                 810                 815

Gly Ala Ser Val Asp Leu Gly Ser Ala Ile Ala Leu Val Asn Lys Tyr
        820                 825                 830

Cys Ala Arg Leu Pro Ser Asp Thr Phe Thr Lys Leu Thr Ala Leu Trp
        835                 840                 845

Arg Cys Thr Arg Asn Glu Arg Ala Gly Val Thr Leu Phe Gln Tyr Thr
850                 855                 860

Leu Arg Leu Pro Ile Asn Ser Pro Leu Lys His Asp Ile Val Gly Leu
865                 870                 875                 880

Pro Met Pro Thr Gln Thr Leu Ala Arg Arg Leu Ala Ala Leu Gln Ala
        885                 890                 895

Cys Val Glu Leu His Arg Ile Gly Glu Leu Asp Asp Gln Leu Gln Pro
        900                 905                 910

Ile Gly Lys Glu Gly Phe Arg Ala Leu Glu Pro Asp Trp Glu Cys Phe
        915                 920                 925

Glu Leu Glu Pro Glu Asp Glu Gln Ile Val Gln Leu Ser Asp Glu Pro
        930                 935                 940

Arg Pro Gly Thr Thr Lys Arg Arg Gln Tyr Tyr Tyr Lys Arg Ile Ala
945                 950                 955                 960

Ser Glu Phe Cys Asp Cys Arg Pro Val Ala Gly Ala Pro Cys Tyr Leu
        965                 970                 975

Tyr Phe Ile Gln Leu Thr Leu Gln Cys Pro Ile Pro Glu Glu Gln Asn
        980                 985                 990

Thr Arg Gly Arg Lys Ile Tyr Pro Pro Glu Asp Ala Gln Gln Gly Phe
        995                 1000                1005

Gly Ile Leu Thr Thr Lys Arg Ile Pro Lys Leu Ser Ala Phe Ser
        1010                1015                1020

Ile Phe Thr Arg Ser Gly Glu Val Lys Val Ser Leu Glu Leu Ala
        1025                1030                1035

Lys Glu Arg Val Ile Leu Thr Ser Glu Gln Ile Val Cys Ile Asn
        1040                1045                1050

Gly Phe Leu Asn Tyr Thr Phe Thr Asn Val Leu Arg Leu Gln Lys
        1055                1060                1065

Phe Leu Met Leu Phe Asp Pro Asp Ser Thr Glu Asn Cys Val Phe
        1070                1075                1080

Ile Val Pro Thr Val Lys Ala Pro Ala Gly Gly Lys His Ile Asp
```

-continued

```
                1085                1090                1095
Trp Gln Phe Leu Glu Leu Ile Gln Ala Asn Gly Asn Thr Met Pro
            1100                1105                1110
Arg Ala Val Pro Asp Glu Glu Arg Gln Ala Gln Pro Phe Asp Pro
            1115                1120                1125
Gln Arg Phe Gln Asp Ala Val Val Met Pro Trp Tyr Arg Asn Gln
            1130                1135                1140
Asp Gln Pro Gln Tyr Phe Tyr Val Ala Glu Ile Cys Pro His Leu
            1145                1150                1155
Ser Pro Leu Ser Cys Phe Pro Gly Asp Asn Tyr Arg Thr Phe Lys
            1160                1165                1170
His Tyr Tyr Leu Val Lys Tyr Gly Leu Thr Ile Gln Asn Thr Ser
            1175                1180                1185
Gln Pro Leu Leu Asp Val Asp His Thr Ser Ala Arg Leu Asn Phe
            1190                1195                1200
Leu Thr Pro Arg Tyr Val Asn Arg Lys Gly Val Ala Leu Pro Thr
            1205                1210                1215
Ser Ser Glu Glu Thr Lys Arg Ala Lys Arg Glu Asn Leu Glu Gln
            1220                1225                1230
Lys Gln Ile Leu Val Pro Glu Leu Cys Thr Val His Pro Phe Pro
            1235                1240                1245
Ala Ser Leu Trp Arg Thr Ala Val Cys Leu Pro Cys Ile Leu Tyr
            1250                1255                1260
Arg Ile Asn Gly Leu Leu Leu Ala Asp Asp Ile Arg Lys Gln Val
            1265                1270                1275
Ser Ala Asp Leu Gly Leu Gly Arg Gln Gln Ile Glu Asp Glu Asp
            1280                1285                1290
Phe Glu Trp Pro Met Leu Asp Phe Gly Trp Ser Leu Ser Glu Val
            1295                1300                1305
Leu Lys Lys Ser Arg Glu Ser Lys Gln Lys Glu Ser Leu Lys Asp
            1310                1315                1320
Asp Thr Ile Asn Gly Lys Asp Leu Ala Asp Val Glu Lys Lys Pro
            1325                1330                1335
Thr Ser Glu Glu Thr Gln Leu Asp Lys Asp Ser Lys Asp Asp Lys
            1340                1345                1350
Val Glu Lys Ser Ala Ile Glu Leu Ile Ile Glu Gly Glu Glu Lys
            1355                1360                1365
Leu Gln Glu Ala Asp Asp Phe Ile Glu Ile Gly Thr Trp Ser Asn
            1370                1375                1380
Asp Met Ala Asp Asp Ile Ala Ser Phe Asn Gln Glu Asp Asp Asp
            1385                1390                1395
Glu Asp Asp Ala Phe His Leu Pro Val Leu Pro Ala Asn Val Lys
            1400                1405                1410
Phe Cys Asp Gln Gln Thr Arg Tyr Gly Ser Pro Thr Phe Trp Asp
            1415                1420                1425
Val Ser Asn Gly Glu Ser Gly Phe Lys Gly Pro Lys Ser Ser Gln
            1430                1435                1440
Asn Lys Gln Gly Gly Lys Gly Lys Ala Lys Gly Pro Ala Lys Pro
            1445                1450                1455
Thr Phe Asn Tyr Tyr Asp Ser Asp Asn Ser Leu Gly Ser Ser Tyr
            1460                1465                1470
Asp Asp Asp Asp Asn Ala Gly Pro Leu Asn Tyr Met His His Asn
            1475                1480                1485
```

```
Tyr Ser Ser Asp Asp Asp Val Ala Asp Ile Asp Ala Gly
    1490            1495            1500

Arg Ile Ala Phe Thr Ser Lys Asn Glu Ala Glu Thr Ile Glu Thr
    1505            1510            1515

Ala Gln Glu Val Glu Lys Arg Gln Lys Gln Leu Ser Ile Ile Gln
    1520            1525            1530

Ala Thr Asn Ala Asn Glu Arg Gln Tyr Gln Gln Thr Lys Asn Leu
    1535            1540            1545

Leu Ile Gly Phe Asn Phe Lys His Glu Asp Gln Lys Glu Pro Ala
    1550            1555            1560

Thr Ile Arg Tyr Glu Glu Ser Ile Ala Lys Leu Lys Thr Glu Ile
    1565            1570            1575

Glu Ser Gly Gly Met Leu Val Pro His Asp Gln Gln Leu Val Leu
    1580            1585            1590

Lys Arg Ser Asp Ala Ala Glu Ala Gln Val Ala Lys Val Ser Met
    1595            1600            1605

Met Glu Leu Leu Lys Gln Leu Leu Pro Tyr Val Asn Glu Asp Val
    1610            1615            1620

Leu Ala Lys Lys Leu Gly Asp Arg Arg Glu Leu Leu Leu Ser Asp
    1625            1630            1635

Leu Val Glu Leu Asn Ala Asp Trp Val Ala Arg His Glu Gln Glu
    1640            1645            1650

Thr Tyr Asn Val Met Gly Cys Gly Asp Ser Phe Asp Asn Tyr Asn
    1655            1660            1665

Asp His His Arg Leu Asn Leu Asp Glu Lys Gln Leu Lys Leu Gln
    1670            1675            1680

Tyr Glu Arg Ile Glu Ile Glu Pro Pro Thr Ser Thr Lys Ala Ile
    1685            1690            1695

Thr Ser Ala Ile Leu Pro Ala Gly Phe Ser Phe Asp Arg Gln Pro
    1700            1705            1710

Asp Leu Val Gly His Pro Gly Pro Ser Pro Ser Ile Ile Leu Gln
    1715            1720            1725

Ala Leu Thr Met Ser Asn Ala Asn Asp Gly Ile Asn Leu Glu Arg
    1730            1735            1740

Leu Glu Thr Ile Gly Asp Ser Phe Leu Lys Tyr Ala Ile Thr Thr
    1745            1750            1755

Tyr Leu Tyr Ile Thr Tyr Glu Asn Val His Glu Gly Lys Leu Ser
    1760            1765            1770

His Leu Arg Ser Lys Gln Val Ala Asn Leu Asn Leu Tyr Arg Leu
    1775            1780            1785

Gly Arg Arg Lys Arg Leu Gly Glu Tyr Met Ile Ala Thr Lys Phe
    1790            1795            1800

Glu Pro His Asp Asn Trp Leu Pro Pro Cys Tyr Tyr Val Pro Lys
    1805            1810            1815

Glu Leu Glu Lys Ala Leu Ile Glu Ala Lys Ile Pro Thr His His
    1820            1825            1830

Trp Lys Leu Ala Asp Leu Leu Asp Ile Lys Asn Leu Ser Ser Val
    1835            1840            1845

Gln Ile Cys Glu Met Val Arg Glu Lys Ala Asp Ala Leu Gly Leu
    1850            1855            1860

Glu Gln Asn Gly Gly Ala Gln Asn Gly Gln Leu Asp Asp Ser Asn
    1865            1870            1875

Asp Ser Cys Asn Asp Phe Ser Cys Phe Ile Pro Tyr Asn Leu Val
    1880            1885            1890
```

Ser Gln His Ser Ile Pro Asp Lys Ser Ile Ala Asp Cys Val Glu
1895                1900                1905

Ala Leu Ile Gly Ala Tyr Leu Ile Glu Cys Gly Pro Arg Gly Ala
1910                1915                1920

Leu Leu Phe Met Ala Trp Leu Gly Val Arg Val Leu Pro Ile Thr
1925                1930                1935

Arg Gln Leu Asp Gly Gly Asn Gln Glu Gln Arg Ile Pro Gly Ser
1940                1945                1950

Thr Lys Pro Asn Ala Glu Asn Val Val Thr Val Tyr Gly Ala Trp
1955                1960                1965

Pro Thr Pro Arg Ser Pro Leu Leu His Phe Ala Pro Asn Ala Thr
1970                1975                1980

Glu Glu Leu Asp Gln Leu Leu Ser Gly Phe Glu Glu Phe Glu Glu
1985                1990                1995

Ser Leu Gly Tyr Lys Phe Arg Asp Arg Ser Tyr Leu Leu Gln Ala
2000                2005                2010

Met Thr His Ala Ser Tyr Thr Pro Asn Arg Leu Thr Asp Cys Tyr
2015                2020                2025

Gln Arg Leu Glu Phe Leu Gly Asp Ala Val Leu Asp Tyr Leu Ile
2030                2035                2040

Thr Arg His Leu Tyr Glu Asp Pro Arg Gln His Ser Pro Gly Ala
2045                2050                2055

Leu Thr Asp Leu Arg Ser Ala Leu Val Asn Asn Thr Ile Phe Ala
2060                2065                2070

Ser Leu Ala Val Arg His Gly Phe His Lys Phe Phe Arg His Leu
2075                2080                2085

Ser Pro Gly Leu Asn Asp Val Ile Asp Arg Phe Val Arg Ile Gln
2090                2095                2100

Gln Glu Asn Gly His Cys Ile Ser Glu Glu Tyr Tyr Leu Leu Ser
2105                2110                2115

Glu Glu Glu Cys Asp Asp Ala Glu Asp Val Glu Val Pro Lys Ala
2120                2125                2130

Leu Gly Asp Val Phe Glu Ser Ile Ala Gly Ala Ile Phe Leu Asp
2135                2140                2145

Ser Asn Met Ser Leu Asp Val Val Trp His Val Tyr Ser Asn Met
2150                2155                2160

Met Ser Pro Glu Ile Glu Gln Phe Ser Asn Ser Val Pro Lys Ser
2165                2170                2175

Pro Ile Arg Glu Leu Leu Glu Leu Glu Pro Glu Thr Ala Lys Phe
2180                2185                2190

Gly Lys Pro Glu Lys Leu Ala Asp Gly Arg Val Arg Val Thr
2195                2200                2205

Val Asp Val Phe Cys Lys Gly Thr Phe Arg Gly Ile Gly Arg Asn
2210                2215                2220

Tyr Arg Ile Ala Lys Cys Thr Ala Ala Lys Cys Ala Leu Arg Gln
2225                2230                2235

Leu Lys Lys Gln Gly Leu Ile Ala Lys Lys Asp
2240                2245

<210> SEQ ID NO 5
<211> LENGTH: 1145
<212> TYPE: PRT
<213> ORGANISM: Drosophila melanogaster

<400> SEQUENCE: 5

```
Met Gly Lys Lys Asp Lys Asn Lys Lys Gly Gly Gln Asp Ser Ala Ala
1               5                   10                  15

Ala Pro Gln Pro Gln Gln Gln Lys Gln Gln Gln Arg Gln Gln
            20                  25                  30

Gln Pro Gln Gln Leu Gln Gln Pro Gln Gln Leu Gln Gln Pro Gln Gln
            35                  40                  45

Leu Gln Gln Pro Gln Gln Gln Gln Gln Pro His Gln Gln Gln
50                      55                  60

Gln Gln Ser Ser Arg Gln Gln Pro Ser Thr Ser Ser Gly Gly Ser Arg
65                  70                  75                  80

Ala Ser Gly Phe Gln Gln Gly Gln Gln Gln Lys Ser Gln Asp Ala
                85                  90                  95

Glu Gly Trp Thr Ala Gln Lys Lys Gln Gly Lys Gln Gln Val Gln Gly
            100                 105                 110

Trp Thr Lys Gln Gly Gln Gln Gly Gly His Gln Gln Gly Arg Gln Gly
            115                 120                 125

Gln Asp Gly Gly Tyr Gln Gln Arg Pro Gly Gln Gln Gln Gly Gly
        130                 135                 140

His Gln Gln Gly Arg Gln Gly Gln Glu Gly Gly Tyr Gln Gln Arg Pro
145                 150                 155                 160

Pro Gly Gln Gln Gln Gly Gly His Gln Gln Gly Arg Gln Gly Gln Glu
                165                 170                 175

Gly Gly Tyr Gln Gln Arg Pro Ser Gly Gln Gln Gln Gly Gly His Gln
            180                 185                 190

Gln Gly Arg Gln Gly Gln Glu Gly Gly Tyr Gln Gln Arg Pro Pro Gly
        195                 200                 205

Gln Gln Gln Gly Gly His Gln Gln Gly Arg Gln Gly Gln Glu Gly Gly
        210                 215                 220

Tyr Gln Gln Arg Pro Ser Gly Gln Gln Gln Gly Gly His Gln Gln Gly
225                 230                 235                 240

Arg Gln Gly Gln Glu Gly Gly Tyr Gln Gln Arg Pro Ser Gly Gln Gln
                245                 250                 255

Gln Gly Gly His Gln Gln Gly Arg Gln Gly Gln Glu Gly Gly Tyr Gln
            260                 265                 270

Gln Arg Pro Ser Gly Gln Gln Gln Gly Gly His Gln Gln Gly Arg Gln
        275                 280                 285

Gly Gln Glu Gly Gly Tyr Gln Gln Arg Pro Pro Gly Gln Gln Pro Asn
        290                 295                 300

Gln Thr Gln Ser Gln Gly Gln Tyr Gln Ser Arg Gly Pro Pro Gln Gln
305                 310                 315                 320

Gln Gln Ala Ala Pro Leu Pro Leu Pro Pro Gln Pro Ala Gly Ser Ile
            325                 330                 335

Lys Arg Gly Thr Ile Gly Lys Pro Gly Gln Val Gly Ile Asn Tyr Leu
            340                 345                 350

Asp Leu Asp Leu Ser Lys Met Pro Ser Val Ala Tyr His Tyr Asp Val
            355                 360                 365

Lys Ile Met Pro Glu Arg Pro Lys Lys Phe Tyr Arg Gln Ala Phe Glu
            370                 375                 380

Gln Phe Arg Val Asp Gln Leu Gly Gly Ala Val Leu Ala Tyr Asp Gly
385                 390                 395                 400

Lys Ala Ser Cys Tyr Ser Val Asp Lys Leu Pro Leu Asn Ser Gln Asn
                405                 410                 415

Pro Glu Val Thr Val Thr Asp Arg Asn Gly Arg Thr Leu Arg Tyr Thr
```

```
                    420             425             430
Ile Glu Ile Lys Glu Thr Gly Asp Ser Thr Ile Asp Leu Lys Ser Leu
            435                 440                 445

Thr Thr Tyr Met Asn Asp Arg Ile Phe Asp Lys Pro Met Arg Ala Met
    450                 455                 460

Gln Cys Val Glu Val Val Leu Ala Ser Pro Cys His Asn Lys Ala Ile
465                 470                 475                 480

Arg Val Gly Arg Ser Phe Phe Lys Met Ser Asp Pro Asn Asn Arg His
                485                 490                 495

Glu Leu Asp Asp Gly Tyr Glu Ala Leu Val Gly Leu Tyr Gln Ala Phe
            500                 505                 510

Met Leu Gly Asp Arg Pro Phe Leu Asn Val Asp Ile Ser His Lys Ser
        515                 520                 525

Phe Pro Ile Ser Met Pro Met Ile Glu Tyr Leu Glu Arg Phe Ser Leu
    530                 535                 540

Lys Ala Lys Ile Asn Asn Thr Thr Asn Leu Asp Tyr Ser Arg Arg Phe
545                 550                 555                 560

Leu Glu Pro Phe Leu Arg Gly Ile Asn Val Val Tyr Thr Pro Pro Gln
                565                 570                 575

Ser Phe Gln Ser Ala Pro Arg Val Tyr Arg Val Asn Gly Leu Ser Arg
            580                 585                 590

Ala Pro Ala Ser Ser Glu Thr Phe Glu His Asp Gly Lys Lys Val Thr
        595                 600                 605

Ile Ala Ser Tyr Phe His Ser Arg Asn Tyr Pro Leu Lys Phe Pro Gln
    610                 615                 620

Leu His Cys Leu Asn Val Gly Ser Ser Ile Lys Ser Ile Leu Leu Pro
625                 630                 635                 640

Ile Glu Leu Cys Ser Ile Glu Glu Gly Gln Ala Leu Asn Arg Lys Asp
                645                 650                 655

Gly Ala Thr Gln Val Ala Asn Met Ile Lys Tyr Ala Ala Thr Ser Thr
            660                 665                 670

Asn Val Arg Lys Arg Lys Ile Met Asn Leu Leu Gln Tyr Phe Gln His
        675                 680                 685

Asn Leu Asp Pro Thr Ile Ser Arg Phe Gly Ile Arg Ile Ala Asn Asp
    690                 695                 700

Phe Ile Val Val Ser Thr Arg Val Leu Ser Pro Pro Gln Val Glu Tyr
705                 710                 715                 720

His Ser Lys Arg Phe Thr Met Val Lys Asn Gly Ser Trp Arg Met Asp
                725                 730                 735

Gly Met Lys Phe Leu Glu Pro Lys Pro Lys Ala His Lys Cys Ala Val
            740                 745                 750

Leu Tyr Cys Asp Pro Arg Ser Gly Arg Lys Met Asn Tyr Thr Gln Leu
        755                 760                 765

Asn Asp Phe Gly Asn Leu Ile Ile Ser Gln Gly Lys Ala Val Asn Ile
    770                 775                 780

Ser Leu Asp Ser Asp Val Thr Tyr Arg Pro Phe Thr Asp Asp Glu Arg
785                 790                 795                 800

Ser Leu Asp Thr Ile Phe Ala Asp Leu Lys Arg Ser Gln His Asp Leu
                805                 810                 815

Ala Ile Val Ile Ile Pro Gln Phe Arg Ile Ser Tyr Asp Thr Ile Lys
            820                 825                 830

Gln Lys Ala Glu Leu Gln His Gly Ile Leu Thr Gln Cys Ile Lys Gln
        835                 840                 845
```

-continued

```
Phe Thr Val Glu Arg Lys Cys Asn Asn Gln Thr Ile Gly Asn Ile Leu
850                 855                 860

Leu Lys Ile Asn Ser Lys Leu Asn Gly Ile Asn His Lys Ile Lys Asp
865                 870                 875                 880

Asp Pro Arg Leu Pro Met Met Lys Asn Thr Met Tyr Ile Gly Ala Asp
                885                 890                 895

Val Thr His Pro Ser Pro Asp Gln Arg Glu Ile Pro Ser Val Val Gly
            900                 905                 910

Val Ala Ala Ser His Asp Pro Tyr Gly Ala Ser Tyr Asn Met Gln Tyr
                915                 920                 925

Arg Leu Gln Arg Gly Ala Leu Glu Glu Ile Glu Asp Met Phe Ser Ile
930                 935                 940

Thr Leu Glu His Leu Arg Val Tyr Lys Glu Tyr Arg Asn Ala Tyr Pro
945                 950                 955                 960

Asp His Ile Ile Tyr Tyr Arg Asp Gly Val Ser Asp Gly Gln Phe Pro
                965                 970                 975

Lys Ile Lys Asn Glu Glu Leu Arg Cys Ile Lys Gln Ala Cys Asp Lys
                980                 985                 990

Val Gly Cys Lys Pro Lys Ile Cys Cys Val Ile Val Val Lys Arg His
            995                 1000                1005

His Thr Arg Phe Phe Pro Ser Gly Asp Val Thr Thr Ser Asn Lys
    1010                1015                1020

Phe Asn Asn Val Asp Pro Gly Thr Val Val Asp Arg Thr Ile Val
    1025                1030                1035

His Pro Asn Glu Met Gln Phe Phe Met Val Ser His Gln Ala Ile
    1040                1045                1050

Gln Gly Thr Ala Lys Pro Thr Arg Tyr Asn Val Ile Glu Asn Thr
    1055                1060                1065

Gly Asn Leu Asp Ile Asp Leu Leu Gln Gln Leu Thr Tyr Asn Leu
    1070                1075                1080

Cys His Met Phe Pro Arg Cys Asn Arg Ser Val Ser Tyr Pro Ala
    1085                1090                1095

Pro Ala Tyr Leu Ala His Leu Val Ala Ala Arg Gly Arg Val Tyr
    1100                1105                1110

Leu Thr Gly Thr Asn Arg Phe Leu Asp Leu Lys Lys Glu Tyr Ala
    1115                1120                1125

Lys Arg Thr Ile Val Pro Glu Phe Met Lys Lys Asn Pro Met Tyr
    1130                1135                1140

Phe Val
1145

<210> SEQ ID NO 6
<211> LENGTH: 22
<212> TYPE: RNA
<213> ORGANISM: Photinus pyralis

<400> SEQUENCE: 6
ucgaaguacu cagcguaagu ga                                           22

<210> SEQ ID NO 7
<211> LENGTH: 22
<212> TYPE: RNA
<213> ORGANISM: Photinus pyralis

<400> SEQUENCE: 7
cuuacgcuga guacuucgaa au                                           22
```

```
<210> SEQ ID NO 8
<211> LENGTH: 81
<212> TYPE: RNA
<213> ORGANISM: Photinus pyralis

<400> SEQUENCE: 8
caucgacuga aaucccuggu aauccguuug gggcucugcc cugcuauggg auaaauggau      60
uaucagggau uuuagucgau g                                               81

<210> SEQ ID NO 9
<211> LENGTH: 62
<212> TYPE: RNA
<213> ORGANISM: Photinus pyralis

<400> SEQUENCE: 9
caucgacuga aaucccuggu aauccguugu uaacaacgga uuaccaggga uuucagucga      60
ug                                                                    62

<210> SEQ ID NO 10
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
taatacgact cactataggg caaggtcata gttcctgcca gctg                       44

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
taatacgact cactataggg cagatatttt cttaccaccc accc                       44

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
taatacgact cactataggg ttaagtttaa caggagaagc tgga                       44

<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
taatacgact cactataggg aaatcattgc tttcctgata atgc                       44

<210> SEQ ID NO 14
<211> LENGTH: 44
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 14
taatacgact cactataggg tagatttccg cagccccagt gttc                    44

<210> SEQ ID NO 15
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
taatacgact cactataggg gttgcctctc atttttccett gatt                   44

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
taatacgact cactataggg tattttagac tgattacttt tataa                   45

<210> SEQ ID NO 17
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
taatacgact cactataggg tcacatgttt tggctaagac ctat                    44
```